United States Patent
Krieg

(10) Patent No.: US 10,682,365 B2
(45) Date of Patent: Jun. 16, 2020

(54) COMBINATION TUMOR IMMUNOTHERAPY

(71) Applicant: CHECKMATE PHARMACEUTICALS, INC., Cambridge, MA (US)

(72) Inventor: Arthur M. Krieg, Cambridge, MA (US)

(73) Assignee: CHECKMATE PHARMACEUTICALS, INC., Cambridge, MA (US)

(*) Notice: Subject to any disclaimer, the term of this patent is extended or adjusted under 35 U.S.C. 154(b) by 0 days.

(21) Appl. No.: 15/540,913

(22) PCT Filed: Dec. 22, 2015

(86) PCT No.: PCT/US2015/067269
§ 371 (c)(1),
(2) Date: Jun. 29, 2017

(87) PCT Pub. No.: WO2016/109310
PCT Pub. Date: Jul. 7, 2016

(65) Prior Publication Data
US 2018/0000851 A1 Jan. 4, 2018

Related U.S. Application Data

(60) Provisional application No. 62/118,165, filed on Feb. 19, 2015, provisional application No. 62/106,526, filed on Jan. 22, 2015, provisional application No. 62/098,568, filed on Dec. 31, 2014.

(51) Int. Cl.
| | |
|---|---|
| A61K 31/70 | (2006.01) |
| A61K 38/21 | (2006.01) |
| C12N 15/63 | (2006.01) |
| C12N 15/117 | (2010.01) |
| A61K 39/395 | (2006.01) |
| C07K 16/10 | (2006.01) |
| C07K 16/28 | (2006.01) |
| A61P 35/00 | (2006.01) |
| A61K 45/06 | (2006.01) |
| A61K 31/713 | (2006.01) |
| A61K 39/00 | (2006.01) |

(52) U.S. Cl.
CPC ............ *A61K 31/70* (2013.01); *A61K 31/713* (2013.01); *A61K 39/39541* (2013.01); *A61K 45/06* (2013.01); *A61P 35/00* (2018.01); *C07K 16/10* (2013.01); *C07K 16/2818* (2013.01); *C12N 15/117* (2013.01); *A61K 39/00* (2013.01); *A61K 2039/505* (2013.01); *C12N 2310/17* (2013.01); *C12N 2320/31* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,469,863 A | 9/1984 | Ts'o et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,397 A | 3/1989 | Boss et al. |
| 4,816,567 A | 3/1989 | Cabilly et al. |
| 5,023,243 A | 6/1991 | Tullis |
| 5,177,198 A | 1/1993 | Spielvogel et al. |
| 5,658,738 A | 8/1997 | Nadeau et al. |
| 5,668,265 A | 9/1997 | Nadeau et al. |
| 5,703,057 A | 12/1997 | Johnston et al. |
| 5,759,808 A | 6/1998 | Casterman et al. |
| 5,770,429 A | 6/1998 | Lonberg et al. |
| 5,837,243 A | 11/1998 | Deo et al. |
| 5,859,231 A | 1/1999 | Shaw et al. |
| 5,916,771 A | 6/1999 | Hori et al. |
| 5,922,845 A | 7/1999 | Deo et al. |
| 6,028,182 A | 2/2000 | Uhlmann et al. |

(Continued)

FOREIGN PATENT DOCUMENTS

| | | |
|---|---|---|
| EP | 0 338 841 A1 | 10/1989 |
| EP | 0 216 846 B1 | 1/1990 |

(Continued)

OTHER PUBLICATIONS

Bode et al., CpG DNA as a vaccine adjuvant Expert. Rev. Vaccines 10(4), 499-511 (2011).*
Ahonen et al., Combined TLR and CD40 Triggering Induces Potent CD8+ T Cell Expansion with Variable Dependence on Type I IFNJ. Exp. Med vol. 199, No. 6, Mar. 15, 2004 775-784.*
Arima et al. (2014) "Cyclodextrin/Dendrimer conjugates as DNA and oligonucleotide carriers," Curr. Top. Med. Chem. 14(4):465-77.
Barnes et al. (2001) "Characterization of the stability of recombinant protein production in the GS-NS0 expression system," Biotech. Bioeng. 73:261-270.
Beeh et al. (Feb. 4, 2013) "The novel TLR-9 agonist QbG10 shows clinical efficacy in persistent allergic asthma," J. Allergy Clin. Immunol. 131:866-74.

(Continued)

*Primary Examiner* — Maria G Leavitt
(74) *Attorney, Agent, or Firm* — Marshall, Gerstein & Borun LLP

(57) ABSTRACT

Provided are methods for treating cancer using local administration of certain CpG oligonucleotides (CpG ODN) and systemic administration of a checkpoint inhibitor such as an anti-PD-1 antibody, an anti-PD-L1 antibody, and/or an anti-CTLA-4 antibody. In preferred embodiments, the CpG ODN are selected based on their propensity to induce high amounts of interferon alpha (IFN-α) and T-cell activation relative to interleukin-10 (IL-10) and B-cell activation. In certain embodiments, the methods further include pretreatment with radiotherapy, to potentiate the combination immunotherapy.

15 Claims, 11 Drawing Sheets

Specification includes a Sequence Listing.

(56) References Cited

U.S. PATENT DOCUMENTS

| | | | |
|---|---|---|---|
| 6,160,109 | A | 12/2000 | Just et al. |
| 6,194,388 | B1 | 2/2001 | Krieg et al. |
| 6,207,819 | B1 | 3/2001 | Manoharan et al. |
| 6,239,116 | B1 | 5/2001 | Krieg et al. |
| 6,451,563 | B1 | 9/2002 | Wittig et al. |
| 6,451,593 | B1 | 9/2002 | Wittig et al. |
| 6,602,684 | B1 | 8/2003 | Umaña et al. |
| 6,682,736 | B1 | 1/2004 | Hanson et al. |
| 6,765,087 | B1 | 7/2004 | Casterman et al. |
| 6,808,710 | B1 | 10/2004 | Wood et al. |
| 6,849,725 | B2 | 2/2005 | Junghans et al. |
| 6,949,520 | B1 | 9/2005 | Hartmann et al. |
| 7,074,772 | B2 | 7/2006 | Wittig et al. |
| 7,488,802 | B2 | 2/2009 | Collins et al. |
| 7,517,520 | B2 | 4/2009 | Manolova et al. |
| 7,566,703 | B2 | 7/2009 | Krieg et al. |
| 7,635,468 | B2 | 12/2009 | Dobric et al. |
| 7,776,344 | B2 | 8/2010 | Hartmann et al. |
| 7,795,235 | B2 | 9/2010 | Krieg et al. |
| 7,943,743 | B2 | 5/2011 | Korman et al. |
| 8,017,591 | B2 | 9/2011 | Brzezicha et al. |
| 8,198,251 | B2 | 6/2012 | Vollmer et al. |
| 8,283,328 | B2 | 10/2012 | Krieg et al. |
| 8,304,396 | B2 | 11/2012 | Krieg et al. |
| 8,541,559 | B2 | 9/2013 | Kinzler et al. |
| 8,574,564 | B2 * | 11/2013 | Renner .............. A61K 39/39 424/93.2 |
| 8,580,268 | B2 | 11/2013 | Debelak et al. |
| 8,586,728 | B2 | 11/2013 | Sproat |
| 8,728,474 | B2 | 5/2014 | Honjo et al. |
| 8,834,900 | B2 | 9/2014 | Krieg et al. |
| 2002/0086014 | A1 | 7/2002 | Korman et al. |
| 2002/0088014 | A1 | 7/2002 | Fang et al. |
| 2003/0086930 | A1 | 5/2003 | Mueller et al. |
| 2003/0099668 | A1 | 5/2003 | Bachmann et al. |
| 2003/0125279 | A1 | 7/2003 | Junghans et al. |
| 2003/0157108 | A1 | 8/2003 | Presta |
| 2003/0207336 | A1 | 11/2003 | Jardieu et al. |
| 2003/0207346 | A1 | 11/2003 | Arathoon et al. |
| 2004/0063911 | A1 | 4/2004 | Defrees et al. |
| 2004/0072290 | A1 | 4/2004 | Umana et al. |
| 2004/0120948 | A1 | 6/2004 | Mikayama et al. |
| 2004/0132640 | A1 | 7/2004 | Defrees et al. |
| 2004/0142856 | A1 | 7/2004 | Defrees et al. |
| 2004/0198680 | A1 | 10/2004 | Krieg |
| 2007/0184068 | A1 | 8/2007 | Renner et al. |
| 2008/0045473 | A1 | 2/2008 | Uhlmann et al. |
| 2009/0082295 | A1 | 3/2009 | Jungnelius et al. |
| 2009/0117132 | A1 | 5/2009 | Readett et al. |
| 2010/0098722 | A1 | 4/2010 | Bachmann et al. |
| 2012/0003179 | A1 | 1/2012 | Readett et al. |
| 2012/0251494 | A1 | 10/2012 | Kedl et al. |
| 2012/0301499 | A1 * | 11/2012 | Bachmann .............. A61K 39/00 424/196.11 |
| 2014/0163213 | A1 | 6/2014 | Debelak et al. |

FOREIGN PATENT DOCUMENTS

| | | |
|---|---|---|
| EP | 0 256 055 B1 | 8/1991 |
| EP | 0 092 574 B1 | 4/1992 |
| EP | 0 323 997 B1 | 4/1993 |
| EP | 1 262 193 A1 | 12/2002 |
| WO | 1993/000431 A1 | 1/1993 |
| WO | 1995/001363 A1 | 1/1995 |
| WO | 1996/002555 A1 | 2/1996 |
| WO | 1998/018810 A1 | 5/1998 |
| WO | 1998/058964 A1 | 12/1998 |
| WO | 1999/022764 A1 | 5/1999 |
| WO | 2000/006588 A1 | 2/2000 |
| WO | 2000/024893 A2 | 5/2000 |
| WO | 2000/032231 A1 | 6/2000 |
| WO | 2000/037504 A2 | 6/2000 |
| WO | 2001/014424 A2 | 3/2001 |
| WO | 2001/081405 A2 | 11/2001 |
| WO | 2003/024481 A2 | 3/2003 |
| WO | 2003/031464 A2 | 4/2003 |
| WO | 2004/084940 A1 | 10/2004 |
| WO | 2007/068747 A1 | 6/2007 |
| WO | 2007/144150 A1 | 12/2007 |
| WO | 2008/073960 A2 | 6/2008 |
| WO | WO 2012/006634 A2 | 1/2012 |

OTHER PUBLICATIONS

Brody et al. (2010) "In situ vaccination with a TLR9 agonist induces systemic lymphoma regression: a phase I/II study," J. Clin. Oncol. 28(28):4324-4332.

Burnette et al. (2011) "The efficacy of radiotherapy relies upon induction of type i interferon-dependent innate and adaptive immunity," Cancer Res. 71:2488-2496.

Butt et al. (Oct. 21, 2013) "Immunosuppressive networks and checkpoints controlling antitumor immunity and their blockade in the development of cancer immunotherapeutics and vaccines," Oncogene. 33(38):4623-31.

Chen et al. (2008) "The indoleamine 2,3-dioxygenase pathway is essential for human plasmacytoid dendritic cell-induced adaptive T regulatory cell generation," J. Immunol. 181(8):5396-5404.

Chen et al. (Jul. 25, 2013) "Oncology meets immunology: the cancer-immunity cycle," Immunity. 39(1):1-10.

Crooke et al. (1996) "Progress in antisense oligonucleotide therapeutics," Annu. Rev. Pharmacol. Toxicol. 36:107-129.

Durand et al. (1992) "Triple-helix formation by an oligonucleotide containing one (dA)12 and two (dT)12 sequences bridged by two hexaethylene glycol chains," Biochemistry. 31(38):9197-204.

Fontanel et al. (1994) "Sterical recognition by T4 polynucleotide kinase of non-nucleosidic moieties 5'-attached to oligonucleotides," Oligonucleotides Research. 22(11):2022-7.

Fransen et al. (Oct. 10, 2013) "Local immunomodulation for cancer therapy: Providing treatment where needed," Oncoimmunology. 2(11):e26493.

Froehler et al. (1992) "Triple-helix formation by oligodeoxynucleotides containing the carbocyclic analogs of thymidine and 5-methyl-2'-deoxycytidine," J. Am. Chem. Soc. 114:8320-8322.

Goodchild (1990) "Conjugates of oligonucleotides and modified oligonucleotides: a review of their synthesis and properties," Bioconjugate Chem. 1:165-87.

Grimaldi et al. (May 14, 2014) "Abscopal effects of radiotherapy on advanced melanoma patients who progressed after ipilimumab immunotherapy," Oncoimmunology. 3:e28780.

Hartmann et al. (2003) "Rational design of new CpG oligonucleotides that combine B cell activation with high IFN-alpha induction in plasmacytoid dendritic cells," Eur. J. Immunol. 33:1633-1641.

Herbst et al. (Nov. 26, 2014) "Predictive correlates of response to the anti-PD-L1 antibody MPDL3280A in cancer patients," Nature. 515:563-567.

Hunziker et al. (1995) "Nucleic acid analogues: synthesis and properties," In; Modern Synthetic Methods. Verlag Helvetica Chimica Acta. pp. 331-417.

Jiang et al. (1999) "Pseudo-cyclic oligonucleotides: in vitro and in vivo properties," Bioorganic & Medicinal Chemistry. 7(12):2727-2735.

Joshi et al. (2012) "Biodegradable particles as vaccine delivery systems: size matters," AAPS. J. 15(1):85-94.

Kapp et al. (Jun. 24, 2014) "Genuine Immunomodulation With dSLIM," Mol. Ther. Nucleic Acids. 3:e170.

Karbach et al. (2010) "Tumor-reactive CD8+ T-cell responses after vaccination with NY-ESO-1 peptide, CpG 7909 and Montanide ISA-51: association with survival," Int. J. Cancer. 126(4):909-18.

Karbach et al. (2011) "Efficient in vivo priming by vaccination with recombinant NY-ESO-1 protein and CpG in antigen naive prostate cancer patients," Clin. Cancer Res. 17(4):861-70.

Kim et al. (2012) "In situ vaccination against mycosis fungoides by intratumoral injection of a TLR9 agonist combined with radiation: a phase 1/2 study," Blood. 119(2):355-363.

Kim et al. (Oct. 2014) "The path to reactivation of antitumor immunity and checkpoint immunotherapy," Cancer Immunol. Res. 2:926-936.

(56) References Cited

OTHER PUBLICATIONS

Kortylewski et al. (2009) "In vivo delivery of siRNA to immune cells by conjugation to a TLR9 agonist enhances antitumor immune responses," Nat Biotechnol. 27(10):925-932.
Krieg (2002) "CpG motifs in bacterial DNA and their immune effects," Annu. Rev. Immunol. 20:709-60.
Krieg (2006) "Therapeutic potential of Toll-like receptor 9 activation," Nat. Rev. Drug Discov. 5(6):471-84.
Krieg (2012) "CpG still rocks! Update on an accidental drug," Nucleic Acid Ther. 22(2):77-89.
Krieg et al. (2003) "P-chirality-dependent immune activation by phosphorothioate CpG oligodeoxynucleotides," Oligonucleotides. 13(6):491-499.
Krieg et al. (2004) "Induction of systemic TH1-like innate immunity in normal volunteers following subcutaneous but not intravenous administration of CPG 7909, a synthetic B-class CpG oligodeoxynucleotide TLR9 agonist," J. Immunother. 27:460-471.
Krug et al. (2001) "Identification of CpG oligonucleotide sequences with high induction of IFN-alpha/beta in plasmacytoid dendritic cells," Eur. J. Immunol. 31(7):2154-63.
Kruit et al. (May 28, 2013) "Selection of Immunostimulant AS15 for Active Immunization With MAGE-A3 Protein: Results of a Randomized Phase II Study of the European Organisation for Research and Treatment of Cancer Melanoma Group in Metastatic Melanoma," J. Clin. Oncol. 31(19):2413-20.
Lovgren et al. (2012) "Enhanced cytotoxicity and decreased CD8 dependence of human cancer-specific cytotoxic T lymphocytes after vaccination with low peptide dose," Cancer Immunol. Immunother. 61(6):817-26.
Lu (Mar. 3, 2014) "TLR agonists for cancer immunotherapy: tipping the balance between the immune stimulatory and inhibitory effects," Front. Immunol. 5:83.
Mangsbo et al. (2010) "Enhanced tumor eradication by combining CTLA-4 or PD-1 blockade with CpG therapy," J. Immunother. 33:225-35.
Marshall et al. (2003) "Identification of a novel CpG DNA class and motif that optimally stimulate B cell and plasmacytoid dendritic cell functions," J. Leukocyte Biol. 73:781-792.
Marshall et al. (2003) "Novel chimeric immunomodulatory compounds containing short CpG oligodeoxyribonucleotides have differential activities in human cells," Nucleic Acids Res. 31(17):5122-33.
Marshall et al. (2005) "Superior activity of the type C class of ISS in vitro and in vivo across multiple species," DNA Cell Biol. 24(2):63-72.
Millward et al. (May 7, 2013) "Phase I study of tremelimumab (CP-675 206) plus PF-3512676 (CPG 7909) in patients with melanoma or advanced solid tumours," Br. J. Cancer 108(10):1998-2004.
Molenkamp et al. (2007) "Intradermal CpG-B activates both plasmacytoid and myeloid dendritic cells in the sentinel lymph node of melanoma patients," Clin. Cancer Res. 13(10):2961-2969.
Moseman et al. (2004) "Human plasmacytoid dendritic cells activated by CpG oligodeoxynucleotides induce the jeneration of CD4+CD25+ regulatory T cells," J. Immunol. 173(7):4433-4442.
Mumm et al. (May 13, 2013) "Pegylated IL-10 induces cancer immunity: the surprising role of IL-10 as a potent inducer of IFN-γ-mediated CD8(+) T cell cytotoxicity," Bioessays. 35(7):623-631.
Nielsen et al. (1994) "Peptide nucleic acid (PNA). A DNA mimic with a peptide backbone," Bioconjug. Chem. 5:3-7.
Ortigao et al. (1992) "Antisense effect of oligodeoxynucleotides with inverted terminal internucleotidic linkages: a minimal modification protecting against nucleolytic degradation," Antisense Research and Development 2:129-46.
Postow et al. (2012) "Immunologic correlates of the abscopal effect in a patient with melanoma," N. Engl. J. Med. 366(10):925-31.
Powles et al. (Nov. 27, 2014) "MPDL3280A (anti-PD-L1) treatment leads to clinical activity in metastatic bladder cancer," Nature. 515:558-62.
Prasanna et al. (Apr. 2014) "Exploiting sensitization windows of opportunity in hyper and hypo-fractionated radiation therapy," J. Thoracic Dis. 6(4):287-302.
Rajasagi et al. (Jun. 2, 2014) "Systematic identification of personal tumor-specific neoantigens in chronic lymphocytic leukemia," Blood. 124(3):453-462.
Sato et al. (2011) "Interleukin 10 in the Tumor Microenvironment: A Target for Anticancer Immunotherapy," Immunol. Res. 51(2-3):170-182.
Schmidt et al. (2006) "Cytokine and lg-production by CG-containing sequences with phosphorodiester backbone and lumbbell-shape," Allergy. 61:56-63.
Siegal et al. (1999) "The nature of the principal type 1 interferon-producing cells in human blood," Science. 284(5421):1835-7.
Speiser et al. (2005) "Rapid and strong human CD8+ T cell responses to vaccination with peptide, IFA, and CpG oligodeoxynucleotide 7909," J. Clin. Ivest. 115(3):739-46.
Speiser et al. (2010) "Memory and effector CD8 T-cell responses after nanoparticle vaccination of melanoma patients," J. Immunother. 33(8):848-58.
Tarhini et al. (2012) "Differing patterns of circulating regulatory T cells and myeloid-derived suppressor cells in metastatic melanoma patients receiving anti-CTLA4 antibody and interferon-α or TLR-9 agonist and GM-CSF with peptide vaccination," J. Immunother. 35(9):702-10.
Taube et al. (Apr. 8, 2014) "Association of PD-1, PD-1 ligands, and other features of the tumor immune microenvironment with response to anti-PD-1 therapy," Clin. Cancer Res. 20(19):5064-74.
Tumeh et al. (Nov. 27, 2014) "PD-1 blockade induces responses by inhibiting adaptive immune resistance," Nature. 515:568-571.
Uhlmann et al. (1990) "Antisense oligonucleotides: a new therapeutic principle," Chem. Rev. 90(4):543-584.
Vicari et al. (2004) "Interleukin-10 in viral diseases and cancer: exiting the labyrinth?" Immunol. Rev. 202:223-36.
Vollmer et al. (2004) "Characterization of three CpG oligodeoxynucleotide classes with distinct immunostimulatory activities," Eur. J. Immunol. 34:251-262.
International Search Report with Written Opinion corresponding to International Patent Application No. PCT/US2015/067269, dated Mar. 11, 2016.
Supplementary European Search Report for EP15876030 dated Jun. 26, 2018.
Nierkens, Stefan et al. (Jan. 1, 2009) "Route of administration of the TLR9 agonist CpG critically determines the efficacy of cancer immunotherapy in mice," PLOS ONE, vol. 4, No. 12, pp. e8368.
Wong, R M et al. (Dec. 2, 2009) "TLR-9 signaling and TCR stimulation co-regulate CD8+ T cell-associated PD-1 expression," Immunology Letters, vol. 127, No. 1, pp. 60-67.

* cited by examiner

A

B

SEQUENCE LISTING

<160> NUMBER OF SEQ ID NOS: 550

<210> SEQ ID NO 1
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine

<400> SEQUENCE: 1
ggggacganc gtcggggg                                              18

<210> SEQ ID NO 2

```
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine

<400> SEQUENCE: 2
ggggacgana tcgtcggggg                                               20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: 5-iodo-2'-deoxyuridine

<400> SEQUENCE: 3
ggggacgagc ngctcggggg                                               20

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine

<400> SEQUENCE: 4
ggggncaccg gtgaggggg                                                19

<210> SEQ ID NO 5
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine

<400> SEQUENCE: 5
ggggncgacg tacgtcgagg ggg                                           23

<210> SEQ ID NO 6
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (11)..(11)
<223> OTHER INFORMATION: 5-iodo-2'-deoxyuridine

<400> SEQUENCE: 6
```
ggggncgacg nacgtcgagg ggg                                    23

<210> SEQ ID NO 7
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (15)..(15)
<223> OTHER INFORMATION: 5-iodo-2'-deoxyuridine

<400> SEQUENCE: 7
ggggncgacg tacgncgagg ggg                                    23

<210> SEQ ID NO 8
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (11)..(11)
<223> OTHER INFORMATION: 5-iodo-2'-deoxyuridine
<220> FEATURE:
<221> NAME/KEY: misc_feature
<222> LOCATION: (15)..(15)
<223> OTHER INFORMATION: 5-iodo-2'-deoxyuridine

<400> SEQUENCE: 8
ggggncgacg nacgncgagg ggg                                    23

<210> SEQ ID NO 9
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (9)..(9)
<223> OTHER INFORMATION: 5-iodo-2'-deoxyuridine

<400> SEQUENCE: 9
ggggacgncg acgtgggg                                          18

<210> SEQ ID NO 10
<211> LENGTH: 26
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine

```
<400> SEQUENCE: 10
ggggncgacg tcgacgtcga gggggg                                             26

<210> SEQ ID NO 11
<211> LENGTH: 26
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (11)..(11)
<223> OTHER INFORMATION: 5-iodo-2'-deoxyuridine

<400> SEQUENCE: 11
ggggncgacg ncgacgtcga gggggg                                             26

<210> SEQ ID NO 12
<211> LENGTH: 26
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (17)..(17)
<223> OTHER INFORMATION: 5-iodo-2'-deoxyuridine

<400> SEQUENCE: 12
ggggncgacg tcgacgncga gggggg                                             26

<210> SEQ ID NO 13
<211> LENGTH: 26
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (11)..(11)
<223> OTHER INFORMATION: 5-iodo-2'-deoxyuridine
<220> FEATURE:
<221> NAME/KEY: misc_feature
<222> LOCATION: (17)..(17)
<223> OTHER INFORMATION: 5-iodo-2'-deoxyuridine

<400> SEQUENCE: 13
ggggncgacg ncgacgncga gggggg                                             26

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: 5-iodo-2'-deoxyuridine
```

```
<220> FEATURE:
<221> NAME/KEY: misc_feature
<222> LOCATION: (14)..(14)
<223> OTHER INFORMATION: 5-iodo-2'-deoxyuridine

<400> SEQUENCE: 14
ggggacgacg ncgnggggggg                                              20

<210> SEQ ID NO 15
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine

<400> SEQUENCE: 15
ggggncgtcg acgaggggg                                                19

<210> SEQ ID NO 16
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: 5-iodo-2'-deoxyuridine

<400> SEQUENCE: 16
ggggtcgncg acgaggggg                                                19

<210> SEQ ID NO 17
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (8)..(8)
<223> OTHER INFORMATION: 5-iodo-2'-deoxyuridine

<400> SEQUENCE: 17
ggggncgncg acgaggggg                                                19

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: 5-iodo-2'-deoxyuridine

<400> SEQUENCE: 18
ggggacgagc ncgtcggggg g                                             21

<210> SEQ ID NO 19
```

```
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: 5-iodo-2'-deoxyuridine

<400> SEQUENCE: 19
gggggacgag cncgtcgggg g                                            21

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: 5-iodo-2'-deoxyuridine

<400> SEQUENCE: 20
ggggacgagc ncgtcggggg                                              20

<210> SEQ ID NO 21
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: 5-iodo-2'-deoxyuridine

<400> SEQUENCE: 21
ggggacgagc ncgtcgggg                                               19

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine

<400> SEQUENCE: 22
ggggacganc gtcggggggg                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: 5-iodo-2'-deoxyuridine

<400> SEQUENCE: 23
gggggacgan cgtcggggg                                               20
```

```
<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine

<400> SEQUENCE: 24
ggggacganc gtcgggggg                                                19

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine
<220> FEATURE:
<221> NAME/KEY: misc_feature
<222> LOCATION: (12)..(12)
<223> OTHER INFORMATION: 5-iodo-2'-deoxyuridine

<400> SEQUENCE: 25
ggggacganc gncggggggg                                               20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: 5-iodo-2'-deoxyuridine
<220> FEATURE:
<221> NAME/KEY: misc_feature
<222> LOCATION: (13)..(13)
<223> OTHER INFORMATION: 5-iodo-2'-deoxyuridine

<400> SEQUENCE: 26
gggggacgan cgncgggggg                                               20

<210> SEQ ID NO 27
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine
<220> FEATURE:
<221> NAME/KEY: misc_feature
<222> LOCATION: (12)..(12)
<223> OTHER INFORMATION: 5-iodo-2'-deoxyuridine

<400> SEQUENCE: 27
ggggacganc gncgggggg                                                19

<210> SEQ ID NO 28
<211> LENGTH: 18
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine
<220> FEATURE:
<221> NAME/KEY: misc_feature
<222> LOCATION: (12)..(12)
<223> OTHER INFORMATION: 5-iodo-2'-deoxyuridine

<400> SEQUENCE: 28
ggggacganc gncgggg                                                      18

<210> SEQ ID NO 29
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine

<400> SEQUENCE: 29
ggggacganc gaacgtgggg gg                                                22

<210> SEQ ID NO 30
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine

<400> SEQUENCE: 30
ggggacganc gaacgtgggg g                                                 21

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine

<400> SEQUENCE: 31
ggggacganc gaacgtgggg                                                   20

<210> SEQ ID NO 32
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine
<220> FEATURE:
<221> NAME/KEY: misc_feature
<222> LOCATION: (16)..(16)
<223> OTHER INFORMATION: 5-iodo-2'-deoxyuridine
```

<400> SEQUENCE: 32
ggggacganc gaacgngggg gg                                                            22

<210> SEQ ID NO 33
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine
<220> FEATURE:
<221> NAME/KEY: misc_feature
<222> LOCATION: (16)..(16)
<223> OTHER INFORMATION: 5-iodo-2'-deoxyuridine

<400> SEQUENCE: 33
ggggacganc gaacgngggg g                                                             21

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine
<220> FEATURE:
<221> NAME/KEY: misc_feature
<222> LOCATION: (16)..(16)
<223> OTHER INFORMATION: 5-iodo-2'-deoxyuridine

<400> SEQUENCE: 34
ggggacganc gaacgngggg                                                               20

<210> SEQ ID NO 35
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine

<400> SEQUENCE: 35
ggggncgacg tcgacgtcga ggggggg                                                       27

<210> SEQ ID NO 36
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine

<400> SEQUENCE: 36
ggggncgacg tcgacgtcga ggggg                                                         25

<210> SEQ ID NO 37

```
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (11)..(11)
<223> OTHER INFORMATION: 5-iodo-2'-deoxyuridine

<400> SEQUENCE: 37
ggggncgacg ncgacgtcga ggggggg                                27

<210> SEQ ID NO 38
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (11)..(11)
<223> OTHER INFORMATION: 5-iodo-2'-deoxyuridine

<400> SEQUENCE: 38
ggggncgacg ncgacgtcga ggggg                                  25

<210> SEQ ID NO 39
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (17)..(17)
<223> OTHER INFORMATION: 5-iodo-2'-deoxyuridine

<400> SEQUENCE: 39
ggggncgacg tcgacgncga ggggggg                                27

<210> SEQ ID NO 40
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (17)..(17)
<223> OTHER INFORMATION: 5-iodo-2'-deoxyuridine

<400> SEQUENCE: 40
ggggncgacg tcgacgncga ggggg                                  25
```

```
<210> SEQ ID NO 41
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (11)..(11)
<223> OTHER INFORMATION: 5-iodo-2'-deoxyuridine
<220> FEATURE:
<221> NAME/KEY: misc_feature
<222> LOCATION: (17)..(17)
<223> OTHER INFORMATION: 5-iodo-2'-deoxyuridine

<400> SEQUENCE: 41
ggggncgacg ncgacgncga ggggggg                                      27

<210> SEQ ID NO 42
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 5-iodo-2'-deoxyuridine
<220> FEATURE:
<221> NAME/KEY: misc_feature
<222> LOCATION: (11)..(11)
<223> OTHER INFORMATION: 5-iodo-2'-deoxyuridine
<220> FEATURE:
<221> NAME/KEY: misc_feature
<222> LOCATION: (17)..(17)
<223> OTHER INFORMATION: 5-iodo-2'-deoxyuridine

<400> SEQUENCE: 42
ggggncgacg ncgacgncga ggggg                                        25

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ggggtcaacg ttgaggggggg                                             20

<210> SEQ ID NO 44
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 44
tcgtcgtttt gtcgttttgt cgtt                                         24

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 45
ggggtcgtcg ttttgggggg                                              20

<210> SEQ ID NO 46
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 46
tcgtcgtttt gtcgttttgg gggg                                         24

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
ggggtcgacg tcgagggggg                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ggggtcatcg atgaggggggg                                             20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
gggggacgat cgtcgggggg                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gggggtcgta cgacggggggg                                             20

<210> SEQ ID NO 51
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 51
gggggacgat atcgtcgggg gg                                           22

<210> SEQ ID NO 52
<211> LENGTH: 22
```

```
<212> TYPE: DNA
<213> ORGANISM: Artificial sequence
<220> FEATURE:
<223> OTHER INFORMATION: Synthetic oligonucleotide

<400> SEQUENCE: 52
gggggacgac gtcgtcgggg gg                                            22

<210> SEQ ID NO 53
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 53
gggggacgag ctgctcgggg gg                                            22

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gggggacgta cgtcggggg                                                20

<210> SEQ ID NO 55
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 55
gggggacgat cgttgggggg g                                             21

<210> SEQ ID NO 56
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 56
ggggaacgat cgtcggggg                                                19

<210> SEQ ID NO 57
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 57 gggggggacga tcgtcggggg g                                            21

<210> SEQ ID NO 58
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 58
```

```
gggggacgat cgtcggggggg g                                          21
```

<210> SEQ ID NO 59
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 59

```
gggggtcatc gatgaggggg g                                           21
```

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60

```
ggggtcgtcg acgaggggg                                              20
```

<210> SEQ ID NO 61
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 61

```
ggggtcgttc gaacgagggg gg                                          22
```

<210> SEQ ID NO 62
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 62

```
ggggacgttc gaacgtgggg gg                                          22
```

<210> SEQ ID NO 63
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 63

```
ggggaacgac gtcgttgggg gg                                          22
```

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64

```
ggggaacgta cgtcggggg                                              20
```

<210> SEQ ID NO 65
<211> LENGTH: 24
<212> TYPE: DNA
<213> ORGANISM: Artificial sequence -continued

```
<220> FEATURE:
<223> OTHER INFORMATION: Synthetic oligonucleotide

<400> SEQUENCE: 65
ggggaacgta cgtacgttgg gggg                                              24

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ggggtcaccg gtgagggggg                                                   20

<210> SEQ ID NO 67
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 67
ggggtcgacg tacgtcgagg gggg                                              24

<210> SEQ ID NO 68
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 68
ggggaccggt accggtgggg gg                                                22

<210> SEQ ID NO 69
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 69
gggtcgacgt cgagggggg                                                    19

<210> SEQ ID NO 70
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 70
ggggtcgacg tcgagggg                                                     18

<210> SEQ ID NO 71
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 71
ggggaacgtt aacgttgggg gg                                                22
```

<210> SEQ ID NO 72
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 72
ggggacgtcg acgtggggg                                              19

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
gggggtcgtt cgttggggggg                                            20

<210> SEQ ID NO 74
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 74
gggacgatcg tcggggggg                                              19

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gggtcgtcga cgagggggggg                                            20

<210> SEQ ID NO 76
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 76
ggtcgtcgac gaggggggg                                              19

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
ggggacgatc gtcggggggg                                             20

<210> SEQ ID NO 78
<211> LENGTH: 27
<212> TYPE: DNA
<213> ORGANISM: Artificial sequence
<220> FEATURE:
<223> OTHER INFORMATION: Synthetic oligonucleotide

```
<400> SEQUENCE: 78
ggggtcgacg tcgacgtcga ggggggg                                          27

<210> SEQ ID NO 79
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 79
ggggacgacg tcgtggggg g                                                 21

<210> SEQ ID NO 80
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 80
gggggacgag ctcgtcgggg gg                                               22

<210> SEQ ID NO 81
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 81
ggggacgatc gaacgtgggg gg                                               22

<210> SEQ ID NO 82
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 82
gggggggggg gacgatcgtc gggggggggg                                       30

<210> SEQ ID NO 83
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 83
tcgtcgtttt cggcgcgcgc cg                                               22

<210> SEQ ID NO 84
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 84
tcgtcgtttt cggcggccgc cg                                               22

<210> SEQ ID NO 85
```

```
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 85
tcgtcgtttt cggcgcgccg cg                                              22

<210> SEQ ID NO 86
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 86
tcgtcgtttt cggcgccggc cg                                              22

<210> SEQ ID NO 87
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 87
tcgtcgtttt cggcccgcgc gg                                              22

<210> SEQ ID NO 88
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 88
tcgtcgtttt cggcgcgcgc cgttttt                                         27

<210> SEQ ID NO 89
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 89
tcctgacgtt cggcgcgcgc cg                                              22

<210> SEQ ID NO 90
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: m5c
<220> FEATURE:
<221> NAME/KEY: misc_feature
<222> LOCATION: (5)..(5)
<223> OTHER INFORMATION: m5c
<220> FEATURE:
<221> NAME/KEY: misc_feature
<222> LOCATION: (11)..(11)
<223> OTHER INFORMATION: m5c
<220> FEATURE:
<221> NAME/KEY: misc_feature
```

```
<222> LOCATION: (14)..(14)
<223> OTHER INFORMATION: m5c
<220> FEATURE:
<221> NAME/KEY: misc_feature
<222> LOCATION: (16)..(16)
<223> OTHER INFORMATION: m5c
<220> FEATURE:
<221> NAME/KEY: misc_feature
<222> LOCATION: (18)..(18)
<223> OTHER INFORMATION: m5c
<220> FEATURE:
<221> NAME/KEY: misc_feature
<222> LOCATION: (20)..(21)
<223> OTHER INFORMATION: m5c

<400> SEQUENCE: 90
tngtngtttt nggngngngn ng                                              22

<210> SEQ ID NO 91
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 91
tcctgacgtt cggcgcgcgc cc                                              22

<210> SEQ ID NO 92
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 92
tcggcgcgcg ccgtcgtcgt tt                                              22

<210> SEQ ID NO 93
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 93
tcgtcgtttt cggcggccga cg                                              22

<210> SEQ ID NO 94
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 94
tcgtcgtttt cgtcggccgc cg                                              22

<210> SEQ ID NO 95
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 95
tcgtcgtttt cgacggccgc cg                                              22
```

<210> SEQ ID NO 96
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 96
tcgtcgtttt cggcggccgt cg                                              22

<210> SEQ ID NO 97
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 97
tcgtcgtttc gacggccgtc g                                               21

<210> SEQ ID NO 98
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 98
tcgtcgtttc gacgatcgtc g                                               21

<210> SEQ ID NO 99
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 99
tcgtcgtttc gacgtacgtc g                                               21

<210> SEQ ID NO 100
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 100
tcgtcgcgac ggccgtcg                                                   18

<210> SEQ ID NO 101
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 101
tcgtcgcgac gatcgtcg                                                   18

<210> SEQ ID NO 102
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 102
tcgtcgcgac gtacgtcg                                                    18

<210> SEQ ID NO 103
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 103
tcgttttttt cgacggccgt cg                                               22

<210> SEQ ID NO 104
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 104
tcgttttttt cgacgatcgt cg                                               22

<210> SEQ ID NO 105
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 105
tcgttttttt cgacgtacgt cg                                               22

<210> SEQ ID NO 106
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 106
tttcgtcgtt tcgtcgtt                                                    18

<210> SEQ ID NO 107
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 107
tcgtcgttcg gcgcgccg                                                    18

<210> SEQ ID NO 108
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 108
tcgtcgtcgt tcggcgcgcg ccg                                              23

<210> SEQ ID NO 109

-continued

```
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 109
tcgtcgacga tcggcgcgcg ccg                                          23

<210> SEQ ID NO 110
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 110
ttcgtcgttt tgtcgtt                                                 17

<210> SEQ ID NO 111
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 111
tcgtcgtcgt tcggcgcgcg cc                                           22

<210> SEQ ID NO 112
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 112
tcgtcgtcgt tcggcgc                                                 17

<210> SEQ ID NO 113
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 113
tcgtcgtcgt tcggcgcgcg c                                            21

<210> SEQ ID NO 114
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 114
cgtcgtcgtt cggcgcgcgc cg                                           22

<210> SEQ ID NO 115
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 115
```
gtcgtcgttc ggcgcgcgcc g                                              21

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
tcgtcgttcg gcgcgcgccg                                                20

<210> SEQ ID NO 117
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 117
cgtcgttcgg cgcgcgccg                                                 19

<210> SEQ ID NO 118
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 118
gtcgttcggc gcgcgccg                                                  18

<210> SEQ ID NO 119
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 119
tcgttcggcg cgcgccg                                                   17

<210> SEQ ID NO 120
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 120
tcgtcgacga ttttacgacg tcgttttt                                       28

<210> SEQ ID NO 121
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 121
tcgtcgacga ttttacgacg tcgtttt                                        27

<210> SEQ ID NO 122
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 122
tcgtcgacga acgacgtcgt                                                    20

<210> SEQ ID NO 123
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 123
tcgtcgacga tttttcgtcg acgattt                                            27

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
tcgtcgacga tcgtcgacga                                                    20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
cgcgcgcgcg cgcgcgcgcg                                                    20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: biotin appended

<400> SEQUENCE: 126
gagaacgctc gaccttcgat                                                    20

<210> SEQ ID NO 127
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 127
agctccatgg tgctcactg                                                     19

<210> SEQ ID NO 128
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 128
tctcccagcg tgcgccat                                              18

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
tccatgacgt tcctgaggtt                                            20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
tccaggactt ctctcaggtt                                            20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
tccacgacgt tttcgacgtt                                            20

<210> SEQ ID NO 132
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 132
tcgtcgtttt gacgttttga cgtt                                       24

<210> SEQ ID NO 133
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 133
tcgcgtgcgt tttgtcgttt tgacgtt                                    27

<210> SEQ ID NO 134
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 134
tcgcgacgtt cggcgcgcgc cg                                         22

<210> SEQ ID NO 135
```

```
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: digoxygenin appended

<400> SEQUENCE: 135
ccggccggcc ggccggccgg                                          20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: digoyxgenin appended

<400> SEQUENCE: 136
cgcgcgcgcg cgcgcgcgcg                                          20

<210> SEQ ID NO 137
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 137
tccaggactt ctctcaggtt tttt                                     24

<210> SEQ ID NO 138
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 138
gtgctcgagg atgcgcttcg c                                        21

<210> SEQ ID NO 139
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 139
gccgaggtcc atgtcgtacg c                                        21

<210> SEQ ID NO 140
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 140
accgataccg gtgccggtga cggcaccacg                               30
```

```
<210> SEQ ID NO 141
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 141
accgataacg ttgccggtga cggcaccacg                              30

<210> SEQ ID NO 142
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 142
accgatgacg tcgccggtga cggcaccacg                              30

<210> SEQ ID NO 143
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 143
cggcgcgcgc cgcggcgcgc gccg                                    24

<210> SEQ ID NO 144
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 144
tcgatcgttt ttcgtgcgtt ttt                                     23

<210> SEQ ID NO 145
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 145
tcgtccagga cttctctcag gtt                                     23

<210> SEQ ID NO 146
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 146
tcgtcgtcca ggacttctct caggtt                                  26

<210> SEQ ID NO 147
<211> LENGTH: 22
<212> TYPE: DNA
<213> ORGANISM: Artificial sequence
<220> FEATURE:
<223> OTHER INFORMATION: Synthetic oligonucleotide
```

```
<400> SEQUENCE: 147
tcgtgacggg cggcgcgcgc cc                                        22

<210> SEQ ID NO 148
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 148
acgacgtcgt tcggcggccg ccg                                       23

<210> SEQ ID NO 149
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 149
ggggacgacg tcgtgcggcg gccgccg                                   27

<210> SEQ ID NO 150
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 150
ccacgacgtc gtcgaagacg acgtcgtgg                                 29

<210> SEQ ID NO 151
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 151
ctgcagctgc agctgcagct gcag                                      24

<210> SEQ ID NO 152
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 152
cggccgctgc agcggccgct gcag                                      24

<210> SEQ ID NO 153
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 153
catgacgttt ttgatgtt                                             18

<210> SEQ ID NO 154
<211> LENGTH: 17
```

```
<212> TYPE: DNA
<213> ORGANISM: Artificial sequence
<220> FEATURE:
<223> OTHER INFORMATION: Synthetic oligonucleotide

<400> SEQUENCE: 154
atgacgtttt tgatgtt                                                    17

<210> SEQ ID NO 155
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 155
tgacgttttt gatgtt                                                     16

<210> SEQ ID NO 156
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 156
atgacgtttt tgatgttgt                                                  19

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
tccatgacgt ttttgatgtt                                                 20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
tccatgcgtt tttgaatgtt                                                 20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
tccatgacgt ctttgatgtc                                                 20

<210> SEQ ID NO 160
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (22)..(22)
```

```
<223> OTHER INFORMATION: cholesterol appended

<400> SEQUENCE: 160
acgacgtcgt tcacgacgtc gt                                              22

<210> SEQ ID NO 161
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (25)..(27)
<223> OTHER INFORMATION: 1'2'-dideoxyribose (D spacer)

<400> SEQUENCE: 161
acgacgtcgt ggccacgacg tcgtnnn                                         27

<210> SEQ ID NO 162
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)

<400> SEQUENCE: 162
acgacgtcgt nnnnacgacg tcgtnnn                                         27

<210> SEQ ID NO 163
<211> LENGTH: 30
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: 1'2'-dideoxyribose (D spacer)
<220> FEATURE:
<221> NAME/KEY: misc_feature
<222> LOCATION: (14)..(17)
<223> OTHER INFORMATION: 1'2'-dideoxyribose (D spacer)
<220> FEATURE:
<221> NAME/KEY: misc_feature
<222> LOCATION: (28)..(30)
<223> OTHER INFORMATION: 1'2'-dideoxyribose (D spacer)

<400> SEQUENCE: 163
nnnacgacgt cgtnnnnacg acgtcgtnnn                                      30

<210> SEQ ID NO 164
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: 1'2'-dideoxyribose (D spacer)
<220> FEATURE:
<221> NAME/KEY: misc_feature
```

```
<222> LOCATION: (14)..(17)
<223> OTHER INFORMATION: 1'2'-dideoxyribose (D spacer)
<220> FEATURE:
<221> NAME/KEY: misc_feature
<222> LOCATION: (27)..(27)
<223> OTHER INFORMATION: cholesterol appended

<400> SEQUENCE: 164
nnnacgacgt cgtnnnnacg acgtcgt                                            27

<210> SEQ ID NO 165
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 165
gggacgacgt cgtggccacg acgtcgtccc                                         30

<210> SEQ ID NO 166
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 166
cccacgacgt cgtggg                                                        16

<210> SEQ ID NO 167
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 167
cccvacgacg tcgtgggg                                                      18

<210> SEQ ID NO 168
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 168
atgacgtttt tgacgtt                                                       17

<210> SEQ ID NO 169
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 169
acgacgtttt tgatgtt                                                       17

<210> SEQ ID NO 170
<211> LENGTH: 17
<212> TYPE: DNA
<213> ORGANISM: Artificial sequence
<220> FEATURE:
<223> OTHER INFORMATION: Synthetic oligonucleotide
```

-continued

<400> SEQUENCE: 170
atgatgtttt tgatgtt                                                    17

<210> SEQ ID NO 171
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 171
atgacgtttt gatgtt                                                     16

<210> SEQ ID NO 172
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 172
atgacgtttg tgatgtt                                                    17

<210> SEQ ID NO 173
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 173
ttgacgtttt tgatgtt                                                    17

<210> SEQ ID NO 174
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 174
atgagctttt gtatgtt                                                    17

<210> SEQ ID NO 175
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 175
tcgacgtttt cggcggccgc cg                                              22

<210> SEQ ID NO 176
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 176
tcctgacgtt ttcggcggcc gccg                                            24

<210> SEQ ID NO 177
<211> LENGTH: 22

```
<212> TYPE: DNA
<213> ORGANISM: Artificial sequence
<220> FEATURE:
<223> OTHER INFORMATION: Synthetic oligonucleotide

<400> SEQUENCE: 177
tcctgacgtt cggcggccgc cg                                              22

<210> SEQ ID NO 178
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 178
tccatgacgt tcggcgcgcg ccc                                             23

<210> SEQ ID NO 179
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 179
tcctgacgtt cggcgcgcgc c                                               21

<210> SEQ ID NO 180
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 180
tcgacgtttt cggcgcgcgc cg                                              22

<210> SEQ ID NO 181
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 181
tcgacgtcga cgttagggtt aggg                                            24

<210> SEQ ID NO 182
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 182
acgacgtcgt tagggttagg g                                               21

<210> SEQ ID NO 183
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 183
```

```
gtcggcgttg ac                                                         12
```

<210> SEQ ID NO 184
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(16)
<223> OTHER INFORMATION: 1'2'-dideoxyribose (D spacer)

<400> SEQUENCE: 184

```
acgacgtcgt cgnnnncggc cgccg                                           25
```

<210> SEQ ID NO 185
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 185

```
tcgtcgacga cgtcgtcg                                                   18
```

<210> SEQ ID NO 186
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(22)
<223> OTHER INFORMATION: 1'2'-dideoxyribose (D spacer)

<400> SEQUENCE: 186

```
tcgtcgacga cgtcgtcgnn nn                                              22
```

<210> SEQ ID NO 187
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (25)..(25)
<223> OTHER INFORMATION: triethylene glycol

<400> SEQUENCE: 187

```
acgacgtcgt ttttacgacg tcgtn                                           25
```

<210> SEQ ID NO 188
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (25)..(27)
<223> OTHER INFORMATION: 1'2'-dideoxyribose (D spacer)

<400> SEQUENCE: 188

```
acgacgtcgt ttttacgacg tcgtnnn                                         27
```

```
<210> SEQ ID NO 189
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 189
acgacgtcgt ttttacgacg tcgtttt                                27

<210> SEQ ID NO 190
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 190
acgacgtcgt ttttacgacg tcgt                                   24

<210> SEQ ID NO 191
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(25)
<223> OTHER INFORMATION: hexaethylene glycol

<400> SEQUENCE: 191
acgacgtcgt nnnnacgacg tcgtn                                  25

<210> SEQ ID NO 192
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: hexaethylene glycol
<220> FEATURE:
<221> NAME/KEY: misc_feature
<222> LOCATION: (22)..(22)
<223> OTHER INFORMATION: hexaethylene glycol

<400> SEQUENCE: 192
acgacgtcgt nacgacgtcg tn                                     22

<210> SEQ ID NO 193
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(12)
<223> OTHER INFORMATION: triethylene glyccol
<220> FEATURE:
<221> NAME/KEY: misc_feature
<222> LOCATION: (23)..(23)
<223> OTHER INFORMATION: triethylene glyccol
```

```
<400> SEQUENCE: 193
acgacgtcgt nnacgacgtc gtn                                           23

<210> SEQ ID NO 194
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(13)
<223> OTHER INFORMATION: 1'2'-dideoxyribose (D spacer)
<220> FEATURE:
<221> NAME/KEY: misc_feature
<222> LOCATION: (23)..(25)
<223> OTHER INFORMATION: 1'2'-dideoxyribose (D spacer)

<400> SEQUENCE: 194
cgacgtcgtn nnnacgacgt cgnnn                                         25

<210> SEQ ID NO 195
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(13)
<223> OTHER INFORMATION: 1'2'-dideoxyribose (D spacer)
<220> FEATURE:
<221> NAME/KEY: misc_feature
<222> LOCATION: (23)..(25)
<223> OTHER INFORMATION: 1'2'-dideoxyribose (D spacer)

<400> SEQUENCE: 195
acgacgtcgn nnncgacgtc gtnnn                                         25

<210> SEQ ID NO 196
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(12)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t

<400> SEQUENCE: 196
cgacgtcgnn nncgacgtcg nnn                                           23

<210> SEQ ID NO 197
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)
```

<400> SEQUENCE: 197
tcgacgtcgt nnnnacgacg tcgannn                                               27

<210> SEQ ID NO 198
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)

<400> SEQUENCE: 198
acgtcgtcgt nnnnacgacg acgtnnn                                               27

<210> SEQ ID NO 199
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)

<400> SEQUENCE: 199
tcgtcgacgt nnnnacgtcg acgannn                                               27

<210> SEQ ID NO 200
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)

<400> SEQUENCE: 200
tcgacgtcgt nnnnacgacg tcgtnnn                                               27

<210> SEQ ID NO 201
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)

<223> OTHER INFORMATION: 1'2'-dideoxyribose (D spacer)

<400> SEQUENCE: 201
acgacgtcgt nnnnacgtcg tcgtnnn         27

<210> SEQ ID NO 202
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(12)
<223> OTHER INFORMATION: 1'2'-dideoxyribose (D spacer)
<220> FEATURE:
<221> NAME/KEY: misc_feature
<222> LOCATION: (21)..(23)
<223> OTHER INFORMATION: 1'2'-dideoxyribose (D spacer)

<400> SEQUENCE: 202
acgacgttnn nnaacgtcgt nnn         23

<210> SEQ ID NO 203
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(11)
<223> OTHER INFORMATION: 1'2'-dideoxyribose (D spacer)
<220> FEATURE:
<221> NAME/KEY: misc_feature
<222> LOCATION: (19)..(21)
<223> OTHER INFORMATION: 1'2'-dideoxyribose (D spacer)

<400> SEQUENCE: 203
acgtcgtnnn nacgacgtnn n         21

<210> SEQ ID NO 204
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(12)
<223> OTHER INFORMATION: 1'2'-dideoxyribose (D spacer)
<220> FEATURE:
<221> NAME/KEY: misc_feature
<222> LOCATION: (21)..(23)
<223> OTHER INFORMATION: 1'2'-dideoxyribose (D spacer)

<400> SEQUENCE: 204
ggcggccgnn nncggccgcc nnn         23

<210> SEQ ID NO 205
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(12)
<223> OTHER INFORMATION: 1'2'-dideoxyribose (D spacer)
<220> FEATURE:
<221> NAME/KEY: misc_feature
<222> LOCATION: (21)..(23)
<223> OTHER INFORMATION: 1'2'-dideoxyribose (D spacer)

<400> SEQUENCE: 205
gcggccggnn nnccggccgc nnn                                           23

<210> SEQ ID NO 206
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(11)
<223> OTHER INFORMATION: 1'2'-dideoxyribose (D spacer)
<220> FEATURE:
<221> NAME/KEY: misc_feature
<222> LOCATION: (22)..(24)
<223> OTHER INFORMATION: 1'2'-dideoxyribose (D spacer)

<400> SEQUENCE: 206
acgtcgtnnn nacgacgtcg tnnn                                          24

<210> SEQ ID NO 207
<211> LENGTH: 26
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 1'2'-dideoxyribose (D spacer)
<220> FEATURE:
<221> NAME/KEY: misc_feature
<222> LOCATION: (12)..(15)
<223> OTHER INFORMATION: 1'2'-dideoxyribose (D spacer)
<220> FEATURE:
<221> NAME/KEY: misc_feature
<222> LOCATION: (26)..(26)
<223> OTHER INFORMATION: 1'2'-dideoxyribose (D spacer)

<400> SEQUENCE: 207
nacgacgtcg tnnnnacgac gtcgtn                                        26

<210> SEQ ID NO 208
<211> LENGTH: 28
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (26)..(27)
<223> OTHER INFORMATION: 1'2'-dideoxyribose (D spacer)

<400> SEQUENCE: 208
acgacgtcgt cgaagacgac gtcgtnnt                                      28

<210> SEQ ID NO 209
<211> LENGTH: 28
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (26)..(27)
<223> OTHER INFORMATION: 1'2'-dideoxyribose (D spacer)

<400> SEQUENCE: 209
tcgacgtcgt cgaagacgtc gtcgtnnt                                              28

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 1'2'-dideoxyribose (D spacer)

<400> SEQUENCE: 210
tccangacgt ttttgatgtt                                                       20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: 1'2'-dideoxyribose (D spacer)

<400> SEQUENCE: 211
tccatgacgt tnttgatgtt                                                       20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 1,3-propane diol

<400> SEQUENCE: 212
tccangacgt ttttgatgtt                                                       20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: 1,3-propane diol

<400> SEQUENCE: 213
tccatgacgt tnttgatgtt                                                       20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: bis-hydroxypropyl-3,3,3',3'-tetramethy-4, 5-benzindocarbocyanine chloride appended

<400> SEQUENCE: 214
tccatgacgt ttttgatgtt                                          20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: 1,3-propane diol

<400> SEQUENCE: 215
nnnnngacgt ttttgatgtt                                          20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 1,3-propane diol
<220> FEATURE:
<221> NAME/KEY: misc_feature
<222> LOCATION: (12)..(12)
<223> OTHER INFORMATION: 1,3-propane diol

<400> SEQUENCE: 216
tccangacgt tnttgatgtt                                          20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 1'2'-dideoxyribose (D spacer)
<220> FEATURE:
<221> NAME/KEY: misc_feature
<222> LOCATION: (12)..(12)
<223> OTHER INFORMATION: 1'2'-dideoxyribose (D spacer)

<400> SEQUENCE: 217
tccangacgt tnttgatgtt                                          20

<210> SEQ ID NO 218
<211> LENGTH: 28
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)
<220> FEATURE:
<221> NAME/KEY: misc_feature
<222> LOCATION: (28)..(28)
<223> OTHER INFORMATION: ribouracil

<400> SEQUENCE: 218
acgacgtcgt nnnnacgacg tcgtnnnn					28

<210> SEQ ID NO 219
<211> LENGTH: 28
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)
<220> FEATURE:
<221> NAME/KEY: misc_feature
<222> LOCATION: (28)..(28)
<223> OTHER INFORMATION: riboguanidine

<400> SEQUENCE: 219
acgacgtcgt nnnnacgacg tcgtnnng					28

<210> SEQ ID NO 220
<211> LENGTH: 28
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)
<220> FEATURE:
<221> NAME/KEY: misc_feature
<222> LOCATION: (28)..(28)
<223> OTHER INFORMATION: riboadenine

<400> SEQUENCE: 220
acgacgtcgt nnnnacgacg tcgtnnna					28

<210> SEQ ID NO 221
<211> LENGTH: 31
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: 1'2'-dideoxyribose (D spacer)
<220> FEATURE:
<221> NAME/KEY: misc_feature
<222> LOCATION: (14)..(17)
<223> OTHER INFORMATION: 1'2'-dideoxyribose (D spacer)
<220> FEATURE:
<221> NAME/KEY: misc_feature
<222> LOCATION: (28)..(30)
<223> OTHER INFORMATION: 1'2'-dideoxyribose (D spacer)
<220> FEATURE:
<221> NAME/KEY: misc_feature
<222> LOCATION: (31)..(31)
<223> OTHER INFORMATION: ribouracil

```
<400> SEQUENCE: 221
nnnacgacgt cgtnnnnacg acgtcgtnnn n                              31

<210> SEQ ID NO 222
<211> LENGTH: 31
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)
<220> FEATURE:
<221> NAME/KEY: misc_feature
<222> LOCATION: (28)..(31)
<223> OTHER INFORMATION: riboadenine

<400> SEQUENCE: 222
acgacgtcgt nnnnacgacg tcgtnnnaaa a                              31

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
tcgatgacgt tcctgacgtt                                           20

<210> SEQ ID NO 224
<211> LENGTH: 31
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (14)..(17)
<223> OTHER INFORMATION: 1'2'-dideoxyribose (D spacer)
<220> FEATURE:
<221> NAME/KEY: misc_feature
<222> LOCATION: (28)..(30)
<223> OTHER INFORMATION: 1'2'-dideoxyribose (D spacer)
<220> FEATURE:
<221> NAME/KEY: misc_feature
<222> LOCATION: (31)..(31)
<223> OTHER INFORMATION: ribouracil

<400> SEQUENCE: 224
tttacgacgt cgtnnnnacg acgtcgtnnn n                              31

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
tcgcgacgtt cgcgcgcgcg                                           20

<210> SEQ ID NO 226
<211> LENGTH: 20
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 1'2'-dideoxyribose (D spacer)

<400> SEQUENCE: 226
nccatgacgt ttttgatgtt                                               20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 1'2'-dideoxyribose (D spacer)

<400> SEQUENCE: 227
tncatgacgt ttttgatgtt                                               20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 1'2'-dideoxyribose (D spacer)

<400> SEQUENCE: 228
tcnatgacgt ttttgatgtt                                               20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 1'2'-dideoxyribose (D spacer)

<400> SEQUENCE: 229
tccntgacgt ttttgatgtt                                               20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (14)..(14)
<223> OTHER INFORMATION: 1'2'-dideoxyribose (D spacer)

<400> SEQUENCE: 230
tccatgacgt tttngatgtt                                               20

<210> SEQ ID NO 231
```

```
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: 1'2'-dideoxyribose (D spacer)

<400> SEQUENCE: 231
tccatgacgt ttntgatgtt                                           20

<210> SEQ ID NO 232
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 232
tcgaacgttc ggcgcgcgcc g                                         21

<210> SEQ ID NO 233
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 233
tcgtcgaacg ttcggcgcgc gccg                                      24

<210> SEQ ID NO 234
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 234
tcgtcgaacg ttcggcgctg cgccg                                     25

<210> SEQ ID NO 235
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 235
tcgcgacgtt cgttgcgcgc gccg                                      24

<210> SEQ ID NO 236
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 236
tacgtcgttc ggcgcgcgcc g                                         21

<210> SEQ ID NO 237
<211> LENGTH: 23
<212> TYPE: DNA
<213> ORGANISM: Artificial sequence
```

```
<220> FEATURE:
<223> OTHER INFORMATION: Synthetic oligonucleotide

<400> SEQUENCE: 237
ttcgcgacgt tcggcgcgcg ccg                                           23

<210> SEQ ID NO 238
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 238
tcggcgcgcg ccgtcgcgac gt                                            22

<210> SEQ ID NO 239
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 239
tagcgtgcgt tttgacgttt tttt                                          24

<210> SEQ ID NO 240
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 240
tagcgagcgt tttgacgttt tttt                                          24

<210> SEQ ID NO 241
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 241
ttgcgagcgt tttgacgttt tttt                                          24

<210> SEQ ID NO 242
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 242
atgcgtgcgt tttgacgttt tttt                                          24

<210> SEQ ID NO 243
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 243
ttacgtgcgt tttgacgttt tttt                                          24
```

<210> SEQ ID NO 244
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 244
ttgcatgcgt tttgacgttt tttt                                            24

<210> SEQ ID NO 245
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 245
ttgcgtacgt tttgacgttt tttt                                            24

<210> SEQ ID NO 246
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 246
ttgcgtgcat tttgacgttt tttt                                            24

<210> SEQ ID NO 247
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 247
ttgcgtgcga tttgacgttt tttt                                            24

<210> SEQ ID NO 248
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 248
ttgcgcgcgt tttgacgttt tttt                                            24

<210> SEQ ID NO 249
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 249
ttgcgtgcgc tttgacgttt tttt                                            24

<210> SEQ ID NO 250
<211> LENGTH: 24
<212> TYPE: DNA
<213> ORGANISM: Artificial sequence
<220> FEATURE:
<223> OTHER INFORMATION: Synthetic oligonucleotide

```
<400> SEQUENCE: 250
ttgcgtgcgt ttcgacgttt tttt                                              24

<210> SEQ ID NO 251
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 251
tcgtcggacg ttcggcgctg cgccg                                             25

<210> SEQ ID NO 252
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 252
tggcgacgtt cgttgcgcgc gccg                                              24

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
tcgcgacgtt ttgcgcgcgc                                                   20

<210> SEQ ID NO 254
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 254
tcgcgacgtc gttgcgcgcg ccg                                               23

<210> SEQ ID NO 255
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 255
tcgcgacgtt cgaagcgcgc gccg                                              24

<210> SEQ ID NO 256
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 256
tcgcgacgaa cgttgcgcgc gccg                                              24

<210> SEQ ID NO 257
```

```
<211> LENGTH: 27
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)

<400> SEQUENCE: 257
tcgacgtcgt nnnntcgacg tcgtnnn                                27

<210> SEQ ID NO 258
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 258
tcgtcgttag ctcgttagct cgtt                                   24

<210> SEQ ID NO 259
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 259
tcgtcgttac gtaattacgt cgtt                                   24

<210> SEQ ID NO 260
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 260
tcgtcgttac gtcgttacgt aatt                                   24

<210> SEQ ID NO 261
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 261
tcgtcgttac gtaattacgt aatt                                   24

<210> SEQ ID NO 262
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 262
tcgacgtcga cgtgacggg                                         19
```

-continued

```
<210> SEQ ID NO 263
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 263
tcgcgacgtt cggcgcgctg ccg                                              23

<210> SEQ ID NO 264
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 264
tcgcgacgtt cggcgcgtcg ccg                                              23

<210> SEQ ID NO 265
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 265
tcgcgacgtt cggcggctcg ccg                                              23

<210> SEQ ID NO 266
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: vitamin E appended

<400> SEQUENCE: 266
tcgacgtcgt                                                             10

<210> SEQ ID NO 267
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 267
tcgacgtcga cgtgacgtc                                                   19

<210> SEQ ID NO 268
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 268
tcgacgtcga cgtgacg                                                     17

<210> SEQ ID NO 269
<211> LENGTH: 10
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: vitamin E appended

<400> SEQUENCE: 269
tcgacgtcga                                                                  10

<210> SEQ ID NO 270
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 270
tcgtcgttac gtaactacgt cgtt                                                  24

<210> SEQ ID NO 271
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 271
tcgtcgttac gtaacgacgt cgtt                                                  24

<210> SEQ ID NO 272
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 272
tcgtcgttag ctaattagct cgtt                                                  24

<210> SEQ ID NO 273
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 273
tcgtcgttac gtaattagct cgtt                                                  24

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
cccatgacgt tcctgacgtt                                                       20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 275
gccatgacgt tcctgacgtt                                                    20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
accatgacgt tcctgacgtt                                                    20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
tggatgacgt tcctgacgtt                                                    20

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278
tttatgacgt tcctgacgtt                                                    20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
taaatgacgt tcctgacgtt                                                    20

<210> SEQ ID NO 280
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 280
ccatgacgtt cctgacgtt                                                     19

<210> SEQ ID NO 281
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 281
catgacgttc ctgacgtt                                                      18

<210> SEQ ID NO 282
```

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 282
atgacgttcc tgacgtt                                                    17

<210> SEQ ID NO 283
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 283
tgacgttcct gacgtt                                                     16

<210> SEQ ID NO 284
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (24)..(24)
<223> OTHER INFORMATION: cholesterol appended

<400> SEQUENCE: 284
tcgacgtcga nnnntcgacg tcga                                            24

<210> SEQ ID NO 285
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: triethylene glycol
<220> FEATURE:
<221> NAME/KEY: misc_feature
<222> LOCATION: (12)..(15)
<223> OTHER INFORMATION: n is a, c, g, or t
<220> FEATURE:
<221> NAME/KEY: misc_feature
<222> LOCATION: (22)..(22)
<223> OTHER INFORMATION: cholesterol appended

<400> SEQUENCE: 285
nagctgcagc tnnnntcgac ga                                              22

<210> SEQ ID NO 286
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 286
tcgcgacgtt cgggcgcgcc g                                               21
```

```
<210> SEQ ID NO 287
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 287
tcgtcgacgt tcggcgcgcg ccg                                       23

<210> SEQ ID NO 288
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 288
tcggacgttc ggcgcgcgcc g                                         21

<210> SEQ ID NO 289
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 289
tcggacgttc ggcgcgccg                                            19

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
tcgcgacgtt cggcgcgccg                                           20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 291
tcgacgttcg gcgcgcgccg                                           20

<210> SEQ ID NO 292
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 292
tcgacgttcg gcgcgccg                                             18

<210> SEQ ID NO 293
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 293
tcgcgacgtt cggcgccg                                                  18

<210> SEQ ID NO 294
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 294
tcgcgacgtt cggccg                                                    16

<210> SEQ ID NO 295
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 295
tcgacgttcg gcgccg                                                    16

<210> SEQ ID NO 296
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 296
tcgtcgacgt tcggcgggcc g                                              21

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
tcgtcgacgt tcgggcgccg                                                20

<210> SEQ ID NO 298
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 298
tcgacgacgt tcggcgcgcg ccg                                            23

<210> SEQ ID NO 299
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 299
tcgacgtcgt tcggcgcgcg ccg                                            23

<210> SEQ ID NO 300
<211> LENGTH: 23
```

```
<212> TYPE: DNA
<213> ORGANISM: Artificial sequence
<220> FEATURE:
<223> OTHER INFORMATION: Synthetic oligonucleotide

<400> SEQUENCE: 300
tcgtcgacgt tcgccgcgcg gcg                                              23

<210> SEQ ID NO 301
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 301
tcgtcgacgt tcggcgccgt gccg                                             24

<210> SEQ ID NO 302
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 302
tcgtcgacgt tcgactcgag tcg                                              23

<210> SEQ ID NO 303
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 303
tcgacgtcga cgtgacgtt                                                   19

<210> SEQ ID NO 304
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 304
tcgtcgacgt tcggcgcgcc g                                                21

<210> SEQ ID NO 305
<211> LENGTH: 28
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(14)
<223> OTHER INFORMATION: 1'2'-dideoxyribose (D spacer)
<220> FEATURE:
<221> NAME/KEY: misc_feature
<222> LOCATION: (25)..(27)
<223> OTHER INFORMATION: 1'2'-dideoxyribose (D spacer)
<220> FEATURE:
<221> NAME/KEY: misc_feature
<222> LOCATION: (28)..(28)
<223> OTHER INFORMATION: inverse orientation ribouracil

<400> SEQUENCE: 305
```
acgacgtcgt nnnnacgacg tcgtnnnn    28

<210> SEQ ID NO 306
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 306
tcgtcgacga tcgggcgccg tgccg    25

<210> SEQ ID NO 307
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 307
tcgtcgacga tcggcgccgt gccg    24

<210> SEQ ID NO 308
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 308
tcgtcgacga cggcgccgtg ccg    23

<210> SEQ ID NO 309
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 309
tcgtcgacga cgtgtcgat    19

<210> SEQ ID NO 310
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 310
tcgtcgacga cggcgccgtg ccgt    24

<210> SEQ ID NO 311
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 311
tcgtcgacga tcggcggcgt gccgt    25

<210> SEQ ID NO 312
<211> LENGTH: 25
<212> TYPE: DNA
<213> ORGANISM: Artificial sequence

```
<220> FEATURE:
<223> OTHER INFORMATION: Synthetic oligonucleotide

<400> SEQUENCE: 312
tcgtcgacgt tcggcgccgt gccgt                                              25

<210> SEQ ID NO 313
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 313
tcgtcgacgt cggcgccgtg ccgt                                               24

<210> SEQ ID NO 314
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 314
tcgtcgacgc ggcgccgtgc cgt                                                23

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
tcgtcgacga agtcgacgat                                                    20

<210> SEQ ID NO 316
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 316
tcgtcgacga gaatcgtcga cgat                                               24

<210> SEQ ID NO 317
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 317
tcgtcgtacg gcgccgtgcc gt                                                 22

<210> SEQ ID NO 318
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 318
tcgtcgacga tcggcgccgt gccgt                                              25
```

<210> SEQ ID NO 319
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 319
tcgtcgacga cgtgtcgat                                            19

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
tcgacgtcga agacgtcgat                                           20

<210> SEQ ID NO 321
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 321
tcgacgtcga gaatcgacgt cgat                                      24

<210> SEQ ID NO 322
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 322
tcgtcgacga cggcgaagcc g                                         21

<210> SEQ ID NO 323
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 323
tcgtcgacga cggcgaagcc gt                                        22

<210> SEQ ID NO 324
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 324
tcgacgtcga cgtgacgttg t                                         21

<210> SEQ ID NO 325
<211> LENGTH: 23
<212> TYPE: DNA
<213> ORGANISM: Artificial sequence
<220> FEATURE:
<223> OTHER INFORMATION: Synthetic oligonucleotide

```
<220> FEATURE:
<221> NAME/KEY: misc_feature
<222> LOCATION: (23)..(23)
<223> OTHER INFORMATION: butyrate appended

<400> SEQUENCE: 325
tcgtcgacga tcggcgcgcg ccg                                              23

<210> SEQ ID NO 326
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 326
acgacgtttt cgacgtt                                                     17

<210> SEQ ID NO 327
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 327
tcgtcgacga tcggcgcgcg cccgt                                            25

<210> SEQ ID NO 328
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 328
ttcgtcgacg atcggcgcgc gcccgt                                           26

<210> SEQ ID NO 329
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 329
tcgtcgacga tcgacgcgcg tcg                                              23

<210> SEQ ID NO 330
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 330
tcgtcgacga tcaacgcgcg ttg                                              23

<210> SEQ ID NO 331
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 331
```
tcgtcgacga tcggcacgtg ccg                                               23

<210> SEQ ID NO 332
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 332
tcgtcgacga tcggcatatg ccg                                               23

<210> SEQ ID NO 333
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 333
tcgtcgacga tgccgcgcgc ggc                                               23

<210> SEQ ID NO 334
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 334
tcgtcgacga tgccgcgctg cggc                                              24

<210> SEQ ID NO 335
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 335
tcgtcgtacg atgccgcgcg cggc                                              24

<210> SEQ ID NO 336
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 336
tcgtcgtacg atgccgcgct gcggc                                             25

<210> SEQ ID NO 337
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 337
tcgtcgacga tcggcgcgcg ccgt                                              24

<210> SEQ ID NO 338
<211> LENGTH: 23
<212> TYPE: DNA
<213> ORGANISM: Artificial sequence

```
<220> FEATURE:
<223> OTHER INFORMATION: Synthetic oligonucleotide

<400> SEQUENCE: 338
tcgtgcacga tcggcgcgcg ccg                                              23

<210> SEQ ID NO 339
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: m5c

<400> SEQUENCE: 339
tngtcgacga tcggcgcgcg ccg                                              23

<210> SEQ ID NO 340
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: m5c

<400> SEQUENCE: 340
tcgtngacga tcggcgcgcg ccg                                              23

<210> SEQ ID NO 341
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: m5c

<400> SEQUENCE: 341
tcgtcganga tcggcgcgcg ccg                                              23

<210> SEQ ID NO 342
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: m5c

<400> SEQUENCE: 342
tcgtcgacga tnggcgcgcg ccg                                              23

<210> SEQ ID NO 343
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 343
tcgacgtcga cgtcgacg                                        18

<210> SEQ ID NO 344
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 344
tcgtcgacgt tcggcgccgt gccgt                                25

<210> SEQ ID NO 345
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 345
gccgcgcgcg gctagcagct gct                                  23

<210> SEQ ID NO 346
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 346
cggcgcgcgc cgtagcagct gct                                  23

<210> SEQ ID NO 347
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 347
cggcgccgtg ccgttgcagc tgct                                 24

<210> SEQ ID NO 348
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 348
gccgtgccgc ggcttgcagc tgct                                 24

<210> SEQ ID NO 349
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 349
tcggcgcgcg ccgatagcag ctgct                                25

<210> SEQ ID NO 350
<211> LENGTH: 25
```

```
<212> TYPE: DNA
<213> ORGANISM: Artificial sequence
<220> FEATURE:
<223> OTHER INFORMATION: Synthetic oligonucleotide

<400> SEQUENCE: 350
tcggcgccgt gccgttgcag ctgct                                          25

<210> SEQ ID NO 351
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: n is a, c, g, or t

<400> SEQUENCE: 351
cggcgcngcg ccg                                                       13

<210> SEQ ID NO 352
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 352
tcgtcgacga cggcgcgcgc cg                                             22

<210> SEQ ID NO 353
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: 1,3-propane diol

<400> SEQUENCE: 353
tcgtcgacga ncggcgcgcg ccg                                            23

<210> SEQ ID NO 354
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: hexaethylene glycol
<220> FEATURE:
<221> NAME/KEY: misc_feature
<222> LOCATION: (11)..(11)
<223> OTHER INFORMATION: 1'2'-dideoxyribose (D spacer)

<400> SEQUENCE: 354
tcgtcgacga ncggcgcgcg ccg                                            23

<210> SEQ ID NO 355
<211> LENGTH: 23
<212> TYPE: DNA
<213> ORGANISM: Artificial sequence
<220> FEATURE:
```

<223> OTHER INFORMATION: Synthetic oligonucleotide
<220> FEATURE:
<221> NAME/KEY: misc_feature
<222> LOCATION: (11)..(11)
<223> OTHER INFORMATION: n is a, c, g, or t

<400> SEQUENCE: 355
tcgtcgacga ncggcgcgcg ccg                                              23

<210> SEQ ID NO 356
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 356
tcgacgtcgt ggggg                                                       15

<210> SEQ ID NO 357
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 357
tccaggactt ctctca                                                      16

<210> SEQ ID NO 358
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 2'-O-methyl guanidine
<220> FEATURE:
<221> NAME/KEY: misc_feature
<222> LOCATION: (7)..(7)
<223> OTHER INFORMATION: 2'-O-methyl adenine
<220> FEATURE:
<221> NAME/KEY: misc_feature
<222> LOCATION: (9)..(9)
<223> OTHER INFORMATION: 2'-O-methyl guanidine
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: misc_feature
<222> LOCATION: (13)..(14)
<223> OTHER INFORMATION: 2'-O-methyl guanidine
<220> FEATURE:
<221> NAME/KEY: misc_feature
<222> LOCATION: (16)..(16)
<223> OTHER INFORMATION: 2'-O-methyl guanidine
<220> FEATURE:
<221> NAME/KEY: misc_feature
<222> LOCATION: (18)..(18)
<223> OTHER INFORMATION: 2'-O-methyl guanidine
<220> FEATURE:
<221> NAME/KEY: misc_feature
<222> LOCATION: (20)..(20)
<223> OTHER INFORMATION: 2'-O-methyl guanidine
<220> FEATURE:
<221> NAME/KEY: misc_feature
<222> LOCATION: (23)..(23)
<223> OTHER INFORMATION: 2'-O-methyl guanidine

<400> SEQUENCE: 358
tcgtcnncnn tcnncncncn ccn                                              23

<210> SEQ ID NO 359
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 2'-O-methyl guanidine
<220> FEATURE:
<221> NAME/KEY: misc_feature
<222> LOCATION: (6)..(6)
<223> OTHER INFORMATION: 2'-O-methyl guanidine
<220> FEATURE:
<221> NAME/KEY: misc_feature
<222> LOCATION: (7)..(7)
<223> OTHER INFORMATION: 2'-O-methyl adenine
<220> FEATURE:
<221> NAME/KEY: misc_feature
<222> LOCATION: (9)..(9)
<223> OTHER INFORMATION: 2'-O-methyl guanidine
<220> FEATURE:
<221> NAME/KEY: misc_feature
<222> LOCATION: (10)..(10)
<223> OTHER INFORMATION: 2'-O-methyl adenosine
<220> FEATURE:
<221> NAME/KEY: misc_feature
<222> LOCATION: (13)..(14)
<223> OTHER INFORMATION: 2'-O-methyl guanidine
<220> FEATURE:
<221> NAME/KEY: misc_feature
<222> LOCATION: (16)..(16)
<223> OTHER INFORMATION: 2'-O-methyl guanidine
<220> FEATURE:
<221> NAME/KEY: misc_feature
<222> LOCATION: (18)..(18)
<223> OTHER INFORMATION: 2'-O-methyl guanidine
<220> FEATURE:
<221> NAME/KEY: misc_feature
<222> LOCATION: (20)..(20)
<223> OTHER INFORMATION: 2'-O-methyl guanidine
<220> FEATURE:
<221> NAME/KEY: misc_feature
<222> LOCATION: (23)..(23)
<223> OTHER INFORMATION: 2'-O-methyl guanidine

<400> SEQUENCE: 359
tcntcnncnn tcnncncncn ccn                                              23

<210> SEQ ID NO 360
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 2,4-difluorotoluene

<400> SEQUENCE: 360
tgncgttttt tttttttttt                                                  20

<210> SEQ ID NO 361
<211> LENGTH: 20
<212> TYPE: DNA
<213> ORGANISM: Artificial sequence
<220> FEATURE:
<223> OTHER INFORMATION: Synthetic oligonucleotide
<220> FEATURE:

```
<221> NAME/KEY: misc_feature
<222> LOCATION: (6)..(6)
<223> OTHER INFORMATION: 2,4-difluorotoluene

<400> SEQUENCE: 361
tgtcgntttt tttttttttt                                               20

<210> SEQ ID NO 362
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 2,4-difluorotoluene
<220> FEATURE:
<221> NAME/KEY: misc_feature
<222> LOCATION: (6)..(6)
<223> OTHER INFORMATION: 2,4-difluorotoluene

<400> SEQUENCE: 362
tgncgntttt tttttttttt                                               20

<210> SEQ ID NO 363
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 2,4-difluorotoluene

<400> SEQUENCE: 363 tgtngtttt tttttttttt                                                20

<210> SEQ ID NO 364
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 2,4-difluorotoluene

<400> SEQUENCE: 364 tgtcntttt tttttttttt                                                20

<210> SEQ ID NO 365
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 2,4-difluorotoluene

<400> SEQUENCE: 365
tncgtttttt tttttttttt                                               20

<210> SEQ ID NO 366
<211> LENGTH: 20
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: 2,4-difluorotoluene

<400> SEQUENCE: 366
tgtcgtnttt tttttttttt                                              20

<210> SEQ ID NO 367
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-bromo-2'-deoxyuridine

<400> SEQUENCE: 367
tgncgttttt tttttttttt                                              20

<210> SEQ ID NO 368
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 5-bromo-2'-deoxyuridine

<400> SEQUENCE: 368
tgtcgntttt tttttttttt                                              20

<210> SEQ ID NO 369
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-bromo-2'-deoxyuridine
<220> FEATURE:
<221> NAME/KEY: misc_feature
<222> LOCATION: (6)..(6)
<223> OTHER INFORMATION: 5-bromo-2'-deoxyuridine

<400> SEQUENCE: 369
tgncgntttt tttttttttt                                              20

<210> SEQ ID NO 370
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine

<400> SEQUENCE: 370
```

```
tgncgttttt ttttttttt                                                19
```

```
<210> SEQ ID NO 371
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 5-iodo-2'-deoxyuridine

<400> SEQUENCE: 371
tgtcgntttt tttttttttt                                               20
```

```
<210> SEQ ID NO 372
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine
<220> FEATURE:
<221> NAME/KEY: misc_feature
<222> LOCATION: (6)..(6)
<223> OTHER INFORMATION: 5-iodo-2'-deoxyuridine

<400> SEQUENCE: 372
tgncgntttt tttttttttt                                               20
```

```
<210> SEQ ID NO 373
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: uridine

<400> SEQUENCE: 373
tgncgttttt tttttttttt                                               20
```

```
<210> SEQ ID NO 374
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: uridine

<400> SEQUENCE: 374
tgtcgntttt tttttttttt                                               20
```

```
<210> SEQ ID NO 375
<211> LENGTH: 19
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
```

```
<222> LOCATION: (3)..(3)
<223> OTHER INFORMATION: uridine
<220> FEATURE:
<221> NAME/KEY: misc_feature
<222> LOCATION: (6)..(6)
<223> OTHER INFORMATION: uridine

<400> SEQUENCE: 375
tgncgntttt tttttttt                                                    19

<210> SEQ ID NO 376
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 376
ncgtcgtttt tcggtcgttt t                                                21

<210> SEQ ID NO 377
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine
<220> FEATURE:
<221> NAME/KEY: misc_feature
<222> LOCATION: (4)..(4)
<223> OTHER INFORMATION: n is a, c, g, or t

<400> SEQUENCE: 377
tcgncgtttt tcggtcgttt t                                                21

<210> SEQ ID NO 378
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (15)..(15)
<223> OTHER INFORMATION: 5-iodo-2'-deoxyuridine

<400> SEQUENCE: 378
tcgtcgtttt tcggncgttt t                                                21

<210> SEQ ID NO 379
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (4)..(4)
<223> OTHER INFORMATION: 5-iodo-2'-deoxyuridine
```

<400> SEQUENCE: 379
ncgncgtttt tcggtcgttt t                                              21

<210> SEQ ID NO 380
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 5-iodo-2'-deoxyuridine
<220> FEATURE:
<221> NAME/KEY: misc_feature
<222> LOCATION: (7)..(7)
<223> OTHER INFORMATION: 5-iodo-2'-deoxyuridine

<400> SEQUENCE: 380
tcgncgnttt tcggtcgttt t                                              21

<210> SEQ ID NO 381
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (15)..(15)
<223> OTHER INFORMATION: 5-iodo-2'-deoxyuridine
<220> FEATURE:
<221> NAME/KEY: misc_feature
<222> LOCATION: (18)..(18)
<223> OTHER INFORMATION: 5-iodo-2'-deoxyuridine

<400> SEQUENCE: 381
tcgtcgtttt tcggncgntt t                                              21

<210> SEQ ID NO 382
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 382
ncgtcgtttt acggcgccgt gccg                                           24

<210> SEQ ID NO 383
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 5-iodo-2'-deoxyuridine

<400> SEQUENCE: 383
tcgncgtttt acggcgccgt gccg                                           24

<210> SEQ ID NO 384
<211> LENGTH: 20

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 5-ethyl-2'-deoxyuridine

<400> SEQUENCE: 384
tgtcgntttt tttttttttt                                          20

<210> SEQ ID NO 385
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-ethyl-2'-deoxyuridine
<220> FEATURE:
<221> NAME/KEY: misc_feature
<222> LOCATION: (6)..(6)
<223> OTHER INFORMATION: 5-ethyl-2'-deoxyuridine

<400> SEQUENCE: 385
tgncgntttt tttttttttt                                          20

<210> SEQ ID NO 386
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 386
ncgtcgacga tcggcgcgcg ccg                                      23

<210> SEQ ID NO 387
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 5-iodo-2'-deoxyuridine

<400> SEQUENCE: 387
tcgncgacga tcggcgcgcg ccg                                      23

<210> SEQ ID NO 388
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (4)..(4)
```

```
<223> OTHER INFORMATION: 5-iodo-2'-deoxyuridine

<400> SEQUENCE: 388
ncgncgacga tcggcgcgcg ccg                                            23

<210> SEQ ID NO 389
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 389
ncgacgtcgt ggggg                                                     15

<210> SEQ ID NO 390
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: 5-iodo-2'-deoxyuridine

<400> SEQUENCE: 390
tcgacgncgt ggggg                                                     15

<210> SEQ ID NO 391
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: 5-iodo-2'-deoxyuridine
<220> FEATURE:
<221> NAME/KEY: misc_feature
<222> LOCATION: (10)..(10)
<223> OTHER INFORMATION: 5-iodo-2'-deoxyuridine

<400> SEQUENCE: 391
tcgacgncgn ggggg                                                     15

<210> SEQ ID NO 392
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-chloro-2'-deoxyuridine

<400> SEQUENCE: 392
tgncgttttt tttttttttt                                                20

<210> SEQ ID NO 393
<211> LENGTH: 20
<212> TYPE: DNA
<213> ORGANISM: Artificial sequence
```

<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-ethyl-2'-deoxyuridine

<400> SEQUENCE: 393
tgncgttttt ttttttttttt                                          20

<210> SEQ ID NO 394
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (4)..(4)
<223> OTHER INFORMATION: 5-iodo-2'-deoxyuridine

<400> SEQUENCE: 394
ncgncgtttt acggcgccgt gccg                                      24

<210> SEQ ID NO 395
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 5-iodo-2'-deoxyuridine
<220> FEATURE:
<221> NAME/KEY: misc_feature
<222> LOCATION: (7)..(7)
<223> OTHER INFORMATION: 5-iodo-2'-deoxyuridine

<400> SEQUENCE: 395
tcgncgnttt acggcgccgt gccg                                      24

<210> SEQ ID NO 396
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: 5-iodo-2'-deoxyuridine

<400> SEQUENCE: 396
tcttttttgn cgttttttttt tt                                       22

<210> SEQ ID NO 397
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: 5-iodo-2'-deoxyuridine
<220> FEATURE:

```
<221> NAME/KEY: misc_feature
<222> LOCATION: (13)..(13)
<223> OTHER INFORMATION: 5-iodo-2'-deoxyuridine

<400> SEQUENCE: 397
tcttttttgn cgntttttt tt                                                22

<210> SEQ ID NO 398
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 398
ncttttttgt cgtttttttt tt                                               22

<210> SEQ ID NO 399
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: uridine
<220> FEATURE:
<221> NAME/KEY: misc_feature
<222> LOCATION: (11)..(11)
<223> OTHER INFORMATION: n is a, c, g, or t

<400> SEQUENCE: 399
tcttttttgc ngtttttttt tt                                               22

<210> SEQ ID NO 400
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 400
ncgacgtcga tcggcgcgcg ccg                                              23

<210> SEQ ID NO 401
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 401
ncgacgtcga tcggcgcgcg ccgt                                             24

<210> SEQ ID NO 402
<211> LENGTH: 23
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 402
ncgacgtcga tcggcgcgcg ccg                                    23

<210> SEQ ID NO 403
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 403
ncgtcgacga tcggcggccg ccgt                                   24

<210> SEQ ID NO 404
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 404
ncgtcgacga tcggcggccg ccg                                    23

<210> SEQ ID NO 405
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 405
ncgtcgacga tcggcggccg ccg                                    23

<210> SEQ ID NO 406
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 5-fluorodeoxyuridine

<400> SEQUENCE: 406
tgtcgntttt ttttttttt                                         20

<210> SEQ ID NO 407
```

<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-fluorodeoxyuridine
<220> FEATURE:
<221> NAME/KEY: misc_feature
<222> LOCATION: (6)..(6)
<223> OTHER INFORMATION: 5-fluorodeoxyuridine

<400> SEQUENCE: 407
tgncgntttt tttttttttt                                                20

<210> SEQ ID NO 408
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: uridine
<220> FEATURE:
<221> NAME/KEY: misc_feature
<222> LOCATION: (6)..(6)
<223> OTHER INFORMATION: uridine

<400> SEQUENCE: 408
tgncgntttt tttttttttt                                                20

<210> SEQ ID NO 409
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 6-nitro-benzimidizol

<400> SEQUENCE: 409
tgtcnttttt tttttttttt                                                20

<210> SEQ ID NO 410
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 6-nitro-benzimidazol

<400> SEQUENCE: 410
tgtngttttt tttttttttt                                                20

<210> SEQ ID NO 411
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature

```
<222> LOCATION: (1)..(1)
<223> OTHER INFORMATION: 5-iodo-2'-deoxyuridine

<400> SEQUENCE: 411
ngtcgttttt tttttttttt                                              20

<210> SEQ ID NO 412
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (3)..(3)
<223> OTHER INFORMATION: 5-iodo-2'-deoxyuridine

<400> SEQUENCE: 412
ngncgttttt tttttttttt                                              20

<210> SEQ ID NO 413
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(7)
<223> OTHER INFORMATION: 5-iodo-2'-deoxyuridine

<400> SEQUENCE: 413
tgtcgtnttt tttttttttt                                              20

<210> SEQ ID NO 414
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: a,a,a-trifluoro-dT

<400> SEQUENCE: 414
tgncgttttt tttttttttt                                              20

<210> SEQ ID NO 415
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: a,a,a-trifluoro-dT

<400> SEQUENCE: 415
tgtcgntttt tttttttttt                                              20

<210> SEQ ID NO 416
<211> LENGTH: 20
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(6)
<223> OTHER INFORMATION: a,a,a-trifluoro-dT
<220> FEATURE:
<221> NAME/KEY: misc_feature
<222> LOCATION: (6)..(6)
<223> OTHER INFORMATION: a,a,a-trifluoro-dT

<400> SEQUENCE: 416
tgncgntttt tttttttttt                                                20

<210> SEQ ID NO 417
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 5-chloro-2'-deoxyuridine

<400> SEQUENCE: 417
tgtcgntttt tttttttttt                                                20

<210> SEQ ID NO 418
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-chloro-2'-deoxyuridine
<220> FEATURE:
<221> NAME/KEY: misc_feature
<222> LOCATION: (6)..(6)
<223> OTHER INFORMATION: 5-chloro-2'-deoxyuridine

<400> SEQUENCE: 418
tgncgntttt tttttttttt                                                20

<210> SEQ ID NO 419
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 5-iodo-2'-deoxyuridine

<400> SEQUENCE: 419
tncgtttttt tttttttttt                                                20

<210> SEQ ID NO 420
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine
```

<400> SEQUENCE: 420
tgncgttttg tcgtt                                                    15

<210> SEQ ID NO 421
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine

<400> SEQUENCE: 421
ttncgtcgtt tcgtcgtt                                                 18

<210> SEQ ID NO 422
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-bromo-2'-deoxyuridine

<400> SEQUENCE: 422
ncgacgtcgt ggggg                                                    15

<210> SEQ ID NO 423
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine

<400> SEQUENCE: 423
tgngcttttt tttttttttt                                               20

<210> SEQ ID NO 424
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 424
ncgtcgtttt cggcgcgcgc cg                                            22

<210> SEQ ID NO 425
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)

<223> OTHER INFORMATION: 5-iodo-2'-deoxyuridine

<400> SEQUENCE: 425
tcgncgtttt cggcgcgcgc cg                                    22

<210> SEQ ID NO 426
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: 5-iodo-2'-deoxyuridine

<400> SEQUENCE: 426
tcgtcgtttn cggcgcgcgc cg                                    22

<210> SEQ ID NO 427
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (15)..(15)
<223> OTHER INFORMATION: 5-iodo-2'-deoxyuridine

<400> SEQUENCE: 427
ncgtcgtttt tcggncgttt t                                     21

<210> SEQ ID NO 428
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 5-iodo-2'-deoxyuridine
<220> FEATURE:
<221> NAME/KEY: misc_feature
<222> LOCATION: (15)..(15)
<223> OTHER INFORMATION: 5-iodo-2'-deoxyuridine

<400> SEQUENCE: 428
tcgncgtttt tcggncgttt t                                     21

<210> SEQ ID NO 429
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine
<220> FEATURE:
<221> NAME/KEY: misc_feature
<222> LOCATION: (16)..(16)
<223> OTHER INFORMATION: 5-iodo-2'-deoxyuridine

<400> SEQUENCE: 429
tgncgttttt ttttgncgtt                                          20

<210> SEQ ID NO 430
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine

<400> SEQUENCE: 430
tgncgttttt tttttttttt                                          20

<210> SEQ ID NO 431
<211> LENGTH: 15
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (13)..(13)
<223> OTHER INFORMATION: 7-deaza-dG

<400> SEQUENCE: 431
ncgacgtcgt ggngg                                               15

<210> SEQ ID NO 432
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 5-methyl guanidine
<220> FEATURE:
<221> NAME/KEY: misc_feature
<222> LOCATION: (3)..(3)
<223> OTHER INFORMATION: 5-iodo-2'-deoxyuridine

<400> SEQUENCE: 432
tnncgttttt tttttttttt                                          20

<210> SEQ ID NO 433
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine
<220> FEATURE:
<221> NAME/KEY: misc_feature
<222> LOCATION: (5)..(5)
<223> OTHER INFORMATION: 5-methyl guanidine

<400> SEQUENCE: 433
tgncnttttt tttttttttt                                          20

```
<210> SEQ ID NO 434
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 5-methyl guanidine
<220> FEATURE:
<221> NAME/KEY: misc_feature
<222> LOCATION: (3)..(3)
<223> OTHER INFORMATION: 5-iodo-2'-deoxyuridine
<220> FEATURE:
<221> NAME/KEY: misc_feature
<222> LOCATION: (5)..(5)
<223> OTHER INFORMATION: 5-methyl guanidine

<400> SEQUENCE: 434 tnncntttt tttttttttt                                            20

<210> SEQ ID NO 435
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-proynyl-dU

<400> SEQUENCE: 435
tgncgttttt tttttttttt                                           20

<210> SEQ ID NO 436
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 5-proynyl-dU

<400> SEQUENCE: 436 tgtcgnttt tttttttttt                                            20

<210> SEQ ID NO 437
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine

<400> SEQUENCE: 437
tgncgttttc ggcgcgcgcc g                                         21

<210> SEQ ID NO 438
<211> LENGTH: 21
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: misc_feature
<222> LOCATION: (2)..(2)
<223> OTHER INFORMATION: 5-iodo-2'-deoxyuridine

<400> SEQUENCE: 438
tncgttttcg gcgcgcgccg t                                              21

<210> SEQ ID NO 439
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 5-ethyl-2'-deoxyuridine

<400> SEQUENCE: 439
tncgtttttt tttttttttt                                                20

<210> SEQ ID NO 440
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-ethyl-2'-deoxyuridine

<400> SEQUENCE: 440 tgngctttt tttttttttt                                                 20

<210> SEQ ID NO 441
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 441
ncgtcgtttt tcggtcgttt t                                              21

<210> SEQ ID NO 442
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 442
ncgtcgtttt acggcgccgt gccg                                           24

<210> SEQ ID NO 443
<211> LENGTH: 24
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: misc_feature
<222> LOCATION: (4)..(4)
<223> OTHER INFORMATION: 5-ethyl-2'-deoxyuridine

<400> SEQUENCE: 443
tcgncgtttt acggcgccgt gccg                                              24

<210> SEQ ID NO 444
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 444
ncgtcgacga tcggcgcgcg ccg                                               23

<210> SEQ ID NO 445
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 445
nctttttttt ttttttt                                                      17

<210> SEQ ID NO 446
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 446
nctttttttt cgttttttttt tt                                               22

<210> SEQ ID NO 447
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: 5-iodo-2'-deoxyuridine

<400> SEQUENCE: 447
tctttttttn cgttttttttt tt                                               22

<210> SEQ ID NO 448
<211> LENGTH: 22
<212> TYPE: DNA
<213> ORGANISM: Artificial sequence
```

<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (10)..(10)
<223> OTHER INFORMATION: 5-iodo-2'-deoxyuridine

<400> SEQUENCE: 448 ncttttttn cgttttttt tt                                           22

<210> SEQ ID NO 449
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 449
ncgtcgtttc gtcgttttgt cgtt                                       24

<210> SEQ ID NO 450
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: 5-iodo-2'-deoxyuridine

<400> SEQUENCE: 450
tcgtcgtttc gtcgttttgn cgtt                                       24

<210> SEQ ID NO 451
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (20)..(20)
<223> OTHER INFORMATION: 5-iodo-2'-deoxyuridine

<400> SEQUENCE: 451
ncgtcgtttc gtcgttttgn cgtt                                       24

<210> SEQ ID NO 452
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine
<220> FEATURE:

```
<221> NAME/KEY: misc_feature
<222> LOCATION: (5)..(5)
<223> OTHER INFORMATION: 7-deaza-dG

<400> SEQUENCE: 452 tgncntttt tttttttttt                                              20

<210> SEQ ID NO 453
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine
<220> FEATURE:
<221> NAME/KEY: misc_feature
<222> LOCATION: (5)..(5)
<223> OTHER INFORMATION: inosine

<400> SEQUENCE: 453 tgncntttt tttttttttt                                              20

<210> SEQ ID NO 454
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-iodo-2'-deoxyuridine
<220> FEATURE:
<221> NAME/KEY: misc_feature
<222> LOCATION: (4)..(4)
<223> OTHER INFORMATION: m5c

<400> SEQUENCE: 454 tgnngtttt tttttttttt                                              20

<210> SEQ ID NO 455
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: 5-iodo-2'-deoxyuridine

<400> SEQUENCE: 455
tgtcgttntt tttttttttt                                             20

<210> SEQ ID NO 456
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: 5-iodo-2'-deoxyuridine

<400> SEQUENCE: 456
tgtcgtttnt tttttttttt                                             20
```

<210> SEQ ID NO 457
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 457
ncgtcgtttt cggcgcgcgc cgt                                          23

<210> SEQ ID NO 458
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 458
ncgtcgtttt cggcgcgcgc cgt                                          23

<210> SEQ ID NO 459
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 5-ethyl-2'-deoxyuridine

<400> SEQUENCE: 459
tcgncgtttt cggcgcgcgc cgt                                          23

<210> SEQ ID NO 460
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: 5-iodo-2'-deoxyuridine

<400> SEQUENCE: 460
tcgtcgtttn cggcgcgcgc cgt                                          23

<210> SEQ ID NO 461
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: 5-ethyl-2'-deoxyuridine

<400> SEQUENCE: 461

```
tcgtcgtttn cggcgcgcgc cgt                    23
```

```
<210> SEQ ID NO 462
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (10)..(10)
<223> OTHER INFORMATION: 5-ethyl-2'-deoxyuridine

<400> SEQUENCE: 462
ncgtcgtttn cggcgcgcgc cgt                    23
```

```
<210> SEQ ID NO 463
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (4)..(4)
<223> OTHER INFORMATION: 5-ethyl-2'-deoxyuridine

<400> SEQUENCE: 463
ncgncgtttt cggcgcgcgc cgt                    23
```

```
<210> SEQ ID NO 464
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (4)..(4)
<223> OTHER INFORMATION: 5-ethyl-2'-deoxyuridine

<400> SEQUENCE: 464
ncgncgtttt cggcgcgcgc cgt                    23
```

```
<210> SEQ ID NO 465
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 465
ncgtcgtttt gtcgttttgt cgtt                   24
```

```
<210> SEQ ID NO 466
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 466
ncgtcgtttt gtcgttttcg tt                                           22

<210> SEQ ID NO 467
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 5-(d-bromo-vinyl)-uridine

<400> SEQUENCE: 467
tgncgttttt tttttttttt                                              20

<210> SEQ ID NO 468
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 5-(d-bromo-vinyl)-uridine

<400> SEQUENCE: 468
tgtcgntttt tttttttttt                                              20

<210> SEQ ID NO 469
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 469
ncggcggccg ccg                                                     13

<210> SEQ ID NO 470
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (24)..(24)
<223> OTHER INFORMATION: 3'-O-methyl riboguanidine
```

```
<400> SEQUENCE: 470
ncgtcgtttt acggcgccgt gccn                                              24

<210> SEQ ID NO 471
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (24)..(24)
<223> OTHER INFORMATION: 3'-O-methyl riboguanidine

<400> SEQUENCE: 471
ncgtcgtttt acggcgccgt gccn                                              24

<210> SEQ ID NO 472
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (4)..(4)
<223> OTHER INFORMATION: 5-ethyl-2'-deoxyuridine
<220> FEATURE:
<221> NAME/KEY: misc_feature
<222> LOCATION: (24)..(24)
<223> OTHER INFORMATION: 3'-O-methyl riboguanidine

<400> SEQUENCE: 472
ncgncgtttt acggcgccgt gccn                                              24

<210> SEQ ID NO 473
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 473
ncgtcgtttt acggcgccgt gccgt                                             25

<210> SEQ ID NO 474
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (22)..(22)
<223> OTHER INFORMATION: 3'-O-methyl riboguanidine
```

```
<400> SEQUENCE: 474
ncgtcgtttt cggcgcgcgc cn                                           22

<210> SEQ ID NO 475
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (22)..(22)
<223> OTHER INFORMATION: 3'-O-methyl riboguanidine

<400> SEQUENCE: 475
ncgtcgtttt cggcgcgcgc cn                                           22

<210> SEQ ID NO 476
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (4)..(4)
<223> OTHER INFORMATION: 5-ethyl-2'-deoxyuridine
<220> FEATURE:
<221> NAME/KEY: misc_feature
<222> LOCATION: (22)..(22)
<223> OTHER INFORMATION: 3'-O-methyl riboguanidine

<400> SEQUENCE: 476
ncgncgtttt cggcgcgcgc cn                                           22

<210> SEQ ID NO 477
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (10)..(10)
<223> OTHER INFORMATION: 5-ethyl-2'-deoxyuridine
<220> FEATURE:
<221> NAME/KEY: misc_feature
<222> LOCATION: (22)..(22)
<223> OTHER INFORMATION: 3'-O-methyl riboguanidine

<400> SEQUENCE: 477
ncgtcgtttn cggcgcgcgc cn                                           22

<210> SEQ ID NO 478
<211> LENGTH: 22
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (10)..(10)
<223> OTHER INFORMATION: 5-iodo-2'-deoxyuridine
<220> FEATURE:
<221> NAME/KEY: misc_feature
<222> LOCATION: (22)..(22)
<223> OTHER INFORMATION: 3-methyl guanidine
<220> FEATURE:
<221> NAME/KEY: misc_feature
<222> LOCATION: (22)..(22)
<223> OTHER INFORMATION: 3'-O-methyl riboguanidine

<400> SEQUENCE: 478
ncgtcgtttn cggcgcgcgc cn                                          22

<210> SEQ ID NO 479
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: N_region
<222> LOCATION: (1)..(1)
<223> OTHER INFORMATION: 5-ethyl-2'-deoxyuridine
<220> FEATURE:
<221> NAME/KEY: misc_feature
<222> LOCATION: (1)..(1)
<223> OTHER INFORMATION: n is a, c, g, or t

<400> SEQUENCE: 479
ncgtcgtttt cggcgcgcgc cgt                                         23

<210> SEQ ID NO 480
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 480
ncgtcgtttt cggcgcgcgc cgt                                         23

<210> SEQ ID NO 481
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (24)..(24)
<223> OTHER INFORMATION: 3'-O-methyl riboguanidine

<400> SEQUENCE: 481
ncgtcgacgt tcggcgccgt gccn                                        24
```

```
<210> SEQ ID NO 482
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (24)..(24)
<223> OTHER INFORMATION: 3'-O-methyl riboguanidine

<400> SEQUENCE: 482
ncgtcgacgt tcggcgccgt gccn                                            24

<210> SEQ ID NO 483
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (23)..(23)
<223> OTHER INFORMATION: 3'-O-methyl riboguanidine

<400> SEQUENCE: 483
ncgtcgacga tcggcgcgcg ccn                                             23

<210> SEQ ID NO 484
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine
<220> FEATURE:
<221> NAME/KEY: misc_feature
<222> LOCATION: (23)..(23)
<223> OTHER INFORMATION: 3'-O-methyl riboguanidine

<400> SEQUENCE: 484
ncgtcgacga tcggcgcgcg ccn                                             23

<210> SEQ ID NO 485
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 485
ncgtcgacgt tcggcgccgt gccgt                                           25

<210> SEQ ID NO 486
<211> LENGTH: 24
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 486
ncgtcgacga tcggcgcgcg ccgt                                          24

<210> SEQ ID NO 487
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: nitroindole

<400> SEQUENCE: 487
tgncgttttt tttttttttt                                               20

<210> SEQ ID NO 488
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: nitropyrrole

<400> SEQUENCE: 488
tgncgttttt tttttttttt                                               20

<210> SEQ ID NO 489
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: 6-nitro-benzimidazole

<400> SEQUENCE: 489
tgncgttttt tttttttttt                                               20

<210> SEQ ID NO 490
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 490
ncgtcgacga tggcggcgcc gcc                                           23

<210> SEQ ID NO 491
<211> LENGTH: 23
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 491
ncgtcgacga tggcggcgcc gcc                                      23

<210> SEQ ID NO 492
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 492
ttcgttttcg gcgcgcgccg t                                        21

<210> SEQ ID NO 493
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 5-ethyl-2'-deoxyuridine

<400> SEQUENCE: 493
tncgttttcg gcgcgcgccg t                                        21

<210> SEQ ID NO 494
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine

<400> SEQUENCE: 494
ncgttttcgg cgcgcgccgt                                          20

<210> SEQ ID NO 495
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: 5-iodo-2'-deoxyuridine

<400> SEQUENCE: 495
nncgttttcg gcgcgcgccg t                                        21

<210> SEQ ID NO 496
<211> LENGTH: 25
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: misc_feature
<222> LOCATION: (1)..(1)
<223> OTHER INFORMATION: 5-ethyl-2'-deoxyuridine

<400> SEQUENCE: 496
ncgtcgtttt acggcgccgt gccgt                                              25

<210> SEQ ID NO 497
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 5-ethyl-2'-deoxyuridine

<400> SEQUENCE: 497
tncgttttac ggcgccgtgc cgt                                                23

<210> SEQ ID NO 498
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: 5-iodo-2'-deoxyuridine

<400> SEQUENCE: 498
tncgttttac ggcgccgtgc cgt                                                23

<210> SEQ ID NO 499
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5-iodo-2'-deoxyuridine
<220> FEATURE:
<221> NAME/KEY: misc_feature
<222> LOCATION: (12)..(13)
<223> OTHER INFORMATION: uridine
<220> FEATURE:
<221> NAME/KEY: misc_feature
<222> LOCATION: (15)..(15)
<223> OTHER INFORMATION: uridine
<220> FEATURE:
<221> NAME/KEY: misc_feature
<222> LOCATION: (17)..(17)
<223> OTHER INFORMATION: uridine

<400> SEQUENCE: 499
ncgtcgtttt gnngngn                                                       17

<210> SEQ ID NO 500
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
```

```
<222> LOCATION: (1)..(1)
<223> OTHER INFORMATION: 5-ethyl-2'-deoxyuridine

<400> SEQUENCE: 500
ncgtcgacga tcggcggccg ccgt                                      24

<210> SEQ ID NO 501
<211> LENGTH: 116
<212> TYPE: DNA
<213> ORGANISM: Artificial sequence
<220> FEATURE:
<223> OTHER INFORMATION: Synthetic oligonucleotide

<400> SEQUENCE: 501
aggtggtaac ccctaggggt taccaccttc attggaaaac gttcttcggg gcgttcttag    60
gtggtaaccc ctaggggtta ccaccttcat tggaaaacgt tcttcgggc gttctt       116

<210> SEQ ID NO 502
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 502
ggggacgatc gtcggggg                                             18

<210> SEQ ID NO 503
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 503
ggggtcgacg tacgtcgagg ggg                                       23

<210> SEQ ID NO 504
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 504
ggggtcgtcg acgaggggg                                            19

<210> SEQ ID NO 505
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 505
ggggacgagc tcgtcggggg g                                         21

<210> SEQ ID NO 506
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 506
```
gggggacgag ctcgtcgggg g                                         21

<210> SEQ ID NO 507
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 507
ggggacgagc tcgtcggggg                                           20

<210> SEQ ID NO 508
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 508
ggggacgagc tcgtcgggg                                            19

<210> SEQ ID NO 509
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 509
ggggacgatc gtcggggggg                                           19

<210> SEQ ID NO 510
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 510
ggggacgatc gaacgtgggg g                                         21

<210> SEQ ID NO 511
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 511
ggggacgatc gaacgtgggg                                           20

<210> SEQ ID NO 512
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 512
ggggtcgacg tcgacgtcga gggggg                                    26

<210> SEQ ID NO 513
<211> LENGTH: 25
<212> TYPE: DNA
<213> ORGANISM: Artificial sequence

```
<220> FEATURE:
<223> OTHER INFORMATION: Synthetic oligonucleotide

<400> SEQUENCE: 513
ggggtcgacg tcgacgtcga ggggg                                          25

<210> SEQ ID NO 514
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 514
ggggacgacg tcgtggggggg                                               20

<210> SEQ ID NO 515
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 515
ggggacgacg tcgtgggggg                                                19

<210> SEQ ID NO 516
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 516
gggtcgtcga cgaggggg                                                  18

<210> SEQ ID NO 517
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 517
gggggacgag ctcgtcgggg g                                              21

<210> SEQ ID NO 518
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: 5-iodo-2'-deoxyuridine
<220> FEATURE:
<221> NAME/KEY: misc_feature
<222> LOCATION: (14)..(14)
<223> OTHER INFORMATION: 5-iodo-2'-deoxyuridine

<400> SEQUENCE: 518
ggggacgacg ncgnggggggg                                               20

<210> SEQ ID NO 519
<211> LENGTH: 30
<212> TYPE: DNA
```

```
<213> ORGANISM: Artificial sequence
<220> FEATURE:
<223> OTHER INFORMATION: Synthetic oligonucleotide

<400> SEQUENCE: 519
tcgaacgttc gaacgttcga acgttcgaat                                    30

<210> SEQ ID NO 520
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (16)..(20)
<223> OTHER INFORMATION: n is a, c, g, or t

<400> SEQUENCE: 520
nnnnacgacg tcgtgnnnnn                                               20

<210> SEQ ID NO 521
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: n is a, c, g, or t

<400> SEQUENCE: 521
ggggacgacg tcgtgggggn                                               20

<210> SEQ ID NO 522
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 522
ggggacgacg tcgtgggggg tt                                            22

<210> SEQ ID NO 523
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (21)..(22)
<223> OTHER INFORMATION: n is a, c, g, or t

<400> SEQUENCE: 523
ggggacgacg tcgtgggggg nn                                            22

<210> SEQ ID NO 524
<211> LENGTH: 10
<212> TYPE: DNA
<213> ORGANISM: Artificial sequence
<220> FEATURE:
<223> OTHER INFORMATION: Synthetic oligonucleotide
```

-continued

<400> SEQUENCE: 524
tcgtcgacga                                                                    10

<210> SEQ ID NO 525
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 525
gacgatcgtc                                                                    10

<210> SEQ ID NO 526
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 526
acgacgtcgt                                                                    10

<210> SEQ ID NO 527
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 527
gggggagcat gcctgggggg                                                         20

<210> SEQ ID NO 528
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 528 gggggggac gatcgtcggg ggggggg                                                  27

<210> SEQ ID NO 529
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 529
gggggggggg gacgatcgtc ggggggg                                                 27

<210> SEQ ID NO 530
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 530
ggggggggac gatcgtcggg gggg                                                    24

<210> SEQ ID NO 531

```
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 531
gggggggggg tcgtcgacga gggggggggg                                       30

<210> SEQ ID NO 532
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 532
gggggggggg acgagctcgt cgggggggggg g                                    31

<210> SEQ ID NO 533
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 533
gggggggggg acgatcgtcg ggggggggg                                        29

<210> SEQ ID NO 534
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 534
gggggggggg tcgacgtcga cgtcgagggg gggggg                                36

<210> SEQ ID NO 535
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 535
gggggggggg acgacgtcgt gggggggggg                                       30

<210> SEQ ID NO 536
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 536
gggggggggg aacgacgtcg ttgggggggg gg                                    32

<210> SEQ ID NO 537
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 537
```

```
gggggggggg acgacgacga tcgtcgtcgt gggggggggg                40
```

<210> SEQ ID NO 538
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 538

```
gggggggggg cacgacgtcg tggggggggg g                         31
```

<210> SEQ ID NO 539
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 539

```
gggggggggg aacgttcgaa cgttgggggg gggg                      34
```

<210> SEQ ID NO 540
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 540

```
gggggggggg aacgttcgaa cgttcgaacg ttcgaacgtt gggggggggg     50
```

<210> SEQ ID NO 541
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 541

```
gggggggggg ttcgaacgtt cgaagggggg gggg                      34
```

<210> SEQ ID NO 542
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 542

```
gggggggggg acgtcgacgt cgggggggggg g                        31
```

<210> SEQ ID NO 543
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 543

```
gggggggggg tcgacgtcga cgggggggggg g                        31
```

<210> SEQ ID NO 544
<211> LENGTH: 40
<212> TYPE: DNA

<213> ORGANISM: Artificial sequence
<220> FEATURE:
<223> OTHER INFORMATION: Synthetic oligonucleotide

<400> SEQUENCE: 544
gggggggggg acgtcgacgt acgtcgacgt gggggggggg                               40

<210> SEQ ID NO 545
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 545
gggggggggg tacgatatcg tagggggggg gg                                       32

<210> SEQ ID NO 546
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 546
gggggggggg tacgtatacg tagggggggg gg                                       32

<210> SEQ ID NO 547
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 547
gggggggggg cagcatgctg gggggggggg                                          30

<210> SEQ ID NO 548
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 548
acgacgacga                                                                10

<210> SEQ ID NO 549
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 549
acgtcgacgt                                                                10

<210> SEQ ID NO 550
<211> LENGTH: 24
<212> TYPE: DNA

```
<213> ORGANISM: Artificial sequence
<220> FEATURE:
<223> OTHER INFORMATION: Synthetic oligonucleotide

<400> SEQUENCE: 550
tcgtcgttac gtaacgacgt cgtt                                          24
```

COMBINATION TUMOR IMMUNOTHERAPY

RELATED APPLICATIONS

This application is the United States national stage of International Patent Application No. PCT/US2015/067269, filed Dec. 22, 2015, which claims priority from U.S. Provisional Patent Application No. 62/098,568, filed Dec. 31, 2014; U.S. Provisional Patent Application No. 62/106,526, filed Jan. 22, 2015; and U.S. Provisional Patent Application No. 62/118,165, filed Feb. 19, 2015.

SEQUENCE LISTING

The instant application contains a Sequence Listing which has been submitted electronically in ASCII format and is hereby incorporated by reference in its entirety. Said ASCII copy, created on Dec. 22, 2015, is named CPW-00325_ST25 and is 139 kilobytes in size.

BACKGROUND OF THE INVENTION

Many scientists have sought to treat cancer by activating the immune system against the tumor. However, despite occasional successes, durable responses to immune therapy have been rare and limited to just a few tumor types. Current understanding of cancer immunotherapy among those skilled in the art has been summarized in recent review articles, including for example Chen and Mellman, *Immunity* 2013 39(1): 1-10. The cycle for induction of therapeutic immune responses against tumors may be broken down into seven distinct steps (FIG. 1):

1. Release of cancer cell antigens;
2. Presentation of cancer cell antigens by antigen-presenting cells (APC, usually in draining lymph nodes);
3. T-cell priming and activation;
4. Trafficking of $CD8^+$ T cells to tumors;
5. Infiltration of $CD8^+$ T cells into tumors;
6. Recognition of cancer cells by the infiltrating $CD8^+$ T cells; and
7. Killing of cancer cells.

The art teaches that there are multiple negative and positive mediators of each step of the anti-tumor response. Recent research interest has focused on understanding and addressing the role that negative mediators play in inhibiting the anti-tumor immune response. For example, interleukin-10 (IL-10) is a factor that can have complicated effects, locally immune suppressive in the tumor, but systemically can actually have anti-tumor activity (reviewed in Vicari and Trinchieri, *Immunol. Rev.,* 2004). Although Toll-like receptor (TLR) agonists such as TLR9-activating CpG oligonucleotides (CpG ODN) have immune stimulatory effects that can promote anti-tumor responses, they are also known in the art to induce immune suppressive factors such as IL-10 (reviewed in Lu, *Frontiers Immunol,* 2014). The art does not teach designs of TLR9 agonists that have improved anti-tumor effects as a result of inducing lower amounts of IL-10 production. Nevertheless, this increasing recent understanding of the cycle of tumor immunity has heightened awareness that it may be possible to increase the clinical efficacy of cancer immunotherapy by using combinations of agents that act at different points in this cycle for induction of therapeutic immune responses against tumors, but the art does not provide a deep enough understanding of the immunobiology of cancer to predict which of the many different possible combinations will be preferred.

Another possible way to consider the development of the anti-cancer T-cell response is the 3-signal model for the induction of a T-cell response, summarized by Kim and Cantor, *Cancer Immunol Res* 2014 2:929-936) and presented in FIG. 2. In this model signal 1 to the T cell come from the presentation of antigen by an APC on the appropriate MHC to the T cell receptor. Signal 2 is the requirement for a costimulatory signal through the interaction of CD28 on the T cell by B7-1 or B7-2 on the APC (this signal is antagonized by CTLA-4 present on Treg: the efficacy of anti-CTLA-4 antibodies in cancer immunotherapy results from their inhibition of this "off" signal). Finally, signal 3 is the modulation of T cell function resulting from signals via inflammatory cytokine receptors and PD-1. In particular for the induction of optimal $CD8^+$ T cell responses, which are known to be critical for successful cancer immunotherapy, type I IFN signaling is a very positive signal, but when chronic or prolonged also can paradoxically lead to T cell exhaustion and unresponsiveness, which is mediated through upregulation of PD-1 expression. Blocking of PD-1 by antibodies to it, or against its major ligand regulating anti-tumor immunity, PD-L1, therefore restores the ability of the T cell to proliferate and produce cytokines in the tumor microenvironment.

Recently there have been several early clinical successes with the use of "checkpoint inhibitor" (CPI) compounds, such as antibodies, which block the negative immune effects of the checkpoint molecules such as CTLA-4, PD-1, and its ligand, PD-L1. Systemic administration of anti-CTLA-4 antibodies has led to durable responses in ~10% of patients with melanoma, and some encouraging early results in other tumor types, but at the cost of a high rate of adverse effects, including death in some patients. Anti-PD-1/PD-L1 human clinical trials also have been reporting encouraging results, apparently with a lower rate of severe toxicity. However, analyses of the responding patients have revealed that across multiple different types of cancer, responses to anti-PD-L1 therapy are relatively restricted to patients with tumor-infiltrating lymphocytes (TIL) and a Th1 pattern of gene expression in the tumor (Powles et al., *Nature* 2014 515:558; Herbst et al., *Nature* 2014 515:563; Tumeh et al., *Nature* 2014 515:568). That is, responses can be seen in some patients with preexisting immunity to the tumor, but are quite unlikely to occur in patients without this. Aside from melanoma, in which pre-existing anti-tumor immunity is relatively common, TIL are relatively uncommon in most other tumor types, indicating that CPI may be of limited benefit in most types of cancer. Thus, there is a need to improve the efficacy of CPI for cancer therapy.

SUMMARY OF THE INVENTION

The present invention provides methods for promoting immune activation and reducing immune inhibition, thus metaphorically both "stepping on the gas" and "releasing the brakes" of the immune system, to treat cancer. The invention can be used, for example, to convert "cold" (treatment-resistant or -refractory) cancers or tumors to "hot" ones amenable to treatment, including treatment with checkpoint inhibition.

This invention provides specific subtypes of CpG ODN with reduced amounts of phosphorothioate modifications compared to the CpG ODN most widely used in past cancer immunotherapy, and methods for their intratumoral and peritumoral administration in combination with CPI and/or radiotherapy (XRT), for the improved immunotherapy of cancer, including cancers that would be unlikely to respond to any of these therapies alone, or in other combinations.

CpG ODN bind and stimulate TLR9, an innate immune receptor which is constitutively expressed in only two type of human immune cell: B cells, which respond to TLR9 stimulation by proliferating and secreting immunoglobulin; and plasmacytoid dendritic cells (pDC), which respond to TLR9 stimulation by secreting large amounts of type I IFN (IFN-α and IFN-β). The present invention is based, at least in part, on the finding that the IFN-α response to CpG ODN is important for tumor immunotherapy. The present invention is based, at least in part, on the finding that a strong IFN-α response to CpG ODN is important for tumor immunotherapy, including tumor immunotherapy using intratumoral administration of CpG ODN.

Preferred CpG ODN of the invention are characterized, at least in part, by their propensity to induce high amounts of type I IFN.

Type I IFN is believed to play a key role in tumor rejection. For example, Type I IFN augments CD8+ T-cell survival, expansion, and effector differentiation; promotes dendritic cell (DC) maturation, cross-presentation of tumor-associated antigens to CD8+ T cells; is required for immune surveillance against carcinogen-induced tumors; and is required for rejection of implanted tumors. Additionally, levels of type I IFN-related mRNA correlate with tumor-infiltrating lymphocytes (TILs) in human metastases.

In addition to inducing higher levels of type I IFN than anything else, TLR9 ligands such as CpG ODN also activate pDC and induce secretion of hundreds of other Th1-promoting genes and factors; and convert pDC from immature/tolerance-promoting phenotype to mature, activated, cytotoxic T lymphocyte (CTL)-inducing phenotype.

The present invention also is based, at least in part, on the finding that delivery of the CpG ODN into tumors (directly or indirectly) induces the expression of adhesion molecules in the local vasculature in and around the tumor, and promotes the egress of activated T cells (CD4+ and CD8+) from capillaries into the tumor and surrounding region. Some of these T cells will be specific to the unmutated and mutated tumor-associated antigens (TAA). In the absence of checkpoint inhibitors and/or XRT, these T cells may be inhibited by the tumor, but in combination, this creates a much more powerful anti-tumor effect than can be achieved with CpG or the checkpoint inhibitors or XRT on their own.

The present invention in certain aspects is based on the use of CpG ODN classes other than those that have historically been used for cancer immunotherapy. In particular, the present invention in certain aspects is based on the use of high IFN-α secreting classes, the A-class and E-class, with reduced amounts of phosphorothioate (PS) modifications compared to B-class CpG ODN that have been widely used in the past. B-class CpG ODN are typically completely phosphorothioate-modified to increase their resistance to nucleases and the magnitude of the B-cell activation. In contrast, since a focus of the present invention is on achieving a high type I IFN response, rather than B-cell activation, the preferred CpG ODN of the present invention have either no phosphorothioate modifications, or only 1 or 2 phosphorothioate modifications at the 5' end and 1 to 4 phosphorothioate modifications at the 3' end. Preferred E-class ODN of the invention also contain phosphodiester (PO) linkages at the CpG dinucleotides, and optionally at other positions within the ODN, in order to reduce the B cell activation (and concomitant IL-10 and indoleamine 2,3-dioxygenase (IDO) induction), and they also preferably contain one or more palindromes to form duplexes or concatamers.

Those skilled in the art understand that intra- or peritumoral CpG in human cancer patients will activate APC in the tumor draining lymph nodes, enhancing step 2 of the cancer immunity cycle (see FIG. 3). However, what is not well understood by those skilled in the art is that this route of administration of high IFN-inducing CpG ODN will also induce TIL and convert the tumor microenvironment to a more TH1-like state that is more conducive to induction of clinically beneficial anti-tumor immunity. The intratumoral administration of high IFN-inducing CpG ODN induces T cell infiltration into the tumors, notably including CD8− T cell infiltration. The importance of this is that this CD8+ T cell infiltration into tumors is believed to be the best predictor of response to treatment with anti-PD-1 or anti-PD-L1. Because the human clinical trials performed in the past with intratumoral administration of CpG oligonucleotides used B-class ODN, there would have been significant local production of IL-10 in the tumor that would have inhibited the anti-tumor immune response. The present invention features improved preferred CpG ODN as well as designs and screens for identifying the same, which induce lower amounts of IL-10 production and higher amounts of type I IFN secretion compared to the B-class ODN used in the past. Such preferred CpG ODN will provide improved synergy in cancer therapy when combined with checkpoint inhibitors using the methods of the invention.

An aspect of the invention is a method of treating a cancerous tumor, comprising administering to a subject in need thereof an effective amount of a TLR9 agonist and a checkpoint inhibitor (CPI), wherein the TLR9 agonist is administered into or substantially adjacent to the tumor.

An aspect of the invention is a method of treating a cancerous tumor, comprising administering to a subject in need thereof an effective amount of radiotherapy, a TLR9 agonist, and a checkpoint inhibitor (CPI), wherein the radiotherapy is initiated prior to administration of the TLR9 agonist, and the TLR9 agonist is administered into or substantially adjacent to the tumor.

An aspect of the invention is a method of treating a cancerous tumor, comprising administering to a subject in need thereof an effective amount of a TLR9 agonist, a first checkpoint inhibitor (CPI), and a second CPI, wherein the TLR9 agonist and the first CPI are administered into or substantially adjacent to the tumor, and the second CPI is administered systemically.

In certain embodiments, the TLR9 agonist induces IFN-α.

In certain embodiments, the TLR9 agonist is CpG DNA, e.g., CpG ODN.

In certain embodiments, the TLR9 agonist is selected from the group consisting of A-class CpG DNA, C-class CpG DNA, E-class CpG DNA, P-class CpG DNA, and any combination thereof.

In certain embodiments, the TLR9 agonist is an A-class CpG DNA.

In certain embodiments, the sequence of the A-class CpG DNA is GGGGGGGGGGGGAC-GATCGTCGGGGGGGGGG (SEQ ID NO:82).

In certain embodiments, the TLR9 agonist is a C-class CpG DNA.

In certain embodiments, the TLR9 agonist is an E-class CpG DNA.

In certain embodiments, the TLR9 agonist is an A/E-class CpG DNA.

In certain embodiments, the TLR9 agonist is a P-class CpG DNA.

In certain embodiments, the TLR9 agonist including CpG DNA is entirely linked by a phosphodiester backbone.

In certain embodiments, the TLR9 agonist is a CpG DNA with only a single phosphorothioate internucleotide linkage at the 5' end and only a single phosphorothioate internucleotide linkage at the 3' end.

In certain embodiments, the TLR9 agonist is a CpG DNA with a single phosphorothioate linkage.

In certain embodiments, the TLR9 agonist is circular, with a native phosphodiester DNA backbone.

In certain embodiments, the CPI is administered systemically.

In certain embodiments, the CPI is an antibody or antigen-binding fragment thereof which binds specifically to an antigen selected from the group consisting of PD-1, PD-L1, CTLA-4, TIM3, and LAG3.

In certain embodiments, the CPI is an antibody or antigen-binding fragment thereof which binds specifically to one or more antigens selected from the group consisting of PD-1, PD-L1, and CTLA-4.

In certain embodiments, the CPI is an antibody or antigen-binding fragment thereof which binds specifically to an antigen selected from the group consisting of PD-1, PD-L1, and CTLA-4.

In certain embodiments, the CPI is an antibody or antigen-binding fragment thereof which binds specifically to PD-1.

In certain embodiments, the CPI is an antibody or antigen-binding fragment thereof which binds specifically to PD-L1.

In certain embodiments, the CPI is an antibody or antigen-binding fragment thereof which binds specifically to CTLA-4.

In certain embodiments, the cancerous tumor is a lymphoma or a cancerous tumor of an organ or tissue selected from the group consisting of skin, head and neck, esophagus, stomach, liver, colon, rectum, pancreas, lung, breast, cervix, ovary, kidney, bladder, prostate, thyroid, brain, muscle, and bone.

In certain embodiments, the cancerous tumor is melanoma.

In certain embodiments, the cancerous tumor is lymphoma.

In certain embodiments, the cancerous tumor is a cancer of the bone marrow.

In certain embodiments, the cancerous tumor is a carcinoid tumor.

In certain embodiments, the cancerous tumor is neuroblastoma.

In certain embodiments, the subject is a human.

DETAILED DESCRIPTION OF THE INVENTION

Figure 1:
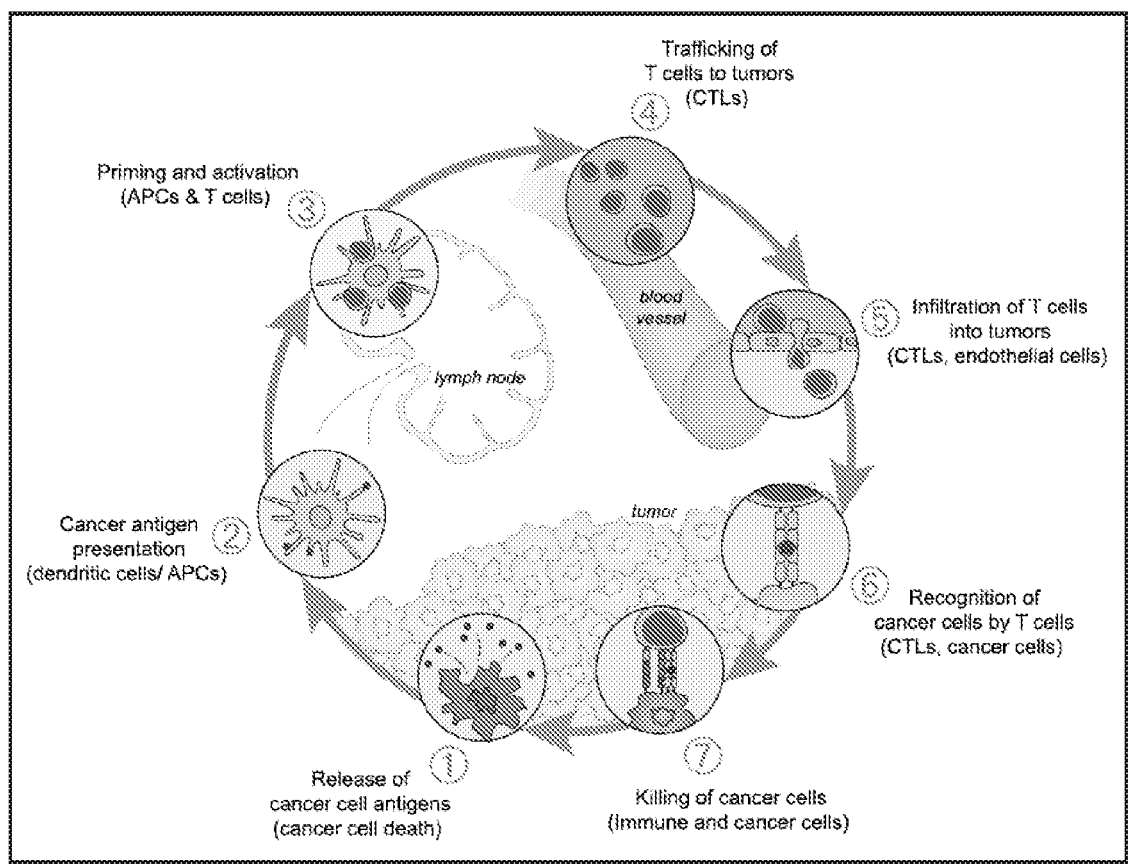
FIG. 1 (prior art) is a schematic representation of the cancer immunity cycle, depicting seven steps. From Chen and Mellman, *Immunity* 2013.
Figure 2:
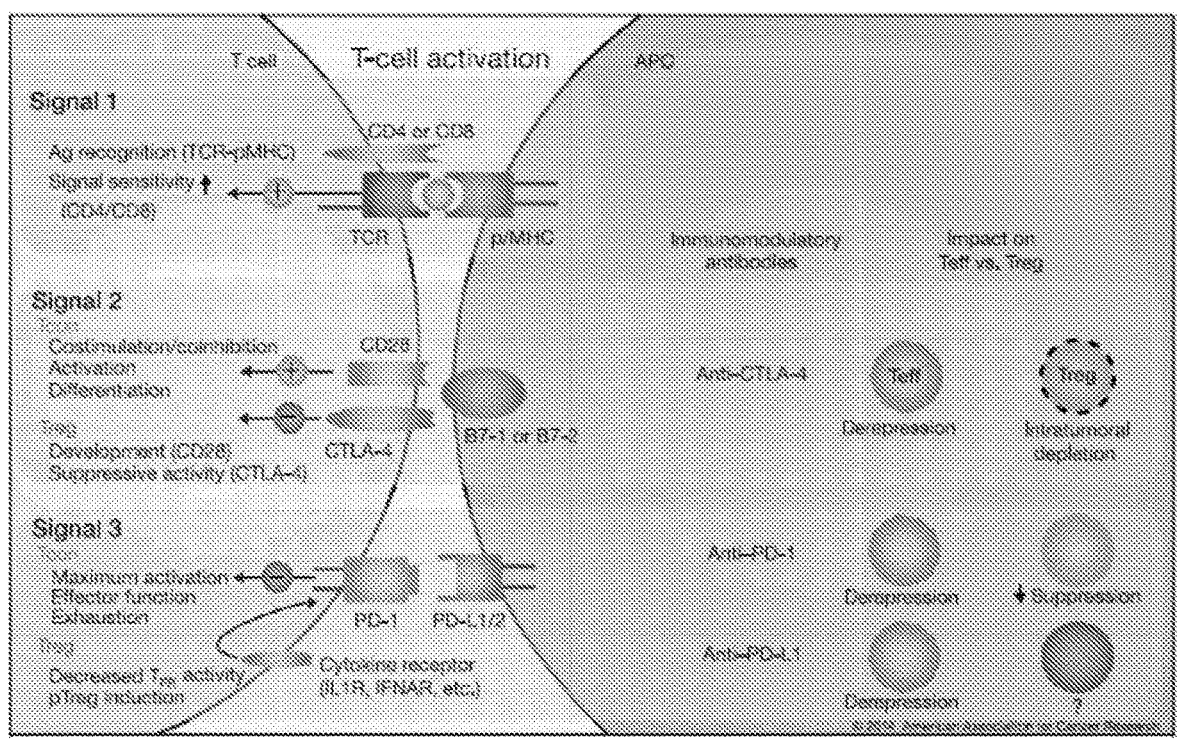
FIG. 2 is a schematic representation of the three signals needed for induction of anti-tumor immunity. Each T cell expresses a unique TCR that recognizes a specific antigen in the context of a specific MHC (signal 1). CD4 and CD8 coreceptors increase the sensitivity of antigen recognition by TCR. Optimal T-cell expansion and acquisition of effector function require signals transduced by costimulatory receptors (signal 2). CD28-BB7-1/B7-2 interaction delivers an activation signal, whereas CTLA-4-B71/B7-2 interaction inhibits T-cell activation. Signaling via CD28 and CTLA-4 is also critical for the development and function of CD4 Treg. Inflammatory signals often induce upregulation of surface cytokine receptors and other receptors, including PD-1 (signal 3). Expression of PD-1 is associated with acquisition of an exhausted phenotype in T cells during infection and cancer. PD-1-PD-L1 interaction is involved in the inhibition of $T_{FR}$ activity and has also been implicated in pTreg generation. Preclinical and clinical data with checkpoint blockade using anti-CTLA-4, anti-PD-1, and anti-PD-L1 Abs suggest that increased antitumor immunity may be achieved by the combined effects of enhanced Teff activity and depletion or reduced suppression by CD4 Treg. From Kim and Cantor, *Cancer Immunol. Res.* 2014 2:926-936.
Figure 3:
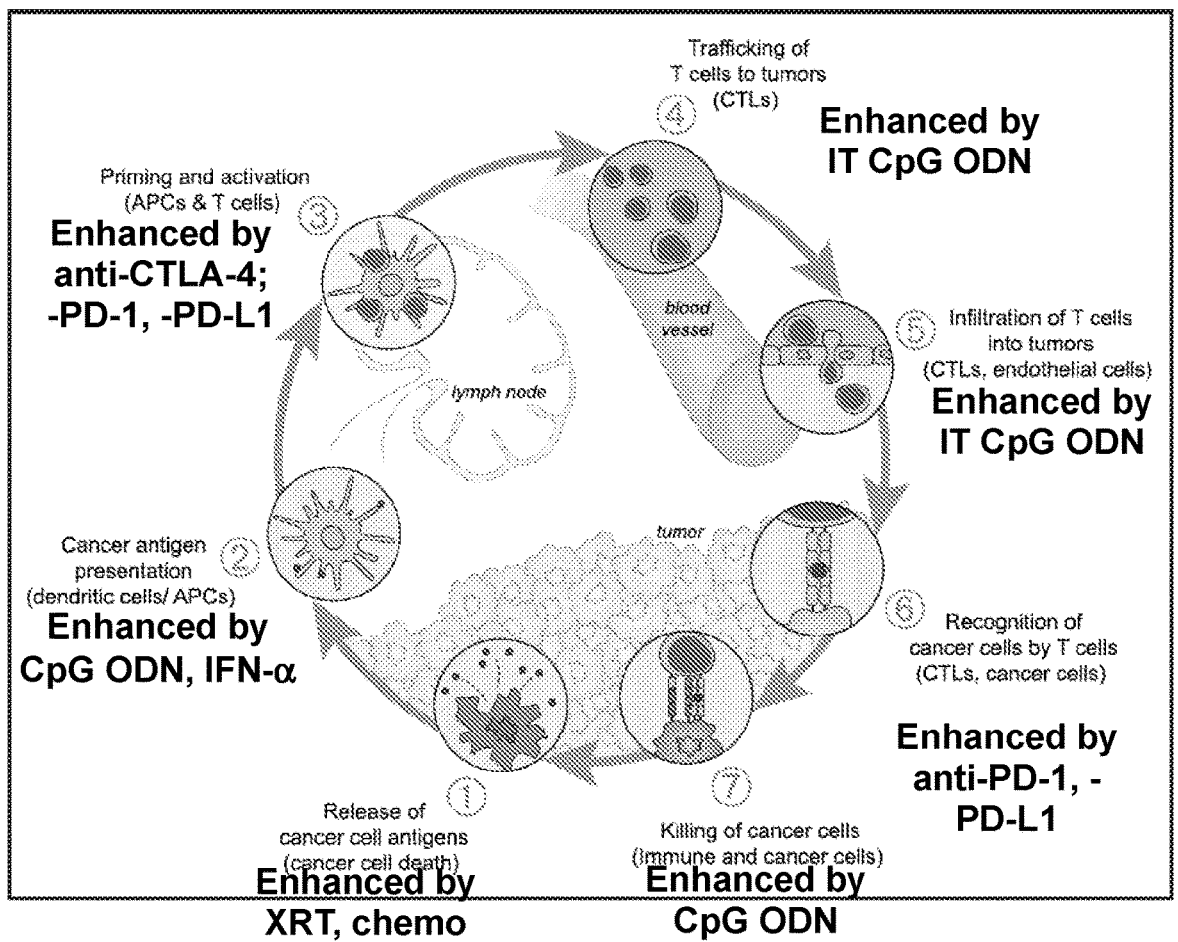
FIG. 3 is a schematic representation of the cancer immunity cycle, depicting roles for CpG ODN, CPI, and XRT. Adapted from Chen and Mellman, *Immunity* 2013.

Toll-like receptor (TLR) ligands in general are known to be potential inducers of the presentation of cancer cell antigens by APC. However, it is not previously known what particular TLR ligands are preferred, and even in the case of TLR9 ligands, it is not previously known which, if any, class of CpG ODN is preferred, nor are their preferred doses and routes of administration previously known. Nearly all human clinical trials of CpG ODN in oncology have used B-class ODN administered via a systemic route, while a few trials have explored intratumoral administration (discussed further below).

The invention of immune stimulatory CpG oligodeoxynucleotides (ODN) and subsequent inventions of various classes and designs of CpG ODN provided new opportunities for cancer immunotherapy. Based on encouraging preclinical data in rodent models, human clinical trials of CpG ODN have been performed in oncology patients using systemic and intratumoral administration of several different CpG ODN alone or in combination with various chemotherapy regimens, vaccines, antibodies, and radiotherapy, but again, clinical responses have been uncommon, and despite some encouraging early clinical trial results, phase 3 trials have so far failed (reviewed in Krieg, *Nucleic Acid Ther.* 2012 22(2): 77-89). Therefore, there exists a need to provide improved oligonucleotide therapeutic approaches to increase the success rate of cancer immunotherapy.

Tumor vaccines in which a cancer patient is vaccinated with a conserved unmutated self antigen together with an adjuvant have been a goal of immuno-oncologists for many years, yet despite successfully inducing immunity against the selected antigen, have almost uniformly failed to deliver clear clinical benefits. B-class CpG ODN have enhanced the induction of anti-tumor CD8$^+$ T cell responses in multiple cancer vaccine clinical trials (for example, Kruit et al., *J Clin Oncol* 2013; Tarhini et al., *J Immunother* 2013; Lovgren et al., *Cancer Immunol Immunother* 2012; Karbach et al., *Clin Cancer Res* 2011; Karbach et al., *Int J Cancer* 2010; Speiser et al., *JCI* 2005, and in a single trial an unmodified A-class CpG ODN was used as a vaccine adjuvant (Speiser et al., *J. Immunother* 2010), yet these have seldom been associated with clinical responses, and a phase 3 clinical trial of this approach conducted by GSK (GlaxoSmithKline) using the MAGE-3 tumor antigen so far appears to have been a failure. In particular it is noteworthy that the vaccine clinical trial using an A-class CpG ODN showed relatively weak induction of a CTL response that increased approximately two-fold from baseline in only about half of the patients, compared to an approximate average 10-fold increased CTL response in those melanoma patients previously vaccinated using B-class CpG ODN, indicating the state of the art. It is possible that the immune system will not easily overcome self-tolerance to unmutated self antigens to a degree sufficient to reject a tumor, leading many of those skilled in the art to search for ways to induce tumor immunity against alternative, mutated tumor antigens. Recent studies using deep sequencing of tumor transcriptomes have revealed that all cancers contain variable numbers of unique mutated antigens, referred to as tumor-specific neoantigens (Rajasagi et al., *Blood* 2014 124(3): 453-462), and those skilled in the art have sought ways to direct the anti-tumor immune response against such antigens. One approach being pursued is to synthesize some or all of these neoantigens as peptides, and to vaccinate a cancer patient with the appropriate antigenic peptides to be presented on Class II MEW in a formulation such as viral-like particle and using a very strong adjuvant, such as a CpG B-class ODN. Such an approach would be extremely complex and expensive to develop. Therefore, there is a need for improved methods to induce anti-tumor immune responses against tumor-specific neoantigens.

The present invention provides a superior approach by turning the tumor itself into a vaccine, due to altering the tumor microenvironment in such a way as to disengage the "brakes" of the checkpoint inhibitors, while inducing strong cell-mediated immunity, using TLR9 agonists.

Radiotherapy has long been used in the treatment of cancer, and it is currently employed in the treatment of approximately 60% of patients with solid tumors (reviewed in Prasanna et al., *J Thoracic Dis.* 2014 6(4):287-302). Although radiotherapy often can shrink tumors, this effect is most commonly palliative, and durable responses are extremely uncommon. Moreover, radiotherapy is generally only suitable for treating one or a small number of tumor lesions, and thus is not generally used in the treatment of metastatic cancer.

In some unusual cases, XRT can lead to regression of distant tumor masses as a result of the induction of a specific immune response against tumor antigens present not only in the irradiated lesion, but also in distant metastases. This has been termed an "abscopal effect", and particularly since a recent case report by Postow et al. (*N. Engl. J. Med.* 2012 366(10): 925-31), this term has come to be used to include other forms of localized tumor therapy besides just radiotherapy.

Abscopal effects can be seen when XRT is given either before or after anti-CTLA-4 therapy: for example, more than half of 21 melanoma patients treated with XRT following anti-CTLA-4 therapy showed evidence for distal tumor regressions (Grimaldi et al., *Oncoimmunol.* 2014 3: e28780).

I. Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to methods well known in the art and as described in various general and more specific references that are cited and discussed throughout the present specification unless otherwise indicated. Such references include, e.g., Sambrook and Russell, Molecular Cloning, A Laboratory Approach, Cold Spring Harbor Press, Cold Spring Harbor, N.Y. 2001), Ausubel et al., Current Protocols in Molecular Biology, John Wiley & Sons, NY (2002), and Harlow and Lane Antibodies: A Laboratory Manual, Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference.

Conventional notation is used herein to portray polypeptide sequences: the left-hand end of a polypeptide sequence is the amino-terminus; the right-hand end of a polypeptide sequence is the carboxyl-terminus.

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, tysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992), incorporated herein by reference. A "moderately conservative" replacement is any change having a nonnegative value in the PAM250 log-likelihood matrix.

Preferred amino acid substitutions are those which: (1) reduce susceptibility to proteolysis, (2) reduce susceptibility to oxidation, (3) alter binding affinity for forming protein complexes, and (4) confer or modify other physicochemical or functional properties of such analogs. Analogs comprising substitutions, deletions, and/or insertions can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts). A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., *Nature* 354:105 (1991), which are each incorporated herein by reference.

Sequence similarity for polypeptides, and similarly sequence identity for polypeptides, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). Another preferred algorithm when comparing a sequence of the invention to a database containing a large number of sequences from different organisms is the computer program BLAST, especially blastp or tblastn, using default parameters. See, e.g., Altschul et al., *J. Mol. Biol.* 215:403-410 (1990); Altschul et al., *Nucleic Acids Res.* 25:3389-402 (1997); incorporated herein by reference.

An intact "antibody" comprises at least two heavy (H) chains and two light (L) chains inter-connected by disulfide bonds. See generally, Fundamental Immunology, Ch. 7 (Paul, W., ed., 2nd ed. Raven Press, N.Y. (1989)) (incorporated herein by reference in its entirety for all purposes). Each heavy chain is comprised of a heavy chain variable region (HCVR or $V_H$) and a heavy chain constant region ($C_H$). The heavy chain constant region is comprised of three domains, CH1, CH2 and CH3. Each light chain is comprised of a light chain variable region (LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The assignment of amino acids to each domain is in accordance with the definitions of Kabat, Sequences of Proteins of Immunological Interest (National Institutes of Health, Bethesda, Md. (1987 and 1991)), or Chothia & Lesk, *J. Mol. Biol.* 196:901-917 (1987); Chothia et al., *Nature* 342:878-883 (1989).

The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" can include antigen-binding portions of an intact antibody that retain capacity to specifically bind the antigen of the intact antibody, e.g., PD-1. Antigen-binding portions may be produced by recombinant DNA techniques or by enzymatic or chemical cleavage of intact antibodies.

Examples of antigen-binding portions include (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain antibody ("dAb"), which consists of a $V_H$ domain as described in Ward et al., *Nature* 341:544-546 1989); and (vi) an isolated complementarity determining region (CDR). Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); See, e.g., Bird et al. *Science* 242:423-426 (1988); and Huston et al. *Proc. Natl. Acad. Sci. USA* 85:5879-5883 (1988)). Such single chain antibodies are included by reference to the term "antibody".

A "bispecific antibody" has two different binding specificities, see, e.g., U.S. Pat. Nos. 5,922,845 and 5,837,243; Zeilderi. *Immunol.* 163:1246-1252 (1999); Somasundaram *Hum. Antibodies* 9:47-54 (1999); Keler *Cancer Res.* 57:4008-4014 (1997). For example, the invention provides bispecific antibodies having one binding site for a cell surface antigen, such as human PD-1, and a second binding site for an Fc receptor on the surface of an effector cell. The invention also provides multi specific antibodies, which have at least three binding sites.

Contemplated by the present invention are bispecific antibodies which bind any two different checkpoint inhibitors. For example, the different CPI may be selected from the group consisting of PD-1, PD-L1, CTLA-4, TIM3, and LAG3. Thus, for example, bispecfic antibodies may bind PD-1 and PD-L1, PD-1 and CTLA-4, PD-1 and TIM3, PD-1 and LAG3, PD-L1 and CTLA-4, PD-L1 and TIM3, PD-L1 and LAG3, CTLA-4 and TIM3, and CTLA-4 and LAG3, or TIM3 and LAG3. In certain embodiments, the bispecfic antibodies may bind PD-1 and PD-L1, PD-1 and CTLA-4, PD-1 and TIM3, or PD-1 and LAG3. In certain embodiments, the bispecific antibodies may bind PD-L1 and CTLA-4, PD-L1 and TIM3, PD-L1 and LAG3. In certain embodiments, the bispecfic antibodies may bind PD-1 and PD-L1, or PD-1 and CTLA-4. In certain embodiments, the bispecfic antibodies may bind PD-1 and PD-L1. In certain embodiments, the bispecfic antibodies may bind PD-L1 and CTLA-4. In certain embodiments, the bispecfic antibodies may bind PD-L1 and CTLA-4.

Also contemplated by the present invention are methods of the invention using bispecific antibodies which bind any two different checkpoint inhibitors. For example, the different CPI may be selected from the group consisting of PD-1, PD-L1, CTLA-4, TIM3, and LAG3. Thus, for example, bispecfic antibodies may bind PD-1 and PD-L1, PD-1 and CTLA-4, PD-1 and TIM3, PD-1 and LAG3, PD-L1 and CTLA-4, PD-L1 and TIM3, PD-L1 and LAG3, CTLA-4 and TIM3, and CTLA-4 and LAG3, or TIM3 and LAG3. In certain embodiments, the bispecfic antibodies may bind PD-1 and PD-L1, PD-1 and CTLA-4, PD-1 and TIM3, or PD-1 and LAG3. In certain embodiments, the bispecific antibodies may bind PD-L1 and CTLA-4, PD-L1 and TIM3, PD-L1 and LAG3. In certain embodiments, the bispecfic antibodies may bind PD-1 and PD-L1, or PD-1 and CTLA-4. In certain embodiments, the bispecfic antibodies may bind PD-1 and PD-L1. In certain embodiments, the bispecfic antibodies may bind PD-L1 and CTLA-4. In certain embodiments, the bispecfic antibodies may bind PD-L1 and CTLA-4.

The term "bispecific antibodies" further includes "diabodies." Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (See, e.g., Holliger et al., *Proc. Natl. Acad. Sci. USA* 90:6444-6448 (1993); Pollak et al., *Structure* 2:1121-1123 (1994)).

The terms "human antibody" or "human sequence antibody", as used interchangeably herein, include antibodies having variable and constant regions (if present) derived from human germline immunoglobulin sequences. The human sequence antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include "chimeric" antibodies in which CDR sequences derived from the germline of another mammalian species, such as a mouse, have been grafted onto human framework sequences (i.e., "humanized" or PRIMATIZED™ antibodies).

The term "chimeric antibody" as used herein means an antibody that comprises regions from two or more different antibodies. For example, in one embodiment, one or more of the CDRs are derived from a human anti-CTLA-4 antibody. In another embodiment, all of the CDRs are derived from a human anti-CTLA-4 antibody. In another embodiment, the CDRs from more than one human anti-CTLA-4 antibody are combined in a chimeric human antibody. For instance, a chimeric antibody may comprise a CDR1 from the light chain of a first human anti-CTLA-4 antibody, a CDR2 from the light chain of a second human anti-CTLA-4 antibody, and a CDR3 from the light chain of a third human anti-CTLA-4 antibody; and similarly the CDRs from the heavy chain may be derived from one or more other anti-CTLA-4 antibodies. Further, the framework regions may be derived from one of the same anti-CTLA-4 antibodies or from one or more different human(s).

As another example, in one embodiment, one or more of the CDRs are derived from a human anti-PD-1 antibody. In another embodiment, all of the CDRs are derived from a human anti-PD-1 antibody. In another embodiment, the CDRs from more than one human anti-PD-1 antibody are combined in a chimeric human antibody. For instance, a chimeric antibody may comprise a CDR1 from the light chain of a first human anti-PD-1 antibody, a CDR2 from the light chain of a second human anti-PD-1 antibody, and a CDR3 from the light chain of a third human anti-PD-1 antibody; and similarly the CDRs from the heavy chain may be derived from one or more other anti-PD-1 antibodies. Further, the framework regions may be derived from one of the same anti-PD-1 antibodies or from one or more different human(s).

As yet another example, in one embodiment, one or more of the CDRs are derived from a human anti-PD-L1 antibody. In another embodiment, all of the CDRs are derived from a human anti-PD-L1 antibody. In another embodiment, the CDRs from more than one human anti-PD-L1 antibody are combined in a chimeric human antibody. For instance, a chimeric antibody may comprise a CDR1 from the light chain of a first human anti-PD-L1 antibody, a CDR2 from the light chain of a second human anti-PD-L1 antibody, and a CDR3 from the light chain of a third human anti-PD-L1 antibody; and similarly the CDRs from the heavy chain may be derived from one or more other anti-PD-L1 antibodies. Further, the framework regions may be derived from one of the same anti-PD-L1 antibodies or from one or more different human(s).

Moreover, as discussed previously herein, chimeric antibody includes an antibody comprising a portion derived from the germline sequences of more than one species.

By the term "compete", as used herein with regard to an antibody, is meant that a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). For instance, cross-competing antibodies can bind to the epitope, or portion of the epitope, to which antibodies of the invention bind. Both competing and cross-competing antibodies are encompassed by the present invention. Regardless of the mechanism by which such competition or cross-competition occurs (e.g., steric hindrance, conformational change, or binding to a common epitope, or portion thereof, and the like), the skilled artisan would appreciate, based upon the teachings provided herein, that such competing and/or cross-competing antibodies are encompassed and can be useful for the methods disclosed herein.

The term "epitope" includes any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents.

By the phrase "specifically binds," as used herein, is meant a compound, e.g., a protein, a nucleic acid, an antibody, and the like, which recognizes and binds a specific molecule, but does not substantially recognize or bind other molecules in a sample. For instance, the phrase "specifically binds" may characterize an antibody or a peptide inhibitor which recognizes and binds a cognate ligand (e.g., an anti-PD-1 antibody that binds with its cognate antigen, PD-1) in a sample, but does not substantially recognize or bind other molecules in the sample. Thus, under designated assay conditions, the specified binding moiety (e.g., an antibody or an antigen-binding portion thereof) binds preferentially to a particular target molecule and does not bind in a significant amount to other components present in a test sample. A variety of assay formats may be used to select an antibody that specifically binds a molecule of interest. For example, solid-phase ELISA immunoassay, immunoprecipitation, BIAcore and Western blot analysis are used to identify an antibody that specifically reacts with PD-1. Typically a specific or selective reaction will be at least twice background signal or noise and more typically more than 10 times background, even more specifically, an antibody is said to "specifically bind" an antigen when the equilibrium dissociation constant ($K_D$) is ≤1 µM, preferably ≤100 nM, and most preferably ≤10 nM.

Preferably, an "antibody which binds specifically to a CPI" is an antibody or antigen-binding fragment thereof, which, in addition to binding its target CPI, interferes with reciprocal interaction between the bound target CPI and its cognate ligand. For example, an antibody which binds specifically to PD-1 preferably is an antibody or antigen-binding fragment thereof, which, in addition to binding PD-1, interferes with reciprocal interaction between PD-1 and its cognate ligand, PD-L1.

The term "$K_D$" refers to the equilibrium dissociation constant of a particular antibody-antigen interaction.

As used herein, "substantially pure" means an object species is the predominant species present (i.e., on a molar basis it is more abundant than any other individual species in the composition), and preferably a substantially purified fraction is a composition wherein the object species (e.g., an anti-PD-1 antibody) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

By the term "therapeutically effective amount," as used herein, is meant an amount that when administered to a mammal, preferably a human, mediates a detectable therapeutic response compared to the response detected in the absence of the compound. A therapeutic response, such as, but not limited to, inhibition of and/or decreased tumor growth (including tumor size stasis), tumor size, metastasis, and the like, can be readily assessed by a plethora of art-recognized methods, including, e.g., such methods as disclosed herein.

The skilled artisan would understand that the effective amount of the compound or composition administered herein varies and can be readily determined based on a number of factors such as the disease or condition being treated, the stage of the disease, the age and health and physical condition of the mammal being treated, the severity of the disease, the particular compound being administered, and the like.

A "therapeutically effective amount" is intended to qualify the amount of an agent required to detectably reduce to some extent one or more of the symptoms of a neoplastic disorder, including, but not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

A "therapeutically effective amount" of a TLR9 agonist can also be defined based on a biomarker response using any of the well-defined blood or tissue markers for TLR9 activation that are well known to those skilled in the art. The CpG ODN of the present invention are broadly similar to other CpG ODN (e.g., B-class) in their induction of a TH1-like cytokine and chemokine response in the serum, plasma, PBMC, and/or tissues or biopsies, which can be measured as described by Krieg et al., *J. Immunother.*, 2004 27:460-471 using for example cytokine assays for IP-10, I-TAC, MIG, MIP-1β, MIP-3β, IL-6, IL-12p40, or IFN-α from serum or plasma collected approximately 24 hr after the treatment, or can also be assessed by RT-PCR assays of PBMC. A therapeutically effective amount of the CpG ODN that is injected intratumorally into a cancer patient will increase serum IP-10 levels by 24 hours to at least 100 pg/ml, and preferably to between 100-100,000 pg/ml, and most preferably to between 1,000 to 10,000 pg/mL.

In contrast to chemotherapy drugs, for which the dose is generally escalated to the maximal tolerated dose (MTD), immune stimulatory drugs such as the CpG ODN of the present invention function best at an optimal biologic dose (OBD), which is generally below the MTD. The serum cytokines and chemokines provide one simple measure to estimate the optimal biologic dose. The intended biologic effect of the CpG ODN of the present invention is to convert the tumor microenvironment (and that of the draining lymph nodes) from immunosuppressive—with a low level of IFN production and lacking in activated TIL—to an immune activated microenvironment that shows increased production of IFN, especially type I IFN, and which now has increased TIL that display activation markers such as PD-L1, as reflected for example in the tumor biopsy characteristics of patients responding to treatment with anti-PD-1 or anti-PD-L1 reported by Tumeh et. al., *Nature* 2014 515:568-571; and by Herbst et al., *Nature* 2014 515:563-567, respectively, or additionally by Taube et al., *Clin Cancer Res.* 2014. Expressed another way, recent studies have demonstrated that anti-PD-1 or anti-PD-L1 therapy is generally only effective in patients who already have TIL, and already have a tumor microenvironment that reflects IFN effects (such as expression of PD-L1, which is induced by IFN). Patients who lack these characteristics on a pre-treatment tumor biopsy are unlikely to respond to therapy with anti-PD-1 or anti-PD-L1 unless they also receive treatment with an agent that induces TIL and high production of type I IFN: the CpG ODN of the present invention are the perfect agent for this purpose.

The major endogenous source of type I IFN in humans and other animals is the plasmacytoid dendritic cell (pDC). pDC produce more than 99% of the type I IFN that is made in response to pathogen infection (Siegal et al., *Science* 1999). Yet very few molecularly-defined stimuli have been shown to activate the pDC to secrete high levels of type I IFN. In fact, to date A-class CpG ODN are by far the strongest stimulus for pDC production of type I IFN that have been reported in the scientific literature, and, surprisingly, the CpG ODN of the present invention are even more effective than those previously known in the art.

Certain preferred CpG ODN induce high or large amounts of type I IFN. Assays for measuring type I IFN are well known in the art and include in vitro enzyme-linked immunosorbent assay (ELISA) and cell-based assays, such as are described herein. Without meaning to be limiting, large or high amounts of type I IFN can refer to greater than or equal to about 1000 pg/mL IFN-α as measured according to such in vitro assays. In certain embodiments, large or high amounts of type I IFN can refer to greater than or equal to about 2000 pg/mL IFN-α as measured according to such in vitro assays. In certain embodiments, large or high amounts of type I IFN can refer to greater than or equal to about 3000 pg/mL IFN-α as measured according to such in vitro assays. In certain embodiments, large or high amounts of type I IFN can refer to greater than or equal to about 4000 pg/mL IFN-α as measured according to such in vitro assays. In certain embodiments, large or high amounts of type I IFN can refer to greater than or equal to about 5,000 pg/mL IFN-α as measured according to such in vitro assays.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the severity of the disease or condition, and the health and size of the subject. One of ordinary skill in the art can empirically determine the effective amount of TLR9 agonist (e.g., CpG ODN), CPI (e.g., anti-PD-1 antibodies, anti-PD-L1 antibodies, anti-CTLA-4 antibodies), and/or other therapeutic agent(s) without necessitating undue experimentation.

For example, a human clinical trial of a B-class CpG ODN together with an anti-CTLA-4 antibody was reported by Millward et al., 2013. The clinical trial demonstrated a way to combine a TLR9 agonist given by subcutaneous injection with an anti-CTLA-4 antibody given systemically that could be used in future clinical trials of other CpG ODN and other checkpoint inhibitors, but the trial failed to demonstrate significant clear clinical benefit from the combination. This failure demonstrates the non-obviousness of the present invention. Even though there have been publications of A-class CpG ODN with high IFN-α secretion, it was not obvious to the investigators running the clinical trial to use such a CpG ODN instead of the B-class CpG ODN. It was not obvious to give the CpG ODN or anti-CTLA-4 antibody locally into the tumor instead of by the systemic route. As a result, the approach was abandoned following the completion of the trial. Likewise, Mangsbo et al. *Immunother* 2010 33:225) reported the combination of an intratumoral B-class CpG ODN with anti-CTLA-4 or anti-PD-1 in mouse tumor models. Positive results were seen with the combinations, but again, there was no guidance to perform such therapy using a high IFN-inducing type of CpG ODN, such as the A-class or other ODN of the present invention.

To date, there appears to be no realization among those skilled in the field of the desirability and advantage to combine a high-IFN-inducing class of CpG ODN together with checkpoint inhibitor therapy. For a combination of agents to have optimal synergy in cancer immunotherapy, the immune suppressive effects of one agent should be reversed by another. For example, IFN induce the expression of PD-L1 on tumors, which suppresses the immune response. High IFN-inducing CpG ODN of the invention induce the expression of PD-L1, but when they are used in combination with an anti-PD-L1 antibody or an anti-PD-L1 antibody, the potential immune suppressive effects of the PD-L1 are overcome by the antibody. On the other hand, the present invention is based, at least in part, on the discovery that the combination of an intratumoral B-class CpG ODN with a systemic checkpoint inhibitor will be less than optimally synergistic (or not synergistic at all) because the induction of IL-10 results in pleiotropic immune suppressive effects that are not reversed by checkpoint inhibitor therapy. Thus, the present invention provides combinations of agents that together provide unexpected, e.g., synergistic, benefits in cancer immunotherapy.

The therapeutically effective amount of CpG ODN and/or antibodies alone or together can be initially determined from in vitro and/or animal models. A therapeutically effective dose can also be determined from human data for the specific CpG ODN and/or specific antibodies or for other compounds which are known to exhibit similar pharmacological activities. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

"Instructional material", as that term is used herein, includes a publication, a recording, a diagram, or any other medium of expression which can be used to communicate the usefulness of the compound, combination, and/or composition of the invention in the kit for affecting, alleviating or treating the various diseases or disorders recited herein. Optionally, or alternately, the instructional material can describe one or more methods of alleviating the diseases or disorders in a cell, a tissue, or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively.

The CpG ODN and/or antibody of the invention may be provided in a medicinal dispenser. A medical dispenser is a package defining a plurality of medicinal storage compartments, each compartment for housing an individual unit of medicament. In an embodiment, an entire medicinal course of treatment is housed in a plurality of medicinal storage compartments.

A package defining a plurality of medicinal storage compartments may be any type of disposable pharmaceutical package or card which holds medicaments in individual compartments. For example, the package is a blister package constructed from a card, which may be made from stiff paper material, a blister sheet and backing sheet. Such cards are well known to those of ordinary skill in the art.

As an example, a medicinal dispenser may house an entire medicinal course of treatment. The dispenser may include the day indicia to indicate which day the individual units of medicament are to be taken. These may be marked along a first side of the medicinal package. The dose indicia may also be marked, for example along a second side of the medicinal package perpendicular to the first side of the medicinal package, thereby indicating the time which the individual unit of medicament should be taken. The unit doses may be contained in the dispenser which is a blister pack.

Except when noted, the terms "patient" or "subject" are used interchangeably and refer to mammals such as human patients and non-human primates, as well as veterinary subjects such as rabbits, rats, and mice, and other animals. Preferably, "patient" or "subject" refers to a human.

In certain embodiments, a subject is an adult human.

In certain embodiments, a subject is a child. In certain embodiments, a subject is less than about 18 years of age. In certain embodiments, a subject is less than about 12 years of age.

As used herein, to "treat" means reducing the frequency with which symptoms of a disease (i.e., tumor growth and/or metastasis, or other effect mediated by the numbers and/or activity of immune cells, and the like) are experienced by a patient. Treatment may be prophylactic (to prevent or delay the onset of the disease, or to prevent the manifestation of clinical or subclinical symptoms thereof) or therapeutic suppression or alleviation of symptoms after the manifestation of the disease. The term "treat" includes the administration of the compounds or agents of the present invention to (i) prevent or delay the onset of the symptoms, complications, or biochemical indicia of, (ii) alleviate the symptoms of, and/or (iii) inhibit or arrest the further development of, the disease, condition, or disorder.

"Combination therapy" embraces the administration of a TLR9 agonist, e.g., certain CpG ODN, and a checkpoint inhibitor as part of a specific treatment regimen intended to provide a beneficial effect from the co-action of these therapeutic agents. In some embodiments, the checkpoint inhibitor is a CPI-specific antibody or antigen-binding fragment thereof. In some embodiments, the checkpoint inhibitor is a bispecific CPI-specific antibody or bispecific antigen-binding fragment thereof. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days, or weeks depending upon the combination selected). "Combination therapy" generally is not intended to encompass the administration of two or more of these therapeutic agents as part of separate monotherapy regimens that incidentally and arbitrarily result in the combinations of the present invention.

"Combination therapy" embraces administration of these therapeutic agents in a sequential manner, that is, wherein each therapeutic agent is administered at a different time, as well as administration of these therapeutic agents, or at least two of the therapeutic agents, in a substantially simultaneous manner. Sequential or substantially simultaneous administration of each therapeutic agent can be effected by any appropriate route as described herein, including, but not limited to, intratumoral and peritumoral routes; systemic routes, e.g., intravenous, intraperitoneal, enteric (including oral), intramuscular, subcutaneous, and transmucosal routes; and topical and transdermal routes. As described herein, generally a first therapeutic agent (e.g., CpG ODN) can be administered by intratumoral or peritumoral injection, and a second agent (e.g., anti-PD-1 antibody) can be administered systemically (e.g., intravenously).

"Combination therapy" also can embrace the administration of the TLR9 agonist, e.g., certain CpG ODN, and checkpoint inhibitor therapeutic agents as described above in further combination with non-drug therapies (such as, but not limited to, radiotherapy (XRT) or surgery). In some embodiments, the checkpoint inhibitor is a CPI-specific antibody or antigen-binding fragment thereof. In some embodiments, the checkpoint inhibitor is a bispecific CPI-specific antibody or bispecific antigen-binding fragment thereof. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, by days or even weeks.

"Combination therapy" also can embrace the administration of the TLR9 agonist, e.g., certain CpG ODN, and checkpoint inhibitor therapeutic agents as described above in further combination with other biologically active ingredients (such as, but not limited to, a further and different antineoplastic agent, a dendritic vaccine or other tumor vaccine). In some embodiments, the checkpoint inhibitor is an antibody or antigen-binding fragment thereof. In some embodiments, the checkpoint inhibitor is a bispecific antibody or bispecific antigen-binding fragment thereof. However, in certain embodiments, "combination therapy" specifically excludes the administration of a dendritic cell or tumor vaccine.

II. CpG DNA

CpG oligonucleotides (CpG DNA; CpG ODN) contain specific sequences found to elicit an immune response. These specific sequences are referred to as "immunostimulatory motifs", and the oligonucleotides that contain immunostimulatory motifs are referred to as "immunostimulatory oligonucleotide molecules" and equivalently, "immunostimulatory oligonucleotides". Immunostimulatory oligonucleotides include at least one immunostimulatory motif, and preferably that motif is an internal motif. The term "internal immunostimulatory motif" refers to the position of the motif sequence within an oligonucleotide sequence which is at least one nucleotide longer (at both the 5' and 3' ends) than the motif sequence.

CpG oligonucleotides include at least one unmethylated CpG dinucleotide. An oligonucleotide containing at least one unmethylated CpG dinucleotide is an oligonucleotide molecule which contains a cytosine-guanine dinucleotide sequence (i.e., "CpG DNA" or DNA containing a 5' cytosine linked by a phosphate bond to a 3' guanine) and activates the immune system. The entire CpG oligonucleotide can be unmethylated or portions may be unmethylated, but at least the C of the 5' CG 3' must be unmethylated.

CpG ODN are generally about 8-100 nucleotides long. In certain embodiments, CpG ODN are about 8-50 nucleotides long, about 8-40 nucleotides long, about 8-30 nucleotides long, about 8-24 nucleotides long, about 8-20 nucleotides long, or about 8-16 nucleotides long.

By 2004, structure-activity relationship studies of CpG ODN had defined three families with distinct structural and biological characteristics (Hartmann et al., *Eur. J. Immunol.* 2003, 33:1633-1641; Marshall et al., *J. Leukocyte Biol.* 2003 73: 781-792; Vollmer et al., *Eur. J. Immunol.* 2004 34:251-262). Typical B-class ODN have a completely phosphorothioate backbone, do not form higher-ordered structures, and are strong B cell stimulators, inducing relatively high levels of IL-10 secretion, but induce relatively little NK activity or IFN-α secretion (Krieg, 2002, and Krieg, unpublished observations). B-class CpG ODN induce immune-suppressive counter-regulatory effects including not only the secretion of IL-10, but also the expression of IDO, which can promote the development of Treg cells in vitro (Moseman et al., *J. Immunol.* 2004 173(7): 4433-4442; Chen et al., *J. Immunol.* 2008 181(8): 5396-5404). The relevance of these in vitro data to in vivo tumor immunotherapy has been uncertain, and has not delayed the clinical development of B-class ODN, but the present invention is based in part on a new discovery that these effects of B-class ODN will suppress anti-tumor immune responses, which can be avoided using other classes of CpG ODN that are structurally designed not to activate the NF-κB pathway leading to IL-10 secretion.

The phosphorothioate backbone used in B-class CpG ODN has multiple complex effects on the resulting immune response compared to that seen with a CpG ODN with the same sequence but without a phosphorothioate backbone. One very important effect of the phosphorothioate (PS) backbone is protection against nuclease degradation. Completely PS-modified ODN are nearly completely stable in serum and tissues for at least 24 hr, whereas unmodified and unprotected ODN are degraded within a few minutes. In serum the major nuclease activity is a 3' exonuclease against which CpG ODN can be protected with just 1 or a few PS linkages at the 3' end of the ODN. But in tissues there also are 5' exonucleases as well as endonucleases, and these can degrade native DNA that is not otherwise protected. Native DNA can be protected against exonucleases by circularization using techniques well described in the literature. See, for example, U.S. Pat. Nos. 8,017,591; 7,635,468; 7,074,772; 6,849,725; 6,451,593; and 6,451,563; and U.S. Published Patent Application No. 2003/0125279; the entire contents of all of which are hereby incorporated by reference. Alternatively or in addition, the native (i.e., otherwise unmodified and unprotected) ODN can be formulated in nanoparticles or other formulations well known in the art to block nuclease access to the ODN.

In general, native CpG DNA (phosphodiester) activates TLR9 in both B cells and pDC. B cells produce cytokine and start to proliferate (this is predominantly driven through NF-κB activation), but unless the TLR9 stimulation is sustained, the proliferation is usually modest, and relatively little stimulation of Ig secretion and class switching occurs. pDC are activated by native CpG DNA to secrete type I IFN and to express costimulatory receptors, but the magnitude of the stimulation depends critically on the form of the DNA. In contrast to these effects of native CpG DNA, B-class phosphorothioate CpG DNA provides a far more powerful and sustained TLR9 signal for B cells, inducing them to proliferate strongly and leading to Ig secretion and class switching as reported in the literature. But the phosphorothioate backbone has a very different effect on the TLR9-mediated pDC response, reducing substantially the IFN secretion (apparently through suppressing IRF7-mediated signaling), but usually still providing strong induction of costimulatory molecule expression. Thus, for the present invention, the use of native DNA usually will provide higher type I IFN responses and will be therapeutically effective as long as the native DNA is protected from degradation. From 1 to 3 phosphorothioate modifications can be added onto the 5' and 3' termini of native DNA to protect it from nuclease degradation without diminishing the type I IFN response.

Early on in the development of CpG ODN for cancer immunotherapy, those skilled in the art generally believed that B-cell activation was desirable, and therefore focused development efforts on the B-class ODN. Indeed, perhaps B-cell activation is desirable for a tumor vaccine, in order to drive the production of anti-tumor Ab, which are well known in the field to be able to contribute to the anti-tumor response. Some early human clinical trials employing intratumoral administration of B-class CpG gave encouraging evidence of dendritic cell activation in the tumor draining lymph nodes (e.g., Molenkamp B G et al., *Clin Cancer Res.* 2007 13(10): 2961-2969). However, clinical responses to this local intratumoral therapy were quite limited, and studies of the total lymphocyte population in the draining lymph nodes showed an approximate two-fold increase in the release of IL-10 in CpG-treated patients (Table 2 in Molenkamp et al.). Considering the negative effects of IL-10 for tumor immunotherapy, and the need for improved CpG ODN that do not induce its production, or which induce a lower level of this production, the present invention further provides improved CpG ODN with reduced induction of IL-10.

Nevertheless, it has now been discovered, in accordance with the present invention, that for intratumoral administration in particular, B cell activation with the concomitant IL-10 and IDO induction, is undesirable, and perhaps deleterious. This is difficult or impossible to demonstrate using mouse models because of the species-specific differences in the TLR9 expression and differences in the cytokine responses. The present invention is based on a new analysis of previously published and unpublished data on the human immune cell responses to various CpG ODN, together with a new analysis of the immune effects and deficiencies of other cancer immunotherapies and XRT.

For cancer immunotherapy IL-10 can sometimes have positive effects (especially with systemic therapy, see for example Mumm and Oft, Bioessays 2013 35(7): 623-631), but IL-10 is generally considered to have negative immune effects in the local tumor microenvironment, inhibiting immune rejection (reviewed in Sato et al., *Immunol Res.* 2011 51(2-3): 170-182). Thus, the present invention is based in part on the discovery that B-class CpG ODN, which induce high levels of IL-10, are not preferred for intratumoral therapy.

The B-class of CpG oligonucleotides is represented by the formula:

$$5'\ X_1CGX_2\ 3'$$

wherein $X_1$ and $X_2$ are nucleotides. In some embodiments, $X_1$ may be adenine, guanine, or thymine and/or $X_2$ may be cytosine, adenine, or thymine.

The B-class of CpG oligonucleotides is also represented by the formula:

$$5'\ X_1X_2CGX_3X_4\ 3'$$

wherein $X_1$, $X_2$, $X_3$, and $X_4$ are nucleotides. $X_2$ may be adenine, guanine, or thymine. $X_3$ may be cytosine, adenine, or thymine.

The B-class of CpG oligonucleotides also includes oligonucleotides represented by at least the formula:

$$5'\ N_1X_1X_2CGX_3X_4N_2\ 3'$$

wherein $X_1$, $X_2$, $X_3$, and $X_4$ are nucleotides and N is any nucleotide and $N_1$ and $N_2$ are oligonucleotide sequences composed of from about 0-25 N's each. $X_1X_2$ may be a dinucleotide selected from the group consisting of: GpT, GpG, GpA, ApA, ApT, ApG, CpT, CpA, CpG, TpA, TpT, and TpG; and $X_3X_4$ may be a dinucleotide selected from the group consisting of: TpT, ApT, TpG, ApG, CpG, TpC, ApC, CpC, TpA, ApA, and CpA.

The B-class of CpG oligonucleotides is disclosed in PCT Published Patent Applications PCT/US95/01570 and PCT/US97/19791, and U.S. Pat. No. 6,194,388 B1 and U.S. Pat. No. 6,239,116 B1, issued Feb. 27, 2001 and May 29, 2001 respectively.

In contrast to the B-class CpG ODN, A-class CpG ODN are potent activators of natural killer cells and IFN-α secretion from plasmacytoid dendritic cells (pDC), but only weakly stimulate B cells, and induce very little IL-10 secretion. Canonical A-class ODN contain polyG motifs at the 5' and/or 3' ends which are capable of forming complex higher-ordered structures known as G-tetrads and a central phosphodiester region containing one or more CpG motifs within a self-complementary palindrome (reviewed in (Krieg, 2006). For example, U.S. Pat. Nos. 6,949,520 and 7,776,344 show that in certain preferred embodiments the A-class CpG ODN has a sequence corresponding to any of the following:

```
                                      (SEQ ID NO: 43)
ggGGTCAACGTTGAgggggG;

(SEQ ID NO: 44)
tcgtcgttttgtcgttttgtcgtt;

(SEQ ID NO: 45)
ggggtcgtcgttttgggggg;

(SEQ ID NO: 46)
tcgtcgttttgtcgttttgggggg;

(SEQ ID NO: 47)
ggggtcgacgtcgagggggg;

(SEQ ID NO: 48)
ggggtcatcgatgagggggg;

(SEQ ID NO: 49)
ggGGGACGATCGTCgggggG;

(SEQ ID NO: 50)
gggggtcgtacgacgggggg;

(SEQ ID NO: 51)
ggGGGACGATATCGTCgggggG;

(SEQ ID NO: 52)
ggGGGACGACGTCGTCgggggG;

(SEQ ID NO: 53)
ggGGGACGAGCTGCTCgggggG;

(SEQ ID NO: 54)
ggGGGACGTACGTCgggggG;

(SEQ ID NO: 55)
ggGGGACGATCGTTgggggG;

(SEQ ID NO: 56)
ggGGAACGATCGTCggggG;

(SEQ ID NO: 57)
ggGGGGACGATCGTCgggggG;

(SEQ ID NO: 58)
ggGGGACGATCGTCGgggggG;

(SEQ ID NO: 59)
ggGGGTCATCGATGAgggggG;

(SEQ ID NO: 60)
ggGGTCGTCGACGAgggggG;

(SEQ ID NO: 61)
ggGGTCGTTCGAACGAgggggG;

(SEQ ID NO: 62)
ggGGACGTTCGAACGTgggggG;

(SEQ ID NO: 63)
ggGGAACGACGTCGTTgggggG;
```

-continued ggGGAACGTACGTCgggggG; (SEQ ID NO: 64)

ggGGAACGTACGTACGTTgggggG; (SEQ ID NO: 65)

ggGGTCACCGGTGAgggggG; (SEQ ID NO: 66)

ggGGTCGACGTACGTCGAgggggG; (SEQ ID NO: 67)

ggGGACCGGTACCGGTgggggG; (SEQ ID NO: 68)

gggGTCGACGTCGAgggggG; (SEQ ID NO: 69)

ggGGTCGACGTCGagggg; (SEQ ID NO: 70)

ggGGAACGTTAACGTTgggggG; (SEQ ID NO: 71)

ggGGACGTCGACGTggggG; (SEQ ID NO: 72)

ggGGGTCGTTCGTTgggggG; (SEQ ID NO: 73)

ggGACGATCGTCGgggggG; (SEQ ID NO: 74)

ggGTCGTCGACGAggggggG; (SEQ ID NO: 75)

ggTCGTCGACGAGgggggG; (SEQ ID NO: 76)

ggGGACGATCGTCGgggggG; (SEQ ID NO: 77)

ggGGTCGACGTCGACGTCGAGgggggG; and (SEQ ID NO: 78)

ggGGACGACGTCGTgggggG, (SEQ ID NO: 79)

wherein each lower case letter represents a nucleotide linked to its 3'-adjacent nucleotide by a phosphorothioate (PS) linkage; and each upper case letter represents a nucleotide linked to its 3'-adjacent nucleotide (if present) by a phosphodiester (PO) linkage, except that the 3'-terminal nucleotide is represented by an upper case letter since it has no 3'-adjacent nucleotide.

In certain more preferred embodiments the immunostimulatory nucleic acid has a sequence corresponding to ggGGGACGAGCTCGTCgggggG; (SEQ ID NO: 80)

ggGGGACGATCGTCgggggG; (SEQ ID NO: 58)

ggGGACGATCGAACGTgggggG; (SEQ ID NO: 81)

ggGGTCGACGTCGACGTCGAGgggggG; or (SEQ ID NO: 78)

ggGGACGACGTCGTgggggG; (SEQ ID NO: 79)

wherein each lower case letter represents a nucleotide linked to its 3'-adjacent nucleotide by a phosphorothioate (PS) linkage; and each upper case letter represents a nucleotide linked to its 3'-adjacent nucleotide (if present) by a phosphodiester (PO) linkage, except that the 3'-terminal nucleotide is represented by an upper case letter since it has no 3'-adjacent nucleotide.

In certain embodiments, an A-class CpG ODN for use in accordance with the methods of the instant invention has a sequence provided as: 5'-GGGGGGGGGGGAC-GATCGTCGGGGGGGGGG-3' (SEQ ID N0:82; also referred to herein as "G10"). Such oligonucleotide and formulations thereof useful in accordance with the present invention are described in WO 2003/024481; US 2003/0099668; US 2012/0301499; WO 2004/084940; U.S. Pat. No. 7,517,520; US 2010/0098722; WO 2007/068747; US 2007/0184068; U.S. Pat. No. 8,574,564; WO 2007/144150; U.S. Pat. No. 8,541,559; WO 2008/073960; and U.S. Pat. No. 8,586,728, the entire contents of each of which is incorporated herein by reference.

The structure of C-class ODN is typically based on a phosphorothioate backbone, but is distinct in that the CpG motifs are followed by a 3' palindrome, which may form a duplex. C-class ODN are described in U.S. Pat. No. 7,566,703 to Krieg et al.; U.S. Pat. No. 8,198,251 to Vollmer et al.; and U.S. Pat. No. 8,834,900 to Krieg et al. The C-class CpG ODN have immune properties intermediate between the A and B classes (Hartmann et al., 2003; Marshall et al., 2003; Marshall et al., 2005; Vollmer et al., 2004).

Examples of C-class ODN include:

TCGTCGTTTTCGGCGCGCGCCG; (SEQ ID NO: 83)

TCGTCGTTTTCGGCGGCCGCCG; (SEQ ID NO: 84)

TCGTCGTTTTCGGCGCGCCGCG; (SEQ ID NO: 85)

TCGTCGTTTTCGGCGCCGGCCG; (SEQ ID NO: 86)

TCGTCGTTTTCGGCCCGCGCGG; (SEQ ID NO: 87)

TCGTCGTTTTCGGCGCGCGCCGTTTTT; (SEQ ID NO: 88)

TCCTGACGTTCGGCGCGCGCCG; (SEQ ID NO: 89)

TZGTZGTTTTZGGZGZGZGZZG; (SEQ ID NO: 90)

TCCTGACGTTCGGCGCGCGCCC; (SEQ ID NO: 91)

TCGGCGCGCGCCGTCGTCGTTT; (SEQ ID NO: 92)

TCGTCGTTTTCGGCGGCCGACG; (SEQ ID NO: 93)

TCGTCGTTTTCGTCGGCCGCCG; (SEQ ID NO: 94)

TCGTCGTTTTCGACGGCCGCCG; (SEQ ID NO: 95)

TCGTCGTTTTCGGCGGCCGTCG; (SEQ ID NO: 96)

TCGTCGTTTCGACGGCCGTCG; (SEQ ID NO: 97)

TCGTCGTTTCGACGATCGTCG; (SEQ ID NO: 98)

TCGTCGTTTCGACGTACGTCG; (SEQ ID NO: 99)

TCGTCGCGACGGCCGTCG; (SEQ ID NO: 100)

TCGTCGCGACGATCGTCG; (SEQ ID NO: 101)

TCGTCGCGACGTACGTCG; (SEQ ID NO: 102)

TCGTTTTTTTCGACGGCCGTCG; (SEQ ID NO: 103)

TCGTTTTTTTCGACGATCGTCG; and (SEQ ID NO: 104)

TCGTTTTTTTCGACGTACGTCG, (SEQ ID NO: 105)

wherein each Z is 5-methylcytosine.

According to certain embodiments the immunostimulatory nucleic acid includes the sequence TCGGCGCGCGC-CGTCGTCGTTT (SEQ ID NO:92).

The oligonucleotide may comprise 5' T*T*T*C_G*T*C_G*T*T*T*C_G*T*C_G*T*T 3' (SEQ ID NO:106), wherein * represents a stabilized internucleotide linkage. Optionally, when specifically stated, 5' may refer to the free 5' end of the oligonucleotide and 3' may refer to the free 3' end of the oligonucleotide.

In some embodiments of the invention the oligonucleotide has one of the following formulas: TCGTCGTTCG-GCGCGCCG (SEQ ID NO:107), TCGTCGTCGTTCG-GCGCGCGCCG (SEQ ID NO:108), TCGTCGACGATCGGCGCGCGCCG (SEQ ID NO:109), TTCGTCGTTTGTCGTT (SEQ ID NO:110), or TTTCGTCGTTTCGTCGTT (SEQ ID NO:106).

In other embodiments of the invention the oligonucleotide has one of the following formulas: TCGTCGTC, CGTCGTCG, GTCGTCGT, TCGTCGTT, CGTCGTTC, GTCGTTCG, TCGTTCGG, CGTTCGGC, GTTCGGCG, TTCGGCGC, TCGGCGCG, CGGCGCGC, GGCGCGCG, GCGCGCGC, CGCGCGCC, or GCGCGCCG.

In other embodiments of the invention the oligonucleotide has one of the following formulas: T*C_G*T*C_G*T*C, C_G*T*C_G*T*C_G, G*T*C_G*T*C_G*T, T*C_G*T*C_G*T*T, C_G*T*C_G*T*T*C, G*T*C_G*T*T*C_G, T*C_G*T*T*C_G*G, C_G*T*T*C_G*G*C, G*T*T*C_G*G*C*G, T*T*C_G*G*C*G*C, T*C_G*G*C*G*C_G, C_G*G*C*G*C_G*C, G*G*C*G*C_G*C*G, G*C*G*C_G*C*G*C, C*G*C_G*C*G*C*C, or G*C_G*C*G*C*C*G, wherein * represents a stabilized internucleotide linkage.

In other embodiments of the invention an oligonucleotide comprising: T*C_G*T*C_G*T*C, wherein * represents a stabilized internucleotide linkage and _ represents phosphodiester or phosphodiester-like internucleotide linkage is provided. Optionally the oligonucleotide may be 5' T*C_G*T*C_G*T*C_G*T*T*C_G*G*C*G*C_G*C*G*C*C 3' (SEQ ID NO:111), 5' T*C_G*T*C_G*T*C_G*T*T*C_G*G*C*G*C 3' (SEQ ID NO:112), or 5' T*C_G*T*C_G*T*C_G*T*T*C_G*G*C*G*C_G*C*G*C 3' (SEQ ID NO:113) wherein 5' refers to the free 5' end of the oligonucleotide and 3' refers to the free 3' end of the oligonucleotide.

In other embodiments an oligonucleotide comprising: T*C_G*T*T*C_G*G, wherein * represents a stabilized internucleotide linkage and _ represents phosphodiester or phosphodiester-like internucleotide linkage is provided. Optionally the oligonucleotide may be 5' C_G*T*C_G*T*C_G*T*T*C_G*G*C*G*C_G*C*G*C*C*G 3' (SEQ ID NO:114); 5' G*T*C_G*T*C_G*T*T*C_G*G*C*G*C_G*C*G*C*C*G 3' (SEQ ID NO:115); 5' T*C_G*T*C_G*T*T*C_G*G*C*G*C_G*C*G*C*C*G 3' (SEQ ID NO:116); 5' G*T*C_G*T*T*C_G*G*C*G*C_G*C*G*C*C*G 3' (SEQ ID NO:117); 5' G*T*C_G*T*T*C_G*G*C*G*C_G*C*G*C*C*G 3' (SEQ ID NO:118); or 5' T*C_G*T*T*C_G*G*C*G*C_G*C*G*C*C*G 3' (SEQ ID NO:119), wherein 5' refers to the free 5' end of the oligonucleotide and 3' refers to the free 3' end of the oligonucleotide.

More recently a new class of CpG oligo was identified with the structural feature of two palindromes (vs the single palindrome in the C-class). See, e.g., U.S. Patent Application Pub. 2008/0045473, the entire content of which is incorporated herein by reference. Because of the two palindromes these P-class CpG ODN are able to form higher-order concatamers, which are hypothesized to interact with TLR9 in a different manner from the linear B-class ODN or duplex C-class ODN, with the observed result that the P-class ODN induce higher levels of type I IFN compared to C-class (or B-class), and substantially lower levels of IL-10.

Examples of P-class ODN include:

T*C-G*T*C-G*A*C-G*A*T*C-G*G*C*G*C-G*C*G*C*C*G; (SEQ ID NO: 109)

T-C-G-T-C-G-A-C-G-A-T*T*T-A-C-G-A-C-G-T-C-G-T-T*T*T; (SEQ ID NO: 120)

T-C-G-T-C-G-A-C-G-A-T-T-T-A-C-G-A-C-G-T-C-G-T-T-T-T; (SEQ ID NO: 121)

T-C-G-T-C-G-A-C-G-A-A-C-G-A-C-G-T-C-G-T; (SEQ ID NO: 122)

T-C-G-T-C-G-A-C-G-A-T*T*T-T-C-G-T-C-G-A-C-G-A-T*T; (SEQ ID NO: 123)

-continued (SEQ ID NO: 123)
T-C-G-T-C-G-A-C-G-A-T-T-T-T-C-G-T-C-G-A-C-G-A-T-T-T;

(SEQ ID NO: 124)
T-C-G-T-C-G-A-C-G-A-T-C-G-T-C-G-A-C-G-A;

(SEQ ID NO: 125)
C*G*C*G*C*G*C*G*C*G*C*G*C*G*C*G*C*G;

(SEQ ID NO: 126)
G*A*G*A*A*C*G*C*T*C*G*A*C*C*T*T*C*G*A*T*biot;

(SEQ ID NO: 127)
A*G*C*T*C*C*A*T*G*G*T*G*C*T*C*A*C*T*G;

(SEQ ID NO: 128)
T*C*T*C*C*C*A*G*C*G*T*G*C*G*C*C*A*T;

(SEQ ID NO: 129)
T*C*C*A*T*G*A*C*G*T*T*C*C*T*G*A*G*G*T*T;

(SEQ ID NO: 130)
T*C*C*A*G*G*A*C*T*T*C*T*C*T*C*A*G*G*T*T;

(SEQ ID NO: 131)
T*C*C*A*C*G*A*C*G*T*T*T*T*C*G*A*C*G*T*T;

(SEQ ID NO: 132)
T*C*G*T*C*G*T*T*T*T*G*A*C*G*T*T*T*T*G*A*C*G*T*T;

(SEQ ID NO: 91)
T*C*C*T*G*A*C*G*T*T*C*G*G*C*G*C*G*C*G*C*C*C;

(SEQ ID NO: 133)
T*C*G*C*G*T*G*C*G*T*T*T*T*G*T*C*G*T*T*T*T*G*A*C*G*T*T;

(SEQ ID NO: 134)
T*C*G*C*G*A*C*G*T*T*C*G*G*C*G*C*G*C*G*C*C*G;

(SEQ ID NO: 135)
dig-C*C*G*G*C*C*G*G*C*C*G*G*C*C*G*G*C*C*G*G;

(SEQ ID NO: 136)
dig-C*G*C*G*C*G*C*G*C*G*C*G*C*G*C*G*C*G;

(SEQ ID NO: 137)
T*C*C*A*G*G*A*C*T*T*C*T*C*T*C*A*G*G*T*T*T*T*T;

(SEQ ID NO: 138)
G*T*G*C*T*C*G*A*G*G*A*T*G*C*G*C*T*T*C*G*C;

(SEQ ID NO: 139)
G*C*C*G*A*G*G*T*C*C*A*T*G*T*C*G*T*A*C*G*C;

(SEQ ID NO: 133)
T-C-G-C-G-T-G-C-G-T-T-T-T-G-T-C-G-T-T-T-T-G-A-C-G-T-T;

(SEQ ID NO: 140)
A*C*C*G*A*T*A*C*C*G*G*T*G*C*C*G*G*T*G*A*C*G*G*C*A*C*C*A*C*G;

(SEQ ID NO: 141)
A*C*C*G*A*T*A*A*C*G*T*T*G*C*C*G*G*T*G*A*C*G*G*C*A*C*C*A*C*G;

(SEQ ID NO: 142)
A*C*C*G*A*T*G*A*C*G*T*C*G*C*C*G*G*T*G*A*C*G*G*C*A*C*C*A*C*G;

(SEQ ID NO: 143)
C*G*G*C*G*C*G*C*G*C*C*G*C*G*G*C*G*C*G*C*C*G;

(SEQ ID NO: 144)
T*C*G*A*T*C*G*T*T*T*T*T*C*G*T*G*C*G*T*T*T*T*T;

(SEQ ID NO: 145)
T*C*G*T*C*C*A*G*G*A*C*T*T*C*T*C*T*C*A*G*G*T*T;

(SEQ ID NO: 146)
T*C*G*T*C*G*T*C*C*A*G*G*A*C*T*T*C*T*C*T*C*A*G*G*T*T;

(SEQ ID NO: 147)
T*C*G*T*G*A*C*G*G*G*C*G*G*C*G*C*G*C*G*C*C*C;

-continued

```
                                                (SEQ ID NO: 148)
A*C*G*A*C*G*T*C*G*T*tC*G*G*C*G*G*C*C*G*C*C*G;

(SEQ ID NO: 149)
G*G*G-G-A-C-G-A-C-G-T-C-G-T-G-C*G*G*C*G*G*C*C*G*C*C*G;

(SEQ ID NO: 149)
G*G*G*G*A*C*G*A*C*G*T*C*G*T*G*C*G*G*C*G*G*C*C*G*C*C*G;

(SEQ ID NO: 150)
C*C-A*C-G*A*C-G*T*C-G*T*C-G-A-A-G*A*C-G*A*C-G*T*C-G*T-G*G;

(SEQ ID NO: 151)
C*T-G*C*A*G-C*T-G-C*A*G-C*T-G-C*A*G-C*T-G*C*A*G;

(SEQ ID NO: 152)
C*G*G-C*C-G*C*T-G*C*A-G-C*G-G*C*C-G*C*T-G*C*A*G;

(SEQ ID NO: 153)
C*A*T*G*A*C*G*T*T*T*T*T*G*A*T*G*T*T;

(SEQ ID NO: 154)
A*T*G*A*C*G*T*T*T*T*T*G*A*T*G*T*T;

(SEQ ID NO: 155)
T*G*A*C*G*T*T*T*T*T*G*A*T*G*T*T;

(SEQ ID NO: 156)
A*T*G*A*C*G*T*T*T*T*T*G*A*T*G*T*T*G*T;

(SEQ ID NO: 157)
T*C*C*A*T*G*A*C-G-T*T*T*T*T*G*A*T*G*T*T;

(SEQ ID NO: 157)
T*C*C*A*T*G*A-C-G-T*T*T*T*T*G*A*T*G*T*T;

(SEQ ID NO: 157)
T*C*C*A*T*G*A*C*G*T*T*T*T*T*G*A*T-G-T*T;

(SEQ ID NO: 157)
T*C*C*A*T*G*A-C-G-T*T*T*T*T*G*A*T-G*T*T;

(SEQ ID NO: 157)
T*C*C*A*T*G*A-C-G-T*T*T*T*T*G*A*T-G*T*T;

(SEQ ID NO: 156)
A*T*G*A*C-G*T*T*T*T*T*G*A*T*G*T*T*G*T;

(SEQ ID NO: 156)
A*T*G*A*C*G*T*T*T*T*T*G*A*T-G*T*T*G*T;

(SEQ ID NO: 156)
A*T*G*A*C-G*T*T*T*T*T*G*A*T-G*T*T*G*T;

(SEQ ID NO: 156)
A*T*G*A-C-G-T*T*T*T*T*G*A-T-G-T*T*G*T;

(SEQ ID NO: 158)
T*C*C*A*T*G*C*G*T*T*T*T*T*G*A*A*T*G*T*T;

(SEQ ID NO: 159)
T*C*C*A*T*G*A*C*G*T*C*T*T*T*G*A*T*G*T*C;

(SEQ ID NO: 160)
A-C-G-A-C-G-T-C-G-T-T-C-A-C-G-A-C-G-T-C-G-T-chol;

(SEQ ID NO: 161)
A-C-G-A-C-G-T-C-G-T-G-G-C-C-A-C-G-A-C-G-T-C-G-T-D-D-D;

(SEQ ID NO: 162)
A-C-G-A-C-G-T-C-G-T-D-D-D-D-A-C-G-A-C-G-T-C-G-T-D-D-D;

(SEQ ID NO: 163)
D-D-D-A-C-G-A-C-G-T-C-G-T-D-D-D-D-A-C-G-A-C-G-T-C-G-T-D-D-D;

(SEQ ID NO: 164)
D-D-D-A-C-G-A-C-G-T-C-G-T-D-D-D-D-A-C-G-A-C-G-T-C-G-T-chol;

(SEQ ID NO: 165)
G*G*G-A-C-G-A-C-G-T-C-G-T-G*G*C*C-A-C-G-A-C-G-T-C-G-T-C*C*C;
```

-continued

C*C*C-A-C-G-A-C-G-T-C-G-T-G*G*G; (SEQ ID NO: 166)

C*C*C*V-A-C-G-A-C-G-T-C-G-T-G*G*G*G; (SEQ ID NO: 167)

T*C*G*A*T*C*G*T*T*T-T-C-G*T*G*C*G*T*T*T*T*T; (SEQ ID NO: 144)

T*C*G*A*T*C*G*T*T-T-T-C-G-T*G*C*G*T*T*T*T*T; (SEQ ID NO: 144)

T*C*G*A*T*C*G*T-T-T-T-C-G-T-G*C*G*T*T*T*T*T; (SEQ ID NO: 144)

T*C*G*A*T*C*G-T-T-T-T-C*G*T*G*C*G*T*T*T*T*T; (SEQ ID NO: 144)

A*T-G*A*C-G*T*T*T*T-G*A*C-G*T*T; (SEQ ID NO: 168)

A*C-G*A*C-G*T*T*T*T-G*A*T-G*T*T; (SEQ ID NO: 169)

A*C-G*A*C-G*T*T*T*T-C-G*A*C-G*T*T; (SEQ ID NO: 326)

A*T-G*A*T-G*T*T*T*T-T-G*A*T-G*T*T; (SEQ ID NO: 170)

A*T-G*A*C-G*T*T*T*T-G-A*T-G-T*T; (SEQ ID NO: 171)

A*T-G*A*C-G*T*T*T*G*T-G*A*T-G*T*T; (SEQ ID NO: 172)

T*T-G*A*C-G*T*T*T*T-G*A*T-G*T*T; (SEQ ID NO: 173)

A*T-G*A*T-G*T*T*T*T-T-G*A*T-G*T*T; (SEQ ID NO: 170)

A*T-G*A*G-C*T*T*T*T-G-T*A*T-G*T*T; (SEQ ID NO: 174)

T*C*G*A*C*G*T*T*T*T*C*G*G*C*G*G*C*C*G*C*C*G; (SEQ ID NO: 175)

T*C*C*T*G*A*C*G*T*T*T*T*C*G*G*C*G*G*C*C*G*C*C*G; (SEQ ID NO: 176)

T*C*C*T*G*A*C*G*T*T*T*C*G*G*C*G*G*C*C*G*C*C*G; (SEQ ID NO: 177)

T*C*C*A*T*G*A*C*G*T*T*C*G*G*C*G*C*G*C*G*C*C*C; (SEQ ID NO: 178)

T*C*C*T*G*A*C*G*T*T*C*G*G*C*G*C*G*C*G*C*C; (SEQ ID NO: 179)

T*C*G*A*C*G*T*T*T-T-C-G-G-C*G*G*C*G*C*C*G; (SEQ ID NO: 180)

T*C*G*A*C*G*T*T*T-T-C-G-G-C*G*G*C*C*G*C*C*G; (SEQ ID NO: 175)

T*C*G*A*C*G*T*C*G-A-C-G-T-T-A-G-G-T-T-A*G*G; (SEQ ID NO: 181)

A*C*G*A*C*G*T*C*G-T-T-A-G-G-G-T-T-A*G*G; (SEQ ID NO: 182)

G*T*C-G*G*C-G*T*T-G*A*C; (SEQ ID NO: 183)

A-C-G-A-C-G-T-C-G-T-C-G-D-D-D-D-C-G-G-C-C-G-C-C-G; (SEQ ID NO: 184)

A-C-G-A-C-G-T-C-G-T-C-G-D-D-D-D-C*G*G*C*C*G*C*C*G; (SEQ ID NO: 184)

-continued

```
                                                       (SEQ ID NO: 185)
T-C-G-T-C-G-A*C*G*A*C*G*T*C*G*T*C*G;

(SEQ ID NO: 186)
T-C-G-T-C-G-A-C-G-A-C-G-T-C-G-T-C-G-D-D-D-D;

(SEQ ID NO: 187)
A-C-G-A-C-G-T-C-G-T-T*T*T-A-C-G-A-C-G-T-C-G-T-teg;

(SEQ ID NO: 162)
A*C*G*A*C*G*T*C*G*T*D*D*D*A*C*G*A*C*G*T*C*G*T*D*D*D;

(SEQ ID NO: 163)
D*D*D*A*C*G*A*C*G*T*C*G*T*D*D*D*A*C*G*A*C*G*T*C*G*T*D*D*D;

(SEQ ID NO: 188)
A-C-G-A-C-G-T-C-G-T-T*T*T-A-C-G-A-C-G-T-C-G-T-D-D-D;

(SEQ ID NO: 189)
A-C-G-A-C-G-T-C-G-T-T*T*T-A-C-G-A-C-G-T-C-G-T-T*T*T;

(SEQ ID NO: 189)
A*C-G-A-C-G-T-C-G-T-T*T*T-A-C-G-A-C-G-T-C-G-T-T*T*T;

(SEQ ID NO: 190)
A*C-G-A-C-G-T-C-G-T-T*T*T-A-C-G-A-C-G-T-C-G*T;

(SEQ ID NO: 191)
A-C-G-A-C-G-T-C-G-T-D-D-D-D-A-C-G-A-C-G-T-C-G-T-L;

(SEQ ID NO: 192)
A-C-G-A-C-G-T-C-G-T-L-A-C-G-A-C-G-T-C-G-T-L;

(SEQ ID NO: 193)
A-C-G-A-C-G-T-C-G-T-teg-teg-A-C-G-A-C-G-T-C-G-T-teg;

(SEQ ID NO: 194)
C-G-A-C-G-T-C-G-T-D-D-D-D-A-C-G-A-C-G-T-C-G-D-D-D;

(SEQ ID NO: 195)
A-C-G-A-C-G-T-C-G-D-D-D-D-C-G-A-C-G-T-C-G-T-D-D-D;

(SEQ ID NO: 196)
C-G-A-C-G-T-C-G-D-D-D-D-C-G-A-C-G-T-C-G-D-D-D;

(SEQ ID NO: 197)
T-C-G-A-C-G-T-C-G-T-D-D-D-D-A-C-G-A-C-G-T-C-G-A-D-D-D;

(SEQ ID NO: 198)
A-C-G-T-C-G-T-C-G-T-D-D-D-D-A-C-G-A-C-G-A-C-G-T-D-D-D;

(SEQ ID NO: 199)
T-C-G-T-C-G-A-C-G-T-D-D-D-D-A-C-G-T-C-G-A-C-G-A-D-D-D;

(SEQ ID NO: 200)
T-C-G-A-C-G-T-C-G-T-D-D-D-D-A-C-G-A-C-G-T-C-G-T-D-D-D;

(SEQ ID NO: 201)
A-C-G-A-C-G-T-C-G-T-D-D-D-D-A-C-G-T-C-G-T-C-G-T-D-D-D;

(SEQ ID NO: 202)
A-C-G-A-C-G-T-T-D-D-D-D-A-A-C-G-T-C-G-T-D-D-D;

(SEQ ID NO: 203)
A-C-G-T-C-G-T-D-D-D-D-A-C-G-A-C-G-T-D-D-D;

(SEQ ID NO: 204)
G-G-C-G-G-C-C-G-D-D-D-D-C-G-G-C-C-G-C-C-D-D-D;

(SEQ ID NO: 205)
G-C-G-G-C-C-G-G-D-D-D-D-C-C-G-G-C-C-G-C-D-D-D;

(SEQ ID NO: 206)
A-C-G-T-C-G-T-D-D-D-D-A-C-G-A-C-G-T-C-G-T-D-D-D;

(SEQ ID NO: 207)
D-A-C-G-A-C-G-T-C-G-T-D-D-D-D-A-C-G-A-C-G-T-C-G-T-D;

(SEQ ID NO: 208)
A*C-G-A-C-G-T-C-G-T-C-G-A-A-G-A-C-G-A-C-G-T-C-G-T-D-D-T;
```

-continued

```
                                             (SEQ ID NO: 209)
T*C-G-A-C-G-T-C-G-T-C-G-A-A-G-A-C-G-T-C-G-T-C-G-T-D-D-T;

(SEQ ID NO: 150)
C*C*A-C-G-A-C-G-T-C-G-T-C-G-A-A-G-A-C-G-A-C-G-T-C-G-T*G*G;

(SEQ ID NO: 210)
T*C*C*A*D*G*A*C*G*T*T*T*T*T*G*A*T*G*T*T;

(SEQ ID NO: 211)
T*C*C*A*T*G*A*C*G*T*T*D*T*T*G*A*T*G*T*T;

(SEQ ID NO: 212)
T*C*C*A*J*G*A*C*G*T*T*T*T*T*G*A*T*G*T*T;

(SEQ ID NO: 213)
T*C*C*A*T*G*A*C*G*T*T*J*T*T*G*A*T*G*T*T;

(SEQ ID NO: 214)
T*C*C*A*T*G*A*C*G*T*T*T*T*T*G*A*T*G*T*T*Cy3;

(SEQ ID NO: 215)
J*J*J*J*J*G*A*C*G*T*T*T*T*T*G*A*T*G*T*T;

(SEQ ID NO: 216)
T*C*C*A*J*G*A*C*G*T*T*J*T*T*G*A*T*G*T*T;

(SEQ ID NO: 217)
T*C*C*A*D*G*A*C*G*T*T*D*T*T*G*A*T*G*T*T;

(SEQ ID NO: 218)
A-C-G-A-C-G-T-C-G-T-D-D-D-D-A-C-G-A-C-G-T-C-G-T-D-D-D-rU;

(SEQ ID NO: 219)
A-C-G-A-C-G-T-C-G-T-D-D-D-D-A-C-G-A-C-G-T-C-G-T-D-D-D-rG;

(SEQ ID NO: 220)
A-C-G-A-C-G-T-C-G-T-D-D-D-D-A-C-G-A-C-G-T-C-G-T-D-D-D-rA;

(SEQ ID NO: 221)
D-D-D-A-C-G-A-C-G-T-C-G-T-D-D-D-D-A-C-G-A-C-G-T-C-G-T-D-D-D-rU;

(SEQ ID NO: 222)
A-C-G-A-C-G-T-C-G-T-D-D-D-D-A-C-G-A-C-G-T-C-G-T-D-D-D-rA-rA-rA-rA;

(SEQ ID NO: 223)
T*C*G*A*T*G*A*C*G*T*T*C*C*T*G*A*C*G*T*T;

(SEQ ID NO: 224)
T-T-T-A-C-G-A-C-G-T-C-G-T-D-D-D-D-A-C-G-A-C-G-T-C-G-T-D-D-D-rU;

(T*C-G-A-C-G-T-C-G-T-)(vitE-)double-teg;

(SEQ ID NO: 175)
T*C*G*A-C-G*T*T*T*T*C-G*G*C*G*G*C-G*C*C*G;

(SEQ ID NO: 180)
T*C*G*A-C-G*T*T*T*T*C-G*G*C*G*C*G*C-G*C*C*G;

(SEQ ID NO: 134)
T*C-G*C-G*A*C-G*T*T*C-G*G*C*G*C-G*C*G*C*C*G;

(SEQ ID NO: 134)
T*C*G*C-G*A*C*G*T*T*C-G*G*C*G*C*G*C*G*C*C*G;

(SEQ ID NO: 134)
T*C*G*C-G*A*C*G*T*T*C-G*G*C*G*C*G*C-G*C*G*C*C*G;

(SEQ ID NO: 134)
T*C*G*C-G*A*C*G*T*T*C-G*G*C*G*C*G*C-G*C*G*C*C*G;

(SEQ ID NO: 134)
T*C*G*C*G*A*C-G*T*T*C-G*G*C*G*C-G*C*G*C*C*G;

(SEQ ID NO: 134)
T*C*G*C*G*A*C-G*T*T*C-G*G*C*G*C-G*C*G*C*C*G;

(SEQ ID NO: 134)
T*C*G*C-G*A*C*G*T*T*C-G*G*C*G*C-G*C*G*C*G*C*C*G;
```

-continued

```
                                          (SEQ ID NO: 134)
T*C*G*C*G*A*C-G*T*T*C-G*G*C*G*C-G*C*G*C*C*G;

(SEQ ID NO: 225)
T*C*G*C*G*A*C-G*T*T*C*G*C*G*C-G*C*G*C*G;

(SEQ ID NO: 226)
D*C*C*A*T*G*A*C*G*T*T*T*T*T*G*A*T*G*T*T;

(SEQ ID NO: 227)
T*D*C*A*T*G*A*C*G*T*T*T*T*T*G*A*T*G*T*T;

(SEQ ID NO: 228)
T*C*D*A*T*G*A*C*G*T*T*T*T*T*G*A*T*G*T*T;

(SEQ ID NO: 229)
T*C*C*D*T*G*A*C*G*T*T*T*T*T*G*A*T*G*T*T;

(SEQ ID NO: 230)
T*C*C*A*T*G*A*C*G*T*T*T*T*D*G*A*T*G*T*T;

(SEQ ID NO: 231)
T*C*C*A*T*G*A*C*G*T*T*T*D*T*G*A*T*G*T*T;

(SEQ ID NO: 232)
T*C*G*A*A*C-G*T*T*C*G*G*C*G*C*G*C*G*C*C*G;

(SEQ ID NO: 233)
T*C*G*T*C*G*A*A*C-G*T*T*C*G*G*C*G*C*G*C*G*C*C*G;

(SEQ ID NO: 234)
T*C*G*T*C*G*A*A*C-G*T*T*C*G*G*C*G*C*T*G*C*G*C*C*G;

(SEQ ID NO: 235)
T*C*G*C*G*A*C-G*T*T*C*G*T*T*G*C*G*C*G*C*G*C*C*G;

(SEQ ID NO: 236)
T*A*C*G*T*C-G*T*T*C*G*G*C*G*C*G*C*G*C*C*G;

(SEQ ID NO: 237)
T*T*C*G*C*G*A*C-G*T*T*C*G*G*C*G*C*G*C*G*C*C*G;

(SEQ ID NO: 238)
T*C*G*G*C*G*C*G*C*G*C*C-G*T*C*G*C*G*A*C*G*T;

(SEQ ID NO: 239)
T*A*G*C-G*T*G*C-G*T*T*T*T*G*A*C-G*T*T*T*T*T*T*T;

(SEQ ID NO: 240)
T*A*G*C-G*A*G*C-G*T*T*T*T*G*A*C-G*T*T*T*T*T*T*T;

(SEQ ID NO: 241)
T*T*G*C-G*A*G*C-G*T*T*T*T*G*A*C-G*T*T*T*T*T*T*T;

(SEQ ID NO: 242)
A*T*G*C-G*T*G*C-G*T*T*T*T*G*A*C-G*T*T*T*T*T*T*T;

(SEQ ID NO: 243)
T*T*A*C-G*T*G*C-G*T*T*T*T*G*A*C-G*T*T*T*T*T*T*T;

(SEQ ID NO: 244)
T*T*G*C-A*T*G*C-G*T*T*T*T*G*A*C-G*T*T*T*T*T*T*T;

(SEQ ID NO: 245)
T*T*G*C-G*T*A*C-G*T*T*T*T*G*A*C-G*T*T*T*T*T*T*T;

(SEQ ID NO: 246)
T*T*G*C-G*T*G*C-A*T*T*T*T*G*A*C-G*T*T*T*T*T*T*T;

(SEQ ID NO: 247)
T*T*G*C-G*T*G*C-G*A*T*T*T*G*A*C-G*T*T*T*T*T*T*T;

(SEQ ID NO: 248)
T*T*G*C-G*C*G*C-G*T*T*T*T*G*A*C-G*T*T*T*T*T*T*T;

(SEQ ID NO: 249)
T*T*G*C-G*T*G*C-G*C*T*T*T*G*A*C-G*T*T*T*T*T*T*T;

(SEQ ID NO: 250)
T*T*G*C-G*T*G*C-G*T*T*T*C*G*A*C-G*T*T*T*T*T*T*T;
```

-continued (SEQ ID NO: 234)
T*C*G*T*C-G*A*A*C*G*T*T*C-G*G*C*G*C*T*G*C*G*C*C*G;

(SEQ ID NO: 234)
T*C*G*T*C-G*A*A*C*G*T*T*C-G*G*C-G*C*T*G*C*G*C*C*G;

(SEQ ID NO: 234)
T*C*G*T*C-G*A*A*C*G*T*T*C-G*G*C*G*C*T*G*C-G*C*C*G;

(SEQ ID NO: 234)
T*C*G*T*C*G*A*A*C-G*T*T*C*G*G*C-G*C*T*G*C*G*C*C*G;

(SEQ ID NO: 251)
T*C*G*T*C-G*G*A*C*G*T*T*C-G*G*C*G*C*T*G*C*G*C*C*G;

(SEQ ID NO: 235)
T*C*G*C*G*A-C-G*T*T*C*G*T*T*G*C-G*C*G*C*G*C*C*G;

(SEQ ID NO: 252)
T*G*G*C-G*A*C*G*T*T*C-G*T*T*G*C-G*C*G*C*G*C*C*G;

(SEQ ID NO: 235)
T*C-G*C*G*A*C*G*T*T*C-G*T*T*G*C*G*C-G*C*G*C*C*G;

(SEQ ID NO: 253)
T*C*G*C*G*A-C-G*T*T*T*T*G*C*G*C-G*C*G*C;

(SEQ ID NO: 254)
T*C*G*C*G*A-C-G*T*C*G*T*T*G*C-G*C*G*C*G*C*C*G;

(SEQ ID NO: 255)
T*C*G*C*G*A-C-G*T*T*C*G*A*A*G*C-G*C*G*C*G*C*C*G;

(SEQ ID NO: 256)
T*C*G*C*G*A*C-G*A*A*C*G*T*T*G*C-G*C*G*C*G*C*C*G;

(SEQ ID NO: 257)
T-C-G-A-C-G-T-C-G-T-D-D-D-D-T-C-G-A-C-G-T-C-G-T-D-D-D;

(SEQ ID NO: 258)
T*C*G*T*C*G*T*T*A*G*C*T*C*G*T*T*A*G*C*T*C*G*T*T;

(SEQ ID NO: 259)
T*C*G*T*C*G*T*T*A*C*G*T*A*A*T*T*A*C*G*T*C*G*T*T;

(SEQ ID NO: 260)
T*C*G*T*C*G*T*T*A*C*G*T*C*G*T*T*A*C*G*T*A*A*T*T;

(SEQ ID NO: 261)
T*C*G*T*C*G*T*T*A*C*G*T*A*A*T*T*A*C*G*T*A*A*T*T;

(SEQ ID NO: 262)
T*C*G*A*C*G*T*C-G-A-C*G*T*G*A*C*G*G;

(T-C-G-A-C-G-T-C-G-T-T-)2doub-but;

(T-C-G-A-C-G-T-C-G-T-T-)2doub-chol;

(T-C-G-A-C-G-T-C-G-T-T-T-)2doub-chol;

T-C-G-A-C-G-T-C-G-T-T-T-chol-T-T-C-G-A-C-G-T-C-G-T-T-but;

(SEQ ID NO: 263)
T*C*G*C-G*A*C*G*T*T*C-G*G*C*G*C-G*C*T*G*C*C*G;

(SEQ ID NO: 264)
T*C*G*C-G*A*C*G*T*T*C-G*G*C*G*C-G*T*C*G*C*C*G;

(SEQ ID NO: 265)
T*C*G*C-G*A*C*G*T*T*C-G*G*C*G*G*C-T*C*G*C*C*G;

(SEQ ID NO: 264)
T*C*G*C*G-A*C*G*T*T*C-G*G*C*G*C-G*T*C*G*C*C*G;

(SEQ ID NO: 265)
T*C*G*C*G-A*C*G*T*T*C-G*G*C*G*G*C-T*C*G*C*C*G;

(SEQ ID NO: 264)
T*C*G-C*G*A*C*G*T*T*C-G*G*C*G*C-G*T*C*G*C*C*G;

-continued

```
                                                    (SEQ ID NO: 265)
T*C*G-C*G*A*C*G*T*T*C-G*C*G*G*C-T*C*G*C*C*G;

(SEQ ID NO: 266)
(T-C-G-A-C-G-T-C-G-T-)(vitE-);

(SEQ ID NO: 262)
T*C-G*A*C-G*T*C-G*A*C*G*T*G*A*C*G*G;

(SEQ ID NO: 262)
T*C*G*A*C*G*T*C*G*A*C*G*T*G*A*C*G*G;

(SEQ ID NO: 267)
T*C*G*A*C*G*T*C*G*A*C*G*T*G*A*C*T*C;

(SEQ ID NO: 268)
T*C*G*A*C*G*T*C*G*A*C*G*T*G*A*C*G;

(SEQ ID NO: 269)
(T-C-G-A-C-G-T-C-G-A-)(vitE-);

(SEQ ID NO: 270)
T*C*G*T*C*G*T*T*A*C*G*T*A*A*C*T*A*C*G*T*C*G*T*T;

(SEQ ID NO: 550)
T*C*G*T*C*G*T*T*A*C*G*T*A*A*C*G*A*C*G*T*C*G*T*T;

(SEQ ID NO: 271)
T*C*G*T*C*G*T*T*A*C*G*T*A*A*C*G*A*C*G*A*C*G*T*T;

(SEQ ID NO: 272)
T*C*G*T*C*G*T*T*A*G*C*T*A*A*T*T*A*G*C*T*C*G*T*T;

(SEQ ID NO: 273)
T*C*G*T*C*G*T*T*A*C*G*T*A*A*T*T*A*G*C*T*C*G*T*T;

(SEQ ID NO: 274)
C*C*C*A*T*G*A*C*G*T*T*C*C*T*G*A*C*G*T*T;

(SEQ ID NO: 275)
G*C*C*A*T*G*A*C*G*T*T*C*C*T*G*A*C*G*T*T;

(SEQ ID NO: 276)
A*C*C*A*T*G*A*C*G*T*T*C*C*T*G*A*C*G*T*T;

(SEQ ID NO: 277)
T*G*G*A*T*G*A*C*G*T*T*C*C*T*G*A*C*G*T*T;

(SEQ ID NO: 278)
T*T*T*A*T*G*A*C*G*T*T*C*C*T*G*A*C*G*T*T;

(SEQ ID NO: 279)
T*A*A*T*G*A*C*G*T*T*C*C*T*G*A*C*G*T*T;

(SEQ ID NO: 280)
C*C*A*T*G*A*C*G*T*T*C*C*T*G*A*C*G*T*T;

(SEQ ID NO: 281)
C*A*T*G*A*C*G*T*T*C*C*T*G*A*C*G*T*T;

(SEQ ID NO: 282)
A*T*G*A*C*G*T*T*C*C*T*G*A*C*G*T*T;

(SEQ ID NO: 283)
T*G*A*C*G*T*T*C*C*T*G*A*C*G*T*T;

(SEQ ID NO: 284)
T-C-G-A-C-G-T-C-G-A-D-D-D-D-T-C-G-A-C-G-T-C-G-A-chol;

(SEQ ID NO: 285)
teg-iA-iG-iC-iT-iG-iC-iA-iG-iC-iT-D-D-D-D-T-C-G-A-C-G-A-chol;

(SEQ ID NO: 286)
T*C-G*C-G*A*C-G*T*T*C-G*G*G*C-G*C*C*G;

(SEQ ID NO: 287)
T*C-G*T*C-G*A*C-G*T*T*C-G*G*C*G*C-G*C*G*C*C*G;

(SEQ ID NO: 288)
T*C-G*G*A*C-G*T*T*C-G*G*C*G*C-G*C*G*C*C*G;
```

-continued

T*C-G*G*A*C-G*T*T*C-G*G*C*G*C*G*C*C*G;  (SEQ ID NO: 289)

T*C-G*C-G*A*C-G*T*T*C-G*G*C*G*C*G*C*C*G;  (SEQ ID NO: 290)

T*C-G*C-G*AC-G*T*T*C-G*C-G*C-G*C-G;  (SEQ ID NO: 225)

T*C-G*A*C-G*T*T*C-G*G*C*G-C-G*C*G*C*G;  (SEQ ID NO: 291)

T*C-G*A*C-G*T*T*C-G*G*C*G*C*G*C*C*G;  (SEQ ID NO: 292)

T*C-G*C-G*A*C-G*T*T*C-G*G*C*G*C*G*C*C*G;  (SEQ ID NO: 293)

T*C-G*C-G*A*C-G*T*T*C-G*G*C*G*C*C*G;  (SEQ ID NO: 294)

T*C-G*A*C-G*T*T*C-G*G*C*G*C*G*C*G;  (SEQ ID NO: 295)

T*C-G*T*C-G*A*C-G*T*T*C-G*G*C*G-G*G*C*C*G;  (SEQ ID NO: 296)

T*C-G*T*C-G*A*C-G*T*T*C-G*G*G*C-G*C*C*G;  (SEQ ID NO: 297)

T*C-G*A*C-G*A*C-G*T*T*C-G*G*C*G*C-G*C*G*C*C*G;  (SEQ ID NO: 298)

T*C-G*A*C-G*T*C-G*T*T*C-G*G*C*G*C*G*C-G*C*G*C*C*G;  (SEQ ID NO: 299)

T*C-G*T*C-G*A*C-G*A*T*C-G*G*C*G*C*G*G-C*G*C*C*G;  (SEQ ID NO: 109)

T*C-G*T*C-G*A*C-G*A*T*C-G*G*C*G*C*G*C-G*C*G*C*C*G;  (SEQ ID NO: 109)

T*C-G*T*C-G*A*C-G*T*T*C-G*C*C*G*C-G*C*G*G*C*G;  (SEQ ID NO: 300)

T*C-G*T*C-G*A*C-G*T*T*C-G*G*C*G*G*C-G*T*G*C*C*G;  (SEQ ID NO: 301)

T*C-G*T*C-G*A*C-G*T*T*C-G*A*C*T*C-G*A*G*T*C*G;  (SEQ ID NO: 302)

T*C-G*T*C-G*T*T*A*C-G*T*A*A*C-G*A*C*G*A-C-G*T*T;  (SEQ ID NO: 271)

T*C*G*T*C-G*T*T*A*C-G*T*A*A*C-G*A*C*G*A*C-G*T*T;  (SEQ ID NO: 271)

T*C*G*A*C*G*T*C*G*A*C*G*T*G*A*C*G*T*T;  (SEQ ID NO: 303)

T*C*G*T*C*G*A*C*G*T*T*C*G*G*C*G*C*G*C*C*G;  (SEQ ID NO: 304)

T*C*G*T*C*G*A*C*G*A*T*C*G*G*C*G*C*G*C*G*C*C*G;  (SEQ ID NO: 109)

A-C-G-A-C-G-T-C-G-T-D-D-D-D-A-C-G-A-C-G-T-C-G-T-D-D-D-D-irU;  (SEQ ID NO: 305)

T*C-G*T*C-G*A*C-G*A*T*C-G*G*G*C*G*C*C-G*T*G*C*C*G;  (SEQ ID NO: 306)

T*C-G*T*C-G*A*C-G*A*T*C-G*G*C*G*C*C-G*T*G*C*C*G;  (SEQ ID NO: 307)

T*C-G*T*C-G*A*C-G*A*C-G*G*C*G*C*C-G*T*G*C*C*G;  (SEQ ID NO: 308)

T*C*G*T*C*G*A*C*G*A*T*C*G*G*C*G*C*C*G*T*G*C*C*G;  (SEQ ID NO: 307)

-continued

```
                                                  (SEQ ID NO: 307)
T*C*G*T*C-G*A*C-G*A*T*C-G*G*C*G*C*C-G*T*G*C*C*G;

(SEQ ID NO: 307)
T*C*G*T*C-G*A*C*G*A*T*C-G*G*C*G*C*C-G*T*G*C*C*G;

(SEQ ID NO: 307)
T*C*G*T*C*G*A*C*G*A-T*C*G*G*C*G*C*C*G*T*G*C*C*G;

(SEQ ID NO: 109)
T*C*G*T*C-G*A*C-G*A*T*C-G*G*C*G*C-G*C*G*C*C*G;

(SEQ ID NO: 109)
T*C*G*T*C-G*A*C*G*A*T*C-G*G*C*G*C-G*C*G*C*C*G;

(SEQ ID NO: 109)
T*C*G*T*C*G*A*C*G*A-T*C*G*G*C*G*C*G*C*G*C*C*G;

(SEQ ID NO: 303)
T*C*G*A*C*G*T*C*G-A-C*G*T*G*A*C*G*T*T;

(SEQ ID NO: 303)
T*C*G*A*C-G*T*C*G*A*C-G*T*G*A*C*G*T*T;

(SEQ ID NO: 303)
T*C*G*A*C-G*T*C*G*A*C*G*TG*A*C*G*T*T;

(SEQ ID NO: 309)
T*C*G*T*C-G*A*C*G*A-C-G*T*G*T*C*G*A*T;

(SEQ ID NO: 303)
T*C*G*A*C*G-T*C*G*A*C*G-T*G*A*C*G*T*T;

(SEQ ID NO: 303)
T*C*G*A-C*G*T*C*G-A*C*G*T*G-A*C*G*T*T;

(SEQ ID NO: 307)
T*C*G*T*C*G*A-C*G*A*T*C*G*G*C*G-C*C*G*T*G*C*C*G;

(SEQ ID NO: 310)
T*C*G*T*C*G*A-C*G*A*C*G*G*C*G*C-C*G*T*G*C*C*G*T;

(SEQ ID NO: 310)
T*C*G*T*C*G*A-C-G*A*C*G*G*C*G*C*C-G*T*G*C*C*G*T;

(SEQ ID NO: 311)
T*C*G*T*C-G*A*C-G*A*T*C-G*G*C*G*G*C-G*T*G*C*C*G*T;

(SEQ ID NO: 312)
T*C-G*T*C-G*A*C-G*T*T*C-G*G*C*G*C*C-G*T*G*C*C*G*T;

(SEQ ID NO: 313)
T*C-G*T*C-G*A*C-G*T*C-G*G*C*G*C*C*-G*T*G*C*C*G*T;

(SEQ ID NO: 314)
T*C-G*T*C-G*A*C-G*C-G*G*C*G*C*C-G*T*G*C*C*G*T;

(SEQ ID NO: 314)
T*C*G*T*C*G*A-C*G*C*G*G*C*G-C*C*G*T*G*C*C*G*T;

(SEQ ID NO: 315)
T*C*G*T*C-G*A*C*G*A-A*G*T*C-G*A*C*G*A*T;

(SEQ ID NO: 316)
T*C*G*T*C-G*A*C*G*A*G-A*T*C*G*T*C-G*A*C*G*A*T;

(SEQ ID NO: 317)
T*C*G*T*C-G*T*A*C-G*G*C*G*C*C-G*T*G*C*C*G*T;

(SEQ ID NO: 307)
T*C*G*T*C*G*A*C-G*A*T*C*G*G*C-G*C*C*G*T*G*C*C*G;

(SEQ ID NO: 307)
T*C*G*T*C*G*A-C*G*A*T*C*G*G*C*G-C*C*G*T*G*C*C*G;

(SEQ ID NO: 307)
T*C*G*T*C*G*A-C*G*A*T*C*G-G*C*G*C-C*G*T*G*C*C*G;

(SEQ ID NO: 310)
T*C*G*T*C*G*A-C*G*A*C*G*G*C*G*C-C*G*T*G*C*C*G*T;
```

-continued

T*C*G*T*C-G*A*C-G*A*T*C-G*G*C*G*C-G*T*G*C*C*G*T; (SEQ ID NO: 318)

T*C*G*T*C*G-A-C*G*A*T*C*G*G*C*G-C*C*G*T*G*C*C*G*T; (SEQ ID NO: 318)

T*C*G*T*C*G*A-C*G*A*C*G*G*C*G*C-C*G*T*G*C*C*G*T; (SEQ ID NO: 310)

T*C-G*T*C-G*A*C-G*T*T*C-G*G*C*G*C-G*T*G*C*C*G*T; (SEQ ID NO: 312)

T*C-G*T*C-G*A*C-G*T*C-G*G*C*G*C-G*T*G*C*C*G*T; (SEQ ID NO: 313)

T*C*G*T*C-G*A*C*G*A-A*G*T*C-G*A*C*G*A*T; (SEQ ID NO: 315)

T*C*G*T*C-G*A*C*G*A*G-A-A*T*C*G*T*C-G*A*C*G*A*T; (SEQ ID NO: 316)

T*C*G*T*C-G*A*C*G*A*C.G*T*G*T*C*G*A*T; (SEQ ID NO: 319)

T*C*G*A*C-G*T*C*G*A-A*G*A*C-G*T*C*G*A*T; (SEQ ID NO: 320)

T*C*G*A*C-G*T*C*G*A*G-A-A*T*C*G*A*C-G*T*C*G*A*T; (SEQ ID NO: 321)

T*C*G*T*C-G*A*C-G*A*C*G*G*C*G-A*A*G*C*C*G; (SEQ ID NO: 322)

T*C*G*T*C-G*A*C-G*A*C*G*G*C*G-A*A*G*C*C*G*T; (SEQ ID NO: 323)

T*C*G*T*C*G-A*C*G*A*C-G-T*G*T*C*G*A*T; (SEQ ID NO: 309)

T*C*G*T*C*G*A*C*G*A*C*G*T*G*T*C*G*A*T; (SEQ ID NO: 309)

T*C*G*A*C-G*T*C*G*A*C-G*T*G*A*C*G-T*T*G*T; (SEQ ID NO: 324)

T*C<G*T*C-G*A*C-G*A*T*C-G*G*C*G*C-G*C*G*C*C*G-but; (SEQ ID NO: 325)

T*C-G*T*C<G*A*C-G*A*T*C-G*G*C*G*C-G*C*G*C*C*G-but; (SEQ ID NO: 325)

T*C-G*T*C-G*A*C*G*A*T*C-G*G*C*G*C-G*C*G*C*C*C*G-iT; (SEQ ID NO: 327)

iT-T*C-G*T*C-G*A*C*G*A*T*C-G*G*C*G*C-G*C*G*C*C*C*G-iT; (SEQ ID NO: 328)

T*C-G*T*C-G*A*C-G*A*T*C-G*A*C*G*C-G*C*G*T*C*G; (SEQ ID NO: 329)

T*C-G*T*C-G*A*C-G*A*T*C-A*A*C*G*C-G*C*G*T*T*G; (SEQ ID NO: 330)

T*C-G*T*C-G*A*C-G*A*T*C-G*G*C*A-C-G*T*G*C*C*G; (SEQ ID NO: 331)

T*C-G*T*C-G*A*C-G*A*T*C-G*G*C*A*T-A*T*G*C*C*G; (SEQ ID NO: 332)

T*C-G*T*C-G*A*C-G*A*T-G-C*C*G*C*G-C*G*C*G*G*C; (SEQ ID NO: 333)

T*C*G*T*C*G*A*C*G*A*T*G*C*C*G*C*G*C*G*C*G*G*C; (SEQ ID NO: 333)

T*C-G*T*C*G*A*C*G*A*T*G*C*C*G*C*G*C*G*C*G*G*C; (SEQ ID NO: 333)

T*C*G*T*C-G*A*C*G*A*T*G*C*C*G*C*G*C*G*C*G*G*C; (SEQ ID NO: 333)

-continued

T*C-G*T*C*G*A*C*G*A*T*G*C*C*G*C*G*C*T*G*C*G*G*C; (SEQ ID NO: 334)

T*C-G*T*C*G*T*A*C*G*A*T*G*C*C*G*C*G*C*G*C*G*G*C; (SEQ ID NO: 335)

T*C-G*T*C*G*T*A*C*G*A*T*G*C*C*G*C*G*C*T*G*C*G*G*C; (SEQ ID NO: 336)

T*C*G*T*C*G*A*C*G*A*T-G*C*C*G*C*G*C*G*C*G*G*C; (SEQ ID NO: 333)

T*C*G*T*C*G*A*C*G*A*T-G-C*C*G*C*G*C*G*C*G*G*C; (SEQ ID NO: 333)

T*C*G*T*C-G*A*C*G*A*T*C*G*G*C*G*C*G*C*G*C*C*G-iT; (SEQ ID NO: 337)

T*C-G*T*C*G*A*C*G*A*T*C*G*G*C*G*C*G*C*G*C*C*G-iT; (SEQ ID NO: 337)

T*C*G*T*C*G*A*C*G*A*T-C*G*G*C*G*C*G*C*G*C*C*G-iT; (SEQ ID NO: 337)

T*C-G*T*G-C*A*C-G*A*T-C-G*G*C*G*C-G*C*G*C*C*G; (SEQ ID NO: 338)

T*Z-G*T*C-G*A*C-G*A*T-C-G*G*C*G*C-G*C*G*C*C*G; (SEQ ID NO: 339)

T*C-G*T*Z-G*A*C-G*A*T-C-G*G*C*G*C-G*C*G*C*C*G; (SEQ ID NO: 340)

T*C-G*T*C-G*A*Z-G*A*T-C-G*G*C*G*C-G*C*G*C*C*G; (SEQ ID NO: 341)

T*C-G*T*C-G*A*C-G*A*T*Z-G*G*C*G*C-G*C*G*C*C*G; (SEQ ID NO: 342)

T*C-G*A*C*G*T-C-G*A*C*G*T-C-G*A*C*G; (SEQ ID NO: 343)

T-C-G-A-C-G-T-C-G-A-C-G-T-C-G-A-C-G; (SEQ ID NO: 343)

T*C*G*A*C*G*T*C*G*A*C*G*T*C*G*A*C*G; (SEQ ID NO: 343)

T*C-G*T*C*G*A*C*G*T*T*C*G*G*C*G*C*C*G*T*G*C*C*G-iT; (SEQ ID NO: 344)

T*C*G*T*C-G*A*C*G*T*T*C*G*G*C*G*C*C*G*T*G*C*C*G-iT; (SEQ ID NO: 344)

T*C*G*T*C*G*A*C*G*T*T-C-G*G*C*G*C*C*G*T*G*C*C*G-iT; (SEQ ID NO: 344)

G*C*C*G*C*G-C*G*C*G-G-C*iT*iA*iG-iC*iA*iG-iC*iT*iG-iC*iT; (SEQ ID NO: 345)

C*G*G*C*G*C-G*C*G*C*C-G*iT*iA*iG-iC*iA*iG-iC*iT*iG-iC*iT; (SEQ ID NO: 346)

G*C*C*G*C*G*C*G*C*G*G*C*iT*iA*iG*iC*iA*iG-iC*iT*iG*iC*iT; (SEQ ID NO: 345)

C*G*G*C*G*C*G*C*G*C*C*G*iT*iA*iG*iC*iA*iG-iC*iT*iG*iC*iT; (SEQ ID NO: 346)

C*G*G*C*G*C-G*T*G*C*C*G*iT*iT*iG*iC*iA*iG-iC*iT*iG*iC*iT; (SEQ ID NO: 347)

G*C*C*G*T*G-C*C*G*C*G-C*iT*iT*iG*iC*iA*iG-iC*iT*iG*iC*iT; (SEQ ID NO: 348)

C*G*G*C*G*C*C*G*T*G*C*C*G*iT*iT*iG*iC*iA*iG-iC*iT*iG*iC*iT; (SEQ ID NO: 347)

G*C*C*G*T*G*C*C*G*C*G*G*C*iT*iT*iG*iC*iA*iG-iC*iT*iG*iC*iT; (SEQ ID NO: 348)

-continued (SEQ ID NO: 349)
T*C*G*G*C*G*C-G*C*G*C*C-G*A*iT*iA*iG-iC*iA*iG-iC*iT*iG-iC*iT;

(SEQ ID NO: 349)
T*C*G*G*C*G*C*G*C*C*G*A*iT*iA*iG*iC*iA*iG-iC*iT*iG*iC*iT;

(SEQ ID NO: 350)
T*C*G*G*C*G*C-G*T*G*C*C*G*iT*iT*iG*iC*iA*iG-iC*iT*iG*iC*iT;

(SEQ ID NO: 350)
T*C*G*G*C*G*C*C*G*T*G*C*C*G*iT*iT*iG*iC*iA*iG-iC*iT*iG*iC*iT;

(SEQ ID NO: 351)
CGGCGCXGCGCCG;

(SEQ ID NO: 287)
T-C_G*T*C_G*A*C_G*T*T*C_G*G*C*G*C_G*C*G*C*C*G;

(SEQ ID NO: 352)
T*C*G*T*C*G*A*C*G*A*C*G*G*C*G*C*G*C*G*C*C*G;

(SEQ ID NO: 353)
T*C*G*T*C*G*A*C*G*A*J*C*G*G*C*G*C*G*C*G*C*C*G;

(SEQ ID NO: 354)
T*C*G*T*C*G*A*C*G*A*L*C*G*G*C*G*C*G*C*G*C*C*G;

(SEQ ID NO: 355)
T*C*G*T*C*G*A*C*G*A*D*C*G*G*C*G*C*G*C*G*C*C*G;

(SEQ ID NO: 79)
G*G*G-A-C-G-A-C-G-T-C-G-T-G-G*G*G*G*G;

(SEQ ID NO: 356)
T*C-G-A-C-G-T-C-G-T-G-G*G*G*G;

(SEQ ID NO: 357)
T*C*C*A*G*G*A*C*T*T*C*T*C*T*C*A;

(SEQ ID NO: 83)
T*C*G*T*C*G*T*T*T*C*G*G*C*G*C*G*C*G*C*C*G;

(SEQ ID NO: 358)
T*C*G*T*C-mG*mA*C*mG*mA*T*C*mG*mG*C*mG*C*mG*C*mG*C*C*mG;

(SEQ ID NO: 359)
T*C*mG*T*C*mG*mA*C*mG*mA*T*C*mG*mG*C*mG*C*mG*C*mG*C*C*mG;

(SEQ ID NO: 358)
T*C*G*T*C-mG*mA*C-mG*mA*T*C-mG*mG*C*mG*C-mG*C*mG*C*C*mG;
and (SEQ ID NO: 359)
T*C-mG*T*C-mG*mA*C-mG*mA*T*C-mG*mG*C*mG*C-mG*C*mG*C*C*mG, wherein: - represents phosphodiester linkage; * represents stabilized internucleotide linkage; biot represents Biotin; but represents butyrate; chol represents Cholesterol; Cy3 represents Bis-hydroxypropyl-3,3,3',3'-tetramethyl-4,5-benzindocarbocyanine chloride (Glen Research); D represents D spacer (1'2'-dideoxyribose, Glen Research, Sterling, Va.); dig represents Digoxygenin; doub- represents doubler; iN represents Inverse nucleotide (inverse orientation: 3' and 5' switched); J represents 1,3-propane-diol; L represents hexaethylene glycol; mN represents 2'-O-methyl nucleoside; rN represents ribonucleoside; teg represents Triethylene glycol; vitE represents Vitamin E; and Z represents 5-methyldeoxycytidine.

Another recently-discovered class of CpG ODN is the E-class, in which halogen-modified nucleotides are placed immediately 5' to the CpG motif as described in U.S. Pat. No. 8,580,268 and U.S. Published Application 2014/0163213, the entire contents of both of which are incorporated herein by reference. These ODN also induce much higher levels of type I IFN relative to the modest IL-10 production.

Examples of E-class ODN include:

(SEQ ID NO: 360)
T*G*FF*C-G*T*T*T*T*T*T*T*T*T*T*T*T*T*T*T;

(SEQ ID NO: 361)
T*G*T*C-G*FF*T*T*T*T*T*T*T*T*T*T*T*T*T*T;

(SEQ ID NO: 362)
T*G*FF*C-G*FF*T*T*T*T*T*T*T*T*T*T*T*T*T*T;

(SEQ ID NO: 363)
T*G*T*FF-G*T*T*T*T*T*T*T*T*T*T*T*T*T*T*T;

(SEQ ID NO: 364)
T*G*T*C-FF*T*T*T*T*T*T*T*T*T*T*T*T*T*T*T;

(SEQ ID NO: 365)
T*FF*C-G*T*T*T*T*T*T*T*T*T*T*T*T*T*T*T;

(SEQ ID NO: 366)
T*G*T*C-G*T*FF*T*T*T*T*T*T*T*T*T*T*T*T*T;

-continued (SEQ ID NO: 367)
T*G*BU*C-G*T*T*T*T*T*T*T*T*T*T*T*T*T*T*T;

(SEQ ID NO: 368)
T*G*T*C-G*BU*T*T*T*T*T*T*T*T*T*T*T*T*T*T;

(SEQ ID NO: 369)
T*G*BU*C-G*BU*T*T*T*T*T*T*T*T*T*T*T*T*T*T;

(SEQ ID NO: 370)
T*G*JU*C-G*T*T*T*T*T*T*T*T*T*T*T*T*T*T*T;

(SEQ ID NO: 371)
T*G*T*C-G*JU*T*T*T*T*T*T*T*T*T*T*T*T*T*T;

(SEQ ID NO: 372)
T*G*JU*C-G*JU*T*T*T*T*T*T*T*T*T*T*T*T*T*T;

(SEQ ID NO: 373)
T*G*U*C-G*T*T*T*T*T*T*T*T*T*T*T*T*T*T*T;

(SEQ ID NO: 374)
T*G*T*C-G*U*T*T*T*T*T*T*T*T*T*T*T*T*T*T;

(SEQ ID NO: 375)
T*G*U*C-G*U*T*T*T*T*T*T*T*T*T*T*T*T*T*T;

(SEQ ID NO: 376)
JU*C*G*T*C*G*T*T*T*T*T*C*G*G*T*C*G*T*T*T*T;

(SEQ ID NO: 377)
T*C*G*JU*C*G*T*T*T*T*T*C*G*G*T*C*G*T*T*T*T;

(SEQ ID NO: 378)
T*C*G*T*C*G*T*T*T*T*T*C*G*G*JU*C*G*T*T*T*T;

(SEQ ID NO: 379)
JU*C*G*JU*C*G*T*T*T*T*T*C*G*G*T*C*G*T*T*T*T;

(SEQ ID NO: 380)
T*C*G*JU*C*G*JU*T*T*T*T*C*G*G*T*C*G*T*T*T*T;

(SEQ ID NO: 381)
T*C*G*T*C*G*T*T*T*T*T*C*G*G*JU*C*G*JU*T*T*T;

(SEQ ID NO: 382)
JU*C-G*T*C*G*T*T*T*T*A*C*G*G*C*G*C*C*G*T*G*C*C*G;

(SEQ ID NO: 383)
T*C*G*JU*C-G*T*T*T*T*A*C*G*G*C*G*C*C*G*T*G*C*C*G;

(SEQ ID NO: 384)
T*G*T*C-G*EU*T*T*T*T*T*T*T*T*T*T*T*T*T*T;

(SEQ ID NO: 385)
T*G*EU*C-G*EU*T*T*T*T*T*T*T*T*T*T*T*T*T*T;

(SEQ ID NO: 386)
JU*C-G*T*C*G*A*C*G*A*T*C*G*G*C*G*C*G*C*G*C*C*G;

(SEQ ID NO: 387)
T*C*G*JU*C-G*A*C*G*A*T*C*G*G*C*G*C*G*C*G*C*C*G;

(SEQ ID NO: 388)
JU*C-G*JU*C*G*A*C*G*A*T*C*G*G*C*G*C*G*C*G*C*C*G;

(SEQ ID NO: 389)
JU*C-G-A-C-G-T-C-G-T-G-G*G*G;

(SEQ ID NO: 390)
T*C-G-A-C-G-JU-C-G-T-G-G*G*G;

(SEQ ID NO: 391)
T*C-G-A-C-G-JU-C-G-JU-G-G*G*G;

G*JU*C-G*T*T;

G*JU*C-G*JU*T;

(SEQ ID NO: 392)
T*G*CU*C-G*T*T*T*T*T*T*T*T*T*T*T*T*T*T*T;

(SEQ ID NO: 393)
T*G*EU*C-G*T*T*T*T*T*T*T*T*T*T*T*T*T*T*T;

(SEQ ID NO: 394)
JU*C-G*JU*C*G*T*T*T*T*A*C*G*G*C*G*C*C*G*T*G*C*C*G;

(SEQ ID NO: 395)
T*C-G*JU*C*G*JU*T*T*T*A*C*G*G*C*G*C*C*G*T*G*C*C*G;

(SEQ ID NO: 396)
T*C*T*T*T*T*T*T*G*JU*C-G*T*T*T*T*T*T*T*T*T;

(SEQ ID NO: 397)
T*C*T*T*T*T*T*T*G*JU*C-G*JU*T*T*T*T*T*T*T*T;

(SEQ ID NO: 398)
JU*C*T*T*T*T*T*T*G*T*C-G*T*T*T*T*T*T*T*T*T;

(SEQ ID NO: 398)
JU*C-T*T*T*T*T*T*G*T*C-G*T*T*T*T*T*T*T*T*T;

(SEQ ID NO: 399)
T*C*T*T*T*T*T*T*G*U*C-G*T*T*T*T*T*T*T*T*T;

(SEQ ID NO: 400)
JU*C-G*A*C*G*T*C*G*A*T*C*G*G*C*G*C*G*C*G*C*C*G;

(SEQ ID NO: 400)
JU*C*G*A*C*G*T*C*G*A*T*C*G*G*C*G*C*G*C*G*C*C*G;

(SEQ ID NO: 401)
JU*C-G*A*C*G*T*C*G*A*T*C*G*G*C*G*C*G*C*G*C*C*G*T;

(SEQ ID NO: 401)
JU*C*G*A*C*G*T*C*G*A*T*C*G*G*C*G*C*G*C*G*C*C*G*T;

(SEQ ID NO: 402)
EU*C-G*A*C*G*T*C*G*A*T*C*G*G*C*G*C*G*C*G*C*C*G;

(SEQ ID NO: 402)
EU*C*G*A*C*G*T*C*G*A*T*C*G*G*C*G*C*G*C*G*C*C*;

(SEQ ID NO: 403)
JU*C-G*T*C*G*A*C*G*A*T*C*G*G*C*G*C*G*C*G*C*C*G*T;

(SEQ ID NO: 403)
JU*C*G*T*C*G*A*C*G*A*T*C*G*G*C*G*C*G*C*G*C*C*G*T;

(SEQ ID NO:404)
EU*C-G*T*C*G*A*C*G*A*T*C*G*G*C*G*C*G*C*G*C*C*G;

(SEQ ID NO: 405)
JU*C-G*T*C*G*A*C*G*A*T*C*G*G*C*G*C*G*C*G*C*C*G;

(SEQ ID NO: 406)
T*G*T*C-G*FU*T*T*T*T*T*T*T*T*T*T*T*T*T*T;

(SEQ ID NO: 407)
T*G*FU*C-G*FU*T*T*T*T*T*T*T*T*T*T*T*T*T*T;

(SEQ ID NO: 408)
T*G*U*C-G*UT*T*T*T*T*T*T*T*T*T*T*T*T*T*T;

(SEQ ID NO: 409)
T*G*T*C-6NB*T*T*T*T*T*T*T*T*T*T*T*T*T*T*T;

(SEQ ID NO: 410)
T*G*T*6NB-G*T*T*T*T*T*T*T*T*T*T*T*T*T*T*T;

(SEQ ID NO: 410)
T*G*T*6NB-G*T*T*T*T*T*T*T*T*T*T*T*T*T*T*T;

(SEQ ID NO: 411)
JU*G*T*C-G*T*T*T*T*T*T*T*T*T*T*T*T*T*T*T;

(SEQ ID NO: 412)
JU*G*JU*C-G*T*T*T*T*T*T*T*T*T*T*T*T*T*T*T;

(SEQ ID NO: 413)
T*G*T*C-G*T*JU*T*T*T*T*T*T*T*T*T*T*T*T*T;

-continued (SEQ ID NO: 414)
T*G*FT*C-G*T*T*T*T*T*T*T*T*T*T*T*T*T*T;

(SEQ ID NO: 415)
T*G*T*C-G*FT*T*T*T*T*T*T*T*T*T*T*T*T*T;

(SEQ ID NO: 416)
T*G*FT*C-G*FT*T*T*T*T*T*T*T*T*T*T*T*T*T;

(SEQ ID NO: 392)
T*G*CU*C-G*T*T*T*T*T*T*T*T*T*T*T*T*T*T;

(SEQ ID NO: 417)
T*G*T*C-G*CU*T*T*T*T*T*T*T*T*T*T*T*T*T;

(SEQ ID NO: 418)
T*G*CU*C-G*CU*T*T*T*T*T*T*T*T*T*T*T*T*T;

(SEQ ID NO: 419)
T*JU*C-G*T*T*T*T*T*T*T*T*T*T*T*T*T*T*T;

T*G*JU*C-G*T*T*T*T;

(SEQ ID NO: 420)
T*G*JU*C-G*T*T*T*T*G*T*C-G*T*T;

(T*G*JU*C-G*T*L)2doub-3mG;

(JU*C*G*T*T*C*G*L)2doub-3mG;

(SEQ ID NO: 421)
T*T*JU*C-G*T*C-G*T*T*T*C-G*T*C-G*T*T;

(SEQ ID NO: 422)
BU*C-G-A-C-G-T-C-G-T-G-G-*G*G;

(SEQ ID NO: 423)
T*G*JU*G-C*T*T*T*T*T*T*T*T*T*T*T*T*T*T*T;

(T*G*JU*C-G*T*L)2doub-teg;

(JU*C*G*T*T*C*G*L)2doub-teg;

(SEQ ID NO: 424)
JU*C-G*T*C*G*T*T*T*T*C*G*G*C*G*C*G*C*C*G;

(SEQ ID NO: 425)
T*C*G*JU*C*G*T*T*T*T*C*G*G*C*G*C*G*C*C*G;

(SEQ ID NO: 426)
T*C*G*T*C*G*T*T*T*JU*C-G*G*C*G*C*G*C*C*G;

(SEQ ID NO: 427)
JU*C*G*T*C*G*T*T*T*T*C*G*G*JU*C*G*T*T*T;

(SEQ ID NO: 428)
T*C*G*JU*C*G*T*T*T*T*C*G*G*JU*C*G*T*T*T;

(SEQ ID NO: 429)
T*G*JU*C-G*T*T*T*T*T*T*T*T*G*JU*C-G*T*T;

(SEQ ID NO: 430)
T*G*JU*C*G*T*T*T*T*T*T*T*T*T*T*T*T*T*T;

(SEQ ID NO: 431)
JU*C-G-A-C-G-T-C-G-T-G-G*E*G;

(SEQ ID NO: 432)
T*mG*JU*C-G*T*T*T*T*T*T*T*T*T*T*T*T*T*T;

(SEQ ID NO: 433)
T*G*JU*C-mG*T*T*T*T*T*T*T*T*T*T*T*T*T*T;

(SEQ ID NO: 434)
T*mG*JU*C-mG*T*T*T*T*T*T*T*T*T*T*T*T*T*T;

(SEQ ID NO: 379)
JU*C-G*JU*C*G*T*T*T*T*T*C*G*G*T*C*G*T*T*T;

(SEQ ID NO: 379)
JU*C*G*JU*C-G*T*T*T*T*T*C*G*T*C*G*T*T*T;

(SEQ ID NO: 435)
T*G*PU*C-G*T*T*T*T*T*T*T*T*T*T*T*T*T*T;

(SEQ ID NO: 436)
T*G*T*C-G*PU*T*T*T*T*T*T*T*T*T*T*T*T*T*T;

(SEQ ID NO: 422)
BU*C-G-A-C-G-T-C-G-T-G-G-*G*G*G;

(SEQ ID NO: 437)
T*G*JU*C-G*T*T*T*T*C*G*G*C*G*C*G*C*G*C*C*G;

(SEQ ID NO: 438)
T*JU*C-G*T*T*T*T*C*G*G*C*G*C*G*C*G*C*C*G*T;

(SEQ ID NO: 439)
T*EU*C-G*T*T*T*T*T*T*T*T*T*T*T*T*T*T*T;

(SEQ ID NO: 440)
T*G*EU*G-C*T*T*T*T*T*T*T*T*T*T*T*T*T*T*T;

(SEQ ID NO: 376)
JU*C-G*T*C*G*T*T*T*T*T*C*G*G*T*C*G*T*T*T;

(SEQ ID NO: 441)
EU*C-G*T*C*G*T*T*T*T*T*C*G*G*T*C*G*T*T*T;

G*JU*C-G*T*T-hex;

G*JU*C-G*JU*T-hex;

G*EU*C-G*EU*T-hex;

(SEQ ID NO: 442)
EU*C-G*T*C*G*T*T*T*T*A*C*G*G*C*G*C*C*G*T*G*C*C*G;

(SEQ ID NO: 443)
T*C*G*EU*C-G*T*T*T*T*A*C*G*G*C*G*C*C*G*T*G*C*C*G;

(SEQ ID NO: 444)
EU*C-G*T*C*G*A*C*G*A*T*C*G*G*C*G*C*G*C*G*C*C*G;

(SEQ ID NO: 445)
JU*C*T*T*T*T*T*T*T*T*T*T*T*T*T*T*T*T*T;

(SEQ ID NO: 446)
JU*C*T*T*T*T*T*T*T*T*C*G*T*T*T*T*T*T*T*T;

(SEQ ID NO: 447)
T*C*T*T*T*T*T*T*T*JU*C*G*T*T*T*T*T*T*T*T;

(SEQ ID NO: 448)
JU*C*T*T*T*T*T*T*T*JU*C*G*T*T*T*T*T*T*T*T;

(SEQ ID NO: 449)
JU*C-G*T*C*G*T*T*T*C*G*T*C*G*T*T*T*G*T*C*G*T*T;

(SEQ ID NO: 450)
T*C*G*T*C*G*T*T*T*C*G*T*C*G*T*T*T*G*JU*C-G*T*T;

(SEQ ID NO: 451)
JU*C-G*T*C*G*T*T*T*C*G*T*C*G*T*T*T*G*JU*C-G*T*T;

(SEQ ID NO: 452)
T*G*JU*C-E*T*T*T*T*T*T*T*T*T*T*T*T*T*T*T;

(SEQ ID NO: 453)
T*G*JU*C-I*T*T*T*T*T*T*T*T*T*T*T*T*T*T*T;

(SEQ ID NO: 454)
T*G*JU*Z-G*T*T*T*T*T*T*T*T*T*T*T*T*T*T*T;

(SEQ ID NO: 455)
T*G*T*C-G*T*T*JU*T*T*T*T*T*T*T*T*T*T*T*T;

(SEQ ID NO: 456)
T*G*T*C-G*T*T*T*JU*T*T*T*T*T*T*T*T*T*T*T;

-continued (SEQ ID NO: 457)
JU*C-G*T*C*G*T*T*T*T*C*G*G*C*G*C*G*C*G*C*C*G*T;

(SEQ ID NO: 458)
EU*C-G*T*C*G*T*T*T*T*C*G*G*C*G*C*G*C*G*C*C*G*T;

(SEQ ID NO: 459)
T*C-G*EU*C*G*T*T*T*T*C*G*G*C*G*C*G*C*G*C*C*G*T;

(SEQ ID NO: 460)
T*C-G*T*C*G*T*T*T*JU*C*G*G*C*G*C*G*C*G*C*C*G*T;

(SEQ ID NO: 461)
T*C-G*T*C*G*T*T*T*EU*C*G*G*C*G*C*G*C*G*C*C*G*T;

(SEQ ID NO: 462)
EU*C-G*T*C*G*T*T*T*EU*C*G*G*C*G*C*G*C*G*C*C*G*T;

(SEQ ID NO: 463)
EU*C-G*EU*C*G*T*T*T*T*C*G*G*C*G*C*G*C*G*C*C*G*T;

(SEQ ID NO: 464)
JU*C-G*EU*C*G*T*T*T*T*C*G*G*C*G*C*G*C*G*C*C*G*T;

(SEQ ID NO: 465)
JU*C-G*T*C*G*T*T*T*T*G*T*C*G*T*T*T*T*G*T*C*G*T*T;

(SEQ ID NO: 466)
EU*C-G*T*C*G*T*T*T*T*G*T*C*G*T*T*T*T*C*G*T*T;

(SEQ ID NO: 467)
T*G*BVU*C-G*T*T*T*T*T*T*T*T*T*T*T*T*T*T*T;

(SEQ ID NO: 468)
T*G*T*C-G*BVU*T*T*T*T*T*T*T*T*T*T*T*T*T*T;

(SEQ ID NO: 469)
JU*C*G*G*C*G*G*C*C*G*C*C*G;

(SEQ ID NO: 470)
JU*C*G*T*C*G*T*T*T*T*A*C*G*G*C*G*C*C*G*T*G*C*C*3mG;

(SEQ ID NO: 471)
EU*C*G*T*C*G*T*T*T*T*A*C*G*G*C*G*C*C*G*T*G*C*C*3mG;

(SEQ ID NO: 472)
EU*C*G*EU*C*G*T*T*T*T*A*C*G*G*C*G*C*C*G*T*G*C*C*3mG;

(SEQ ID NO: 472)
EU*C-G*EU*C*G*T*T*T*T*A*C*G*G*C*G*C*C*G*T*G*C*C*3mG;

(SEQ ID NO: 473)
EU*C*G*T*C*G*T*T*T*T*A*C*G*G*C*G*C*C*G*T*G*C*C*G*iT;

(SEQ ID NO: 474)
JU*C*G*T*C*G*T*T*T*T*C*G*G*C*G*C*G*C*G*C*C*3mG;

(SEQ ID NO: 475)
EU*C*G*T*C*G*T*T*T*T*C*G*G*C*G*C*G*C*G*C*C*3mG;

(SEQ ID NO: 475)
EU*C-G*T*C*G*T*T*T*T*C*G*G*C*G*C*G*C*G*C*C*3mG;

(SEQ ID NO: 476)
EU*C*G*EU*C*G*T*T*T*T*C*G*G*C*G*C*G*C*G*C*C*3mG;

(SEQ ID NO: 476)
EU*C-G*EU*C*G*T*T*T*T*C*G*G*C*G*C*G*C*G*C*C*3mG;

(SEQ ID NO: 477)
EU*C*G*T*C*G*T*T*T*T*EU*C*G*G*C*G*C*G*C*G*C*C*3mG;

(SEQ ID NO: 478)
JU*C*G*T*C*G*T*T*T*T*JU*C*G*G*C*G*C*G*C*G*C*C*3mG;

(SEQ ID NO: 479)
EU*C*G*T*C*G*T*T*T*T*C*G*G*C*G*C*G*C*G*C*C*G*iT;

(SEQ ID NO: 480)
JU*C*G*T*C*G*T*T*T*T*C*G*G*C*G*C*G*C*G*C*C*G*iT;

(SEQ ID NO: 481)
EU*C*G*T*C*G*A*C*G*T*T*C*G*G*C*G*C*C*G*T*G*C*C*3mG;

(SEQ ID NO: 482)
JU*C*G*T*C*G*A*C*G*T*T*C*G*G*C*G*C*C*G*T*G*C*C*3mG;

(SEQ ID NO: 483)
JU*C*G*T*C*G*A*C*G*A*T*C*G*G*C*G*C*G*C*G*C*C*3mG;

(SEQ ID NO:484)
EU*C*G*T*C*G*A*C*G*A*T*C*G*G*C*G*C*G*C*G*C*C*3mG;

(SEQ ID NO: 485)
EU*C*G*T*C*G*A*C*G*T*T*C*G*G*C*G*C*C*G*T*G*C*C*G*iT;

(SEQ ID NO: 486)
EU*C*G*T*C*G*A*C*G*A*T*C*G*G*C*G*C*G*C*G*C*C*G*iT;

(SEQ ID NO: 487)
T*G*NI*C-G*T*T*T*T*T*T*T*T*T*T*T*T*T*T*T;

(SEQ ID NO: 488)
T*G*NP*C-G*T*T*T*T*T*T*T*T*T*T*T*T*T*T*T;

(SEQ ID NO: 489)
T*G*6NB*C-G*T*T*T*T*T*T*T*T*T*T*T*T*T*T*T;

(SEQ ID NO: 441)
EU*C*G*T*C*G*T*T*T*T*T*C*G*G*T*C*G*T*T*T*T;

(SEQ ID NO: 490)
JU*C*G*T*C*G*A*C*G*A*T*G*G*C*G*G*C*G*C*C*G*C*C;

(SEQ ID NO: 491)
EU*C*G*T*C*G*A*C*G*A*T*G*G*C*G*G*C*G*C*C*G*C*C;

(SEQ ID NO: 492)
T*T*C-G*T*T*T*T*C*G*G*C*G*C*G*C*G*C*C*G*T;

(SEQ ID NO: 493)
T*EU*C-G*T*T*T*T*C*G*G*C*G*C*G*C*G*C*C*G*T;

(SEQ ID NO: 494)
JU*C-G*T*T*T*T*C*G*G*C*G*C*G*C*G*C*C*G*T;

(SEQ ID NO: 495)
JU*JU*C-G*T*T*T*T*C*G*G*C*G*C*G*C*G*C*C*G*T;

(SEQ ID NO: 438)
T*JU*C*G*T*T*T*T*C*G*G*C*G*C*G*C*G*C*C*G*T;

(SEQ ID NO: 496)
EU*C*G*T*C*G*T*T*T*T*A*C*G*G*C*G*C*C*G*T*G*C*C*G*T;

(SEQ ID NO: 497)
T*EU*C*G*T*T*T*T*A*C*G*G*C*G*C*C*G*T*G*C*C*G*T;

(SEQ ID NO: 498)
T*JU*C*G*T*T*T*T*A*C*G*G*C*G*C*C*G*T*G*C*C*G*T;

(SEQ ID NO: 499)
JU*C*G*T*C*G*T*T*T*T*rG*rU*rU*rG*rU*rG*rU;

(SEQ ID NO: 500)
EU*C-G*T*C*G*A*C*G*A*T*C*G*G*C*G*C*G*C*G*C*C*G*T;

(SEQ ID NO: 500)
EU*C*G*T*C*G*A*C*G*A*T*C*G*G*C*G*C*G*C*G*C*C*G*T;

(SEQ ID NO: 402)
EU-C-G*A*C*G*T*C*G*A*T*C*G*G*C*G*C*G*C*G*C*C*G;

(SEQ ID NO: 402)
EU-C*G*A*C*G*T*C*G*A*T*C*G*G*C*G*C*G*C*G*C*C*G;

```
                                                  (SEQ ID NO: 373)
T*G*U*C*G*T*T*T*T*T*T*T*T*T*T*T*T*T*T
(SEQ ID NO:); and (SEQ ID NO: 374)
T*G*T*C-G*U*T*T*T*T*T*T*T*T*T*T*T*T*T,
``` wherein: - represents phosphodiester internucleotide linkage; * represents phosphorothioate internucleotide linkage; 2doub represents Doubler2 (Chemgenes); 3mG represents 3'-O-Methyl-rG; 6NB represents 6-nitro-benzimidazol; BU represents 5-bromo-2'-deoxyuridine; BVU represents 5-(d-bromo-vinyl)-uridine; CU represents 5-chloro-2'-deoxyuridine; E represents 7-deaza-dG; EU represents 5-ethyl-2'-deoxyuridine; F represents 5-fluoro-dU; FF represents 2,4-difluorotoluene; FT represents a,a,a-trifluoro-dT; FU represents 5-fluoro-dU; hex represents hexadecylglyceryl; I represents inosine; iT represents inverse nucleotide (3' and 5' switched); JU represents 5-iodo-2'-deoxyuridine; L represents Spacer 18 (hexaethylenglycol phosphate); NI represents nitroindol; NP represents nitropyrrol; PU represents 5-proynyl-dU; teg represents Spacer 9 (triethylenglycol phosphate); U represents Uridine; and Z represents 5-methyl-dC.

Methods to reduce the amount of B cell activation with CpG ODN and increase or maintain the amount of IFN-α induction are not well known to those skilled in the art, but without committing to a particular mechanism of action underlying the invention, it has now been discovered in accordance with the invention that B cell proliferation and IL-10 secretion appear to require a more sustained TLR9 signal compared to that required to induce plasmacytoid dendritic cells (pDC) to secrete IFN-α. Such a sustained TLR9 signal is provided by the B-class CpG ODN to a greater degree than the other CpG ODN classes mentioned above. In addition, the duration of the TLR9 signal can be shortened by positioning phosphodiester (PO) linkages at the CpG ("semi-soft" designs) and or at other positions within the ODN. The "softest" CpG ODN with the least sustained B cell activation are those with completely phosphodiester backbones, but these are so rapidly degraded in vivo that the IFN-α response is also compromised, unless the ODN is circular (to protect against exonucleases), or is delivered in a formulation such as virus-like particles (VLP), nanoparticles (NP), immune stimulating complexes (ISCOMs), or the like, which also protects against nucleases.

The immunostimulatory oligonucleotide molecules may have a homogeneous backbone (e.g., entirely phosphodiester (PO) or entirely phosphorothioate (PS)) or a chimeric backbone. An exception to this is the A-class CpG design (and A/E-class) in which the central portion of the ODN including at least 8 nucleotides and preferably 10 or more nucleotides must be phosphodiester for optimal activity. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. The stabilized linkage(s) is/are preferentially placed at the 5' and 3' ends of the oligonucleotide in order to protect the ends from exonucleases: the phosphorothioate linkages are placed in the middle and contribute to inducing a stronger IFN-α response than can easily be achieved with PS alone.

Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could, in one embodiment, include at least one phosphodiester (phosphodiester or phosphodiester-like) linkage and at least one boranophosphonate (stabilized) linkage. In another embodiment, a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate and methylphosphorothioate. Other stabilized internucleotide linkages include, without limitation, peptide, alkyl, dephospho type linkages, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165. Methods for preparing chimeric oligonucleotides are also known. For instance patents issued to Uhlmann et al. have described such techniques, including, for example, U.S. Pat. Nos. 7,566,703, 7,795,235, 8,283,328, and 8,304,396.

Mixed backbone modified ODN may be synthesized using a commercially available DNA synthesizer and standard phosphoramidite chemistry. F. E. Eckstein, "Oligonucleotides and Analogues—A Practical Approach", IRL Press, Oxford, UK, 1991; and M. D. Matteucci and M. H. Caruthers, Tetrahedron Lett. 21, 719 (1980). After coupling, phosphorothioate (PS) linkages are introduced by sulfurization using the Beaucage reagent (R. P. Iyer, W. Egan, J. B. Regan and S. L. Beaucage, *J. Am. Chem. Soc.* 112, 1253 (1990)) (0.075 M in acetonitrile) or phenyl acetyl disulfide (PADS) followed by capping with acetic anhydride, 2,6-lutidine in tetrahydrofurane (1:1:8; v:v:v) and N-methylimidazole (16% in tetrahydrofurane). This capping step is performed after the sulfurization reaction to minimize formation of undesired phosphodiester (PO) linkages at positions where a phosphorothioate linkage should be located. In the case of the introduction of a phosphodiester linkage, e.g. at a CpG dinucleotide, the intermediate phosphorous-III is oxidized by treatment with a solution of iodine in water/pyridine. After cleavage from the solid support and final deprotection by treatment with concentrated ammonia (15 hrs at 50° C.), the ODN are analyzed by HPLC on a Gen-Pak Fax column (Millipore-Waters) using a NaCl-gradient (e.g. buffer A: 10 mM $NaH_2PO4$ in acetonitrile/water=1:4/v:v pH 6.8; buffer B: 10 mM $NaH_2PO_4$, 1.5 M NaCl in acetonitrile/water=1:4/v:v; 5 to 60% B in 30 minutes at 1 ml/min) or by capillary gel electrophoresis. The ODN can be purified by HPLC or by FPLC on a Source High Performance column (Amersham Pharmacia). HPLC-homogeneous fractions are combined and desalted via a C18 column or by ultrafiltration. The ODN was analyzed by MALDI-TOF mass spectrometry to confirm the calculated mass.

The oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

In some embodiments the oligonucleotides may be "soft" or "semi-soft" oligonucleotides. A soft oligonucleotide is an immunostimulatory oligonucleotide having a partially stabilized backbone, in which phosphodiester or phosphodiester-like internucleotide linkages occur only within and immediately adjacent to at least one internal pyrimidine-purine dinucleotide (YZ). Preferably YZ is YG, a pyrimidine-guanosine (YG) dinucleotide. The at least one internal YZ dinucleotide itself has a phosphodiester or phosphodiester-like internucleotide linkage. A phosphodiester or phosphodiester-like internucleotide linkage occurring immediately adjacent to the at least one internal YZ dinucleotide can be 5', 3', or both 5' and 3' to the at least one internal YZ dinucleotide.

In particular, phosphodiester or phosphodiester-like internucleotide linkages involve "internal dinucleotides". An internal dinucleotide in general shall mean any pair of adjacent nucleotides connected by an internucleotide linkage, in which neither nucleotide in the pair of nucleotides is a terminal nucleotide, i.e., neither nucleotide in the pair of nucleotides is a nucleotide defining the 5' or 3' end of the oligonucleotide. Thus a linear oligonucleotide that is n nucleotides long has a total of n-1 dinucleotides and only n-3 internal dinucleotides. Each internucleotide linkage in an internal dinucleotide is an internal internucleotide linkage. Thus a linear oligonucleotide that is n nucleotides long has a total of n-1 internucleotide linkages and only n-3 internal internucleotide linkages. The strategically placed phosphodiester or phosphodiester-like internucleotide linkages, therefore, refer to phosphodiester or phosphodiester-like internucleotide linkages positioned between any pair of nucleotides in the oligonucleotide sequence. In some embodiments the phosphodiester or phosphodiester-like internucleotide linkages are not positioned between either pair of nucleotides closest to the 5' or 3' end.

Preferably a phosphodiester or phosphodiester-like internucleotide linkage occurring immediately adjacent to the at least one internal YZ dinucleotide is itself an internal internucleotide linkage. Thus for a sequence $N_1$ YZ $N_2$, wherein $N_1$ and $N_2$ are each, independent of the other, any single nucleotide, the YZ dinucleotide has a phosphodiester or phosphodiester-like internucleotide linkage, and in addition (a) $N_1$ and Y are linked by a phosphodiester or phosphodiester-like internucleotide linkage when $N_1$ is an internal nucleotide, (b) Z and $N_2$ are linked by a phosphodiester or phosphodiester-like internucleotide linkage when $N_2$ is an internal nucleotide, or (c) $N_1$ and Y are linked by a phosphodiester or phosphodiester-like internucleotide linkage when $N_1$ is an internal nucleotide and Z and $N_2$ are linked by a phosphodiester or phosphodiester-like internucleotide linkage when $N_2$ is an internal nucleotide.

Soft oligonucleotides according to the instant invention are believed to be relatively susceptible to nuclease cleavage compared to completely stabilized oligonucleotides. Without intending to be bound to a particular theory or mechanism, it is believed that soft oligonucleotides of the invention are susceptible to cleavable resulting in fragments with reduced or no immunostimulatory activity relative to full-length soft oligonucleotides. Incorporation of at least one nuclease-sensitive internucleotide linkage, particularly near the middle of the oligonucleotide, is believed to provide an "off switch" which alters the pharmacokinetics and pharmacodynamics of the oligonucleotide so as to reduce the duration of maximal immunostimulatory activity of the oligonucleotide. In particular, the nuclease-sensitive linkage may reduce the magnitude of NF-κB induction while increasing the magnitude of the IRF3 and/or IRF7 induction. TLR9 activation can lead to strong activation of either or both of the NF-κB pathway (leading to expression of cytokines such as IL-6 and expression of costimulatory molecules) and the IRF3/7 pathways leading to IFN-α secretion. There generally seems to be some antagonism between these pathways. For example, B-class CpG ODN predominantly activate the former, whereas the A-class CpG ODN activate the latter. Strong NF-κB induction is associated with B-class CpG oligos and may lead to increased IL-10 secretion. While this may be useful for systemic CpG oligo therapy, it is not desirable for intratumoral therapy. The increased IRF3/7 induction provided by the nuclease-sensitive internucleotide linkage leads to great production of IFN-α in the tumor microenvironment, which improves the chances for a productive and therapeutic anti-tumor immune response following intratumoral therapy without increasing the production of undesirable IL-10. This reduced half-life of CpG oligos containing nuclease-sensitive linkages can be of particular value in tissues and in clinical applications in which it is desirable to avoid injury related to chronic local inflammation or immunostimulation, e.g., the kidney, since the oligos are less likely to accumulate in the tissue to high concentrations.

A semi-soft oligonucleotide is an immunostimulatory oligonucleotide having a partially stabilized backbone, in which phosphodiester or phosphodiester-like internucleotide linkages occur only within at least one internal pyrimidine-purine (YZ) dinucleotide. Semi-soft oligonucleotides generally possess increased immunostimulatory potency relative to corresponding fully stabilized immunostimulatory oligonucleotides. Due to the greater potency of semi-soft oligonucleotides, semi-soft oligonucleotides may be used, in some instances, at lower effective concentrations and have lower effective doses than conventional fully stabilized immunostimulatory oligonucleotides in order to achieve a desired biological effect.

It is believed that the foregoing properties of semi-soft oligonucleotides generally increase with increasing "dose" of phosphodiester or phosphodiester-like internucleotide linkages involving internal YZ dinucleotides. Thus it is believed, for example, that generally for a given oligonucleotide sequence with four internal YZ dinucleotides, an oligonucleotide with four internal phosphodiester or phosphodiester-like YZ internucleotide linkages is more immunostimulatory than an oligonucleotide with three internal phosphodiester or phosphodiester-like YZ internucleotide linkages, which in turn is more immunostimulatory than an oligonucleotide with two internal phosphodiester or phosphodiester-like YZ internucleotide linkages, which in turn is more immunostimulatory than an oligonucleotide with one internal phosphodiester or phosphodiester-like YZ internucleotide linkage. Importantly, inclusion of even one internal phosphodiester or phosphodiester-like YZ internucleotide linkage often can be advantageous over no internal phosphodiester or phosphodiester-like YZ internucleotide linkage. In addition to the number of phosphodiester or phosphodiester-like internucleotide linkages, the position along the length of the oligonucleotide can also affect potency.

The soft and semi-soft oligonucleotides will generally include, in addition to the phosphodiester or phosphodiester-like internucleotide linkages at preferred internal positions, 5' and 3' ends that are resistant to degradation. Such degradation-resistant ends can involve any suitable modification that results in an increased resistance against exonuclease digestion over corresponding unmodified ends. For instance, the 5' and 3' ends can be stabilized by the inclusion there of at least one phosphate modification of the backbone. In a preferred embodiment, the at least one phosphate modification of the backbone at each end is independently a phosphorothioate, phosphorodithioate, methylphosphonate, or methylphosphorothioate internucleotide linkage. In another embodiment, the degradation-resistant end includes one or more nucleotide units connected by peptide or amide linkages at the 3' end.

A phosphodiester internucleotide linkage is the type of linkage characteristic of oligonucleotides found in nature. The phosphodiester internucleotide linkage includes a phosphorus atom flanked by two bridging oxygen atoms and bound also by two additional oxygen atoms, one charged and the other uncharged. Phosphodiester internucleotide linkage is particularly preferred when it is important to reduce the tissue half-life of the oligonucleotide or to get the strongest possible induction of type I IFN secretion from pDC.

A phosphodiester-like internucleotide linkage is a phosphorus-containing bridging group that is chemically and/or diastereomerically similar to phosphodiester. Measures of similarity to phosphodiester include susceptibility to nuclease digestion and ability to activate RNase H. Thus, for example phosphodiester, but not phosphorothioate, oligonucleotides are susceptible to nuclease digestion, while both phosphodiester and phosphorothioate oligonucleotides activate RNAse H. In a preferred embodiment the phosphodiester-like internucleotide linkage is boranophosphate (or equivalently, boranophosphonate) linkage. U.S. Pat. Nos. 5,177,198; 5,859,231; 6,160,109; 6,207,819; Sergueev at al., (1998) *J Am Chem Soc* 120:9417-27. In another preferred embodiment the phosphodiester-like internucleotide linkage is diastereomerically pure Rp phosphorothioate. It is believed that diastereomerically pure Rp phosphorothioate is more susceptible to nuclease digestion and is better at activating RNAse H than mixed or diastereomerically pure Sp phosphorothioate. Stereoisomers of CpG oligonucleotides are the subject of published PCT application PCT/US99/17100 (WO 00/06588). It is to be noted that for purposes of the instant invention, the term "phosphodiester-like internucleotide linkage" specifically excludes phosphorodithioate and methylphosphonate internucleotide linkages.

As described above the soft and semi-soft oligonucleotides of the invention may have phosphodiester like linkages between C and G. One example of a phosphodiester-like linkage is a phosphorothioate linkage in an Rp conformation. Oligonucleotide p-chirality can have apparently opposite effects on the immune activity of a CpG oligonucleotide, depending upon the time point at which activity is measured. Krieg et al., *Oligonucleotides* 2003 13(6):491-499. At an early time point of 40 minutes, the Rp but not the Sp stereoisomer of phosphorothioate CpG oligonucleotide induces JNK phosphorylation in mouse spleen cells. In contrast, when assayed at a late time point of 44 hr, the Sp but not the Rp stereoisomer is active in stimulating spleen cell proliferation. This difference in the kinetics and bioactivity of the Rp and Sp stereoisomers does not result from any difference in cell uptake, but rather most likely is due to two opposing biologic roles of the p-chirality. First, the enhanced activity of the Rp stereoisomer compared to the Sp for stimulating immune cells at early time points indicates that the Rp may be more effective at interacting with the CpG receptor, TLR9, or inducing the downstream signaling pathways. On the other hand, the faster degradation of the Rp PS-oligonucleotides compared to the Sp results in a much shorter duration of signaling, so that the Sp PS-oligonucleotides appear to be more biologically active when tested at later time points probably because of the greater nuclease-resistance of the Sp linkage, which provided a more sustained signal through TLR9 for B cell proliferation.

Thus the oligonucleotides may be heterogeneous in backbone composition thereby containing any possible combination of polymer units linked together.

The term "oligonucleotide" also encompasses oligonucleotides with substitutions or modifications, such as in the sugars. For example, they include oligonucleotides having backbone sugars that are covalently attached to low molecular weight organic groups other than a hydroxyl group at the 2' position and other than a phosphate group or hydroxy group at the 5' position. Thus modified oligonucleotides may include a 2'-O-alkylated ribose group. In addition, modified oligonucleotides may include sugars such as arabinose or 2'-fluoroarabinose instead of ribose.

The immunostimulatory oligonucleotides of the instant invention can encompass various chemical modifications and substitutions, in comparison to natural RNA and DNA, involving a phosphodiester internucleotide bridge, or a 13-D-ribose unit. Examples of chemical modifications are known to the skilled person and are described, for example, in Uhlmann E et al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Annu Rev Pharmacol Toxicol* 36:107-129; and Hunziker J et al. (1995) Mod Synth Methods 7:331-417. An oligonucleotide according to the invention may have one or more modifications, wherein each modification is located at a particular phosphodiester internucleotide bridge and/or at a particular β-D-ribose unit in comparison to an oligonucleotide of the same sequence which is composed of natural DNA or RNA.

For example, the invention relates to an oligonucleotide which may comprise one or more modifications and wherein each modification is independently selected from: a) the replacement of a phosphodiester internucleotide bridge located at the 3' and/or the 5' end of a nucleotide by a modified internucleotide bridge; b) the replacement of phosphodiester bridge located at the 3' and/or the 5' end of a nucleotide by a dephospho bridge; c) the replacement of a sugar phosphate unit from the sugar phosphate backbone by another unit; and d) the replacement of a β-D-ribose unit by a modified sugar unit.

More detailed examples for the chemical modification of an oligonucleotide are as follows:

A phosphodiester internucleotide bridge located at the 3' and/or the 5' end of a nucleotide can be replaced by a modified internucleotide bridge, wherein the modified internucleotide bridge is for example selected from phosphorothioate, phosphorodithioate, $NR^1R^2$-phosphoramidate, boranophosphate, a-hydroxybenzyl phosphonate, phosphate-$(C_1-C_{21})$-O-alkyl ester, phosphate-$[C_6-C_{12})$aryl-$(C_1-C_{21})$-

O-alkyl]ester, $(C_1-C_8)$alkylphosphonate and/or $(C_6-C_{12})$ arylphosphonate bridges, $(C_7-C_{12})$-α-hydroxymethyl-aryl (e.g., disclosed in WO 95/01363), wherein $(C_6-C_{12})$aryl, $(C_6-C_{20})$aryl and $(C_6-C_{14})$aryl are optionally substituted by halogen, alkyl, alkoxy, nitro, cyano, and where $R^1$ and $R^2$ are, independently of each other, hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleotide by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester internucleotide bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Oligonucleotides Res* 17:6129-41), that is, e.g., the replacement by a morpholino-derivative unit; or to build up a polyamide oligonucleotide ("PNA"; as described for example, in Nielsen P E et al. (1994) *Bioconjug Chem* 5:3-7), that is, e.g., the replacement by a PNA backbone unit, e.g., by 2-aminoethylglycine.

A 3-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, ribose, preferably 2'-O—$(C_1-C_6)$alkyl-ribose is 2'-O-methylribose, 2'-O—$(C_2-C_6)$alkenyl-ribose, 2'-[O—$(C_1-C_6)$alkyl-O—$(C_1-C_6)$alkyl]-ribose, 2'-NH$_2$-2'-deoxyribose, β-D-xylo-furanose, α-arabinofuranose, 2,4-dideoxy-β-D-erythro-hexo-pyranose, and carbocyclic (described, for example, in Froehler J (1992) *J Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

In some embodiments the sugar is 2'-O-methylribose, particularly for one or both nucleotides linked by a phosphodiester or phosphodiester-like internucleotide linkage.

In particular sequences described herein a set of modified bases is defined. For instance the letter Y is used to refer to a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g., 3-nitropyrrole, P-base), an aromatic ring system (e.g., fluorobenzene or difluorobenzene) or a hydrogen atom (dSpacer).

The letter Z is used to refer to guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-(C2-C6)alkynylguanine), 7-deaza-8-substituted guanine, hypoxanthine, N2-substituted guanines (e.g., N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g., N6-methyl-adenine, 8-oxo-adenine) 8-substituted guanine (e.g., 8-hydroxyguanine and 8-bromoguanine), and 6-thioguanine. In another embodiment of the invention, the guanine base is substituted by a universal base (e.g., 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer).

The oligonucleotides may have one or more accessible 5' ends. It is possible to create modified oligonucleotides having two such 5' ends. This may be achieved, for instance by attaching two oligonucleotides through a 3'-3' linkage to generate an oligonucleotide having one or two accessible 5' ends. The 3'3'-linkage may be a phosphodiester, phosphorothioate or any other modified internucleotide bridge. Methods for accomplishing such linkages are known in the art. For instance, such linkages have been described in Seliger, H. et al., Oligonucleotide analogs with terminal 3'-3'- and 5'-5'-internucleotidic linkages as antisense inhibitors of viral gene expression, *Nucleosides & Nucleotides* (1991), 10(1-3), 469-77; and Jiang, et al., Pseudo-cyclic oligonucleotides: in vitro and in vivo properties, *Bioorganic & Medicinal Chemistry* (1999), 7(12), 2727-2735.

Additionally, 3'3'-linked oligonucleotides where the linkage between the 3'-terminal nucleotides is not a phosphodiester, phosphorothioate or other modified bridge, can be prepared using an additional spacer, such as tri- or tetra-ethyleneglycol phosphate moiety (Durand, M. et al, Triple-helix formation by an oligonucleotide containing one $(dA)_{12}$ and two $(dT)_{12}$ sequences bridged by two hexaethylene glycol chains, Biochemistry (1992), 31(38), 9197-204, U.S. Pat. Nos. 5,658,738, and 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 5'-attached to oligonucleotides; *Oligonucleotides Research* (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

The oligonucleotides may be partially resistant to degradation (e.g., are stabilized). A "stabilized oligonucleotide molecule" shall mean an oligonucleotide that is relatively resistant to in vivo degradation (e.g. via an exo- or endo-nuclease). Oligonucleotide stabilization can be accomplished via backbone modifications. Oligonucleotides having phosphorothioate linkages provide maximal protection for the oligonucleotide from degradation by intracellular exo- and endo-nucleases. Other modified oligonucleotides include phosphodiester modified oligonucleotides, combinations of phosphodiester and phosphorothioate oligonucleotide, methylphosphonate, methylphosphorothioate, phosphorodithioate, p-ethoxy, and combinations thereof. Oligonucleotides which contain diol, such as tetraethyleneglycol or hexaethyleneglycol, at either or both termini have also been shown to be substantially resistant to nuclease degradation. Circular ODN are protected against exonuclease degradation. For example, the Mologen double stem-loop immunomodulator MGN1703 (formerly dSLIM-30L1) is a covalently closed 116-nucleotide dumbbell-shaped CpG-containing phosphodiester backbone oligonucleotide having the sequence 5'-AGGTGGTAACCCCTAGGGGTTACCACCTTCAT-TGGAAAACGTTCTTCGGGGC GTTCTTAGGTGG-TAACCCCTAGGGGTTACCACCTTCATTG-GAAAACGTTCTTCG GGGCGTTCTT-3' (SEQ ID NO:501). Schmidt M et al., *Allergy* 2006 61: 56-63; Kapp, K et al., *Mol Ther Nucleic Acids* 2014 3: e170.

The immunostimulatory oligonucleotides may also contain one or more unusual linkages between the nucleotide or nucleotide-analogous moieties. The usual internucleoside linkage is a 3'5'-linkage. All other linkages are considered to be unusual internucleoside linkages, such as 2'5'-, 5'5'-, 3'3'-, 2'2'-, 2'3'-linkages. The nomenclature 2' to 5' is chosen according to the carbon atom of ribose. However, if unnatural sugar moieties are employed, such as ring-expanded sugar analogs (e.g. hexanose, cyclohexene or pyranose) or bi- or tricyclic sugar analogs, then this nomenclature changes according to the nomenclature of the monomer. In 3'-deoxy-β-D-ribopyranose analogs (also called p-DNA), the mononucleotides are e.g. connected via a 4'2'-linkage.

If the oligonucleotide contains one 3'3'-linkage, then this oligonucleotide may have two unlinked 5'-ends. Similarly, if the oligonucleotide contains one 5'5'-linkage, then this oligonucleotide may have two unlinked 3'-ends. The accessibility of unlinked ends of nucleotides may be better accessible by their receptors. Both types of unusual linkages (3'3'- and 5'5') were described by Ramalho Ortigao et al. (*Antisense Research and Development* (1992) 2, 129-46), whereby oligonucleotides having a 3'3'-linkage were reported to show enhanced stability towards cleavage by nucleases.

Different types of linkages can also be combined in one molecule which may lead to branching of the oligomer. If one part of the oligonucleotide is connected at the 3'-end via a 3'3'-linkage to a second oligonucleotide part and at the 2'-end via a 2'3'-linkage to a third part of the molecule, this results e.g. in a branched oligonucleotide with three 5'-ends (3'3'-, 2'3'-branched).

III. Checkpoint Inhibitors

A. PD-1

Programmed death-1 receptor (PD-1), also known as CD279, is a type 1 membrane protein expressed on activated T cells (including CD8$^+$ T cells), B cells, and macrophages. Its cognate ligands are PD-L1 and PD-L2, and binding of PD-1 particularly by PD-L1 blocks "Signal 3" in T cells and potently inhibits the effector arm of an adaptive immune response, for example by leading to the death of T cells expressing PD-1.

In humans, PD-1 is a 268-amino acid polypeptide having an amino acid sequence published as GenBank Accession No. NP_005009. The protein includes an extracellular IgV domain, transmembrane domain, and intracellular domain having two phosphorylation sites.

The $K_D$ for interaction between PD-1 and PD-L1 is 770 nM.

In preferred embodiments of the invention, the antibody inhibits binding between PD-1 and PD-L1. Preferably, the antibody can inhibit binding with PD-L1 with an $IC_{50}$ of about 100 nM or lower; more preferably, about 10 nM or lower, for example about 5 nM or lower; yet more preferably, about 2 nM or lower; or even more preferably, for example, about 1 nM or lower.

Further, in another embodiment, the anti-PD-1 antibody has a binding affinity for PD-1 that is at least as strong as that of PD-L1. In certain embodiments, the anti-PD-1 antibody has a binding affinity for PD-1 that is at least 10 times as strong as that of PD-L1. In certain embodiments, the anti-PD-1 antibody has a binding affinity for PD-1 that is at least 100 times as strong as that of PD-L1. In certain embodiments, the anti-PD-1 antibody has a binding affinity for PD-1 that is at least 1000 times as strong as that of PD-L1.

Anti-PD-1 antibodies are known in the art and include, for example, those disclosed in U.S. Pat. No. 6,808,710 to Wood et al., U.S. Pat. No. 7,488,802 to Collins et al., and U.S. Pat. No. 8,728,474 to Honjo et al. Anti-PD-1 antibodies are commercially available as pembrolizumab (formerly known as lambrolizumab and MK-3475, KEYTRUDA®, Merck, $K_D$ 29 pM) and nivolumab (OPDIVO®, Bristol-Myers Squibb, $K_D$ 2.6 nM). Additional anti-PD-1 antibodies currently under development include pidilizumab (CT-011, Cure Tech).

B. PD-L1

Programmed death-ligand 1 receptor (PD-L1), also known as CD274 and B7 homolog 1 (B7-H1), is a type 1 membrane protein expressed on activated T cells (including CD8$^+$ T cells and so-called tumor-infiltrating lymphocytes (TIL cells)), B cells, macrophages, and dendritic cells, as well as on many types of tumor cells. Its cognate ligands are PD-1 and B7.1 (CD80), and binding of PD-1 by PD-L1 blocks "Signal 3" in T cells and can potently inhibit the T cell effector functions mediating an adaptive immune response, for example by leading to the death of T cells expressing PD-1.

PD-L1 expression is upregulated on T cells, NK cells, macrophages, myeloid dendritic cells, B cells, epithelial cells, and vascular endothelial cells in response to interferon gamma (IFN-γ). PD-L1 expression is also upregulated on tumors, e.g., renal cell carcinoma and ovarian cancer, in response to IFN-γ.

In humans, PD-L1 is expressed in either of two isoforms, a longer isoform a or a shorter isoform b. Isoform a is a 290-amino acid polypeptide having an amino acid sequence published as GenBank Accession No. NP_054862; the mature peptide comprises amino acid residues 19-290, with residues 239-259 representing the transmembrane domain. Isoform b is a 176-amino acid polypeptide having an amino acid sequence published as GenBank NP_001254635; the mature peptide comprises amino acid residues 19-259.

As mentioned above, the $K_D$ for interaction between PD-1 and PD-L1 is 770 nM.

In preferred embodiments of the invention, the antibody inhibits binding between PD-1 and PD-L1. Preferably, the antibody can inhibit binding with PD-1 with an $IC_{50}$ of about 100 nM or lower; more preferably, about 10 nM or lower, for example about 5 nM or lower; yet more preferably, about 2 nM or lower; or even more preferably, for example, about 1 nM or lower.

Further, in another embodiment, the anti-PD-L1 antibody has a binding affinity for PD-L1 that is at least as strong as that of PD-1. In certain embodiments, the anti-PD-L1 antibody has a binding affinity for PD-L1 that is at least 10 times as strong as that of PD-1. In certain embodiments, the anti-PD-L1 antibody has a binding affinity for PD-L1 that is at least 100 times as strong as that of PD-1. In certain embodiments, the anti-PD-L1 antibody has a binding affinity for PD-L1 that is at least 1000 times as strong as that of PD-1.

Anti-PD-L1 antibodies are known in the art and include, for example, those disclosed in U.S. Pat. No. 7,943,743 to Korman et al. While no anti-PD-L1 antibodies are yet approved by the FDA for commercialization in the United States, several anti-PD-L1 antibodies are currently under development in human clinical trials, including MPDL3280A (Genetech/Roche, $K_D$ 0.4 nM), BMS-936559 (Bristol-Myers Squibb), and MEDI-4736 (AstraZeneca).

C. CTLA-4

Cytotoxic T-lymphocyte-associated protein 4 (CTLA-4), also known as CTLA4 or CD152, is a membrane protein expressed on T cells and regulatory T cells (Treg). Its cognate ligands include B7-1 (CD80) and B7-2 (CD86) on antigen-presenting cells (APC). Binding of B7-1 or B7-2 by CTLA-4 blocks "Signal 2" in T cells and inhibits the initiation of an adaptive immune response.

In humans, CTLA-4 is encoded in various isoforms, including one with an amino acid sequence published as GenBank Accession No. NP_001032720.

A preferred anti-CTLA-4 antibody is an antibody that specifically binds to human CTLA-4. More particularly, the anti-CTLA-4 antibody specifically binds to an epitope in the extracellular domain of human CTLA-4 and inhibits binding between CTLA-4 and one or both of its cognate ligands B7-1 and B7-2.

A preferred anti-CTLA-4 antibody is a human antibody that specifically binds to human CTLA-4. More particularly, the anti-CTLA-4 antibody specifically binds to an epitope in the extracellular domain of human CTLA-4 and inhibits binding between CTLA-4 and one or both of its cognate ligands B7-1 and B7-2. Exemplary human anti-CTLA-4 antibodies are described in detail in International Application No. PCT/US99/30895, published on Jun. 29, 2000 as WO 00/37504; European Patent Appl. No. EP 1262193 A1, published Apr. 12, 2002; U.S. patent application Ser. No. 09/472,087, now issued as U.S. Pat. No. 6,682,736, to Hanson et al.; U.S. patent application Ser. No. 09/948,939, published as US 2002/0086014; U.S. patent application Ser. No. 11/988,396, published as US 2009/0117132; and U.S. patent application Ser. No. 13/168,206, published as US 2012/0003179, the entire disclosures of which are incorporated herein by reference. Such antibodies include, but are not limited to, 3.1.1, 4.1.1, 4.8.1, 4.10.2, 4.13.1, 4.14.3, 6.1.1, 11.2.1, 11.6.1, 11.7.1, 12.3.1.1, and 12.9.1.1, as well as MDX-010. Human antibodies provide a substantial advantage in the treatment methods of the present invention, as they are expected to minimize the immunogenic and allergic responses that are associated with use of non-human antibodies in human patients.

Anti-CTLA-4 antibodies specifically include ipilimumab (YERVOY®, Bristol-Myers Squibb).

Characteristics of useful human anti-CTLA-4 antibodies of the invention are extensively discussed in WO 00/37504, EP 1262193, and U.S. Pat. No. 6,682,736 as well as U.S. Patent Application Publication Nos. US2002/0086014 and US2003/0086930, and the amino and nucleic acid sequences set forth therein are incorporated by reference herein in their entirety. Briefly, the antibodies of the invention include antibodies having amino acid sequences of an antibody such as, but not limited to, antibody 3.1.1, 4.1.1, 4.8.1, 4.10.2, 4.13.1, 4.14.3, 6.1.1, 11.2.1, 11.6.1, 11.7.1, 12.3.1.1, 12.9.1.1, and MDX-010. The invention also relates to antibodies having the amino acid sequences of the CDRs of the heavy and light chains of these antibodies, as well as those having changes in the CDR regions, as described in the above-cited applications and patent. The invention also concerns antibodies having the variable regions of the heavy and light chains of those antibodies. In another embodiment, the antibody is selected from an antibody having the full length, variable region, or CDR, amino acid sequences of the heavy and light chains of antibodies 3.1.1, 4.1.1, 4.8.1, 4.10.2, 4.13.1, 4.14.3, 6.1.1, 11.2.1, 11.6.1, 11.7.1, 12.3.1.1, and 12.9.1.1, and MDX-010.

Methods of administering anti-CTLA-4 antibodies are well known in the art. Most commonly the antibodies are given by systemic administration, generally IV. In animal models but not humans, intra-tumoral administration also has been explored as a way to reduce doses and toxicity (Fransen M F et al., *Oncoimmunology* 2013 Nov. 1; 2(11): e26493).

In one embodiment, the invention comprises an antibody-therapeutic agent combination comprising a human anti-CTLA-4 antibody disclosed in U.S. patent application Ser. No. 09/948,939, published as U.S. Patent Application Publication No. 2002/0086014 and No. 2003/0086930, and references cited therein, including, but not limited to, MAb 10D1 (MDX-010, Medarex, Princeton, N.J.). Even more preferably, the anti-CTLA-4 antibody is MDX-010. Alternatively, the anti-CTLA-4 antibody is 11.2.1 (Ticilimumab; CP-675,206).

In preferred embodiments of the invention, the antibody inhibits binding between CTLA-4 and B7-1, B7-2, or both. Preferably, the antibody can inhibit binding with B7-1 with an $IC_{50}$ of about 100 nM or lower; more preferably, about 10 nM or lower, for example about 5 nM or lower; yet more preferably, about 2 nM or lower; or even more preferably, for example, about 1 nM or lower. Likewise, the antibody can inhibit binding with B7-2 with an $IC_{50}$ of about 100 nM or lower; more preferably, 10 nM or lower, for example, even more preferably, about 5 nM or lower; yet more preferably, about 2 nM or lower; or even more preferably, about 1 nM or lower.

Further, in another embodiment, the anti-CTLA-4 antibody has a binding affinity for CTLA-4 that is at least as strong as that of B7-1. In certain embodiments, the anti-CTLA-4 antibody has a binding affinity for CTLA-4 that is at least 10 times as strong as that of B7-1. In certain embodiments, the anti-CTLA-4 antibody has a binding affinity for CTLA-4 that is at least 100 times as strong as that of B7-1. In certain embodiments, the anti-CTLA-4 antibody has a binding affinity for CTLA-4 that is at least 1000 times as strong as that of B7-1.

Further, in another embodiment, the anti-CTLA-4 antibody has a binding affinity for CTLA-4 that is at least as strong as that of B7-2. In certain embodiments, the anti-CTLA-4 antibody has a binding affinity for CTLA-4 that is at least 10 times as strong as that of B7-2. In certain embodiments, the anti-CTLA-4 antibody has a binding affinity for CTLA-4 that is at least 100 times as strong as that of B7-2. In certain embodiments, the anti-CTLA-4 antibody has a binding affinity for CTLA-4 that is at least 1000 times as strong as that of B7-2.

Further, in another embodiment, the anti-CTLA-4 antibody has a binding affinity for CTLA-4 of about $10^{-8}$ M, or greater affinity, more preferably, about $10^{-9}$ M or greater affinity, more preferably, about $10^{-10}$ M or greater affinity, and even more preferably, about $10^{-11}$ M or greater affinity.

In certain embodiments, the anti-CTLA-4 antibody can compete for binding with an antibody having heavy and light chain amino acid sequences of an antibody selected from the group consisting of 4.1.1, 6.1.1, 11.2.1, 4.13.1 and 4.14.3. Further, in certain embodiments, the anti-CTLA-4 antibody can compete for binding with an MDX-010 antibody.

In another embodiment, the anti-CTLA-4 antibody preferably cross-competes with an antibody having a heavy and light chain sequence, a variable heavy and a variable light chain sequence, and/or the heavy and light CDR sequences of antibody 4.1.1, 4.13.1, 4.14.3, 6.1.1 or 11.2.1. For example, the antibody can bind to the epitope to which an antibody that has heavy and light chain amino acid sequences, variable sequences and/or CDR sequences, of an antibody selected from the group consisting of 4.1.1, 4.13.1, 4.14.3, 6.1.1, or 11.2.1 binds. In another embodiment, the anti-CTLA-4 antibody cross-competes with an antibody having heavy and light chain sequences, or antigen-binding sequences, of MDX-010.

In another embodiment, the invention is practiced using an anti-CTLA-4 antibody that comprises a heavy chain comprising the amino acid sequences of CDR1, CDR2, and CDR3, and a light chain comprising the amino acid sequences of CDR1, CDR2, and CDR3, of an antibody selected from the group consisting of 3.1.1, 4.1.1, 4.8.1, 4.10.2, 4.13.1, 4.14.3, 6.1.1, 11.2.1, 11.6.1, 11.7.1, 12.3.1.1, and 12.9.1.1, or sequences having changes from said CDR sequences selected from the group consisting of conservative changes, wherein the conservative changes are selected from the group consisting of replacement of nonpolar residues by other nonpolar residues, replacement of polar charged residues other polar uncharged residues, replacement of polar charged residues by other polar charged residues, and substitution of structurally similar residues; non-conservative substitutions, wherein the non-conservative substitutions are selected from the group consisting of substitution of polar charged residue for polar uncharged residues and substitution of nonpolar residues for polar residues, additions and deletions.

In a further embodiment of the invention, the antibody contains fewer than 10, 7, 5, or 3 amino acid changes from the germline sequence in the framework or CDR regions. In another embodiment, the antibody contains fewer than 5 amino acid changes in the framework regions and fewer than 10 changes in the CDR regions. In one preferred embodiment, the antibody contains fewer than 3 amino acid changes in the framework regions and fewer than 7 changes in the CDR regions. In a preferred embodiment, the changes in the framework regions are conservative and those in the CDR regions are somatic mutations.

In another embodiment, the antibody has at least 80%, more preferably, at least 85%, even more preferably, at least 90%, yet more preferably, at least 95%, more preferably, at least 99%, sequence identity over the heavy and light chain CDR1, CDR2 and CDR3 sequences with the CDR sequences of antibody 3.1.1, 4.1.1, 4.8.1, 4.10.2, 4.13.1, 4.14.3, 6.1.1, 11.2.1, 11.6.1, 11.7.1, 12.3.1.1, and 12.9.1.1. Even more preferably, the antibody shares 100% sequence identity over the heavy and light chain CDR1, CDR2 and CDR3 with the sequence of antibody 3.1.1, 4.1.1, 4.8.1, 4.10.2, 4.13.1, 4.14.3, 6.1.1, 11.2.1, 11.6.1, 11.7.1, 12.3.1.1, and 12.9.1.1.

In yet another embodiment, the antibody has at least 80%, more preferably, at least 85%, even more preferably, at least 90%, yet more preferably, at least 95%, more preferably, at least 99%, sequence identity over the heavy and light chain variable region sequences with the variable region sequences of antibody 3.1.1, 4.1.1, 4.8.1, 4.10.2, 4.13.1, 4.14.3, 6.1.1, 11.2.1, 11.6.1, 11.7.1, 12.3.1.1, and 12.9.1.1. Even more preferably, the antibody shares 100% sequence identity over the heavy and light chain variable region sequences with the sequences of antibody 3.1.1, 4.1.1, 4.8.1, 4.10.2, 4.13.1, 4.14.3, 6.1.1, 11.2.1, 11.6.1, 11.7.1, 12.3.1.1, and 12.9.1.1.

D. Other Checkpoint Inhibitors

In addition to those listed above, other checkpoints are known in the art and their inhibitors are included in the invention. For example, BTLA provides a negative signal in response to HVEM, and TIM3 provides a negative signal in response to Ga19. Adenosine can trigger suppressive effects through the adenosine A2a receptor, and IDO and TDO are well known immunosuppressive pathways thought to be involved in anti-tumor immunity. LAG3 binds to MHC class II with higher affinity than CD4. LAG3 negatively regulates cellular proliferation, activation, and homeostasis of T cells, in a fashion similar to CTLA-4 and PD-1, and it has been reported to play a role in Treg suppressive function. LAG3 also helps maintain CD8$^+$ T cells in a tolerogenic state and, working with PD-1, helps maintain CD8 exhaustion during chronic viral infection. LAG3 is known to be involved in the maturation and activation of dendritic cells. Additional checkpoint inhibitors for use in the invention include, without limitation, antibodies and antigen-binding fragments thereof, capable of binding specifically to any one or more of BTLA, TIM3, and LAG3. Also contemplated by the invention are bispecific antibodies and bispecific antigen-binding fragments thereof which are capable of binding specifically to any one or more of BTLA, TIM3, and LAG3.

The invention contemplates combinations of a TLR9 agonist and a checkpoint inhibitor, where the checkpoint inhibitor can be a single CPI or any combination of two or more CPI. While it is likely that in clinical use only one or only a pair of CPI will be used, the invention contemplates using any one, any two, any three, or any four or more CPI selected from, for example, inhibitors of CTLA-4, PD-1, PD-L1, TIM3, LAG3, or BTLA.

E. Origin of Antibodies

While the anti-PD-1, anti-PD-L1, and anti-CTLA-4 antibodies discussed previously herein may be preferred, the skilled artisan, based upon the disclosure provided herein, would appreciate that the invention encompasses a wide variety of anti-PD-1, anti-PD-L1, and anti-CTLA-4 antibodies and is not limited to these particular antibodies. More particularly, while human antibodies are preferred for use in humans, the invention is in no way limited to human antibodies; rather, the invention encompasses useful antibodies regardless of species origin, and includes, among others, chimeric humanized and/or primatized antibodies. Also, although certain of the antibodies exemplified herein were obtained using a transgenic mammal, e.g., a mouse comprising a human immune repertoire, the skilled artisan, based upon the disclosure provided herein, would understand that the present invention is not limited to an antibody produced by this or by any other particular method. Instead, the invention includes an anti-PD-1, anti-PD-L1, or anti-CTLA-4 antibody produced by any method, including, but not limited to, a method known in the art (e.g., screening phage display libraries, and the like) or to be developed in the future for producing an anti-PD-1, anti-PD-L1, or anti-CTLA-4 antibody of the invention. Based upon the extensive disclosure provided herein and in, e.g., U.S. Pat. No. 6,682,736 to Bedian et al., and U.S. Pat. App. Pub. No. 2002/0088014, one skilled in the art can readily produce and identify an anti-PD-1, anti-PD-L1, or anti-CTLA-4 antibody useful for treatment of cancer in combination with a CpG ODN using the novel methods disclosed herein.

The present invention encompasses human antibodies produced using a transgenic non-human mammal, i.e., XenoMouse™ (Abgenix, Inc., Fremont, Calif.) as disclosed in the U.S. Pat. No. 6,682,736, to Hanson et al.

Another transgenic mouse system for production of "human" antibodies is referred to as "HuMAb-Mouse™" (Medarex, Princeton, N.J.), which contain human immunoglobulin gene miniloci that encode unrearranged human heavy (mu and gamma) and kappa light chain immunoglobulin sequences, together with targeted mutations that inactivate the endogenous mu and kappa chain loci (Lonberg et al. Nature 368:856-859 (1994), and U.S. Pat. No. 5,770, 429).

However, the invention uses human anti-PD-1, anti-PD-L1, or anti-CTLA-4 antibodies produced using any transgenic mammal such as, but not limited to, the Kirin TC Mouse™ (Kirin Beer Kabushiki Kaisha, Tokyo, Japan) as described in, e.g., Tomizuka et al., Proc Natl Acad Sci USA 97:722 (2000); Kuroiwa et al., Nature Biotechnol 18:1086 (2000); U.S. Patent Application Publication No. 2004/0120948, to Mikayama et al.; and the HuMAb-Mouse™ (Medarex, Princeton, N.J.) and XenoMouse™ (Abgenix, Inc., Fremont, Calif.), supra. Thus, the invention encompasses using an anti-PD-1, anti-PD-L1, or anti-CTLA-4 antibody produced using any transgenic or other non-human animal.

Moreover, while the preferred method of producing a human anti-PD-1, anti-PD-L1, or anti-CTLA-4 antibody comprises generation of the antibodies using a non-human transgenic mammal comprising a human immune repertoire, the present invention is in no way limited to this approach. Rather, as would be appreciated by one skilled in the art once armed with the disclosure provided herein, the invention encompasses using any method for production of a human, or any other antibody specific for PD-1, PD-L1, or CTLA-4 produced according to any method known in the art or to be developed in the future for production of antibodies that specifically bind an antigen of interest Human antibodies can be developed by methods that include, but are not limited to, use of phage display antibody libraries. For example, using these techniques, antibodies can be generated to CTLA-4-expressing cells, CTLA-4 itself, forms of CTLA-4, epitopes or peptides thereof, and expression libraries thereto (see e.g. U.S. Pat. No. 5,703, 057), which can thereafter be screened for the activities described above.

In another embodiment, the antibodies employed in methods of the invention are not fully human, but "humanized". In particular, murine antibodies or antibodies from other species can be "humanized" or "primatized" using techniques well known in the art. See, e.g., Winter and Harris Immunol. Today 14:43-46 (1993), Wright et al. Crit. Reviews in Immunol. 12:125-168 (1992), and U.S. Pat. No. 4,816,567, to Cabilly et al., and Mage and Lamoyi in Monoclonal Antibody Production Techniques and Applications pp. 79-97, Marcel Dekker, Inc., New York, N.Y. (1987).

As will be appreciated based upon the disclosure provided herein, antibodies for use in the invention can be obtained from a transgenic non-human mammal, and hybridomas derived therefrom, but can also be expressed in cell lines other than hybridomas.

Mammalian cell lines available as hosts for expression are well known in the art and include many immortalized cell lines available from the American Type Culture Collection (ATCC), including but not limited to Chinese hamster ovary (CHO) cells, NSO, HeLa cells, baby hamster kidney (BHK) cells, monkey kidney cells (COS), and human hepatocellular carcinoma cells (e.g., Hep G2). Non-mammalian prokaryotic and eukaryotic cells can also be employed, including bacterial, yeast, insect, and plant cells.

Various expression systems can be used as well known in the art, such as, but not limited to, those described in e.g., Sambrook and Russell, Molecular Cloning, A Laboratory Approach, Cold Spring Harbor Press, Cold Spring Harbor, N.Y. (2001), and Ausubel et al., Current Protocols in Molecular Biology, John Wiley & Sons, NY (2002). These expression systems include dihydrofolate reductase (DHFR)-based systems, among many others. The glutamine synthetase system of expression is discussed in whole or part in connection with European Patents Nos. EP 216 846, EP 256 055, and EP 323 997 and European Patent Application 89303964. In one embodiment, the antibody used is made in NSO cells using a glutamine synthetase system (GS-NSO). In another embodiment, the antibody is made in CHO cells using a DHFR system. Both systems are well-known in the art and are described in, among others, Barnes et al. Biotech & Bioengineering 73:261-270 (2001), and references cited therein.

Site-directed mutagenesis of the antibody CH2 domain to eliminate glycosylation may be preferred in order to prevent changes in either the immunogenicity, pharmacokinetic, and/or effector functions resulting from non-human glycosylation. Further, the antibody can be deglycosylated by enzymatic (see, e.g., Thotakura et al. *Meth. Enzymol.* 138: 350 (1987)) and/or chemical methods (see, e.g., Hakimuddin et al., *Arch. Biochem. Biophys.* 259:52 (1987)).

Further, the invention encompasses using an anti-PD-1 antibody, anti-PD-L1 antibody, or anti-CTLA-4 antibody comprising an altered glycosylation pattern. The skilled artisan would appreciate, based upon the disclosure provided herein, that an anti-PD-1 antibody, anti-PD-L1 antibody, or anti-CTLA-4 antibody can be modified to comprise additional, fewer, or different glycosylation sites compared with the corresponding unaltered antibody. Such modifications are described in, e.g., U.S. Patent Application Publication Nos. 2003/0207336, and 2003/0157108, and International Patent Publication Nos. WO 01/81405 and 00/24893.

Additionally, the invention comprises using an anti-PD-1 antibody, anti-PD-L1 antibody, or anti-CTLA-4 antibody regardless of the glycoform, if any, present on the antibody. Moreover, methods for extensively remodeling the glycoform present on a glycoprotein are well-known in the art and include, e.g., those described in International Patent Publication Nos. WO 03/031464, WO 98/58964, and WO 99/22764, and US Patent Application Publication Nos. 2004/0063911, 2004/0132640, 2004/0142856, 2004/0072290, and U.S. Pat. No. 6,602,684 to Umana et al.

Further, the invention encompasses using an anti-PD-1 antibody, anti-PD-L1 antibody, or anti-CTLA-4 antibody with any art-known covalent and non-covalent modification, including, but not limited to, linking the polypeptide to one of a variety of nonproteinaceous polymers, e.g., polyethylene glycol, polypropylene glycol, or polyoxyalkylenes, in the manner set forth in, for example, U.S. Patent Application Publication Nos. 2003/0207346 and 2004/0132640, and U.S. Pat. Nos. 4,640,835; 4,496,689; 4,301,144; 4,670,417; 4,791,192; and 4,179,337.

Additionally, the invention encompasses using an anti-PD-1 antibody, anti-PD-L1 antibody, or anti-CTLA-4 antibody, or antigen-binding portion thereof, chimeric protein comprising, e.g., a human serum albumin polypeptide, or fragment thereof. Whether the chimeric protein is produced using recombinant methods by, e.g., cloning of a chimeric nucleic acid encoding the chimeric protein, or by chemical linkage of the two peptide portions, the skilled artisan would understand once armed with the teachings provided herein that such chimeric proteins are well-known in the art and can confer desirable biological properties such as, but not limited to, increased stability and serum half-life to the antibody of the invention and such molecules are therefore included herein.

Antibodies that are generated for use in the invention need not initially possess a particular desired isotype. Rather, the antibody as generated can possess any isotype and can be isotype switched thereafter using conventional techniques. These include direct recombinant techniques (see, e.g., U.S. Pat. No. 4,816,397), and cell-cell fusion techniques (see e.g., U.S. Pat. No. 5,916,771).

The effector function of the antibodies of the invention may be changed by isotype switching to an IgG1, IgG2, IgG3, IgG4, IgD, IgA, IgE, or IgM for various therapeutic uses. Furthermore, dependence on complement for cell killing can be avoided through the use of bispecifics, immunotoxins, or radiolabels, for example.

Therefore, while the preferred anti-CTLA-4 antibodies used in the invention are exemplified by antibodies having the amino acid sequences of 3.1.1, 4.1.1, 4.8.1, 4.10.2, 4.13.1, 4.14.3, 6.1.1, 11.2.1, 11.6.1, 11.7.1, 12.3.1.1, 12.9.1.1, and MDX-010, or, e.g., the sequences of the V regions or CDRs thereof, the present invention is not limited in any way to using these, or any other, particular anti-CTLA-4 antibodies. Preferably, the antibody is 4.1.1, 4.13.1, 11.2.1, and/or MDX-010. However, any anti-CTLA-4 antibody, or antigen-binding portion thereof, as described elsewhere herein, or as known in the art or developed in the future, can be used in a method of the invention. More particularly, humanized chimeric antibodies, anti-CTLA-4 antibodies derived from any species (including single chain antibodies obtained from camelids as described in, e.g., U.S. Pat. Nos. 5,759,808 and 6,765,087, to Casterman and Hamers), as well as any human antibody, can be combined with a CpG ODN to practice the novel methods disclosed herein.

The invention also encompasses such antibodies as disclosed in, inter alia, International Patent Publication Nos. WO 00/37504 (published Jun. 29, 2000); WO 01/14424 (published Mar. 1, 2001); WO 93/00431 (published Jan. 7, 1993); and WO 00/32231 (published Jun. 8, 2000), among many others.

Thus, the skilled artisan, once provided with the teachings provided herein, would readily appreciate that the anti-CTLA-4 antibody-therapeutic agent combination of the invention can comprise a wide plethora of anti-CTLA-4 antibodies.

Further, one skilled in the art, based upon the disclosure provided herein, would understand that the invention is not limited to administration of only a single antibody; rather, the invention encompasses administering at least one anti-CTLA-4 antibody, e.g., 4.1.1, 4.13.1 and 11.2.1, in combination with a CpG ODN. Moreover, the invention encompasses administering any combination of any known anti-CTLA-4 antibody, including, but not limited to, administering a CpG ODN in combination with, e.g., 4.1.1, 4.13.1, 11.2.1 and MDX-010. Thus, any combination of anti-CTLA-4 antibodies can be combined with at least one therapeutic agent and the present invention encompasses any such combination and permutation thereof.

IV. CpG DNA and Checkpoint Inhibitor Combination Immunotherapy

The present invention relates to combination tumor immunotherapy comprising locally administering CpG ODN into or in proximity to a cancerous tumor, and systemically administering a checkpoint inhibitor, such as an anti-PD-1 antibody, an anti-PD-L1 antibody, or an anti-CTLA-4 antibody, to treat cancer. A single human clinical trial has been reported in which patients were treated with a combination of a CpG ODN (B-class, dosed subcutaneously up to 0.15 mg/kg/wk) and an anti-CTLA-4 antibody (Millward M et al., Br. J. Cancer 2013 108(10): 1998-2004). This study established an MTD for a weekly combination of IV anti-CTLA-4 and subcutaneous CpG over 12 weeks of therapy in 21 patients with stage IV melanoma. Although the results of the study were not considered encouraging enough to warrant continued development of TLR9 agonists in oncology (all immune-oncology drug development by the sponsor was terminated), several interesting findings from the study support the utility of the present invention. First, the combination of a TLR9 agonist and a checkpoint inhibitor is relatively well tolerated—there was no observed systemic autoimmune disease, and only three patients developed dose-limiting toxicities during the prespecified initial 6 week period, two of whom were in the highest dose group of the anti-CTLA-4 antibody. Second, there was no induction of antibody response against the anti-CTLA-4 antibody from the combination regimen. Third, two patients achieved partial responses to the treatment, and several others had unusually prolonged stable disease.

Combination of high IFN-inducing CpG ODN and anti-PD-1, anti-PD-L1, or anti-CTLA-4 is useful for treatment of primary and secondary (i.e., metastatic) cancers. More specifically, among many potential treatment options, CpG ODN and anti-checkpoint combination therapy can be used to treat cancer. In certain embodiments, the cancer to be treated is or includes a cancerous tumor. A "cancerous tumor" as used herein refers to an abnormal swelling or macroscopic collection of cells comprising abnormal cells characterized by their growth or proliferation without regulation by normal external signals. In certain embodiments, a cancerous tumor is a carcinoma, sarcoma, or adenocarcinoma; these are sometimes referred to as solid tumors. In certain embodiments, a cancerous tumor excludes hematologic malignancies. In certain embodiments, a cancerous tumor includes certain hematologic malignancies, e.g., lymphomas.

Representative cancers treatable by the methods of the invention specifically include, without limitation, cancers of skin, head and neck, esophagus, stomach, liver, colon, rectum, pancreas, lung, breast, cervix, ovary, kidney, bladder, prostate, thyroid, brain, muscle, and bone. Also specifically included among cancers treatable by the methods of the invention are melanoma, renal cell carcinoma, and non-small cell lung cancer (NSCLC). Also specifically included among cancers treatable by the methods of the invention are lymphoma, cancer of the bone marrow, carcinoid tumor, and neuroblastoma.

While in some embodiments the foregoing cancers are preferred, the present invention relates to treatment of a wide variety of malignant cell proliferative disorders, including, but not limited to Kaposi's sarcoma, synovial sarcoma, mesothelioma, hepatobiliary (hepatic and biliary duct), a primary or secondary brain tumor, lung cancer (NSCLC and SCLC), bone cancer, skin cancer, cancer of the head or neck, cutaneous or intraocular melanoma, cancer of the anal region, stomach (gastric) cancer, gastrointestinal (gastric, colorectal, and duodenal) cancer, colon cancers, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, prostate cancer, cancer of the penis, testicular cancer, cancer of the bladder, cancer of the kidney or ureter, carcinoma of the renal pelvis, pancreatic cancers, neoplasms of the central nervous system (CNS) including primary or secondary CNS tumor, spinal axis tumors, brain stem glioma, glioblastoma, meningioma, myoblastoma, astrocytoma, pituitary adenoma, adrenocortical cancer, gall bladder cancer, cholangiocarcinoma, fibrosarcoma, neuroblastoma, and retinoblastoma; as well as, in some embodiments, non-Hodgkin's lymphoma (NHL, including indolent and aggressive), Hodgkin's lymphoma, cutaneous T-cell lymphoma, lymphocytic lymphomas, primary CNS lymphoma, chronic or acute myeloid leukemia, chronic or acute lymphocytic leukemia, erythroblastoma, and multiple myeloma; or a combination of two or more of the foregoing cancers.

The cancers to be treated may be refractory cancers. A refractory cancer as used herein is a cancer that is resistant to the ordinary standard of care prescribed. These cancers may appear initially responsive to a treatment (and then recur), or they may be completely non-responsive to the treatment. The ordinary standard of care will vary depending upon the cancer type, and the degree of progression in the subject. It may be a chemotherapy, an immunotherapy, surgery, radiation, or a combination thereof. Those of ordinary skill in the art are aware of such standards of care. Subjects being treated according to the invention for a refractory cancer therefore may have already been exposed to another treatment for their cancer. Alternatively, if the cancer is likely to be refractory (e.g., given an analysis of the cancer cells or history of the subject), then the subject may not have already been exposed to another treatment.

In certain embodiments, refractory cancers include cancers which are refractory to treatment with a checkpoint inhibitor. Cancers of this type are sometimes referred to as "cold". Methods of the instant invention can be used to treat such "cold" cancers or tumors to convert them into "hot" ones, i.e., cancers or tumors which respond to treatment, including treatment with a checkpoint inhibitor, even the same checkpoint inhibitor.

Examples of refractory cancers include but are not limited to melanomas, renal cell carcinomas, colon cancer, liver (hepatic) cancers, pancreatic cancer, non-Hodgkin's lymphoma, lung cancer, and leukemias.

The methods of the invention in certain instances may be useful for replacing existing surgical procedures or drug therapies, although in other instances the present invention is useful in improving the efficacy of existing therapies for treating such conditions. Accordingly combination therapy may be used to treat subjects that are undergoing or that will undergo a treatment for cancer. For example, the agents may be administered to a subject in combination with another anti-proliferative (e.g., an anti-cancer) therapy. Suitable anti-cancer therapies include surgical procedures to remove the tumor mass, chemotherapy, or localized radiation. The other anti-proliferative therapy may be administered before, concurrent with, or after treatment with the CpG ODN/CPI combination of the invention. There may also be a delay of several hours, days, and in some instances weeks between the administration of the different treatments, such that the CpG ODN/CPI combination may be administered before or after the other treatment. The invention further contemplates the use of the CpG ODN/CPI combination in cancer subjects prior to and following surgery, radiation or chemotherapy.

In one embodiment, the invention provides compositions and methods of producing or increasing an anti-tumor response using a CpG ODN-CPI combination, wherein CpG ODN enhances an anti-tumor response by an amount of CPI which is otherwise sub-optimal for inducing the same level of anti-tumor response when used alone. In certain embodiments, when the CpG ODN is not used in conjunction with a CPI to elicit an anti-tumor response, administering CpG ODN alone does not produce or increase the anti-tumor response. In alternate embodiments, both the CpG ODN and the CPI can elicit an anti-tumor response alone and/or when administered in combination.

In one embodiment, the invention provides compositions and methods of producing or increasing an anti-tumor response using a CpG ODN-CPI antibody combination, wherein CpG ODN enhances an anti-tumor response by an amount of antibody which is otherwise sub-optimal for inducing the same level of anti-tumor response when used alone. In certain embodiments, when the CpG ODN is not used in conjunction with a CPI antibody to elicit an anti-tumor response, administering CpG ODN alone does not produce or increase the anti-tumor response. In alternate embodiments, both the CpG ODN and the CPI antibody can elicit an anti-tumor response alone and/or when administered in combination.

In certain embodiments, the CpG ODN may enhance the effects of the CPI (or vice-versa) in an additive manner. In a preferred embodiment, the CpG ODN enhances the effects of the CPI (or vice versa) in a synergistic manner. In another embodiment, the CPI enhances the effect of a CpG ODN in an additive manner. Preferably, the effects are enhanced in a synergistic manner. Thus, in certain embodiments, the invention encompasses methods of disease treatment or prevention that provide better therapeutic profiles than expected based on administration of CpG ODN alone and CPI alone.

In certain embodiments, the CpG ODN may enhance the effects of the CPI antibody (or vice-versa) in an additive manner. In a preferred embodiment, the CpG ODN enhances the effects of the CPI antibody (or vice versa) in a synergistic manner. In another embodiment, the CPI antibody enhances the effect of a CpG ODN in an additive manner. Preferably, the effects are enhanced in a synergistic manner. Thus, in certain embodiments, the invention encompasses methods of disease treatment or prevention that provide better therapeutic profiles than expected based on administration of CpG ODN alone and CPI antibody alone.

In certain embodiments, the CpG ODN is administered with CPI (with or without other modalities such as radiotherapy) as a part of a neoadjuvant therapeutic regimen to achieve an anti-tumor effect that will make possible curative surgery.

In certain embodiments, the CpG ODN is administered together with CPI (with or without other modalities such as radiotherapy) following surgical resection of a primary or metastatic tumor or in the setting of minimal residual disease in order to prevent tumor recurrence.

Also encompassed by the invention are combination therapies that have additive potency or an additive therapeutic effect while reducing or avoiding unwanted or adverse effects. The invention also encompasses synergistic combinations where the therapeutic efficacy is greater than additive, while unwanted or adverse effects are reduced or avoided. In certain embodiments, the methods of the invention permit treatment or prevention of diseases and disorders wherein treatment is improved by an enhanced anti-tumor response using lower and/or less frequent doses of CpG ODN and/or CPI to reduce the incidence of unwanted or adverse effects caused by the administration of CpG ODN alone and/or CPI alone, while maintaining or enhancing efficacy of treatment, preferably increasing patient compliance, improving therapy, and/or reducing unwanted or adverse effects.

Methods of the Invention

An aspect of the invention is a method of treating a cancerous tumor, comprising administering to a subject in need thereof an effective amount of a TLR9 agonist and a checkpoint inhibitor (CPI), wherein the TLR9 agonist is administered into or substantially adjacent to the tumor.

In certain embodiments, the TLR9 agonist induces IFN-α.

In certain embodiments, the TLR9 agonist is CpG DNA.

In certain embodiments, the TLR9 agonist is selected from the group consisting of A-class CpG DNA, C-class CpG DNA, E-class CpG DNA, P-class CpG DNA, and any combination thereof.

In certain embodiments, the TLR9 agonist is an A-class CpG DNA.

In certain embodiments, the TLR9 agonist is a C-class CpG DNA.

In certain embodiments, the TLR9 agonist is an E-class CpG DNA.

In certain embodiments, the TLR9 agonist is an A/E-class CpG DNA.

In certain embodiments, the TLR9 agonist is a P-class CpG DNA.

In certain embodiments, the TLR9 agonist has a sequence provided as:

```
                                            (SEQ ID NO: 82)
5'-GGGGGGGGGGGACGATCGTCGGGGGGGGGG-3'.
```

In certain embodiments the TLR9 agonist is a circular CpG DNA with a native backbone, e.g., MGN1703.

In certain embodiments the TLR9 agonist is an unmodified native CpG DNA administered in a formulation comprising a nanoparticle, VLP, ISCOM or other nuclease-resistant delivery vehicle.

In certain embodiments, the CPI is administered systemically.

In certain embodiments, the CPI is an antibody or antigen-binding fragment thereof which binds specifically to an antigen selected from the group consisting of PD-1, PD-L1, and CTLA-4.

In certain embodiments, the CPI is an antibody or antigen-binding fragment thereof which binds specifically to PD-1.

In certain embodiments, the CPI is an antibody or antigen-binding fragment thereof which binds specifically to PD-L1.

In certain embodiments, the CPI is an antibody or antigen-binding fragment thereof which binds specifically to CTLA-4.

In certain embodiments, the CPI is not an antibody or antigen-binding fragment thereof which binds specifically to PD-1.

In certain embodiments, the CPI is not an antibody or antigen-binding fragment thereof which binds specifically to PD-L1.

In certain embodiments, the CPI is not an antibody or antigen-binding fragment thereof which binds specifically to CTLA-4.

In certain embodiments, the CPI comprises (i) a first antibody or antigen-binding fragment thereof which binds specifically to CTLA-4, and (ii) a second antibody or antigen-binding fragment thereof which binds specifically to an antigen selected from the group consisting of PD-1 and PD-L1.

In certain embodiments, the CPI comprises (i) a first antibody or antigen-binding fragment thereof which binds specifically to CTLA-4, and (ii) a second antibody or antigen-binding fragment thereof which binds specifically to PD-1.

In certain embodiments, the CPI comprises (i) a first antibody or antigen-binding fragment thereof which binds specifically to CTLA-4, and (ii) a second antibody or antigen-binding fragment thereof which binds specifically to PD-L1.

In certain embodiments, the CPI comprises (i) a first antibody or antigen-binding fragment thereof which binds specifically to CTLA-4, and (ii) a second antibody or antigen-binding fragment thereof which binds specifically to TIM3.

In certain embodiments, the CPI comprises (i) a first antibody or antigen-binding fragment thereof which binds specifically to CTLA-4, and (ii) a second antibody or antigen-binding fragment thereof which binds specifically to LAG3.

In certain embodiments, the CPI comprises (i) a first antibody or antigen-binding fragment thereof which binds specifically to PD-1, and (ii) a second antibody or antigen-binding fragment thereof which binds specifically to PD-L1.

In certain embodiments, the CPI comprises (i) a first antibody or antigen-binding fragment thereof which binds specifically to PD-1, and (ii) a second antibody or antigen-binding fragment thereof which binds specifically to TIM3.

In certain embodiments, the CPI comprises (i) a first antibody or antigen-binding fragment thereof which binds specifically to PD-1, and (ii) a second antibody or antigen-binding fragment thereof which binds specifically to LAG3.

In certain embodiments, the CPI comprises (i) a first antibody or antigen-binding fragment thereof which binds specifically to PD-L1, and (ii) a second antibody or antigen-binding fragment thereof which binds specifically to TIM3.

In certain embodiments, the CPI comprises (i) a first antibody or antigen-binding fragment thereof which binds specifically to PD-L1, and (ii) a second antibody or antigen-binding fragment thereof which binds specifically to LAG3.

In certain embodiments, the CPI comprises (i) a first antibody or antigen-binding fragment thereof which binds specifically to TIM3, and (ii) a second antibody or antigen-binding fragment thereof which binds specifically to LAG3.

In certain embodiments, the CPI comprises a bispecific antibody or bispecific antigen-binding fragment thereof which binds specifically to CTLA-4 and to an antigen selected from the group consisting of PD-1 and PD-L1.

In certain embodiments, the CPI comprises a bispecific antibody or bispecific antigen-binding fragment thereof which binds specifically to CTLA-4 and to PD-1.

In certain embodiments, the CPI comprises a bispecific antibody or bispecific antigen-binding fragment thereof which binds specifically to CTLA-4 and to PD-L1.

In certain embodiments, the CPI comprises a bispecific antibody or bispecific antigen-binding fragment thereof which binds specifically to CTLA-4 and to TIM3.

In certain embodiments, the CPI comprises a bispecific antibody or bispecific antigen-binding fragment thereof which binds specifically to CTLA-4 and to LAG3.

In certain embodiments, the CPI comprises a bispecific antibody or bispecific antigen-binding fragment thereof which binds specifically to PD-1 and to PD-L1.

In certain embodiments, the CPI comprises a bispecific antibody or bispecific antigen-binding fragment thereof which binds specifically to PD-1 and to TIM3.

In certain embodiments, the CPI comprises a bispecific antibody or bispecific antigen-binding fragment thereof which binds specifically to PD-1 and to LAG3.

In certain embodiments, the CPI comprises a bispecific antibody or bispecific antigen-binding fragment thereof which binds specifically to PD-L1 and to TIM3.

In certain embodiments, the CPI comprises a bispecific antibody or bispecific antigen-binding fragment thereof which binds specifically to PD-L1 and to LAG3.

In certain embodiments, the CPI comprises a bispecific antibody or bispecific antigen-binding fragment thereof which binds specifically to TIM3 and to LAG3.

In certain embodiments, the TLR9 agonist is administered prior to administration of the CPI.

In certain embodiments, the TLR9 agonist and the CPI are administered substantially at the same time.

In certain embodiments, the cancerous tumor is a lymphoma or a cancerous tumor of a tissue selected from the group consisting of skin, head and neck, esophagus, stomach, liver, colon, rectum, pancreas, lung, breast, cervix, ovary, kidney, bladder, prostate, thyroid, brain, muscle, and bone.

In certain embodiments, the cancerous tumor is melanoma.

In certain embodiments, the cancerous tumor is lymphoma.

In certain embodiments, the cancerous tumor is a cancer of the bone marrow.

In certain embodiments, the cancerous tumor is a carcinoid tumor.

In certain embodiments, the cancerous tumor is neuroblastoma.

In certain embodiments, the subject is a human.

An aspect of the invention is a method of treating a cancerous tumor, comprising administering to a subject in need thereof an effective amount of radiotherapy, a TLR9 agonist, and a checkpoint inhibitor (CPI), wherein the radiotherapy is initiated prior to administration of the TLR9 agonist, and the TLR9 agonist is administered into or substantially adjacent to the tumor.

In certain embodiments, the radiotherapy is radiotherapy.

In certain embodiments, the radiotherapy is hypofractionated radiotherapy.

In certain embodiments, the TLR9 agonist induces IFN-α.

In certain embodiments, the TLR9 agonist is CpG DNA.

In certain embodiments, the TLR9 agonist is selected from the group consisting of A-class CpG DNA, C-class CpG DNA, E-class CpG DNA, P-class CpG DNA, and any combination thereof.

In certain embodiments, the TLR9 agonist is an A-class CpG DNA.

In certain embodiments, the TLR9 agonist is a C-class CpG DNA.

In certain embodiments, the TLR9 agonist is an E-class CpG DNA.

In certain embodiments, the TLR9 agonist is an A/E-class CpG DNA.

In certain embodiments, the TLR9 agonist is a P-class CpG DNA.

In certain embodiments, the TLR9 agonist has a sequence provided as:

```
                                        (SEQ ID NO: 82)
  5'-GGGGGGGGGGGACGATCGTCGGGGGGGGGG-3'.
```

In certain embodiments the TLR9 agonist is a circular CpG DNA with a native backbone, e.g., MGN1703.

In certain embodiments the TLR9 agonist is an unmodified native CpG DNA administered in a formulation comprising a nanoparticle, VLP, ISCOM or other nuclease-resistant delivery vehicle.

In certain embodiments, the CPI is administered systemically.

In certain embodiments, the CPI is an antibody or antigen-binding fragment thereof which binds specifically to an antigen selected from the group consisting of PD-1, PD-L1, and CTLA-4.

In certain embodiments, the CPI is an antibody or antigen-binding fragment thereof which binds specifically to PD-1.

In certain embodiments, the CPI is an antibody or antigen-binding fragment thereof which binds specifically to PD-L1.

In certain embodiments, the CPI is an antibody or antigen-binding fragment thereof which binds specifically to CTLA-4.

In certain embodiments, the CPI is not an antibody or antigen-binding fragment thereof which binds specifically to PD-1.

In certain embodiments, the CPI is not an antibody or antigen-binding fragment thereof which binds specifically to PD-L1.

In certain embodiments, the CPI is not an antibody or antigen-binding fragment thereof which binds specifically to CTLA-4.

In certain embodiments, the CPI comprises (i) a first antibody or antigen-binding fragment thereof which binds specifically to CTLA-4, and (ii) a second antibody or antigen-binding fragment thereof which binds specifically to an antigen selected from the group consisting of PD-1 and PD-L1.

In certain embodiments, the CPI comprises (i) a first antibody or antigen-binding fragment thereof which binds specifically to CTLA-4, and (ii) a second antibody or antigen-binding fragment thereof which binds specifically to PD-1.

In certain embodiments, the CPI comprises (i) a first antibody or antigen-binding fragment thereof which binds specifically to CTLA-4, and (ii) a second antibody or antigen-binding fragment thereof which binds specifically to PD-L1.

In certain embodiments, the CPI comprises (i) a first antibody or antigen-binding fragment thereof which binds specifically to CTLA-4, and (ii) a second antibody or antigen-binding fragment thereof which binds specifically to TIM3.

In certain embodiments, the CPI comprises (i) a first antibody or antigen-binding fragment thereof which binds specifically to CTLA-4, and (ii) a second antibody or antigen-binding fragment thereof which binds specifically to LAG3.

In certain embodiments, the CPI comprises (i) a first antibody or antigen-binding fragment thereof which binds specifically to PD-1, and (ii) a second antibody or antigen-binding fragment thereof which binds specifically to PD-L1.

In certain embodiments, the CPI comprises (i) a first antibody or antigen-binding fragment thereof which binds specifically to PD-1, and (ii) a second antibody or antigen-binding fragment thereof which binds specifically to TIM3.

In certain embodiments, the CPI comprises (i) a first antibody or antigen-binding fragment thereof which binds specifically to PD-1, and (ii) a second antibody or antigen-binding fragment thereof which binds specifically to LAG3.

In certain embodiments, the CPI comprises (i) a first antibody or antigen-binding fragment thereof which binds specifically to PD-L1, and (ii) a second antibody or antigen-binding fragment thereof which binds specifically to TIM3.

In certain embodiments, the CPI comprises (i) a first antibody or antigen-binding fragment thereof which binds specifically to PD-L1, and (ii) a second antibody or antigen-binding fragment thereof which binds specifically to LAG3.

In certain embodiments, the CPI comprises (i) a first antibody or antigen-binding fragment thereof which binds specifically to TIM3, and (ii) a second antibody or antigen-binding fragment thereof which binds specifically to LAG3.

In certain embodiments, the CPI comprises a bispecific antibody or bispecific antigen-binding fragment thereof which binds specifically to CTLA-4 and to an antigen selected from the group consisting of PD-1 and PD-L1.

In certain embodiments, the CPI comprises a bispecific antibody or bispecific antigen-binding fragment thereof which binds specifically to CTLA-4 and to PD-1.

In certain embodiments, the CPI comprises a bispecific antibody or bispecific antigen-binding fragment thereof which binds specifically to CTLA-4 and to PD-L1.

In certain embodiments, the CPI comprises a bispecific antibody or bispecific antigen-binding fragment thereof which binds specifically to CTLA-4 and to TIM3.

In certain embodiments, the CPI comprises a bispecific antibody or bispecific antigen-binding fragment thereof which binds specifically to CTLA-4 and to LAG3.

In certain embodiments, the CPI comprises a bispecific antibody or bispecific antigen-binding fragment thereof which binds specifically to PD-1 and to PD-L1.

In certain embodiments, the CPI comprises a bispecific antibody or bispecific antigen-binding fragment thereof which binds specifically to PD-1 and to TIM3.

In certain embodiments, the CPI comprises a bispecific antibody or bispecific antigen-binding fragment thereof which binds specifically to PD-1 and to LAG3.

In certain embodiments, the CPI comprises a bispecific antibody or bispecific antigen-binding fragment thereof which binds specifically to PD-L1 and to TIM3.

In certain embodiments, the CPI comprises a bispecific antibody or bispecific antigen-binding fragment thereof which binds specifically to PD-L1 and to LAG3.

In certain embodiments, the CPI comprises a bispecific antibody or bispecific antigen-binding fragment thereof which binds specifically to TIM3 and to LAG3.

In certain embodiments, the TLR9 agonist is administered prior to administration of the CPI.

In certain embodiments, the TLR9 agonist and the CPI are administered substantially at the same time.

In certain embodiments, the cancerous tumor is a lymphoma or a cancerous tumor of a tissue selected from the group consisting of skin, head and neck, esophagus, stomach, liver, colon, rectum, pancreas, lung, breast, cervix, ovary, kidney, bladder, prostate, thyroid, brain, muscle, and bone.

In certain embodiments, the cancerous tumor is melanoma.

In certain embodiments, the cancerous tumor is lymphoma.

In certain embodiments, the cancerous tumor is a cancer of the bone marrow.

In certain embodiments, the cancerous tumor is a carcinoid tumor.

In certain embodiments, the cancerous tumor is neuroblastoma.

In certain embodiments, the subject is a human.

An aspect of the invention is a method of treating a cancerous tumor, comprising administering to a subject in need thereof an effective amount of a TLR9 agonist, a first checkpoint inhibitor (CPI), and a second CPI, wherein the TLR9 agonist and the first CPI are administered into or substantially adjacent to the tumor, and the second CPI is administered systemically.

In certain embodiments, the TLR9 agonist induces IFN-α.

In certain embodiments, the TLR9 agonist is CpG DNA.

In certain embodiments, the TLR9 agonist is selected from the group consisting of A-class CpG DNA, C-class CpG DNA, E-class CpG DNA, P-class CpG DNA, and any combination thereof.

In certain embodiments, the TLR9 agonist is an A-class CpG DNA.

In certain embodiments, the TLR9 agonist is a C-class CpG DNA.

In certain embodiments, the TLR9 agonist is an E-class CpG DNA.

In certain embodiments, the TLR9 agonist is an A/E-class CpG DNA.

In certain embodiments, the TLR9 agonist is a P-class CpG DNA.

In certain embodiments, the TLR9 agonist has a sequence provided as:

```
                                            (SEQ ID NO: 82)
  5'-GGGGGGGGGGGACGATCGTCGGGGGGGGGG-3'.
```

In certain embodiments the TLR9 agonist is a circular CpG DNA with a native backbone, e.g., MGN1703.

In certain embodiments the TLR9 agonist is an unmodified native CpG DNA administered in a formulation comprising a nanoparticle, VLP, ISCOM or other nuclease-resistant delivery vehicle.

In certain embodiments, the first CPI is an antibody or antigen-binding fragment thereof which binds specifically to CTLA-4.

In certain embodiments, the first CPI is an antibody or antigen-binding fragment thereof which binds specifically to CTLA-4; and the second CPI is an antibody or antigen-binding fragment thereof which binds specifically to PD-1.

In certain embodiments, the first CPI is an antibody or antigen-binding fragment thereof which binds specifically to CTLA-4; and the second CPI is an antibody or antigen-binding fragment thereof which binds specifically to PD-L1.

In certain embodiments, the first CPI is an antibody or antigen-binding fragment thereof which binds specifically to CTLA-4; and the second CPI is an antibody or antigen-binding fragment thereof which binds specifically to TIM3.

In certain embodiments, the first CPI is an antibody or antigen-binding fragment thereof which binds specifically to CTLA-4; and the second CPI is an antibody or antigen-binding fragment thereof which binds specifically to LAG3.

In certain embodiments, the first CPI is an antibody or antigen-binding fragment thereof which binds specifically to PD-1.

In certain embodiments, the first CPI is an antibody or antigen-binding fragment thereof which binds specifically to PD-1; and the second CPI is an antibody or antigen-binding fragment thereof which binds specifically to CTLA-4.

In certain embodiments, the first CPI is an antibody or antigen-binding fragment thereof which binds specifically to PD-1; and the second CPI is an antibody or antigen-binding fragment thereof which binds specifically to PD-L1.

In certain embodiments, the first CPI is an antibody or antigen-binding fragment thereof which binds specifically to PD-1; and the second CPI is an antibody or antigen-binding fragment thereof which binds specifically to TIM3.

In certain embodiments, the first CPI is an antibody or antigen-binding fragment thereof which binds specifically to PD-1; and the second CPI is an antibody or antigen-binding fragment thereof which binds specifically to LAG3.

In certain embodiments, the first CPI is an antibody or antigen-binding fragment thereof which binds specifically to PD-L1.

In certain embodiments, the first CPI is an antibody or antigen-binding fragment thereof which binds specifically to PD-L1; and the second CPI is an antibody or antigen-binding fragment thereof which binds specifically to CTLA-4.

In certain embodiments, the first CPI is an antibody or antigen-binding fragment thereof which binds specifically to PD-L1; and the second CPI is an antibody or antigen-binding fragment thereof which binds specifically to PD-1.

In certain embodiments, the first CPI is an antibody or antigen-binding fragment thereof which binds specifically to PD-L1; and the second CPI is an antibody or antigen-binding fragment thereof which binds specifically to TIM3.

In certain embodiments, the first CPI is an antibody or antigen-binding fragment thereof which binds specifically to PD-L1; and the second CPI is an antibody or antigen-binding fragment thereof which binds specifically to LAG3.

In certain embodiments, the first CPI is an antibody or antigen-binding fragment thereof which binds specifically to TIM3.

In certain embodiments, the first CPI is an antibody or antigen-binding fragment thereof which binds specifically to TIM3; and the second CPI is an antibody or antigen-binding fragment thereof which binds specifically to CTLA-4.

In certain embodiments, the first CPI is an antibody or antigen-binding fragment thereof which binds specifically to TIM3; and the second CPI is an antibody or antigen-binding fragment thereof which binds specifically to PD-1.

In certain embodiments, the first CPI is an antibody or antigen-binding fragment thereof which binds specifically to TIM3; and the second CPI is an antibody or antigen-binding fragment thereof which binds specifically to PD-L1.

In certain embodiments, the first CPI is an antibody or antigen-binding fragment thereof which binds specifically to TIM3; and the second CPI is an antibody or antigen-binding fragment thereof which binds specifically to LAG3.

In certain embodiments, the first CPI is an antibody or antigen-binding fragment thereof which binds specifically to LAG3.

In certain embodiments, the first CPI is an antibody or antigen-binding fragment thereof which binds specifically to LAG3; and the second CPI is an antibody or antigen-binding fragment thereof which binds specifically to CTLA-4.

In certain embodiments, the first CPI is an antibody or antigen-binding fragment thereof which binds specifically to LAG3; and the second CPI is an antibody or antigen-binding fragment thereof which binds specifically to PD-1.

In certain embodiments, the first CPI is an antibody or antigen-binding fragment thereof which binds specifically to LAG3; and the second CPI is an antibody or antigen-binding fragment thereof which binds specifically to PD-L1.

In certain embodiments, the first CPI is an antibody or antigen-binding fragment thereof which binds specifically to LAG3; and the second CPI is an antibody or antigen-binding fragment thereof which binds specifically to TIM3.

In certain embodiments, the TLR9 agonist is administered prior to administration of the first CPI.

In certain embodiments, the TLR9 agonist and the first CPI are administered substantially at the same time.

In certain embodiments, the TLR9 agonist is administered after administration of the first CPI.

In certain embodiments, the cancerous tumor is a lymphoma or a cancerous tumor of a tissue selected from the group consisting of skin, head and neck, esophagus, stomach, liver, colon, rectum, pancreas, lung, breast, cervix, ovary, kidney, bladder, prostate, thyroid, brain, muscle, and bone.

In certain embodiments, the cancerous tumor is melanoma.

In certain embodiments, the cancerous tumor is lymphoma.

In certain embodiments, the cancerous tumor is a cancer of the bone marrow.

In certain embodiments, the cancerous tumor is a carcinoid tumor.

In certain embodiments, the cancerous tumor is neuroblastoma.

In certain embodiments, the subject is a human.

In certain embodiments, the method includes administering to a subject in need thereof an effective amount of radiotherapy (XRT). Standard XRT doses are in the range of 1.8 to 2.2 Gy/day, but recent studies indicate that the immune effects of XRT on tumors may be increased through the use of XRT at doses of 3-20 Gy/d for 1-3 days. Those expert in the art will recognize that different tumors have differing levels of radio-sensitivity, and will adjust the amount and intensity of the XRT accordingly.

In certain embodiments, the radiotherapy is radiotherapy.

In certain embodiments, the radiotherapy is hypofractionated radiotherapy.

V. Additional Combination Therapy

Methods of the invention can be used in conjunction with other anti-cancer therapies, including chemotherapy, other immunotherapy, radiotherapy, hormone therapy, and the like. Conventional chemotherapeutics and targeted antineoplastic agents have been developed based on the simplistic notion that cancer constitutes a cell-autonomous genetic or epigenetic disease. However, it is becoming clear that many of the available anticancer drugs that have collectively saved millions of life-years mediate therapeutic effects by eliciting de novo or reactivating pre-existing tumor-specific immune responses. Accumulating evidence indicates that the therapeutic efficacy of several antineoplastic agents relies on their capacity to influence the tumor-host interaction, tipping the balance toward the activation of an immune response specific for malignant cells.

For example, Table 1 lists certain FDA-approved anticancer agents whose efficacy is reduced by immune deficiencies (Zitvogel L. et al., *Immunity* 2013 39(1):74-88).

TABLE 1

| Agent | Tumor | Immune Defects |
|---|---|---|
| 5-fluorouracil | EL4 lymphomas | Nu/Nu genotype |
| anthracyclines | CT26 colorectal carcinomas, MCA205 fibrosarcomas, MCA-induced tumors | Nu/Nu genotype, depletion of $CD8^+$ or $\gamma/\delta$ T cells, blockade of CD11b, neutralization of IL-1, IL-17, or IFN-$\gamma$ |
| ATRA ± arsenic trioxide | murine APLs | SCID phenotype |
| arsenic trioxide | CT26 colorectal cancers | Nu/Nu genotype |
| cisplatin + digoxin | MCA205 fibrosarcomas | Nu/Nu genotype |
| cyclophosphamide | AB1-HA mesotheliomas | $Ifngr2^{-/-}$, $Tnfsf10^{-/-}$, depletion of $CD8^+$ T cells or NK cells |
| dasatinib | P815 mastocytomas | depletion of $CD4^+$ or $CD8^+$ T cells |
| gemcitabine | AB12 mesotheliomas, EJ-6-2 fibrosarcomas, EL4 lymphomas, TC1 insulinomas | Nu/Nu genotype |
| imatinib | AK7 mesotheliomas, B16 melanomas, RMA-S lymphomas GISTs developing in $Kit^{V558/+}$ mice | depletion of NK cells $Rag1^{-/-}$, depletion of $CD8^+$ T cells |
| mitomycin C + digoxin | MCA205 fibrosarcomas | Nu/Nu genotype |
| oxaliplatin | CT26 colorectal carcinomas, MCA205 fibrosarcomas | Nu/Nu genotype |
| paclitaxel | Ret-driven melanomas | depletion of $CD8^+$ T cells |
| PLX4720 (BRAF inhibitor) | SM1WT1 melanomas | $Ccr2^{-/-}$, $Ifng^{-/-}$, $Prf1^{-/-}$, depletion of $CD8^+$ T cells |

Table 1 Abbreviations:
APL, acute promyelocytic leukemia;
ATRA, all-trans retinoic acid;
BRAF, B-Raf;
GIST, gastrointestinal stromal tumor;
IFN, interferon;
IL, interleukin;
MCA, 3-methylcholanthrene;
NK, natural killer;
SCID, severe combined immunodeficient

VI. Dosage Regimens

Dosage regimens can be adjusted to provide the optimum desired response. For example, a single bolus can be administered, several divided doses can be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient can also be determined, as can the temporal requirements for administering each agent to provide a detectable therapeutic benefit to the patient. Accordingly, while certain dose and administration regimens are exemplified herein, these examples in no way limit the dose and administration regimen that can be provided to a patient in practicing the present invention. Further, one skilled in the art would understand, once armed with the teachings provided herein, that a therapeutic benefit, such as, but not limited to, detectable decrease in tumor size and/or metastasis, and increased time to recurrence, among many other parameters, can be assessed by a wide variety of methods known in the art for assessing the efficacy of treatment of cancer, and these methods are encompassed herein, as well as methods to be developed in the future.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the active compound or compounds are well-known in the relevant art and would be understood to be encompassed by the skilled artisan once provided the teachings disclosed herein.

CpG ODN Dosing

In accordance with the methods of the present invention, CpG ODN is administered locally to the cancerous tumor, i.e., by intratumoral or peritumoral administration. Alternatively or in addition, in certain embodiments CpG ODN is administered locally to the cancerous tumor by, for example, intraperitoneal injection or infusion or intravesicular instillation.

Most of the prior art with CpG used subcutaneous administration, not intratumoral or peritumoral. Intratumoral therapy in oncology is generally preferred only for the treatment of primary lesions, not in the situation of metastatic disease. The reason for this is that most intratumoral therapies have only a local effect. In some unusual cases, intratumoral therapies can lead to regression of distant tumor masses as a result of the induction of a specific immune response against tumor antigens present not only in the injected lesion, but also in distant metastases. In the case of radiotherapy (XRT), this has been termed an "abscopal effect" as described above. Some authors have noted cases in which abscopal effects have been induced by TLR agonists, including intratumoral TLR9 (Brody et al, *J. Clin. Oncol.* 2010 28(28): 4324-4332; Kim et al., *Blood* 2012 119(2): 355-363), but these responses have been uncommon and generally of brief duration.

The immune effects of XRT given prior to CpG ODN administration will disrupt the inhibitory mechanisms that normally limit the efficacy of the CpG-induced response, increasing the potential for clinical response. In addition, the production of IFN-α in the tumor has been associated with and is required for an improved response to XRT (Burnette et al, *Cancer Res.* 2011 71: 2488-2496), providing further evidence for benefit from the use of intratumoral high IFN CpG following XRT.

In one form, the present invention comprises a method for improving the induction of abscopal responses from XRT by administering XRT, preferably hypofractionated XRT (as described in Prasanna et al.), to a cancer patient and then administering an intratumoral or peritumoral high IFN-inducing CpG ODN in the same region or lymphatic drainage. Preferred peritumoral injections are in the same lymphatic drainage as the tumor, in order to facilitate that the same APC are exposed both to the tumor Ag released following XRT to the tumor, and to the TLR ligand.

Methods of intratumoral or peritumoral delivery of CpG ODN include not only direct injection, but also can include topical delivery intraperitoneal delivery for abdominal tumors such as ovarian, pancreatic, colon, or gastric), intraocular for eye malignancies, oral for gastric and intestinal cancer, and intravesicular administration for bladder cancer. Also contemplated for intratumoral administration of CpG ODN is systemic delivery using tumor delivery vehicles such as tumor-targeted aptamers, antibody conjugates, nanoparticles, ISCOMS, VLP, multilaminar vesicles, pH-sensitive peptides, and cationic peptides.

For systemic therapy, CpG ODN can be variably dosed based on weight, body surface area, or using a fixed dose. For intratumoral or peritumoral administration, the CpG ODN dose typically is fixed. Doses of CpG ODN for parenteral (including intratumoral and peritumoral) delivery for inducing an immune response when CpG ODN is administered in combination with other therapeutic agents, such as the CPI of the invention, typically range from about 1 μg to 100 mg per administration, which depending on the application could be given daily, weekly, or monthly and any other amount of time therebetween.

In certain embodiments, subject doses of CpG ODN for intratumoral and peritumoral delivery typically range from about 10 μg to about 100 mg per administration, which depending on the application could be given daily, weekly, or monthly and any other amount of time therebetween. In certain embodiments, subject doses of CpG ODN for intratumoral and peritumoral delivery typically range from about 100 μg to about 100 mg per administration, which depending on the application could be given daily, weekly, or monthly and any other amount of time therebetween. In certain embodiments, subject doses of CpG ODN for intratumoral and peritumoral delivery typically range from about 1 mg to about 100 mg per administration, which depending on the application could be given daily, weekly, or monthly and any other amount of time therebetween. In certain embodiments, subject doses of CpG ODN for intratumoral and peritumoral delivery typically range from about 10 mg to about 100 mg per administration, which depending on the application could be given daily, weekly, or monthly and any other amount of time therebetween.

In yet other embodiments, doses of CpG ODN for parenteral (including intratumoral and peritumoral) delivery for inducing an immune response when CpG ODN is administered in combination with other therapeutic agents, such as the CPI of the invention, typically range from about 1 μg to about 50 mg per administration, which depending on the application could be given daily, weekly, or monthly and any other amount of time therebetween. In certain embodiments, subject doses of CpG ODN for intratumoral and peritumoral delivery typically range from about 10 μg to about 50 mg per administration, which depending on the application could be given daily, weekly, or monthly and any other amount of time therebetween. In certain embodiments, subject doses of CpG ODN for intratumoral and peritumoral delivery typically range from about 100 μg to about 50 mg per administration, which depending on the application could be given daily, weekly, or monthly and any other amount of time therebetween. In certain embodiments, subject doses of CpG ODN for intratumoral and peritumoral delivery typically range from about 1 mg to about 50 mg per administration, which depending on the application could be given daily, weekly, or monthly and any other amount of time therebetween. In certain embodiments, subject doses of CpG ODN for intratumoral and peritumoral delivery typically range from about 10 mg to about 50 mg per administration, which depending on the application could be given daily, weekly, or monthly and any other amount of time therebetween.

In yet other embodiments, doses of CpG ODN for parenteral (including intratumoral and peritumoral) delivery for inducing an immune response when CpG ODN is administered in combination with other therapeutic agents, such as the CPI of the invention, typically range from about 1 μg to about 10 mg per administration, which depending on the application could be given daily, weekly, or monthly and any other amount of time therebetween. In certain embodiments, subject doses of CpG ODN for intratumoral and peritumoral delivery typically range from about 10 μg to about 10 mg per administration, which depending on the application could be given daily, weekly, or monthly and any other amount of time therebetween. In certain embodiments, subject doses of CpG ODN for intratumoral and peritumoral delivery typically range from about 100 μg to about 10 mg per administration, which depending on the application could be given daily, weekly, or monthly and any other amount of time therebetween. In certain embodiments, subject doses of CpG ODN for intratumoral and peritumoral delivery typically range from about 1 mg to about 10 mg per administration, which depending on the application could be given daily, weekly, or monthly and any other amount of time therebetween.

In yet other embodiments, doses of CpG ODN for parenteral (including intratumoral and peritumoral) delivery for inducing an immune response when CpG ODN is administered in combination with other therapeutic agents, such as the CPI of the invention, typically range from about 1 µg to about 1 mg per administration, which depending on the application could be given daily, weekly, or monthly and any other amount of time therebetween. In certain embodiments, subject doses of CpG ODN for intratumoral and peritumoral delivery typically range from about 10 µg to about 1 mg per administration, which depending on the application could be given daily, weekly, or monthly and any other amount of time therebetween. In certain embodiments, subject doses of CpG ODN for intratumoral and peritumoral delivery typically range from about 100 µg to about 1 mg per administration, which depending on the application could be given daily, weekly, or monthly and any other amount of time therebetween.

For each of the fixed doses described above, in certain embodiments the dose will be administered in a volume of less than or equal to about 1 mL. In certain embodiments, the dose will be administered in a volume of about 0.1 mL up to about 1 mL. In other embodiments, the dose volume will be up to 4 mL, which is commonly used for intratumoral injection of certain oncolytic viruses, such as talimogene laherparepvec (T-vec).

In certain embodiments of the invention, a sustained release delivery system, including for example nanoparticles, ISCOMS, VLP, and dendrimers (reviewed in, for example, Gomes Dos Santos A L et al., *Curr Pharm Biotechnol.* 2005 6(1): 7-15; Joshi V B et al., *AAPS* 2013 15(1): 85-94; and Arima H et al., *Curr Top Med Chem.* 2014 14(4): 465-77), may be used to administer a single intratumoral or peritumoral therapeutic dose of the CpG ODN. In certain embodiments of the invention, a sustained release delivery system, including for example nanoparticles, ISCOMS, VLP, and dendrimers, may be used to administer a single intratumoral or peritumoral therapeutic dose of the CpG ODN, with no further CpG ODN required.

As is well known in the art, individual doses are increased when using a sustained delivery system of any of the types well described in the literature.

In certain embodiments using a single administration of a sustained release formulation of CpG ODN, the subject dose of CpG ODN for intratumoral and peritumoral delivery typically ranges from about 0.1 mg to about 500 mg per administration, and it is given within one week of XRT; within one week of a checkpoint inhibitor; or within one week of both XRT and a checkpoint inhibitor. In certain embodiments using a single administration of a sustained release formulation of CpG ODN, the subject dose of CpG ODN for intratumoral and peritumoral delivery typically ranges from about 1 mg to about 500 mg per administration, and it is given within one week of XRT; within one week of a checkpoint inhibitor; or within one week of both XRT and a checkpoint inhibitor. In certain embodiments using a single administration of a sustained release formulation of CpG ODN, the subject dose of CpG ODN for intratumoral and peritumoral delivery typically ranges from about 10 mg to about 500 mg per administration, and it is given within one week of XRT; within one week of a checkpoint inhibitor; or within one week of both XRT and a checkpoint inhibitor. In certain embodiments using a single administration of a sustained release formulation of CpG ODN, the subject dose of CpG ODN for intratumoral and peritumoral delivery typically ranges from about 100 mg to about 500 mg per administration, and it is given within one week of XRT; within one week of a checkpoint inhibitor; or within one week of both XRT and a checkpoint inhibitor.

In certain embodiments using a single administration of a sustained release formulation of CpG ODN, the subject doses of CpG ODN for intratumoral and peritumoral delivery typically range from about 0.1 mg to about 250 mg per administration, and it is given within one week of XRT; within one week of a checkpoint inhibitor; or within one week of both XRT and a checkpoint inhibitor. In certain embodiments using a single administration of a sustained release formulation of CpG ODN, the subject dose of CpG ODN for intratumoral and peritumoral delivery typically ranges from about 1 mg to about 250 mg per administration, and it is given within one week of XRT; within one week of a checkpoint inhibitor; or within one week of both XRT and a checkpoint inhibitor. In certain embodiments using a single administration of a sustained release formulation of CpG ODN, the subject dose of CpG ODN for intratumoral and peritumoral delivery typically ranges from about 10 mg to about 250 mg per administration, and it is given within one week of XRT; within one week of a checkpoint inhibitor; or within one week of both XRT and a checkpoint inhibitor. In certain embodiments using a single administration of a sustained release formulation of CpG ODN, the subject dose of CpG ODN for intratumoral and peritumoral delivery typically ranges from about 100 mg to about 250 mg per administration, and it is given within one week of XRT; within one week of a checkpoint inhibitor; or within one week of both XRT and a checkpoint inhibitor.

In certain embodiments using a single administration of a sustained release formulation of CpG ODN, the subject dose of CpG ODN for intratumoral and peritumoral delivery typically ranges from about 0.1 mg to about 100 mg per administration, and it is given within one week of XRT; within one week of a checkpoint inhibitor; or within one week of both XRT and a checkpoint inhibitor. In certain embodiments using a single administration of a sustained release formulation of CpG ODN, the subject dose of CpG ODN for intratumoral and peritumoral delivery typically ranges from about 1 mg to about 100 mg per administration, and it is given within one week of XRT; within one week of a checkpoint inhibitor; or within one week of both XRT and a checkpoint inhibitor. In certain embodiments using a single administration of a sustained release formulation of CpG ODN, the subject dose of CpG ODN for intratumoral and peritumoral delivery typically ranges from about 10 mg to about 100 mg per administration, and it is given within one week of XRT; within one week of a checkpoint inhibitor; or within one week of both XRT and a checkpoint inhibitor.

The desired clinical effect of the administered dose of CpG ODN can readily be followed using standard assays and methods well known to those skilled in the art. For example, biomarker responses to TLR9 stimulation can be measured as described elsewhere herein.

CPI Antibody Dosing

Certain commercially available anti-PD-1 antibodies are currently approved in the United States for intravenous infusion dosing at 2 mg/kg body weight once every three weeks. Other commercially available anti-PD-1 antibodies are currently approved in the United States for intravenous infusion dosing at 3 mg/kg body weight once every two weeks. Commercially available anti-CTLA-4 antibodies are currently approved in the United States for intravenous infusion dosing at 3 mg/kg body weight once every three weeks.

In accordance with the methods of the present invention, in certain embodiments, CPI antibody is administered, at least in part, systemically, e.g., intravenously.

Exemplary, non-limiting doses for a therapeutically effective amount of a CPI antibody systemically administered according to the invention are: at least about 0.1 mg/kg body weight, at least about 0.3 mg/kg body weight, at least about 0.5 mg/kg body weight, at least about 1 mg/kg body weight, at least about 2 mg/kg body weight, at least about 3 mg/kg body weight, at least about 4 mg/kg body weight, at least about 5 mg/kg body weight, and at least about 6 mg/kg body weight.

In certain embodiments, a therapeutically effective amount of systemically administered CPI antibody can range from about 0.1 to about 30 mg/kg body weight, about 0.3 to about 25 mg/kg body weight, about 1 to about 20 mg/kg body weight, about 2 to about 20 mg/kg body weight, about 3 to about 20 mg/kg body weight, about 5 to about 20 mg/kg body weight, about 10 to about 20 mg/kg body weight, about 1 to about 15 mg/kg body weight, about 2 to about 15 mg/kg body weight, about 3 to about 15 mg/kg body weight, about 5 to about 15 mg/kg body weight, about 10 to about 15 mg/kg body weight, about 1 to about 10 mg/kg body weight, about 2 to about 10 mg/kg body weight, about 3 to about 10 mg/kg body weight, or about 5 to about 10 mg/kg body weight.

In certain embodiments, the CPI antibody is systemically administered at a dose of at least about 0.3 mg/kg body weight, at least about 1 mg/kg body weight, at least about 2 mg/kg body weight, at least about 3 mg/kg body weight, at least about 5 mg/kg body weight, at least about 6 mg/kg body weight, at least 10 mg/kg body weight, at least about 15 mg/kg body weight, or at least about 20 mg/kg body weight.

In certain embodiments, the CPI antibody is administered by intravenous (i.v.) infusion at a dose ranging from about 0.1 to about 50 mg/kg body weight, from about 0.3 to about 20 mg/kg body weight, from about 1 to about 15 mg/kg body weight, from about 2 to about 15 mg/kg body weight, from about 3 to about 15 mg/kg body weight, or from about 6 to about 15 mg/kg body weight.

In certain embodiments, the CPI antibody is administered in an intravenous formulation as a sterile aqueous solution containing about 5 to about 20 mg/mL of CPI antibody, in an appropriate buffer system.

In accordance with the methods of the present invention, in certain embodiments, CPI antibody is administered, at least in part, locally to the cancerous tumor, i.e., by intratumoral or peritumoral administration. In certain embodiments, such local administration is by direct injection, while in other embodiments, such administration can be topical delivery, intraperitoneal delivery for abdominal tumors such as ovarian, pancreatic, intraocular delivery for eye malignancies, oral delivery for gastric and intestinal cancer, and intravesicular administration for bladder cancer. Also contemplated for intratumoral administration of CPI antibody is systemic delivery using tumor delivery vehicles such as tumor-targeted aptamers, nanoparticles, ISCOMS, VLP, and cationic peptides.

For local, i.e., intratumoral or peritumoral, administration, the CPI antibody advantageously can be administered at a dose about 10-fold less to about 20-fold less than the systemic doses just listed above.

In accordance with the present invention, CPI antibody dosing will typically be less frequent than CpG ODN dosing. For example, anti-PD-1 antibody may be administered about once every three weeks to about once every three months. Similarly, anti-PD-L1 antibody may be administered about once every three weeks to about once every three months. Similarly, anti-CTLA-4 antibody may be administered about once every three weeks to about once every three months. The invention further specifically contemplates CPI antibody dosing that is more frequent than about once every three weeks and less frequent than about once every three months.

Intratumoral or peritumoral CpG and systemic CPI can be given on the same or different days. For example, intratumoral or peritumoral CpG and the intravenous anti-PD-1 or anti-PD-L1 can be given on the same or different days.

Further, an exemplary dose escalation protocol with respect to CpG ODN, CPI antibody, or both CpG ODN and CPI antibody can be used to determine the maximum tolerated dose (MTD), to assess dose-limiting toxicity (DLT), if any, associated with administration of CpG ODN-CPI antibody combination therapy. For example, with respect to CPI antibody dose escalation at a given dose of CpG ODN, such protocol can comprise administering increasing doses, such as, but not limited to about 0.1 mg/kg, 0.3 mg/kg, 1 mg/kg, 2 mg/kg, 3 mg/kg, 4 mg/kg, 5 mg/kg, 6 mg/kg, 7 mg/kg, 10 mg/kg, 12 mg/kg, 15 mg/kg, or more than 15 mg/kg, or any combination thereof, more preferably, successive doses of 0.1 mg/kg, 0.3 mg/kg, 1 mg/kg, 2 mg/kg, 3 mg/kg, 6 mg/kg, 10 mg/kg, 15 mg/kg or 20 mg/kg are administered and the patient is assessed for toxicity, if any, as well as for efficacy of treatment, among other parameters. Such studies to determine toxicity and efficacy of dose regimens are well-known in the art. See, for example, Millward M. et al., *Br. J. Cancer* 2013 108(10):1998-2004.

VII. Pharmaceutical Compositions

In certain embodiments, the CpG ODN is formulated with a marker, e.g., a radio-opaque marker or dye, that facilitates visualization of the CpG ODN administration into and/or adjacent to the tumor to be treated. Alternatively the CpG ODN is covalently conjugated to or otherwise labeled with a compound that enables the detection of the area of administration. Examples of such labels are well known in the art, and include fluorescent dyes, aptamers, fluorescent RNAs such as spinach and derivatives thereof, quantum dots, gold and other nanoparticles, antibodies, etc.

CpG ODN may be directly administered to the subject or may be administered in conjunction with a nucleic acid delivery complex. A nucleic acid delivery complex shall mean a nucleic acid molecule associated with (e.g., ionically or covalently bound to; or encapsulated within) a targeting means (e.g., a molecule that results in higher affinity binding to target cell. Examples of nucleic acid delivery complexes include oligonucleotides associated with a sterol (e.g. cholesterol), a lipid (e.g., a cationic lipid, virosome, or liposome), or a target cell-specific binding agent (e.g., a ligand recognized by target cell specific receptor). Preferred complexes may be sufficiently stable in vivo to prevent significant uncoupling prior to internalization by the target cell.

However, the complex can be cleavable under appropriate conditions within the cell so that the nucleic acid is released in a functional form.

Delivery vehicles or delivery devices for delivering oligonucleotides and/or antigens to surfaces have been described. The CpG ODN and/or the antigen and/or other therapeutics may be administered alone (e.g., in saline or buffer) or using any delivery vehicles known in the art. For instance the following delivery vehicles have been described: Cochleates; Emulsomes, ISCOMs; Liposomes; Live bacterial vectors (e.g., *Salmonella, Escherichia coli, Bacillus Calmette-Guerin, Shigella, Lactobacillus*); Live viral vectors (e.g., Vaccinia, adenovirus, Herpes Simplex); Microspheres; Oligonucleotide vaccines; Polymers; Polymer rings; Proteosomes; Sodium Fluoride; Transgenic plants; Virosomes; Virus-like particles, and cationic lipids, peptides, or other carriers that have a charge interaction with the polyanionic oligonucleotide. Other delivery vehicles are known in the art and some additional examples are provided below in the discussion of vectors.

In one embodiment, the CPI is administered parenterally (e.g., intravenously) in an aqueous solution while the CpG ODN is administered by intratumoral or peritumoral injection. Preferred formulations and dosage forms of the CpG ODN are described in U.S. Patent Application Publication No. US 2004/0198680, the disclosure of which is incorporated herein by reference in its entirety. However, the skilled artisan would understand, based upon the disclosure provided herein, that the invention is not limited to these, or any other, formulations, doses, routes of administration, and the like. Thus, the following discussion describes various formulations for practicing the methods of the invention comprising administration of any CPI antibody in combination with a CpG ODN, but the invention is not limited to these formulations, but comprises any formulation as can be readily determined by one skilled in the art once armed with the teachings provided herein for use in the methods of the invention.

The antibodies employed in the invention can be incorporated into pharmaceutical compositions suitable for administration to a subject. Typically, the pharmaceutical composition comprises the antibody and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, trehalose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion.

The antibodies may be in a variety of forms. These include, for example, liquid, semi solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the antibody in the required amount in an appropriate solvent with one or a combination of ingredients enumerated above, as required, followed by filter sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The CpG ODN can be administered by a variety of methods known in the art, including, without limitation, local injection or infusion into and/or adjacent to a tumor. As used herein, "into a tumor" or "intratumoral" means anywhere generally within the margins of a tumor. As used herein, "adjacent to a tumor" or "peritumoral" means anywhere generally within about a 2.5 cm thick zone surrounding the margins of a tumor. The invention also contemplates local injection or infusion of the CpG ODN into and/or adjacent to a tumor bed following surgical resection of a tumor. Non-needle injection may be employed, if desired. In certain embodiments the CpG ODN can be administered locally to lung by inhalation or bronchoalveolar lavage. As will be appreciated by the skilled artisan, the route and/or mode of administration will vary depending upon the desired results.

The CPI can be administered by a variety of methods known in the art, including, without limitation, oral, parenteral, mucosal, by-inhalation, topical, buccal, nasal, and rectal. For certain therapeutic applications, the preferred route/mode of administration is subcutaneous, intramuscular, intravenous or infusion. Non-needle injection may be employed, if desired. As will be appreciated by the skilled artisan, the route and/or mode of administration will vary depending upon the desired results.

Dosage regimens may be adjusted to provide the optimum desired response. For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the antibody and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated, and may include single or multiple doses. It is to be further understood that for any particular subject, specific dosage regimens may be adjusted over time according to the individual need and the professional judgment of the person administering or supervising the administration of the compositions, and that dosage ranges set forth herein are exemplary only and are not intended to limit the scope or practice of the claimed composition.

In one embodiment, the antibody is administered in an intravenous formulation as a sterile aqueous solution containing 5 or 10 mg/mL of antibody, with sodium acetate, polysorbate 80, and sodium chloride at a pH ranging from about 5 to 6. Preferably, the intravenous formulation is a sterile aqueous solution containing 5 or 10 mg/mL of antibody, with 20 mM sodium acetate, 0.2 mg/ml polysorbate 80, and 140 mM sodium chloride at pH 5.5.

In one embodiment, part of the dose is administered by an intravenous bolus and the rest by infusion of the antibody formulation. For example, a 0.01 mg/kg intravenous injection of the antibody may be given as a bolus, and the rest of a predetermined antibody dose may be administered by intravenous injection. A predetermined dose of the antibody may be administered, for example, over a period of an hour and a half to two hours to five hours.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics, anti-diarrheals, chemotherapeutic agents, cytokines, and the like.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, intraperitoneal, intramuscular, subcutaneous, intracisternal, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (e.g., powder or granular) form for reconstitution with a suitable vehicle (e.g., sterile pyrogen-free water) prior to parenteral administration of the reconstituted composition.

A composition of the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, (1978). Pharmaceutical compositions are preferably manufactured under GMP conditions.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The CpG ODN and CPI active ingredient components of the invention can be administered to an animal, preferably a mammal, more preferably a human. The precise dosage administered of each active ingredient will vary depending upon any number of factors, including but not limited to, the type of animal and type of disease state being treated, the age of the animal and the route(s) of administration.

The CpG ODN and CPI active ingredient components of the invention may be co-administered with any of numerous other compounds (antihormonal therapy agents, cytokines, anti-cytokine antibodies, or anti-cytokine receptor antibodies, inhibitors of indoleamine 2,3-dioxygenase (IDO) or tryptophan 2,3-dioxygenase (TDO), chemotherapeutic, antibiotic and/or antiviral drugs, among many others). Alternatively, such other compound(s) may be administered an hour, a day, a week, a month, or even more, in advance of the CpG ODN-CPI combination, or any permutation thereof. Further, such other compound(s) may be administered an hour, a day, a week, or even more, after administration of radiation, stem cell transplant, or administration of any therapeutic agent (e.g., cytokine, chemotherapeutic compound, and the like), or any permutation thereof. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds, and the like. Several instructive examples demonstrating methods of co-administering CpG ODN-CPI combination to treat cancer are provided, but the invention is not limited in any way to these examples, which merely serve to illustrate methods encompassed by the invention.

VIII. Kits

The invention includes various kits for treatment of cancer. The kits comprise a therapeutically effective amount of CpG ODN and a therapeutically effective amount of a CPI, along with instructional materials which describe use of the combination to perform the methods of the invention. In certain embodiments, the kits comprise a therapeutically effective amount of CpG ODN and a therapeutically effective amount of a CPI antibody, along with instructional materials which describe use of the combination to perform the methods of the invention. Although exemplary kits are described below, the contents of other useful kits will be apparent to the skilled artisan in light of the present disclosure. Each of these kits is included within the invention.

In one embodiment, the invention encompasses a kit comprising any combination of CpG ODN and an anti-PD-1 antibody. While such kit is preferred, the invention is not limited to this particular combination. Further, the kit can comprise a wide plethora of additional agents for treatment of cancer. Such agents are set forth previously and include chemotherapeutic compounds, cancer vaccines, TLR agonists other than a CpG ODN, other CpG ODNs, receptor tyrosine kinase inhibitors (such as, but not limited to, SU11248), agents useful in treating abnormal cell growth or cancer, antibodies or other ligands that inhibit tumor growth by binding to IGF-1R, a chemotherapeutic agent (taxane, vinca alkaloid, platinum compound, intercalating antibiotics, among many others), and cytokines, among many others, as well as palliative agents to treat, e.g., any toxicities that arise during treatment such as, but not limited to, an anti-diarrheal, an anti-emetic, and the like.

In one embodiment, the invention encompasses a kit comprising any combination of CpG ODN and an anti-PD-L1 antibody. While such kit is preferred, the invention is not limited to this particular combination. Further, the kit can comprise a wide plethora of additional agents for treatment of cancer. Such agents are set forth previously and include chemotherapeutic compounds, cancer vaccines, TLR agonists other than a CpG ODN, other CpG ODNs, receptor tyrosine kinase inhibitors (such as, but not limited to, SU11248), agents useful in treating abnormal cell growth or cancer, antibodies or other ligands that inhibit tumor growth by binding to IGF-1R, a chemotherapeutic agent (taxane, vinca alkaloid, platinum compound, intercalating antibiotics, among many others), and cytokines, among many others, as well as palliative agents to treat, e.g., any toxicities that arise during treatment such as, but not limited to, an anti-diarrheal, an anti-emetic, and the like.

In one embodiment, the invention encompasses a kit comprising any combination of CpG ODN and an anti-CTLA-4 antibody. In one embodiment the kit is used for both agents to be administered together via an intratumoral or peritumoral route, weekly for a course of therapy. When the anti-CTLA-4 antibody is delivered by intratumoral or peritumoral administration instead of systemic, the dose will be adjusted as familiar to those skilled in the art: preferred doses of intratumoral anti-CTLA-4 antibody are given as a fixed dose, generally in the range from 0.1 mg to 10 mg, and most preferably in the range from 1 mg to 5 mg. A course of therapy may vary in duration as is standard in the art, but will typically be at least 12 weeks in duration. As long as patients do not develop serious toxicity, and continue to have measurable tumor, the treatment can be continued, even for a period of several years. Drug holidays and breaks from treatment are encompassed as well. Breaks in treatment may be 1 week, 2 weeks, or longer, and may be provided every month, or less often, or provided depending on patient tolerability. While such kit is preferred, the invention is not limited to this particular combination. Further, the kit can comprise a wide plethora of additional agents for treatment of cancer. Such agents are set forth previously and include chemotherapeutic compounds, cancer vaccines, TLR agonists other than a CpG ODN, other CpG ODNs, receptor tyrosine kinase inhibitors (such as, but not limited to, SU11248), agents useful in treating abnormal cell growth or cancer, antibodies or other ligands that inhibit tumor growth by binding to IGF-1R, a chemotherapeutic agent (taxane, vinca alkaloid, platinum compound, intercalating antibiotics, among many others), and cytokines, among many others, as well as palliative agents to treat, e.g., any toxicities that arise during treatment such as, but not limited to, an anti-diarrheal, an anti-emetic, and the like.

Having now described the present invention in detail, the same will be more clearly understood by reference to the following examples, which are included herewith for purposes of illustration only and are not intended to be limiting of the invention.

EXAMPLES

Example 1

In order to achieve optimal synergy for a combination of a CpG ODN and checkpoint inhibitor (+/−XRT), the CpG ODN should be designed to induce the maximal level of type I IFN possible, with the lowest level of IL-10 possible. Of the CpG ODN classes described above, the closest to this ideal is the A-class. In order to improve the A-class ODN, they can be understood in terms of two semi-independent components: (i) the 5' and 3' termini of the A-class CpG ODN, and (ii) the core palindrome. The purpose of the polyG domains in the 5' and 3' termini is to form G tetrads that self-assemble into nanoparticles, positioning the palindromes in a favorable way to activate TLR9, and providing a very strong multimerization of TLR9 in the early endosomes, leading to strong IRF3/7 activation (and downstream IFN-α secretion) without triggering a more sustained signal that would lead to B cell activation and strong IL-10 production. The G tetrads formed by the polyG domains may also help to stabilize the ODN extracellularly and improve ODN uptake into dendritic cells (DC) and other APC by interacting with scavenger receptors and other cell surface receptors that bind G tetrads. The polyG domains often have one or a few PS linkages at the 5' and 3' ends, but this is not required for high level stimulation of pDC IFN-α secretion, especially if the dosage is increased, or the ODN is delivered using a stabilizing formulation, such as a nanoparticle, VLP, ISCOM, or the like. The purpose of the palindrome is to form a duplex outside the cell, stabilizing a structure that will be taken up effectively by the target DC into endosomes and then will activate TLR9 in a transient manner to induce IRF3/7 without strong NF-κB activation.

Optimization of the 5' and 3' Termini of A-Class ODN

1. Number of Gs.

A-class ODN described in the prior art nearly always contain 5 or more consecutive Gs at both ends, or at least at one end. However this is not required for the ODN activity, and in fact including fewer Gs makes the ODN much easier to synthesize, and does not necessarily dramatically impact the amount of IFN-α induced. In accordance with the instant invention, certain preferred A-class ODN have 4 Gs at one or both ends, while other preferred A-class ODN have more than 6 Gs, 10 Gs, or more than 10 Gs, at the 5' and 3' ends, or at least at the 3' end of the ODN.

2. Number of Phosphorothioate (PS) Linkages.

Some A-class ODN described in the prior art contain no phosphorothioate linkages at all, but usually they have two phosphorothioate internucleotide linkages at the 5' end of the ODN and five at the 3' end. While these phosphorothioate linkages do stabilize the ODN against nucleases and increase protein binding and cell surface uptake to some degree, they also introduce chiral centers and increase the complexity of manufacturing. Certain preferred A-class ODN of the invention contain 0, 1, or 2 PS linkages at the 5' end, and 2, 3, or 4 PS linkages at the 3' end. In certain embodiments, preferred A-class ODN of the invention contain 1 or 2 PS linkages at the 5' end, and 2, 3, or 4 PS linkages at the 3' end.

3. Chirality of the Phosphorothioate (PS) Linkages.

When A-class ODN disclosed in the prior art have PS linkages, they have always been stereo-random. However, the two stereoisomers have quite different immune effects on the TLR9 signaling, as published previously (Krieg A M et al., *Oligonucleotide* 2003 13(6): 491-9). Improved A-class CpG may have all R, all S, or specified R and S chirality at each position within the polyG domains. When the CpG ODN contains any PS linkage, preferably at least the 3' end of the CpG ODN has a Sp linkage because of its greater resistance to nuclease degradation.

Optimization of the Palindrome of A-Class CpG ODN

1. Positioning of Deoxyadenosine Nucleotides.

Preferred palindromes contain at least one, and preferably two or more deoxyadenosines. These are preferably located in the 5' half of the palindrome, with the consequence that the complementary thymidines are located in the 3' half of the preferred palindromes (except that when the thymidines are modified by a halogen, as described in point 3 below, the preferred palindromes may have deoxyadenosine or thymidine in the 5' or 3' or both regions of the palindrome).

2. Position of CpG Dinucleotides.

Preferred palindromes contain at least one CpG dinucleotide that is preceded by a 5'T and/or at least one CpG dinucleotide preceded by a 5' A.

3. Modifications of Thymidine Nucleosides.

We have defined in the current invention a new type of A-class CpG ODN, which we now call A/E-class CpG ODN, that contains not only the novel design features listed above, but also the modifications to one or more thymidine nucleosides previously described as E-class CpG ODN, as described in U.S. Pat. No. 8,580,268 and U.S. Published Application 2014/0163213. Specifically, preferred A/E-class CpG ODN of the invention contain a halogen-modified uracil in place of one or more of the thymidines in the palindrome. The halogen-modified uracil is most preferably 5-iodo-2'-deoxyuridine ("I"), but also may be 5-bromo-2'-deoxyuridine, or 5-chloro-2'-deoxyuridine.

Examples of preferred A-class CpG ODN are:

```
                                           (SEQ ID NO: 80)
ggGGGACGAGCTCGTCgggggG;

(SEQ ID NO: 58)
ggGGGACGATCGTCGgggggG;

(SEQ ID NO: 81)
ggGGACGATCGAACGTgggggG;

(SEQ ID NO: 78)
ggGGTCGACGTCGACGTCGAGgggggG;
and (SEQ ID NO: 79)
ggGGACGACGTCGTGgggggG,
``` where each lower case letter represents a nucleotide linked to its 3'-adjacent nucleotide by a phosphorothioate (PS) linkage; and each upper case letter represents a nucleotide linked to its 3'-adjacent nucleotide (if present) by a phosphodiester (PO) linkage, except that the 3'-terminal nucleotide is represented by an upper case letter since it has no 3'-adjacent nucleotide.

Examples of preferred novel A-class CpG ODN sequences are:

```
                                           (SEQ ID NO: 502)
gGGGACGATCGTCGgggG;

(SEQ ID NO: 503)
ggGGTCGACGTACGTCGAggggG;

(SEQ ID NO: 504)
gGGGTCGTCGACGAggggG;

(SEQ ID NO: 505)
ggGGACGAGCTCGTCgggggG;

(SEQ ID NO: 506)
ggGGGACGAGCTCGTCgggggG;

(SEQ ID NO: 507)
gGGGACGAGCTCGTCgggggG;

(SEQ ID NO: 508)
gGGGACGAGCTCGTCgggG;
```

```
                                      (SEQ ID NO: 77)
ggGGACGATCGTCGggggG;

(SEQ ID NO: 49)
ggGGGACGATCGTCGggggG;

(SEQ ID NO: 509)
gGGGACGATCGTCGggggG;

(SEQ ID NO: 502)
gGGGACGATCGTCGgggG;

(SEQ ID NO: 81)
gGGGACGATCGAACGTgggggG;

(SEQ ID NO: 510)
ggGGACGATCGAACGTggggG;

(SEQ ID NO: 510)
gGGGACGATCGAACGTggggG;

(SEQ ID NO: 511)
gGGGACGATCGAACGTgggG;

(SEQ ID NO: 78)
gGGGTCGACGTCGACGTCGAGgggggG;

(SEQ ID NO: 512)
ggGGTCGACGTCGACGTCGAGggggG;

(SEQ ID NO: 512)
gGGGTCGACGTCGACGTCGAGggggG;

(SEQ ID NO: 513)
gGGGTCGACGTCGACGTCGAGgggG;

(SEQ ID NO: 514)
gGGGACGACGTCGTGgggGG;

(SEQ ID NO: 79)
gGGGACGACGTCGTGggggG;

(SEQ ID NO: 514)
ggGGACGACGTCGTGggggG;

(SEQ ID NO: 514)
gGGGACGACGTCGTGggggG;

(SEQ ID NO: 515)
gGGGACGACGTCGTGgggG;
and (SEQ ID NO: 516)
ggGTCGTCGACGAggggG,
``` where again each lower case letter represents a nucleotide linked to its 3'-adjacent nucleotide by a phosphorothioate (PS) linkage; and each upper case letter represents a nucleotide linked to its 3'-adjacent nucleotide (if present) by a phosphodiester (PO) linkage, except that the 3'-terminal nucleotide is represented by an upper case letter since it has no 3'-adjacent nucleotide.

Examples of preferred novel A/E-class CpG ODN sequences are:

```
                                      (SEQ ID NO: 1)
gGGGACGAICGTCGgggG;

(SEQ ID NO: 2)
gGGGACGAIATCGTCGggggG;

(SEQ ID NO: 3)
gGGGACGAGCIGCTCGggggG;

(SEQ ID NO: 4)
ggGGICACCGGTGAggggG;

(SEQ ID NO: 5)
ggGGICGACGTACGTCGAggggG;

(SEQ ID NO: 6)
ggGGICGACGIACGTCGAggggG;

(SEQ ID NO: 7)
ggGGICGACGTACGICGAggggG;

(SEQ ID NO: 8)
ggGGICGACGIACGICGAggggG;

(SEQ ID NO: 9)
ggGGACGICGACGTgggG;

(SEQ ID NO: 10)
ggGGICGACGTCGACGTCGAGggggG;

(SEQ ID NO: 11)
ggGGICGACGICGACGTCGAGggggG;

(SEQ ID NO: 12)
ggGGICGACGTCGACGICGAGggggG;

(SEQ ID NO: 13)
ggGGICGACGICGACGICGAGggggG;

(SEQ ID NO: 14)
gGGGACGACGICGIGgggGG;

(SEQ ID NO: 15)
gGGGICGTCGACGAggggG;

(SEQ ID NO: 16)
gGGGTCGICGACGAggggG;

(SEQ ID NO: 17)
gGGGICGICGACGAggggG;

(SEQ ID NO: 18)
ggGGACGAGCICGTCgggggG;

(SEQ ID NO: 19)
ggGGGACGAGCICGTCggggG (SEQ ID NO: 20)
gGGGACGAGCICGTCggggG;

(SEQ ID NO: 21)
gGGGACGAGCICGTCgggG;

(SEQ ID NO: 22)
ggGGACGAICGTCGgggggG;

(SEQ ID NO: 23)
ggGGGACGAICGTCGggggG;

(SEQ ID NO: 24)
gGGGACGAICGTCGggggG;

(SEQ ID NO: 1)
gGGGACGAICGTCGgggG;

(SEQ ID NO: 25)
ggGGACGAICGICGgggggG;

(SEQ ID NO: 26)
ggGGGACGAICGICGggggG;

(SEQ ID NO: 27)
gGGGACGAICGICGggggG;

(SEQ ID NO: 28)
gGGGACGAICGICGgggG;

(SEQ ID NO: 29)
gGGGACGAICGAACGTgggggG;

(SEQ ID NO: 30)
ggGGACGAICGAACGTggggG;
```

```
                                    (SEQ ID NO: 30)
gGGGACGAICGAACGTggggG;

(SEQ ID NO: 31)
gGGGACGAICGAACGTgggG;

(SEQ ID NO: 32)
gGGGACGAICGAACGIgggggG;

(SEQ ID NO: 33)
ggGGGACGAICGAACGIggggG;

(SEQ ID NO: 33)
gGGGACGAICGAACGIggggG;

(SEQ ID NO: 34)
gGGGACGAICGAACGIgggG;

(SEQ ID NO: 35)
gGGGICGACGTCGACGTCGAGggggG;

(SEQ ID NO: 10)
ggGGGICGACGTCGACGTCGAGggggG;

(SEQ ID NO: 10)
gGGGICGACGTCGACGTCGAGggggG;

(SEQ ID NO: 36)
gGGGICGACGTCGACGTCGAGgggG;

(SEQ ID NO: 37)
gGGGICGACGICGACGTCGAGggggG;

(SEQ ID NO: 11)
ggGGGICGACGICGACGTCGAGggggG;

(SEQ ID NO: 11)
gGGGICGACGICGACGTCGAGggggG;

(SEQ ID NO: 38)
gGGGICGACGICGACGTCGAGgggG;

(SEQ ID NO: 39)
gGGGICGACGTCGACGICGAGggggG;

(SEQ ID NO: 12)
ggGGGICGACGTCGACGICGAGggggG;

(SEQ ID NO: 12)
gGGGICGACGTCGACGICGAGggggG;

(SEQ ID NO: 40)
gGGGICGACGTCGACGICGAGgggG;

(SEQ ID NO: 41)
gGGGICGACGICGACGICGAGggggG;

(SEQ ID NO: 13)
ggGGGICGACGICGACGICGAGggggG;

(SEQ ID NO: 13)
gGGGICGACGICGACGICGAGggggG;
and (SEQ ID NO: 42)
gGGGICGACGICGACGICGAGgggG,
``` where "I" represents 5-iodo-2'-deoxyuridine; each lower case letter represents a nucleotide linked to its 3'-adjacent nucleotide by a phosphorothioate (PS) linkage; and each upper case letter represents a nucleotide linked to its 3'-adjacent nucleotide (if present) by a phosphodiester (PO) linkage, except that the 3'-terminal nucleotide is represented by an upper case letter since it has no 3'-adjacent nucleotide.

The preferred CpG ODN of the present invention will be synthesized using standard methods well known in the art and described above. The activity of the ODN will be evaluated using in vitro dose-response assays on human peripheral blood mononuclear cells (PBMC) for IFN-α and IL-10 secretion as described in the A-class and E-class patents (for example, U.S. Pat. No. 8,580,268, FIG. 27 for IFN-α, and U.S. Pat. No. 7,795,235, FIG. 27 for IL-10). Because humans show inter-individual variation in the magnitude of the IFN-α response to TLR9 stimulation, PBMC from a minimum of 3 different individuals will be tested for all cytokine, chemokine, and IFN assays. Freshly collected PBMC are strongly preferred for maximal responsiveness—after 24 hr the magnitude of the in vitro responses to TLR9 ligation will be significantly lower. A-class CpG ODN are typically tested on human PBMC at concentrations from approximately 0.1 µM to approximately 10 µM. Supernatants are collected after approximately 24, 48, or 72 hr and tested by enzyme-linked immunosorbent assay (ELISA) or other standard assay for amount of IFN-α (usually the assay just measures one or more of the many isoforms of IFN-α) and/or other IFN-induced chemokines and cytokines.

Preferred A-class and A/E-class CpG ODN of the invention will induce an average of greater than 1000 pg/ml of IFN-α at the most effective concentration in the assay (potency is less important in this regard than peak efficacy), or more preferably greater than 3,000 pg/ml of IFN-α and most preferably greater than 10,000 pg/ml of IFN-α; in any case preferred ODN induce the production of at least greater than 10 times the IFN-α induced by a positive control B-class CpG ODN. Supernatants from the same experiments are also tested for IL-10 secretion using similar ELISA assays. Preferred A or A/E-class ODN of the present invention will induce less than 1000 pg/ml, preferably less than 300 pg/ml, and most preferably less than 100 pg/ml of IL-10 secretion under these assay conditions.

The most preferred CpG ODN selected from these in vitro assays will then be evaluated in mouse tumor models, using standard systems well known in the art. The mouse assays are not used to select the most active ODN to be taken into human clinical trials, since the rank-order of the ODN will differ, as a result of structural differences between mouse and human TLR9 and species-specific differences in the cell types expressing TLR9. For these reasons the primary selection for a lead candidate CpG ODN to take into human clinical trials will be based on the results from the in vitro assays using human cells.

Example 2

In vitro experiments were performed to examine the effects of changes in palindrome sequence, number of 5' and 3' G, number of 5' and 3' phosphorothioate internucleotide linkages, and substitution of 5-iodo-2'-deoxyuridine within the palindromes on IFN-α secretion by human peripheral blood mononuclear cells (PBMCs).

Figure 4:
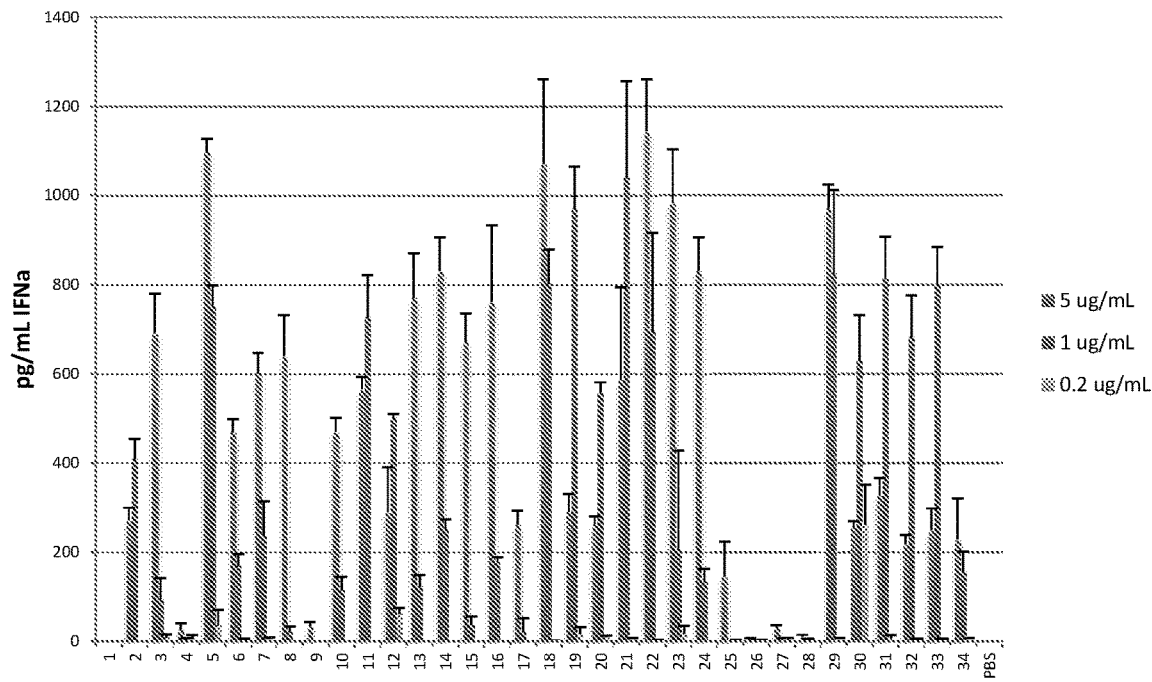
FIG. 4 is a graph depicting IFN-α induction for Set 1 CpG-A oligonucleotides. PBS, phosphate buffered saline control.
Figure 5:
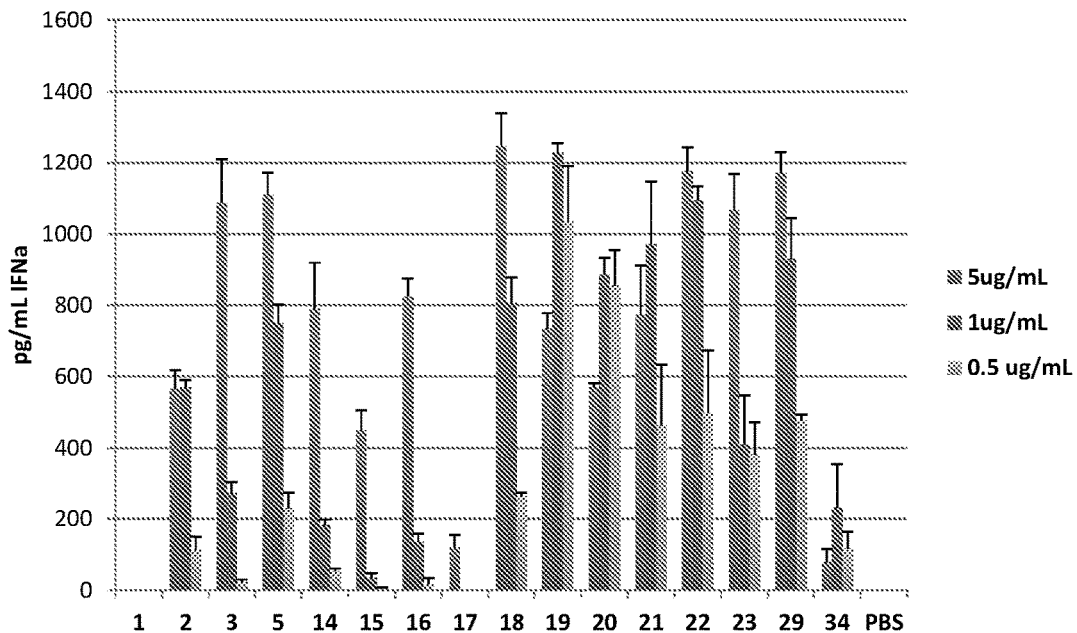
FIG. 5 is a graph depicting IFN-α induction for selected Set 1 CpG-A oligonucleotides. PBS, phosphate buffered saline control.

PBMCs from a normal human donor were cultured in the presence or absence of the indicated ODN in triplicate and results plotted as mean+/−standard deviation (SD) in FIGS. 4 and 5, for two different human donors. PBMCs were isolated over histopaque-1077 (Sigma) and plated at 1.25× $10^6$/mL, 220 µL/well in RPMI 1640 (10% FBS, glutamine, Pen/Strep) in a 96-well U-bottom tissue culture plate. ODN were added to a final concentration of 5, 1 or 0.2 µg/mL (FIG. 4) or at a lowest concentration of 0.5 µg/mL (FIG. 5) and cells were incubated for 48 hours. Cells were then spun down and supernatants transferred to new plates and frozen at −20° C. until use. Supernatants were subsequently thawed and used for an IFN-α ELISA (PBL Verikine human IFN-α) following the manufacturer's instructions.

TABLE 2

Set 1 CpG-A oligos made and tested

| # | Sequence | ODN | IFN-a | SEQ ID NO: |
|---|---|---|---|---|
| 1 | tcgtcgttttgtcgttttgtcgtT | 2006 | low | 44 |
| 2 | ggGGGACGATCGTCgggggG | 2216 | 2+ | 49 |
| 3 | gGGGACGATCGTCGgggG | 2216b | 2+ | 502 |
| 4 | ggGGTCGACGTACGTCGAggggG | 2301a | +/− | 503 |
| 5 | gGGGTCGTCGACGAggggG | 2329a | 3+ | 504 |
| 6 | ggGGACGAGCTCGTCgggggG | 2247a | 2+ | 505 |
| 7 | gGGGACGAGCTCGTCggggG | 2247b | 2+ | 517 |
| 8 | gGGGACGAGCTCGTCggggG | 2247c | 2+ | 507 |
| 9 | gGGGACGAGCTCGTCgggG | 2247d | +/− | 508 |
| 10 | ggGGACGATCGTCGgggggG | 2255a | 2+ | 77 |
| 11 | ggGGGACGATCGTCGgggggG | 2255b | 2+ | 49 |
| 12 | gGGGACGATCGTCGgggggG | 2255c | 2+ | 509 |
| 13 | gGGGACGATCGTCGgggG | 2255d | 2+ | 502 |
| 14 | gGGGTCGACGTCGACGTCGAggggggG | 2334a | 2+ | 78 |
| 15 | ggGGTCGACGTCGACGTCGAggggG | 2334b | 2+ | 512 |
| 16 | gGGGTCGACGTCGACGTCGAggggG | 2334c | 2+ | 512 |
| 17 | gGGGTCGACGTCGACGTCGAgggG | 2334d | 1+ | 513 |
| 18 | gGGGACGACGTCGTGgggGG | 2336a | 3+ | 514 |
| 19 | gGGGACGACGTCGTGgggggG | 2336b | 3+ | 79 |
| 20 | ggGGACGACGTCGTGgggggG | 2336c | 2+ | 514 |
| 21 | gGGGACGACGTCGTGggggG | 2336d | 3+ | 514 |
| 22 | gGGGACGACGTCGTGgggG | 2336e | 3+ | 515 |
| 23 | ggGTCGTCGACGAggggG | 2329e | 2+ | 516 |
| 24 | gGGGACGAICGTCGgggG | 2216a | 2+ | 1 |
| 25 | ggGGICGACGTACGTCGAggggG | 2301b | +/− | 5 |
| 26 | ggGGICGACGIACGTCGAggggG | 2301c | low | 6 |
| 27 | ggGGICGACGTACGICGAggggG | 2301d | low | 7 |
| 28 | ggGGICGACGIACGICGAggggG | 2301e | low | 8 |
| 29 | gGGGTCGTCGACGAggggG | 2329a | 3+ | 504 |
| 30 | gGGGICGTCGACGAggggG | 2329b | 3+ | 15 |
| 31 | gGGGTCGICGACGAggggG | 2329c | 3+ | 16 |
| 32 | gGGGICGICGACGAggggG | 2329d | 3+ | 17 |
| 33 | gGGGACGACGICGIGgggGG | 2336b | 3+ | 518 |
| 34 | tcgaacgttcgaacgttcgaacgttcgaat | SD-101 | 1+ | 519 |

1 (ODN 2006) is control CpG-B
2 (ODN 2216) is control CpG-A
34 (ODN SD-101) is control CpG-C
3-23 are novel A-class oligos
24-33 are CpG-A oligos containing 5-iodo-2'-deoxyuridine ("I")
lower case = PS linkage (others are PO)

Data from this set of experiments suggests:

Greater than four G on the 3' end of oligo confer good activity: compare, e.g., ODN 2247a-c (five or more 3'G) to ODN 2247d (with four 4G on 3' end).

Five G on 3' end may be inferior to six G (compare ODN 2334d with 5G to ODN 2334a-c with six or more 3' G).

It doesn't matter whether there are one or two PS linkages on 5' end: compare ODN 2334b (2 PS) to ODN 2334c (1 PS).

One PS linkage on 5' end appears to be superior to two PS on 5' end in at least some cases: ODN 2336c is the only version of 2336 that has two 5' PS linkages, and appears to be weaker for IFN-α induction than the other versions, which have one PS.

As long as there are at least five G at the 3' end, three PS on 3' end appears to be just as strong as four PS: compare ODN 2336a and 2336e (three PS at 3' end) to ODN 2336b and 2336d with five or four PS, respectively.

The palindrome present in ODN 2301 is weak (but still stronger than the CpG-B) regardless of other elements: therefore not all palindromes work well.

One or two halogen substitutions within the palindrome are tolerated well in CpG-A, but do not increase IFN-α-inducing activity (e.g., compare ODN 2329a to 2329b, c, d; or ODN 2336a to 2336b; or ODN 2216 to 2216a).

Example 3

In vitro experiments were performed to examine the effects of changes in palindrome sequence, number of 5' and 3' phosphorothioate internucleotide linkages, formulation of a native DNA CpG-A ODN in a virus-like particle (VLP), and substitution of 2-O-methyl sugars within the 3' end of the CpG-A ODN on potency and peak IFN-α secretion by human PBMC.

Experimental conditions were generally as in Example 2, except that in this case the indicated ODN were cultured with the PBMC in triplicate at the concentrations of 5 µg/mL (concentration or "conc A" in FIGS. 6 and 7); 1 µg/mL ("conc B" in FIGS. 6 and 7) and 0.5 µg/mL ("conc C") for all of the ODN except for two samples:

1. The completely PO ODN G10 (labeled as "CYT003" in FIGS. 6 and 7) was cultured at ODN concentrations of 50 µg/mL ("conc A" in FIGS. 6 and 7), 10 µg/mL ("conc B") and 2 µg/mL ("conc C"); and 2. Samples labeled as "CytQbAb" in FIGS. 6 and 7 contained the G10 ODN packaged within a virus-like particle comprising the bacteriophage protein Qb as previously described by and in clinical development sponsored by Cytos under the name CYT003 or QbG10 (Beeh et al., *J Allergy Clin Immunol* 2013; 131:866-74) together with an anti-Qb antibody to facilitate uptake of the VLP into immune cells. The VLP in these samples was cultured like G10 at 50 µg/mL ("conc A" in FIGS. 6 and 7), 10 µg/mL ("conc B"), and 2 µg/mL ("conc C"), but since the dose was based on the whole VLP, yet only 20% of the mass of the VLP comprises G10, the actual mass of G10 in each well was closer to 10 µg/mL ("conc A" in FIGS. 6 and 7), 2 µg/mL ("conc B") and 0.5 µg/mL ("conc C").

TABLE 3

Set 2 CpG-A oligos made and tested

| # | Sequence | ODN | IFN-α | SEQ ID NO: |
|---|----------|-----|-------|------------|
| 1 | ggGGGACGATCGTCgggggG | 2216 | 2+ | 49 |
| 2 | gGGGACGACGTCGTGgggGG | 2336a | 3+ | 514 |
| 3 | gGGGACGACGTCGTGgggGG | 2336a1 | 3+ | 514 |
| 4 | GGGGACGACGTCGTGGGGgG | 2336a2 | 1+ | 514 |
| 5 | GGGGACGACGTCGTGGGGGG | 2336aPO | 1+ | 514 |
| 6 | mGmGmGmGACGACGTCGTGmGmGmGmGmG | 2336m1 | weak | 520 |
| 7 | GGGGACGACGTCGTGGGGGmG | 2336m2 | neg | 521 |
| 8 | GGGGACGACGTCGTGGGGGgtT | 23365T | 1+ | 522 |
| 9 | ggGGACGACGTCGTGggggG | 2336c | 2+ | 514 |
| 10 | gGGGACGACGTCGTGgggG | 2336e | 2+ | 515 |
| 11 | gGGGTCGTCGACGAggggG | 2329a | 2+ | 504 |
| 12 | GGGGTCGTCGACGAGGggG | 2329a1 | weak | 504 |
| 13 | GGGGACGACGTCGTGGGGGGmUmU | 2336mU | neg | 523 |
| 14 | GGGGGGGGGGACGATCGTCGGGGGGGGGG | G10 | 3+ | 82 |

1 (ODN 2216) is control CpG-A
2-13 are novel A-class oligos
lower case = PS linkage (others are PO)
mG = 2'-O-methyl G
mT = 2'-O-methyl T Data from this set of experiments suggests:

Fewer than three PS linkages at the 3' end and no PS linkages on the 5' end leads to a severe reduction in the potency of the CpG-A, but no apparent reduction in the peak achievable IFN-α induction at the highest ODN concentration (compare the very strong IFN-α induction by ODN 2336a and 2336a1 (with three or four PS linkages at 3' end, respectively) which was detectable even at only 0.5 μg/mL to the very similar peak level of IFN-α induction by ODN 2336a2, 2336PO, and 2336ST with 2, 0, or 1 PS linkage, respectively.

There is no apparent potency advantage to having more than one PS at the 5' end and three PS at the 3' end (compare the similar levels of activity between ODN 2336c and 2336e, with a difference of one PS linkage at both ends).

The palindrome in ODN 2329 (TCGTCGACGA) (SEQ ID NO:524) appears to be less potent for IFN-α induction than the palindromes in either ODN 2216 (GACGATCGTC) (SEQ ID NO:525) or the ODN 2336 series (ACGACGTCGT) (SEQ ID NO:526).

of the "naked" G10 ("CYT003") is very similar to the G10 packaged within the VLP, although the latter contains only ~20% of the ODN mass.

Figure 7:
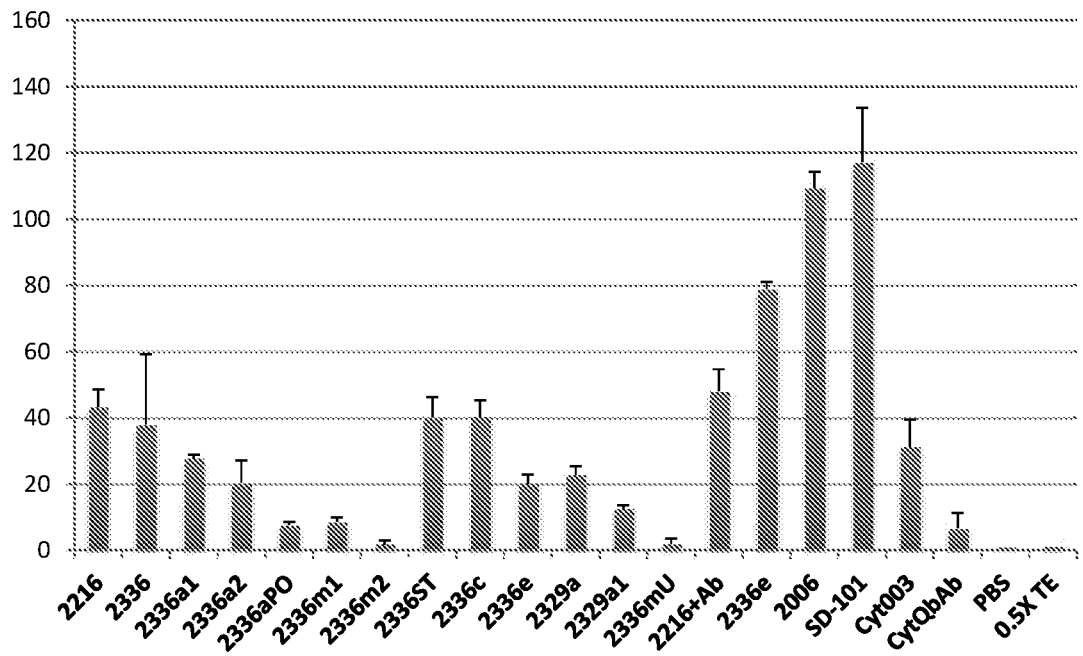
FIG. 7 is a graph depicting interleukin-10 (IL-10) induction for Set 2 CpG-A oligonucleotides. Y-axis, pg/mL IL-10. PBS, phosphate buffered saline control; TE, Tris-EDTA.

In accordance with this invention, the IL-10 induction by the CpG-B ("2006") and CpG-C ("SD-101") control ODN is significantly higher than that of any of the CpG-A ODN (FIG. 7). This supports the use of intratumorally injected CpG-A ODN of the invention for cancer immunotherapy, where local induction of IL-10 (for example, by CpG-B ODN) would be undesirable.

Example 4

In vitro experiments were performed to examine the effects of changes in CpG-A ODN backbone with either phosphorodithioate (PS2) or phosphorothioate (PS) compared to native DNA (PO) on potency and peak IFN-α secretion by normal human PBMC.

Experimental conditions were generally as in Example 2, except that in this case the indicated ODN were cultured with the PBMC in triplicate for 72 hr at the concentrations of 0.5 μg/mL or 5 μg/mL.

TABLE 4

Set 3 CpG-A oligos made and tested

| # | Sequence | ODN | IFN-a | SEQ ID NO: |
|---|---|---|---|---|
| A | G#G#GGGACGATCGTCGGGG#G#G | AF185A | strong | 49 |
| B | G#G#GGGAGCATGCCTGGGG#G#G | AF185B | negative | 527 |
| C | G#G#GGGAC#GATC#GTCGGGG#G#G | AF185C | weak | 49 |
| D | G#G#GGGA#C#GAT#C#GTCGGGG#G#G | AF185D | neg | 49 |
| E | G#G#GGG#ACGA#TCGTCGGGG#G#G | AF185E | weak | 49 |
| F | G#G#GGGACGAT#CGT#CGGGG#G#G | AF185F | weak | 49 |
| G | GGGGGACGATCGTCGGGGGG | AF185G | weak | 49 |
| H | G#GGGGACGATCGTCGGGG#G#G | AF185H | strong | 49 |
| I | GGGGGAC#GATC#GTCGGGGGG | AF185I | weak | 49 |

# = phosphorodithioate (PS2) internucleotide linkage

CpG-A ODN based on a less potent palindrome like that in ODN 2329 may suffer a correspondingly greater reduction in potency if the number of PS linkages is reduced at the 5' and 3' ends (compare ODN 2329a to 2329a1, with reduced PS linkages).

Substitution of one or more 2'-O-methyl bases at the 5' and/or 3' ends of the CpG-A ODN leads to a severe reduction in the potency and peak achievable IFN-α induction (compare the 2-O-methyl-substituted ODN 2336m1, 2336m2, and 2336mU to the original unmethylated versions of ODN 2336).

Figure 6:
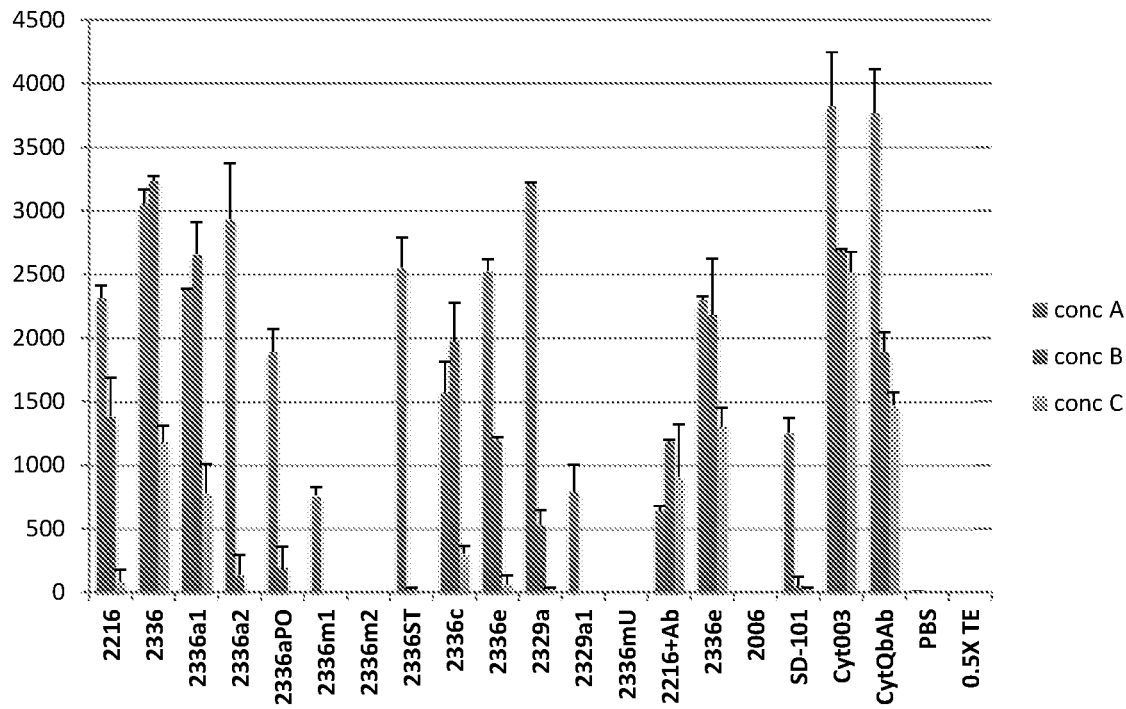
FIG. 6 is a graph depicting IFN-α induction for Set 2 CpG-A oligonucleotides. Y-axis, pg/mL IFN-α. PBS, phosphate buffered saline control; TE, Tris-EDTA.
Figure 8:
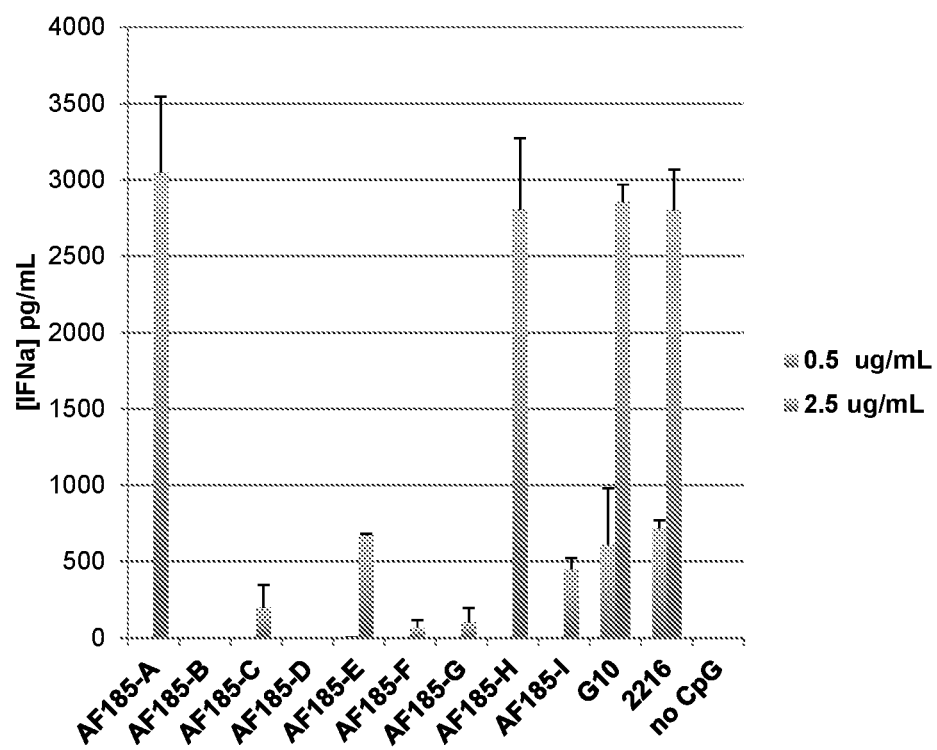
FIG. 8 is a graph depicting effect of phosphorodithioate backbone modification on IFN-α induction by Set 3 CpG-A oligonucleotides.

The highest peak IFN-α induction seen with any of the ODN was from the G10 ("CYT003" in FIG. 6) and from the VLP containing the G10 ("CytQbAb" in FIG. 6). Since G10 is native DNA with no PS modifications at all, this indicates that PS modification is not required for IFN-α induction, as long as either higher concentrations of the CpG-A ODN are used, or the ODN is packaged or delivered in such a way as to protect it against nucleases, such as in a VLP as used in this experiment. The VLP packaging appears to greatly increase the CpG-A ODN potency, since the dose-response Data from this set of experiments suggests (FIG. 8):

CpG-A ODN containing one or two PS2 modifications on the 5' and 3' ends (e.g., ODN AF185A and H) are approximately as effective as PO (G10) or PS ends (ODN 2216 has PS linkages at 5' and 3' ends).

PS2 within palindrome severely reduces activity compared to either no PS2 or PS2 on the ends within the polyG.

It is possible that the PS2 ends may prove superior to PO or PS in vivo due to increased protein binding and nuclease resistance.

Example 5

In vitro experiments were performed to examine the effects of reducing the number of G at the 5' and/or 3' end of the G10 CpG-A ODN, or changing the palindrome while keeping the backbone native DNA.

Experimental conditions were generally as in Example 2, except that in this case the indicated ODN (Table 5) were cultured with PBMC in duplicate for 48 hr at the concentration of 2.5 μg/mL.

TABLE 5

Set 4 CpG-A oligos made and tested

| # | Sequence | IFN-α | SEQ ID NO: |
|---|---|---|---|
| 1 | GGGGGGGGACGATCGTCGGGGGGGGG | ++ | 528 |
| 2 | GGGGGGGGGGGACGATCGTCGGGGGGG | ++ | 529 |
| 3 | GGGGGGGGACGATCGTCGGGGGGG | ++ | 530 |
| 4 | GGGGGGGGGGTCGTCGACGAGGGGGGGGG | - | 531 |
| 5 | GGGGGGGGGGACGAGCTCGTCGGGGGGGGG | + | 532 |
| 6 | GGGGGGGGGGACGATCGTCGGGGGGGGG | + | 533 |
| 7 | GGGGGGGGGGTCGACGTCGACGTCGAGGGGGGGGG | - | 534 |
| 8 | GGGGGGGGGGACGACGTCGTGGGGGGGGG | - | 535 |
| 9 | GGGGGGGGGGAACGACGTCGTTGGGGGGGGG | - | 536 |
| 10 | GGGGGGGGGGACGACGACGATCGTCGTCGTGGGGGGGGG | - | 537 |
| 11 | GGGGGGGGGGCACGACGTCGTGGGGGGGGG | - | 538 |
| 12 | GGGGGGGGGGAACGTTCGAACGTTGGGGGGGGGG | + | 539 |
| 13 | GGGGGGGGGGAACGTTCGAACGTTCGAACGTTGGGGGGGGG | - | 540 |
| 14 | GGGGGGGGGGTTCGAACGTTCGAAGGGGGGGGGG | + | 541 |
| 15 | GGGGGGGGGGACGTCGACGTCGGGGGGGGG | + | 542 |
| 16 | GGGGGGGGGGTCGACGTCGACGGGGGGGGG | ++ | 543 |
| 17 | GGGGGGGGGGACGTCGACGTACGTCGACGTGGGGGGGGG | + | 544 |
| 18 | GGGGGGGGGGTACGATATCGTAGGGGGGGGG | - | 545 |
| 19 | GGGGGGGGGGTACGTATACGTAGGGGGGGGG | - | 546 |
| 20 | GGGGGGGGGGACGTCGACGTCGGGGGGGGG | - | 542 |
| 21 | GGGGGGGGGGCAGCATGCTGGGGGGGGGG | - | 547 |

Figure 9:
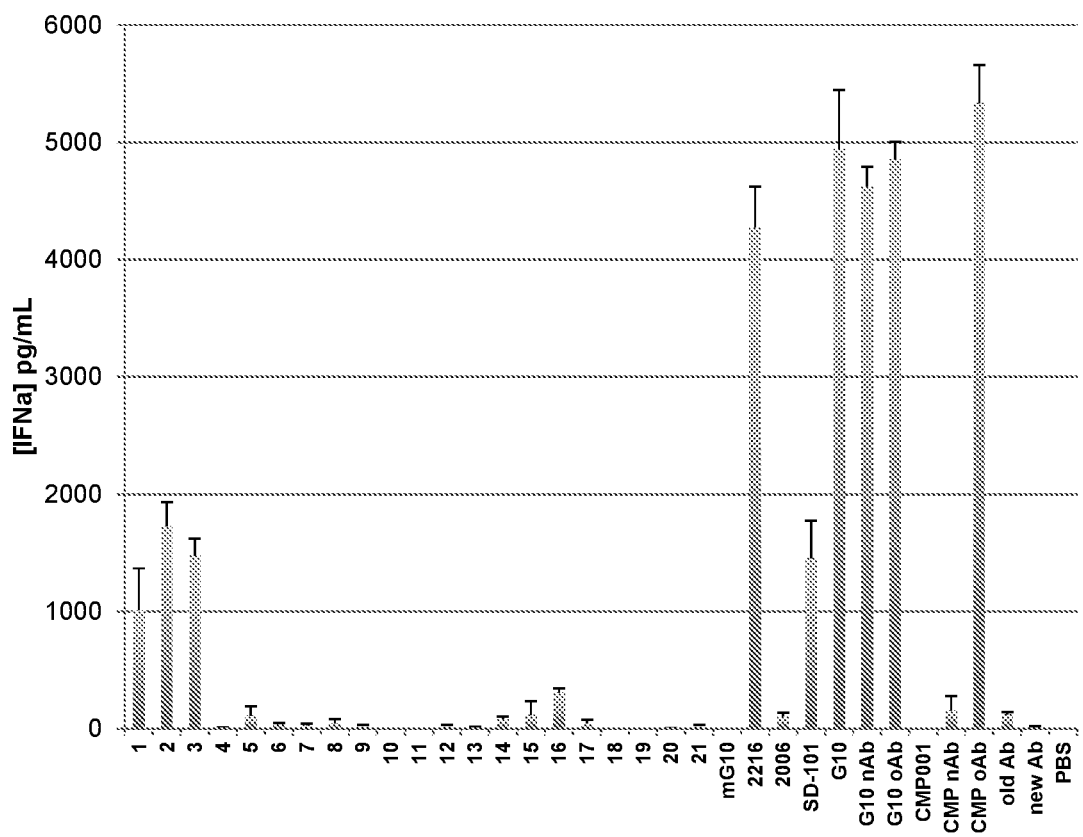
FIG. 9 is a graph depicting structure-activity relationship of reducing the number of 5' and/or 3' G in CpG-A oligonucleotide G10 or changing the palindrome on induction of IFN-α secretion from normal human peripheral blood mononuclear cells (PBMCs). nAb, new anti-Qb antibody; oAb, old anti-Qb antibody; PBS, phosphate buffered saline control.
Figure 10:
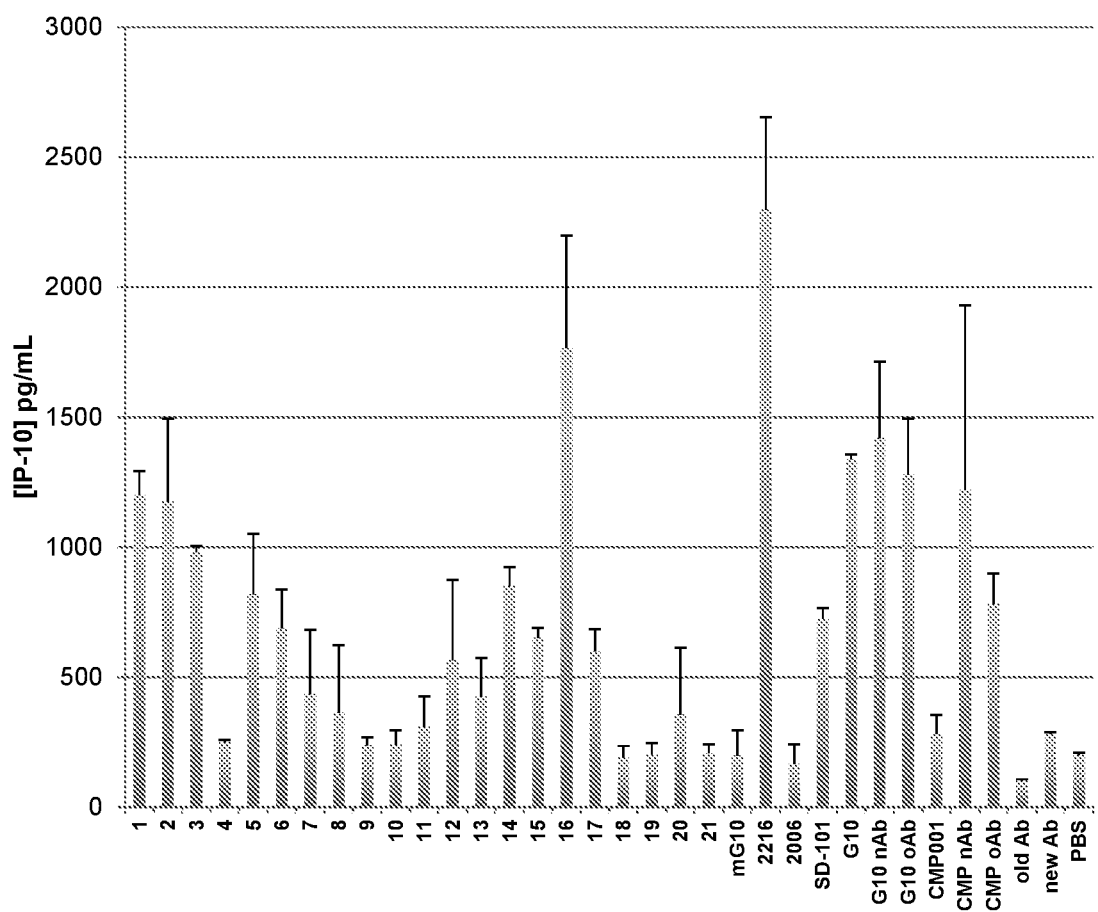
FIG. 10 is a graph depicting structure-activity relationship of reducing the number of 5' and/or 3' G in CpG-A oligonucleotide G10 or changing the palindrome on induction of IP-10 secretion from normal human peripheral blood mononuclear cells (PBMCs). nAb, new anti-Qb antibody; oAb, old anti-Qb antibody; PBS, phosphate buffered saline control.

1 G10 variant: 5' end reduced G
2 G10 variant: 3' end reduced G
3 G10 variant: both ends reduced G
4 TCGGTC palindrome
5 GACGAG palindrome
6 GACGA palindrome
7 TCGACGTC
8 ACGAC
9 AACGAC
10 ACGACGACGA (SEQ ID NO: 548)
11 CACGAC
12 SD-101 palindrome
13 SD-101b
14 TTCGAAC
15 GACGTC
16 GTCGAC
17 ACGTCGACGT (SEQ ID NO: 549)
18 TACGAT low CG
19 TACGCT
20 GACGTC
21 GC control Data from this set of experiments suggests:

Reducing the number of G at the 5' and/or 3' ends of G10 (as in 1-3, Table 5) reduces the induction of IFN-α expression (FIG. 9) without reducing the IP-10 induction (FIG. 10).

Nearly all of the new palindromes when flanked by 10 G at the 5' and 3' ends induced IFN-α and IP-10 secretion that is superior to CpG-B (ODN 2006) but not necessarily superior to the control CpG-C (ODN SD-101).

Figure 11:
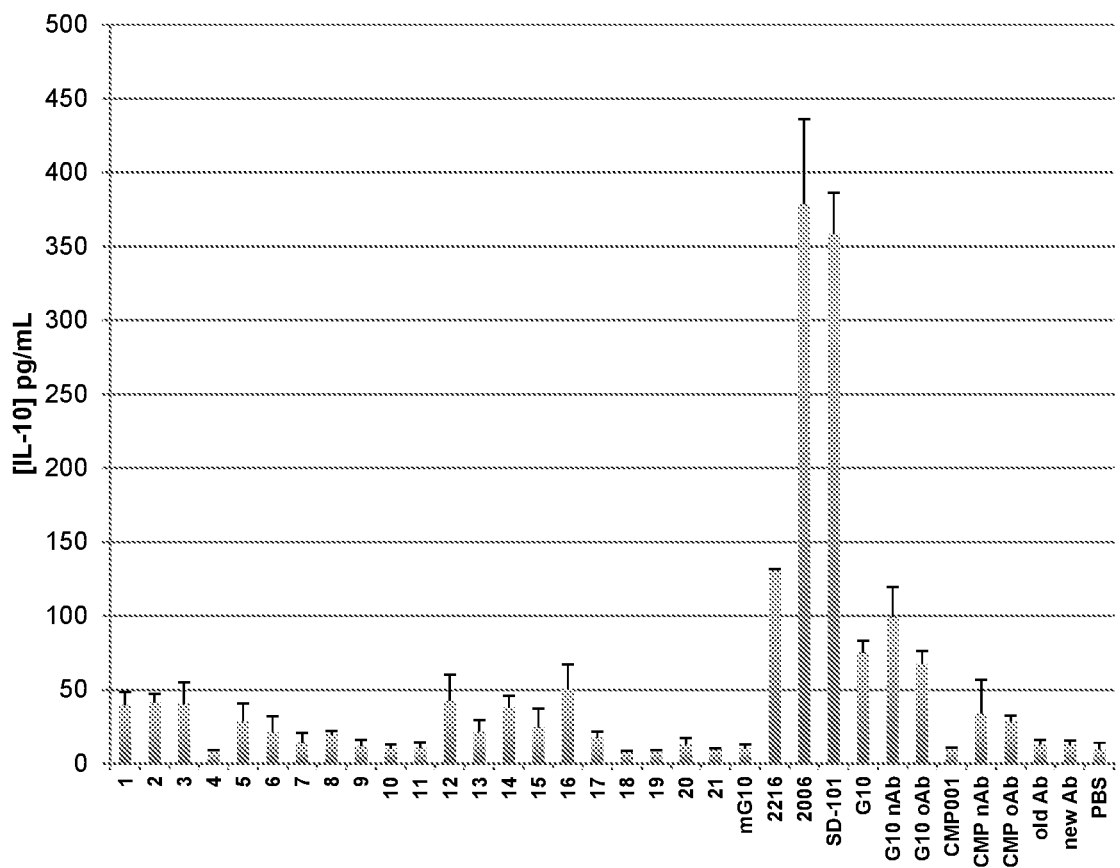
FIG. 11 is a graph depicting structure-activity relationship of reducing the number of 5' and/or 3' G in CpG-A oligonucleotide G10 or changing the palindrome on induction of IL-10 secretion from normal human peripheral blood mononuclear cells (PBMCs). nAb, new anti-Qb antibody; oAb, old anti-Qb antibody; PBS, phosphate buffered saline control.

CpG-B and CpG-C have the undesirable property of inducing higher IL-10 secretion than any of the new CpG-A ODN (FIG. 11).

Example 6

In vivo experiments were performed to evaluate the efficacy of treatment of lymphoma with combination tumor immunotherapy involving intratumoral administration of A-class CpG oligonucleotide and systemic administration of anti-PD-1 checkpoint inhibitor.

Forty female BALB/c mice were primed with CMP001 (CpG-A G10 formulated in VLP) 12.5 µg on day −14. This priming step was included with the aim of inducing an anti-Qb antibody response to the Qb VLP so that with subsequent injections, the VLP would be opsonized and quickly taken up by pDC. Primed mice were then inoculated on each flank with 5×10$^6$ A20 lymphoma cells on day 0. Mice were then divided into four treatment groups, N=10 per group. Mice in Group 1 (negative control) received saline injection directly into lymphoma tumor on one flank on days 7, 12, and 15; and saline injection i.p. twice weekly beginning on day 7. Mice in Group 2 (CpG alone) received CMP001 100 µg injection directly into lymphoma tumor on one flank on days 7, 12, and 15; and saline injection i.p. twice weekly beginning on day 7. Mice in Group 3 (CPI alone) received saline injection directly into lymphoma tumor on one flank on days 7, 12, and 15; and anti-PD-1 antibody 175 µg injection i.p. twice weekly beginning on day 7. Mice in Group 4 (CpG+CPI) received CMP001 100 µg injection directly into lymphoma tumor on one flank on days 7, 12, and 15; and anti-PD-1 antibody 175 µg injection i.p. twice weekly beginning on day 7. All mice were monitored for tumor size (treated and untreated (i.e, distant)) and survival. Results are shown in Table 6 and FIG. 12 and FIG. 13.

TABLE 6

| Treatment | Disease-Free at day 62 | Cause of Death | | |
|---|---|---|---|---|
| | | Treated Tumor | Untreated Tumor | Metastatic Tumor* |
| saline/saline | 0 | 5 | 5 | 0 |
| CMP001/saline | 0 | 2 | 7 | 1 |
| saline/anti-PD-1 | 0 | 3 | 4 | 3 |
| CMP001/anti-PD-1 | 3 | 0 | 3 | 4 |

*Metastatic tumors developed in peripheral lymph nodes and/or in a different location on the back.

Figure 12:
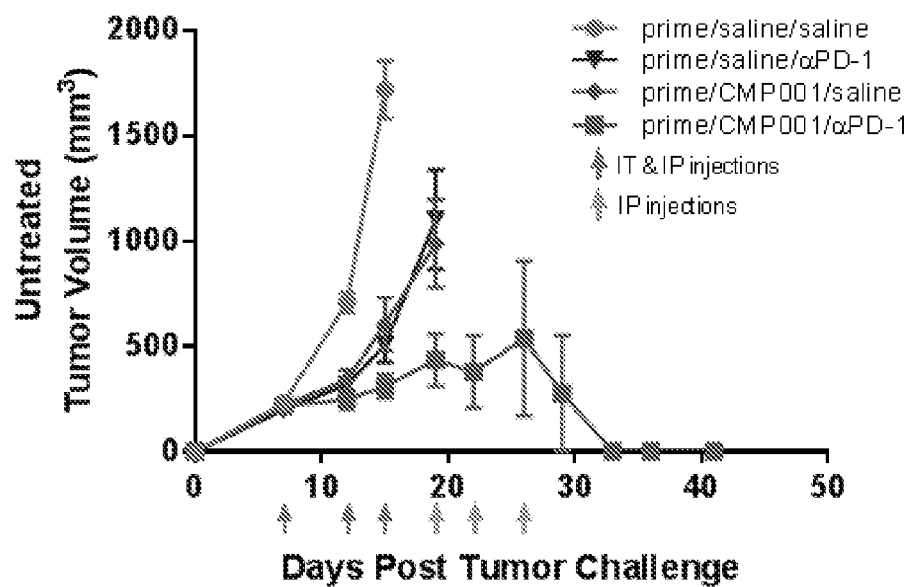
FIG. 12 is a pair of graphs depicting tumor volumes in A20 lymphoma-bearing mice. All mice were primed with a low dose (20 µg) of CMP-001 to induce anti-Qb antibodies so that the virus-like particles (VLP) will be opsonized and activate DC once treatment is initiated. Lymphoma cells were inoculated on both flanks of mice on day 0. Beginning on day 7, tumors on one side (treated) of mice were directly injected with CpG (CMP-001) or saline, while tumors on the other side (untreated) were not. Mice then also received intraperitoneal anti-PD-1 or saline twice weekly, as indicated. The graph in Panel A depicts average tumor volumes for "untreated" (distant) tumors. The graph in Panel B depicts average tumor volumes for "treated" tumors. N=10 for each group.
Figure 12:
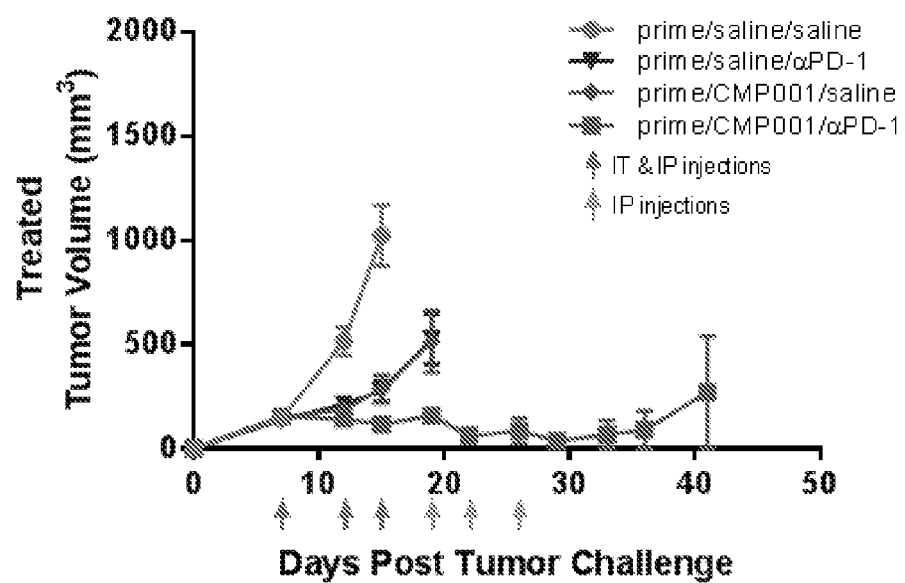

As shown in FIG. 12, both treated and untreated (distant) tumors grew more slowly in Group 2 (CpG alone) and Group 3 (CPI alone) than in the negative controls (Group 1). Significantly, both treated and untreated (distant) tumors grew much more slowly, and in several instances even disappeared, in Group 4 (CpG+CPI), and this effect was clearly synergistic.

Figure 13:
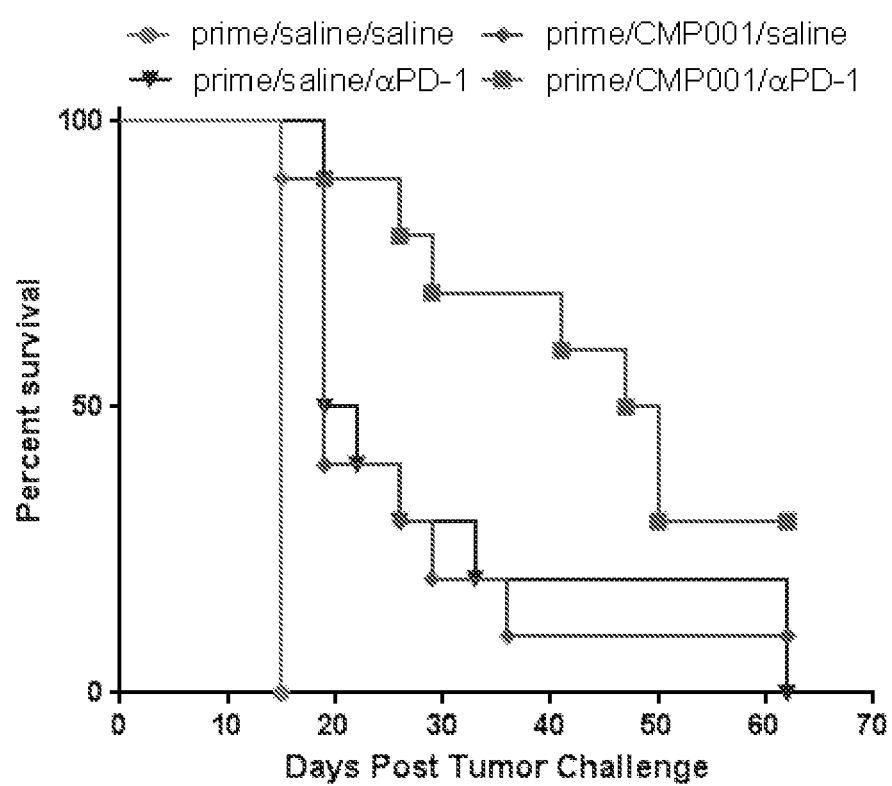
FIG. 13 is a graph depicting survival curves for mice in the experiment in FIG. 12.

As shown in FIG. 13, mice in Group 1 (negative control) had a median survival of 15 days following tumor inoculation ("tumor challenge"); mice in Group 2 (CpG alone) had a median survival of 19 days, with no mice surviving beyond about day 60; mice in Group 3 (CPI alone) had a median survival of 20.5 days, with no mice surviving beyond about day 60; and mice in Group 4 (CpG+CPI) had a median survival of 48.5 days with mice still surviving after more than 60 days.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

I claim:

1. A method of treating a cancerous tumor, comprising administering to a subject in need thereof an effective amount of a TLR9 agonist and a checkpoint inhibitor (CPI), wherein the TLR9 agonist is administered intratumorally or peritumorally, wherein the TLR9 agonist is an A-class CpG DNA of SEQ ID NO:82 and wherein the CPI is an antibody or antigen-binding fragment thereof which binds specifically to an antigen selected from the group consisting of PD-1, PD-L1, CTLA-4, TIM3, LAG3, and BTLA.

2. The method of claim 1, wherein the A-class CpG DNA is formulated as a virus-like particle.

3. The method of claim 1, wherein the CPI is administered systemically.

4. The method of claim 1, wherein the CPI comprises (i) a first antibody or antigen-binding fragment thereof which binds specifically to CTLA-4, and (ii) a second antibody or antigen-binding fragment thereof which binds specifically to an antigen selected from the group consisting of PD-1 and PD-L1.

5. The method of claim 1, wherein the CPI comprises (i) a first antibody or antigen-binding fragment thereof which binds specifically to CTLA-4, and (ii) a second antibody or antigen-binding fragment thereof which binds specifically to PD-1.

6. The method of claim 1, wherein the CPI comprises (i) a first antibody or antigen-binding fragment thereof which binds specifically to CTLA-4, and (ii) a second antibody or antigen-binding fragment thereof which binds specifically to PD-L1.

7. The method of claim 1, wherein the CPI comprises (i) a first antibody or antigen-binding fragment thereof which binds specifically to PD-1, and (ii) a second antibody or antigen-binding fragment thereof which binds specifically to PD-L1.

8. The method of claim 1, wherein the TLR9 agonist is administered prior to administration of the CPI.

9. The method of claim 1, wherein the TLR9 agonist and the CPI are administered substantially at the same time.

10. The method of claim 1, wherein the cancerous tumor is a lymphoma or a cancerous tumor of a tissue or organ selected from the group consisting of skin, head and neck, esophagus, stomach, liver, colon, rectum, pancreas, lung, breast, cervix, ovary, kidney, bladder, prostate, thyroid, brain, muscle, and bone.

11. The method of claim 1, wherein the cancerous tumor is melanoma.

12. The method of claim 10, wherein the cancerous tumor is a lymphoma.

13. The method of claim 1, wherein the cancerous tumor is resistant to a treatment regimen comprising administration of the CPI without administration of the TLR9 agonist.

14. The method of claim 1, wherein the subject is a human.

15. The method of claim 1, further comprising administering to the subject in need thereof an effective amount of radiotherapy, wherein the radiotherapy is initiated prior to administration of the TLR9 agonist.

* * * * *